(12) United States Patent
Peykov et al.

(10) Patent No.: US 10,900,951 B1
(45) Date of Patent: *Jan. 26, 2021

(54) METHODS OF ASSESSING SUITABILITY OF USE OF PHARMACEUTICAL COMPOSITIONS OF ALBUMIN AND PACLITAXEL

(71) Applicant: Abraxis Bioscience, LLC, Summit, NJ (US)

(72) Inventors: Viktor Peykov, San Diego, CA (US); Willard Foss, San Diego, CA (US); Daniel W. Pierce, Belmont, CA (US); Neil P. Desai, Pacific Palisades, CA (US)

(73) Assignee: Abraxis BioScience, LLC, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/517,967

(22) Filed: Jul. 22, 2019

Related U.S. Application Data

(63) Continuation of application No. 15/062,050, filed on Mar. 5, 2016, now Pat. No. 10,527,604.

(60) Provisional application No. 62/129,012, filed on Mar. 5, 2015.

(51) Int. Cl.
| | | |
|---|---|---|
| G01N 33/483 | (2006.01) | |
| G01N 24/08 | (2006.01) | |
| A61K 31/337 | (2006.01) | |
| A61K 9/51 | (2006.01) | |
| G01N 21/35 | (2014.01) | |
| G01N 23/20 | (2018.01) | |
| G01N 21/21 | (2006.01) | |

(52) U.S. Cl.
CPC ....... *G01N 33/4833* (2013.01); *A61K 9/5169* (2013.01); *A61K 31/337* (2013.01); *G01N 21/21* (2013.01); *G01N 21/35* (2013.01); *G01N 23/20* (2013.01); *G01N 24/08* (2013.01); *G01N 2021/3595* (2013.01)

(58) Field of Classification Search
CPC .... G01N 33/4833; G01N 21/21; G01N 21/35; G01N 23/20; G01N 24/08; G01N 2021/3595; A61K 9/5169; A61K 31/337
See application file for complete search history.

(56) References Cited

U.S. PATENT DOCUMENTS

| | | | |
|---|---|---|---|
| 5,362,478 | A | 11/1994 | Desai |
| 5,439,686 | A | 8/1995 | Desai |
| 5,498,421 | A | 3/1996 | Grinstaff |
| 5,505,932 | A | 4/1996 | Grinstaff |
| 5,508,021 | A | 4/1996 | Grinstaff |
| 5,512,268 | A | 4/1996 | Grinstaff |
| 5,560,933 | A | 10/1996 | Soon-Shiong |
| 5,635,207 | A | 6/1997 | Grinstaff |
| 5,639,473 | A | 6/1997 | Grinstaff |
| 5,650,156 | A | 7/1997 | Grinstaff |
| 5,665,382 | A | 9/1997 | Grinstaff |
| 5,665,383 | A | 9/1997 | Grinstaff |
| 5,916,596 | A | 6/1999 | Desai |
| 5,997,904 | A | 12/1999 | Magdassi |
| 6,096,331 | A | 8/2000 | Desai |
| 6,506,405 | B1 | 1/2003 | Desai |
| 6,528,067 | B1 | 3/2003 | Magdassi |
| 6,537,579 | B1 | 3/2003 | Desai |
| 6,565,842 | B1 | 5/2003 | Sojomihardjo |
| 6,652,884 | B2 | 11/2003 | Falciani |
| 6,749,868 | B1 | 6/2004 | Desai |
| 6,753,006 | B1 | 6/2004 | Desai |
| 7,001,885 | B2 | 2/2006 | Adachi |
| 7,223,561 | B2 | 5/2007 | Goodey |
| 7,758,891 | B2 | 7/2010 | Desai |
| 7,771,751 | B2 | 8/2010 | Desai |
| 7,780,984 | B2 | 8/2010 | Desai |
| 7,820,788 | B2 | 10/2010 | Desai |
| 7,923,536 | B2 | 4/2011 | Desai |
| 7,981,445 | B2 | 7/2011 | De |
| 8,034,375 | B2 | 10/2011 | Desai |
| 8,034,765 | B2 | 10/2011 | De |
| 8,137,684 | B2 | 3/2012 | Desai |
| 8,138,229 | B2 | 3/2012 | Desai |
| 8,257,733 | B2 | 9/2012 | Desai |
| 8,268,348 | B2 | 9/2012 | Desai |
| 8,314,156 | B2 | 11/2012 | Desai |
| 8,318,190 | B2 | 11/2012 | Burke |
| 8,415,304 | B2 | 4/2013 | Trieu |
| 8,735,394 | B2 | 5/2014 | Desai |
| 8,846,771 | B2 | 9/2014 | Desai |
| 8,853,260 | B2 | 10/2014 | Desai |

(Continued)

FOREIGN PATENT DOCUMENTS

| | | |
|---|---|---|
| CA | 2395589 A1 | 5/2002 |
| CN | 1406245 A | 3/2003 |

(Continued)

OTHER PUBLICATIONS

Abraxane (TM) (Dec. 2011). "AbraxaneTM Product, FDA Product Label," pp. 1-13.

(Continued)

*Primary Examiner* — Robert A Wax
*Assistant Examiner* — Olga V. Tcherkasskaya
(74) *Attorney, Agent, or Firm* — Morrison & Foerster LLP

(57) ABSTRACT

The present invention provides methods of assessing suitability of a pharmaceutical composition for medical use. The pharmaceutical composition comprises nanoparticles comprising paclitaxel coated with albumin and a non-nanoparticle portion comprising albumin and paclitaxel.

25 Claims, 25 Drawing Sheets

(56) References Cited

U.S. PATENT DOCUMENTS

| | | |
|---|---|---|
| 8,911,786 B2 | 12/2014 | Desai |
| 8,927,019 B2 | 1/2015 | Desai |
| 8,999,396 B2 | 4/2015 | Desai |
| 9,012,518 B2 | 4/2015 | Desai |
| 9,012,519 B2 | 4/2015 | Desai |
| 9,061,014 B2 | 6/2015 | Seward |
| 9,101,543 B2 | 8/2015 | Desai |
| 9,149,455 B2 | 10/2015 | Desai |
| 9,308,180 B2 | 4/2016 | De |
| 9,370,494 B2 | 6/2016 | Yeo |
| 9,393,318 B2 | 7/2016 | Desai |
| 9,399,071 B2 | 7/2016 | Desai |
| 9,399,072 B2 | 7/2016 | Desai |
| 9,446,003 B2 | 9/2016 | Desai |
| 9,511,046 B2 | 12/2016 | Desai |
| 9,561,288 B2 | 2/2017 | Desai |
| 9,585,960 B2 | 3/2017 | Foss |
| 9,597,409 B2 | 3/2017 | Desai |
| 9,675,578 B2 | 6/2017 | Desai |
| 9,724,323 B2 | 8/2017 | Desai |
| 9,820,949 B2 | 11/2017 | Desai |
| 9,855,220 B2 | 1/2018 | Desai |
| 9,884,013 B2 | 2/2018 | Seward |
| 9,962,373 B2 | 5/2018 | Desai et al. |
| 10,076,501 B2 | 9/2018 | Foss et al. |
| 10,258,565 B2 | 4/2019 | Seward |
| 10,328,031 B2 | 6/2019 | Desai |
| 10,413,531 B2 | 9/2019 | Desai |
| 10,527,604 B1 | 1/2020 | Peykov et al. |
| 10,555,912 B2 | 2/2020 | Foss et al. |
| 2003/0185894 A1 | 10/2003 | Zenoni |
| 2003/0187062 A1 | 10/2003 | Zenoni |
| 2003/0199425 A1 | 10/2003 | Desai |
| 2005/0004002 A1 | 1/2005 | Desai |
| 2005/0152979 A1 | 7/2005 | Besman |
| 2005/0282734 A1 | 12/2005 | Kadima |
| 2006/0263434 A1 | 11/2006 | Desai |
| 2007/0087022 A1 | 4/2007 | Desai |
| 2007/0093547 A1 | 4/2007 | Desai |
| 2007/0116761 A1 | 5/2007 | Desai |
| 2007/0117744 A1 | 5/2007 | Desai |
| 2007/0128290 A1 | 6/2007 | Desai |
| 2008/0160095 A1 | 7/2008 | Desai |
| 2008/0161382 A1 | 7/2008 | Desai |
| 2008/0280987 A1 | 11/2008 | Desai |
| 2009/0130163 A1 | 5/2009 | Desai |
| 2009/0263483 A1 | 10/2009 | Desai |
| 2009/0304805 A1 | 12/2009 | Desai |
| 2010/0048499 A1 | 2/2010 | Desai |
| 2010/0166869 A1 | 7/2010 | Desai |
| 2010/0183728 A1 | 7/2010 | Desai |
| 2010/0215751 A1 | 8/2010 | Desai |
| 2010/0297243 A1 | 11/2010 | Desai |
| 2011/0052708 A1 | 3/2011 | Soon-shiong |
| 2011/0118342 A1 | 5/2011 | De |
| 2011/0151012 A1 | 6/2011 | Desai |
| 2012/0070502 A1 | 3/2012 | Desai |
| 2012/0076862 A1 | 3/2012 | Desai |
| 2012/0128732 A1 | 5/2012 | Trieu |
| 2012/0189701 A1 | 7/2012 | Desai |
| 2012/0231082 A1 | 9/2012 | Desai |
| 2012/0283205 A1 | 11/2012 | Desai |
| 2012/0308612 A1 | 12/2012 | De |
| 2013/0045240 A1 | 2/2013 | Tao |
| 2013/0071438 A1 | 3/2013 | Desai |
| 2013/0115296 A1 | 5/2013 | Yeo |
| 2013/0177598 A1 | 7/2013 | Desimone |
| 2013/0195922 A1 | 8/2013 | Desai |
| 2013/0195983 A1 | 8/2013 | Desai |
| 2013/0195984 A1 | 8/2013 | Desai |
| 2013/0202709 A1 | 8/2013 | Desai |
| 2013/0209518 A1 | 8/2013 | Desai |
| 2013/0244952 A1 | 9/2013 | Desai |
| 2013/0266659 A1 | 10/2013 | Desai |
| 2013/0280336 A1 | 10/2013 | Desai |
| 2013/0280337 A1 | 10/2013 | Desai |
| 2014/0017315 A1 | 1/2014 | Desai |
| 2014/0017316 A1 | 1/2014 | Desai |
| 2014/0017323 A1 | 1/2014 | Desai |
| 2014/0023717 A1 | 1/2014 | Desai |
| 2014/0039069 A1 | 2/2014 | Desai |
| 2014/0039070 A1 | 2/2014 | Desai |
| 2014/0056986 A1 | 2/2014 | Desai |
| 2014/0072630 A1 | 3/2014 | Tao |
| 2014/0072631 A1 | 3/2014 | Trieu |
| 2014/0072643 A1 | 3/2014 | Desai |
| 2014/0079787 A1 | 3/2014 | Yeo |
| 2014/0079788 A1 | 3/2014 | Desai |
| 2014/0079793 A1 | 3/2014 | Desai |
| 2014/0080901 A1 | 3/2014 | Desai |
| 2014/0134257 A1 | 5/2014 | Desai |
| 2014/0155344 A1 | 6/2014 | Desai |
| 2014/0170228 A1 | 6/2014 | Desai |
| 2014/0186447 A1 | 7/2014 | Desai |
| 2014/0199403 A1 | 7/2014 | Desai |
| 2014/0199404 A1 | 7/2014 | Heise |
| 2014/0199405 A1 | 7/2014 | Pierce |
| 2014/0271871 A1 | 9/2014 | Desai |
| 2014/0296279 A1 | 10/2014 | Seward |
| 2014/0296353 A1 | 10/2014 | Desai |
| 2014/0302157 A1 | 10/2014 | Desai |
| 2015/0050356 A1 | 2/2015 | Desai |
| 2015/0079177 A1 | 3/2015 | Desai |
| 2015/0079181 A1 | 3/2015 | Desai |
| 2015/0104521 A1 | 4/2015 | Desai |
| 2015/0111960 A1 | 4/2015 | Desai |
| 2015/0157722 A1 | 6/2015 | Foss |
| 2015/0165047 A1 | 6/2015 | Desai |
| 2015/0190519 A1 | 7/2015 | Desai |
| 2015/0190556 A1 | 7/2015 | Desai |
| 2015/0313866 A1 | 11/2015 | Desai |
| 2016/0008330 A1 | 1/2016 | Desai |
| 2016/0015681 A1 | 1/2016 | Desai |
| 2016/0015817 A1 | 1/2016 | Benettaib |
| 2016/0151325 A1 | 6/2016 | Desai |
| 2016/0228401 A1 | 8/2016 | Desai |
| 2016/0374952 A1 | 12/2016 | Yeo |
| 2017/0007569 A1 | 1/2017 | De |
| 2017/0014373 A1 | 1/2017 | Desai |
| 2017/0020824 A1 | 1/2017 | Desai |
| 2017/0049711 A1 | 2/2017 | Desai |
| 2017/0100344 A1 | 4/2017 | Desai |
| 2017/0105951 A1 | 4/2017 | Desai |
| 2017/0157035 A1 | 6/2017 | Seward |
| 2017/0172975 A1 | 6/2017 | Desai |
| 2017/0181988 A1 | 6/2017 | Malhotra |
| 2017/0202782 A1 | 7/2017 | Pierce |
| 2017/0203012 A1 | 7/2017 | Desai |
| 2017/0224627 A1 | 8/2017 | Foss |
| 2017/0333384 A1 | 11/2017 | Desai |
| 2017/0340599 A1 | 11/2017 | Desai |
| 2018/0015181 A1 | 1/2018 | Desai |
| 2018/0064679 A1 | 3/2018 | Pierce |
| 2018/0133157 A1 | 5/2018 | Desai |
| 2018/0147139 A1 | 5/2018 | Seward |
| 2018/0153820 A1 | 6/2018 | Desai |
| 2018/0153863 A1 | 6/2018 | Desai |
| 2018/0169017 A1 | 6/2018 | Desai |
| 2018/0177770 A1 | 6/2018 | Desai |
| 2018/0177771 A1 | 6/2018 | Desai |
| 2018/0214425 A1 | 8/2018 | Desai |
| 2018/0256551 A1 | 9/2018 | Desai et al. |
| 2018/0289620 A1 | 10/2018 | Desai et al. |
| 2018/0374583 A1 | 12/2018 | Goldstein |
| 2019/0022020 A1 | 1/2019 | Desai |
| 2019/0054033 A1 | 2/2019 | Foss |
| 2019/0147986 A1 | 5/2019 | Luo |
| 2019/0167629 A1 | 6/2019 | Desai |
| 2019/0175564 A1 | 6/2019 | Desai |
| 2019/0183789 A1 | 6/2019 | Seward |
| 2019/0184031 A1 | 6/2019 | Desai |
| 2019/0192477 A1 | 6/2019 | Desai |
| 2019/0247357 A1 | 8/2019 | Foss |
| 2019/0307732 A1 | 10/2019 | Desai |

(56) References Cited

U.S. PATENT DOCUMENTS

| | | |
|---|---|---|
| 2019/0343789 A1 | 11/2019 | Desai |
| 2020/0040398 A1 | 2/2020 | Desai et al. |
| 2020/0129469 A1 | 4/2020 | Renschler |
| 2020/0138793 A1 | 5/2020 | Desai et al. |

FOREIGN PATENT DOCUMENTS

| | | |
|---|---|---|
| CN | 101670112 A | 3/2010 |
| CN | 102078306 A | 6/2011 |
| WO | WO9418954 A1 | 9/1994 |
| WO | WO9814174 A1 | 4/1998 |
| WO | WO9814175 A1 | 4/1998 |
| WO | WO9900113 A1 | 1/1999 |
| WO | WO0064437 A1 | 11/2000 |
| WO | WO0071079 A2 | 11/2000 |
| WO | WO0189522 A1 | 11/2001 |
| WO | WO02087545 A1 | 11/2002 |
| WO | WO03096944 A1 | 11/2003 |
| WO | WO2004052401 A2 | 6/2004 |
| WO | WO2004052401 A3 | 2/2005 |
| WO | WO2006089290 A1 | 8/2006 |
| WO | WO2007027819 A2 | 3/2007 |
| WO | WO2007027941 A2 | 3/2007 |
| WO | WO2007027819 A3 | 4/2007 |
| WO | WO2007027941 A3 | 4/2007 |
| WO | WO0071079 A3 | 3/2008 |
| WO | WO2008027055 A1 | 3/2008 |
| WO | WO2008057562 A1 | 5/2008 |
| WO | WO2008076373 A1 | 6/2008 |
| WO | WO2008109163 A1 | 9/2008 |
| WO | WO2008137148 A2 | 11/2008 |
| WO | WO2008150532 A1 | 12/2008 |
| WO | WO2008137148 A3 | 2/2009 |
| WO | WO2009126175 A1 | 10/2009 |
| WO | WO2009126401 A1 | 10/2009 |
| WO | WO2009126938 A1 | 10/2009 |
| WO | WO2010068925 A1 | 6/2010 |
| WO | WO2010105172 A1 | 9/2010 |
| WO | WO2010118365 A1 | 10/2010 |
| WO | WO2010121000 A1 | 10/2010 |
| WO | WO2011025838 A1 | 3/2011 |
| WO | WO2011119988 A1 | 9/2011 |
| WO | WO2011123393 A1 | 10/2011 |
| WO | WO2011123395 A1 | 10/2011 |
| WO | WO2011153009 A1 | 12/2011 |
| WO | WO2011153010 A1 | 12/2011 |
| WO | WO2011156119 A1 | 12/2011 |
| WO | WO2012092712 A1 | 7/2012 |
| WO | WO2012149451 A1 | 11/2012 |
| WO | WO2013090634 A1 | 6/2013 |
| WO | WO2013144554 A1 | 10/2013 |
| WO | WO2014105644 A1 | 7/2014 |
| WO | WO2014110345 A1 | 7/2014 |
| WO | WO2014110408 A1 | 7/2014 |
| WO | WO2014110443 A1 | 7/2014 |
| WO | WO2014123612 A1 | 8/2014 |
| WO | WO2014143613 A1 | 9/2014 |
| WO | WO2014151853 A1 | 9/2014 |
| WO | WO2014159171 A1 | 10/2014 |
| WO | WO2015157120 A1 | 10/2015 |
| WO | WO2016141365 A1 | 9/2016 |
| WO | WO2017004249 A1 | 1/2017 |
| WO | WO2017004264 A1 | 1/2017 |
| WO | WO2017004266 A1 | 1/2017 |
| WO | WO2017004267 A1 | 1/2017 |

OTHER PUBLICATIONS

Abraxane®. (Dec. 2014). "Prescribing Insert for Injectable Suspension (Paclitaxel Protein-Bound Particles for Injectable Suspension) (Albumin-Bound)," 24 pages.
Ahn, H.K. et al. (2014). "A Phase II Trial of Cremorphor EL-Free Paclitaxel (Genexol-PM) and Gemcitabine in Patients With Advanced Non-Small Cell Lung Cancer," Cancer Chemother Pharmacol 74:277-282.
American Society of Health-System Pharmacists. (Jun. 15, 2006). "ASHP Guidelines on Handling Hazardous Drugs. Developed by the ASHP Council on Professional Affairs and Approved by the ASHP Board of Directors on Jan. 12, 2006," Am. J. Health-Syst. Pharm. 63(12):1172-1193.
Amgen Inc. (Jun. 11, 2012). "Reply to Communication Pursuant to Article 94(3) EPC dated Dec. 2, 2011," 7 pages.
Anderson, C.L. et al. (Jul. 2006, e-pub. May 30, 2006). "Perspective—FcRn Transports Albumin: Relevance to Immunology and Medicine," TRENDS in Immunology 27(7):343-348.
Authier, N. et al. (2000). "Description of a Short-term Taxol®-Induced Nociceptive Neuropathy in Rats," Brain Research 887:239-249.
Blum, J.L. (Dec. 2007). "Phase II Study of Weekly Albumin-Bound Paclitaxel for Patients With Metastatic Breast Cancer Heavily Pretreated with Taxanes," Clinical Breast Cancer 7(11):850-856.
CDC Workplace Health and Safety. (Sep. 2004). "NIOSH Alert. Preventing Occupational Exposures to Antineoplastic and Other Hazardous Drugs in Health Care Settings," CDC WorkPlace Health and Safety 58 pages.
Celegene Corporation et al. (Mar. 6, 2015). "Citizen Petition," 116 pages.
Chen, N. et al. (2014). "Pharmacokinetics and Pharmacodynamics of nab-Paclitaxel in Patients With Solid Tumors: Disposition Kinetics and Pharmacology Distinct From Solvent-Based Paclitaxel," The Journal of Clinical Pharmacology 54(10):1097-1107.
Chen, N. et al. (2015). "Albumin-Bound nanoparticle (nab) paclitaxel exhibits enhanced paclitaxel tissue distribution and tumor penetration," Cancer Chemother Pharmacol. 76:699-712.
Chen, N. et. al. (2014). "Population Pharmacokinetics (PK) and Exposure—Neutropenia Relationship of nab-Paclitaxel (nab-P) in Patients (pts) with Solid Tumors," J. Clin. Oncol. 32(15):Abstract 2559, 3 pages.
Commisso, C. et al. (May 20, 2013). "Macropinocytosis of Protein is an Amino Acid Supply Route in Ras-Transformed Cells," Nature 497(7451):1-13.
Cortes, J. et al. (2010). "Nanoparticle Albumin-Bound (nab™)-Paclitaxel: Improving Efficacy and Tolerability by Targeted Drug Delivery in Metastatic Breast Cancer," EJC Supplements 8:1-10.
Dada, O.O. et al. (2017, e-pub. Jun. 17, 2017). "Comparison of SEC and CE-SDS Methods for Monitoring Hinge Fragmentation in IgG1 Monoclonal Antibodies," Journal of Pharmaceutical and Biomedical Analysis 145:91-97.
Desai, N. et al. (Feb. 15, 2006). "Increased Antitumor Activity, Intratumor Paclitaxel Concentrations, and Endothelial Cell Transport of Cremophor-Free, Albumin-Bound Paclitaxel, ABI-007, Compared With Cremophor-Based Paclitaxel," Clin. Cancer Res. 12(4):1317-1324.
Elzoghby, A.O. et al. (2012, e-pub. Aug. 1, 2011). "Albumin-Based Nanoparticles as Potential Controlled Release Drug Delivery Systems," Journal of Controlled Release 157(2):168-182.
EMA. (Mar. 26, 2015). "Reflection Paper on the Data Requirements for Intravenous Iron-Based Nano-Colloidal Products developed With Reference to an Innovator Medicinal Product," 11 pages.
EMA. (May 22, 2013). "Reflection Paper on Surface Coatings: General Issues for Consideration Regarding Parentheral Administration of Coated Nanomedicine Products," 5 pages.
European Search Report and European Search Opinion dated Jul. 6, 2016, for European Patent Application No. 13868481.6, filed on Dec. 19, 2013, 9 pages.
FDA. (2017). "FDA's Approach to Regulation of Nanotechnology Products," 4 pages.
FDA. (Jun. 2014). "Guidance for Industry Considering Whether an FDA-Regulated Product Involves the Application of Nanotechnology," 14 pages.
FDA. (Mar. 7, 2004). Center for Drug Evaluation and Reseach. Pharmacology/Toxicology Review and Evaluation. NDA No. 21-660, Product ABI-007, American Bioscience, Inc., 49 pages.
FDA. (May 16, 2014). "Generic Drug User Fee Amendments of 2012 Regulatory Science Initiatives: Request for Public Input for FY 2015 Generic Drug Research. Part 15 Public Hearing," 4 pages.

(56) References Cited

OTHER PUBLICATIONS

FDA. (Oct. 13, 2010). Petition Response, 12 pages.
FDA. (Oct. 2011). "Draft Guidance on Enoxaparin Sodium," 1 page.
FDA. (Oct. 2011). "Draft Guidance on Zolpidem," 2 pages.
FDA. (Sep. 2012). "Draft Guidance on Methylphenidate Hydrochloride," 6 pages.
FDA. (Sep. 2012). "Draft Guidance on Paclitaxel," 2 pages.
FDANEWS. (2017). "Phase III Trial of Tocosol Paclitaxel Does Not Meet Primary Endpoint," 1 page.
Federal Register. (2014). "Generic Drug User Fee Amendments of 2012; Regulatory Science Initiatives; Public Hearing; Request for Comments," FDA 5 pages.
Final Office Action dated May 31, 2018, for U.S. Appl. No. 15/183,636, filed Jun. 15, 2016, 37 pages.
Frei, E. et al. (2011). "Albumin Binding Ligands and Albumin Conjugate Uptake by Cancer Cells," BioMed Central 3 (11):1-4.
Frese, K.K. et al. (Mar. 2012, e-pub. Feb. 28, 2012). "nab-Paclitaxel Potentiates Gemcitabine Activity by Reducing Cytidine Deaminase Levels in a Mouse Model of Pancreatic Cancer," Cancer Discovery 2(3):260-269.
Fujita, A. et al. (2007). "Anaphylactiod Shock in a Patient Following 5% Human Serum Albumin Infusin During Off-Pump Coronary Artery Bypass Grafting," Journal of Anesthesia 21:396-398.
Gabizon, A. et al. (Feb. 15, 1994). "Prolonged Circulation Time and Enhanced Accumulation in Malignant Exudates of Doxorubicin Encapsulated in Polyethylene-glycol Coated Liposomes," Cancer Research 54:987-992.
Gales, B.J. et al. (1993). "Adverse Reaction to Human Serum Albumin," Ann. Pharmacother. 27:87-94.
Galli, C. (2006, e-pub. Mar. 9, 2016). "Experimental Determination of the Diffusion Boundary Layer Width of Micron and Submicron Particles," International Journal of Pharmaceutics 313:114-122.
Gardner, E.R. et al. (Jul. 1, 2008). "Randomized crossover pharmacokinetic study of solvent-based paclitaxel and nab-paclitaxel," Clin. Cancer Res. 14(13):4200-4205.
Garro, A.G. et al. (2011). "Reversible Exposure of Hydrophobic Residues on Albumin As A Novel Strategy For Formulation of Nanodelivery Vehicles For Taxanes," Int. J. Nanomedicine 6:1193-1200.
GDUFA. (2015). "Regulatory Science Priorities for Fiscal year 2015," 3 pages.
GGPS. (Jan. 6, 2015). "Guidance Agenda: New & Revised Draft Guidances CDER is Planning to Publish During Calendar Year 2015," 5 pages.
Goetz, H. et al. (2004). "Comparison of Selected Analytical Techniques for Protein Sizing, Quantitation and Molecular Weight Determination," J. Biochem. Biophys. Methods 60:281-293.
Gonzalez-Angulo, A.M. et al. (Oct. 1, 2013). "Weekly nab-Rapamycin in Patients With Advanced Nonhematologic Malignancies: Final Results of a Phase I Trial," Clinical Cancer Research 19(19):5474-5484.
Gradishar, W.J. et al. (Nov. 1, 2005). "Phase III Trial of Nanoparticle Albumin-Bound Paclitaxel Compared with Polyethylated Castor Oil-Based Paclitaxel in Women With Breast Cancer," J. Clin. Oncol. 23(31):7794-7803.
Green, M.R. et al. (2006, e-pub. Jun. 1, 2006). "Abraxane®, a novel Cremophore®-free, albumin-bound particle form of paclitaxel for the treatment of advanced non-small-cell lung cancer," Annuals of Oncology 17:1263-1268.
Hanauske, A.R. et al. (2005). "Pharmacokinetics (PK) of Free and Total Paclitaxel After Equal Doses of Paclitaxel Injectable Emulsion and Paclitaxel Injection," J Clin Oncol. 23:Abstract No. 2045, 1 page.
Herr, I. et al. (Jun. 15, 2003). "Glucocorticoid Cotreatment Induces Apoptosis Resistance toward Cancer Therapy in Carcinomas," Cancer Research 63:3112-3120.
Holloway, C. et al. (2012). "Scientific Considerations for Complex Drugs in Light of Established and Emerging Regulatory Guidance," Ann. N.Y. Acad. Sci. 1276:26-36.
Ibrahim, N.K. et al. (Sep. 1, 2006). "Multicenter Phase II Trail of ABI-007, an Albumin-Bound Paclitaxel, in Women With Metastatic Breast Cancer," Journal of Clinical Oncology 23(25):6019-6026.
Infante, J.R. et al. (Jan. 20, 2007). "Peritumoral Fibroblast SPARC Expression and Patient Outcome With Resectable Pancreatic Adenocarcinoma," Journal of Clinical Oncology 25(3):319-325.
International Search Report dated Mar. 18, 2014, for PCT Application No. PCT/US2013/076630, filed on Dec. 19, 2013, 9 pages.
Irizarry, L.D. et al. (Mar. 2009). "Cremophor EL-Containing Paclitaxel-Induced Anaphylaxis: A Call to Action," Community Oncology 6:132-134.
Jain, R.K. et al. (Jan. 7, 2005). "Normalization of Tumor Vasculature: An Emerging Concept in Antiangiogenic Therapy," Science 307:58-62.
Josić, DJ. et al. (1984). "Size-Exclusion High-Performance Liquid Chromatography and Sodium Dodecyl Sulfate-Polyacrylamide Gel Electrophoresis of Protein: A Comparison," Analytical Biochemistry 142:473-479.
Khan, S. et al. (2013). "Activation of NFkB is a Novel Mechanism of Pro-Survival Activity of Glucocorticoids in Breast Cancer Cells," Cancer Letters 337:90-95.
Kranenburg, O. et al. (Nov. 27, 2001). "Regulating c-Ras Function: Cholesterol Depletion Affects Caveolin Association, GTP Loading, and Signaling," Current Biology 11:1880-1884.
Langer, C.J. et al. (2008). "Phase III Trial Comparing Paclitaxel Poliglumex (CT-2103, PPX) in Combination with Carboplatin Versus Standard Paclitaxel and Carboplatin in the Treatment of PS 2 Patients with Chemotherapy-Naive Advanced Non-small Cell Lung Cancer," Journal of Thoracic Oncology 3(6):623-630.
Langer, K. et al. (2008, e-pub. Jun. 23, 2007). "Human Serum Albumin (HSA) Nanoparticles: Reproducibility of Preparation Process and Kinetics of Enzymatic Degradation", International Journal of Pharmaceutics 347 (1-2)109-117.
Lee, K.S. et al. (Mar. 2008). "Multicenter Phase II Trial of Genexol-PM (Cynviloq), a Cremophor-Free, Polymeric Micelle Formulation of Paclitaxel, in Patients With Metastatic Breast Cancer," Breast Cancer Res Treat. 108:241-250.
Li, Y. et al. (Feb. 25, 2015). "Pharmacologic Sensitivity of Paclitaxel to Its Delivery Vehicles Drives Distinct Clinical Outcome of Paclitaxel Formulations. Molecular Pharmaceutics," Molecular Pharmaceutics 12:1308-1317.
Liggins, R.T. et al. (Dec. 1997). "Solid-State Characterization of Paclitaxel," Journal of Pharmaceutical Sciences 86(12):1458-1463.
Lim, W.T. et al. (Feb. 2010, e-pub. Jul. 24, 2009). "Phase I Pharmacokinetic Study of a Weekly Liposomal Paclitaxel Formulation (Genexol®-PM) in Patients with Solid Tumors," Annals of Oncology 21(2):382-388.
Lindfors, L. et al. (Jan. 31, 2006). "Amorphous Drug Nanosuspensions. 1. Inhibition of Ostwald Ripening," Langmuir 22(3):906-910.
Lindfors, L. et al. (Sep. 11, 2007). "Amorphous Drug Nanosuspensions. 3. Particle Dissolution and Crystal Growth," Langmuir 33(19):9866-9874.
Löhr, J.M. et al. (2012, e-pub. Sep. 6, 2011). "Cationic liposomal paclitaxel plus gemcitabine orgemcitabine alone in patients with advanced pancreatic cancer: a randomized controlled phase II trial," Annals of Oncology 23:1214-1222.
Maeda, S. et al. (2011, e-pub. Apr. 1, 2011). "Paclitaxel as Second-Line Chemotherapy in Patients With Gemcitabine-Refractory Pancreatic Cancer: A Retrospective Study," Int. J. Clin. Oncol. 16:539-545.
Makriyannis, A. et al. (2005). "Albumin Enhances the Diffusion of Lipophilic Drugs Into the Membrane Bilayer," Life Sciences 77:1605-1611.
Merisko-Liversidge, E. et al. (1996). "Formulation and Antitumor Activity Evaluation of Nanocrystalline Supensions of Poorly Soluble Anticancer Drugs," Pharmaceutical Research 13(2):272-278.
Merisko-Liversidge, E. et al. (2003). "Nanosizing: A Formulation Approach for Poorly-Water-Soluble Compounds," European Journal of Pharmaceutical Sciences 18:113-120.
Micili, A.J. et al. (Dec. 1987). "Transcytosis of Albumin in Capillary Endothelium," The Journal of Cell Biology 105(Part 6)(Part 1):2603-2612.

(56) References Cited

OTHER PUBLICATIONS

Mielke, S. et al. (2006, epub. Nov. 15, 2005). "Peripheral Neuropathy: A Persisting Challenge in Paclitaxel-Based Regimes," European Journal Of Cancer 42:24-30.
Minshall, R.D. et al. (2002, epub. Jan. 22, 2002). "Vesicle Formation and Trafficking in Endotherlial Cells and Regulation of Endotherlial Barrier Function," Histochem. Cell Biol. 117:105-112.
Müller, B.G. et al. (1996). "Albumin Nanospheres As Carriers For Passive Drug Targeting: An Optimized Manufacturing Technique," Pharmaceutical Research 13(1):32-37.
Non-Final Office Action dated Dec. 5, 2017, for U.S. Appl. No. 15/183,636, filed Jun. 15, 2016, 31 pages.
Non-Final Office Action dated Sep. 11, 2015, for U.S. Appl. No. 13/782,990, filed Mar. 1, 2013, 26 pages.
Pang, D. et al. (Aug. 2006). "Dexamethasone Decreases Xenograft Response to Paclitaxel Through Inhibition of Tumor Cell Apoptosis," Cancer Biology & Therapy 5(8):933-940.
Paál, K. et al. (2001). "High Affinity Binding of Paclitaxel to Human Serum Albumin," Eur. J. Biochem. 268 (7):2187-2191.
Paál, K. et al. (2007). "Paclitaxel Binding to the Fatty Acid-Induced Conformation of Human Serum Albumin-Automated Docking Studies," Boorganic & Medicinal Chemistry 15:7568-7575.
Quilliet, C. et al. (2008). "Anisotropic Colloids Through Non-Trivial Buckling," The European Physical Journal E 27:13-20.
Richly, H et al. (2009). "Plasma and Cellular Pharmacokinetics of Doxorubicin After Intravenous Infusion of Caelyx™/Doxil® in Patients With Hematological Tumors," International Journal of Clinical Pharmacology and Therapeutics 47:55-57.
Ring, J. et al. (1979). "Anaphylactiod Reactions to Infusions of Plasma Protein and Human Serum Albumin," Clinical Allergy 9:89-97.
Rizvi, N.A. et al. (Feb. 1, 2008). "Phase I/II Trial of Weekly Intravenous 130-nm Albumin-Bound Paclitaxel as Initial Chemotherapy in Patients with Stage IV Non-Small-Cell Lung Cancer," J. Clin. Oncol. 26(4):639-643.
Schnitzer, J.E. (Jan. 1992). "Gp60 is an Albumin-Binding Glycoprotein Expressed by Continuous Endothelium Involved in Albumin Transcytosis," Am. J. Physiol. 262(1, Pt. 2):H246-H254.
Schnitzer, J.E. et al. (Apr. 5, 1993). "High Affinity Binding, Endocytosis, and Degradation of Conformationally Modified Albumins," The Journal of Biological Chemistry 268(10):7562-7570.
Schnitzer, J.E. et al. (Dec. 5, 1992). "Preferential Interactiono f Albumin-binding Proteins,g p30 and gp18, with Conformationally Modified Albumins," The Journal of Biological Chemistry 267(34):24544-24553.
Schnitzer, J.E. et al. (Feb. 25, 1994). "Albondin-mediated Capillary Permeability to Albumin. Differential Role of Receptors in Endothelial Transcytosis and Endocytosis of Native and Modified Albumins," The Journal of Biological Chemistry 269(3):6072-6082.
Sheffield, W.P. et al. (Sep. 15, 2000). "Modulation of Clearance of Recombinant Serum Albumin by Either Glycosylation or Truncation," Thromb. Res. 99(6):613-621.
Socinski, M.A. et al. (Apr. 30, 2012). "Weekly nab-Paclitaxel in Combination With Carboplatin Versus Solvent-Based Paclitaxel Plus Carboplatin as First-Line Therapy in Patients With Advanced Non-Small-Cell Lung Cancer: Final Results of a Phase III Trial," Journal of Clinical Oncology 30(17):2055-2062.
Socinski, M.A. et al. (Jun. 2010). "A Dose Finding Study of Weekly and Every-3-Week nab-Paclitaxel Followed by Carboplatin as First-Line Therapy in Patients with Advanced Non-Small Cell Lung Cancer," J. Thorac. Oncol. 5 (6):852-861.
Sparreboom, A. et al. (1998). "Preclinical Pharmacokinetics of Paclitaxel and Docetaxel," Anti-Cancer Drugs 9:1-17.
Sparreboom, A. et al. (Jun. 1, 2005). "Comparative Preclinical and Clinical Pharmacokinetics of a Cremophor-Free, Nanoparticle Albumin-Bound Paclitaxel (ABI-007) and Paclitaxel Formulated in Cremophor (Taxol)," Clin. Cancer Res. 11(11):4136-4143.
Sui, M. et al. (2006, e-pub. Feb. 22, 2006). "Glucocorticoids interfere with therapeutic efficacy of paclitaxel against human breast and ovarian xenograft tumors," Int. J. Cancer 119:712-717.

Surati, M. et al. (2011). "Role of MetMAb (OA-5D5) in C-MET Active Lung Maligiancies," Expert Opinion Bio. Ther. 11(12):1655-1662.
Tacal, O. et al. (2002). "A Comparison Between SDS-PAGE and Size Exclusion Chromatography as Analytical Methods for Determining Product Composition in Protein Conjugation Reactions," J. Biochem. Biophys. Methods 52:161-168.
Tanaka, K. et al. (Nov. 1998). "Purification of Human Albumin by the Combination of the Method of Cohn With Liquid Chromatography," Braz. J. Med. Biol. Res. 31(11):1383-1388.
Tang, L.C. et al. (2013). "Higher rate of skin rash in a phase II trial with weekly nanoparticle albumin-bound paclitaxel and cisplatin combination in Chinese breast cancer patients," BMC Cancer 13(232):1-6.
Taxol®. (Apr. 2011). "Prescribing Insert for Taxol® (paclitaxel) Injection (Patient Information Included)," 53 pages.
Ten Tije, A.J. et al. (2003). "Pharmacological Effects of Formulation Vehicles Implications for Cancer Chemotherapy," Clin. Pharmacokinet 42(7): 665-685.
Tinkle, S. et al. (2014). "Nanomedicines: addressing the scientific and regulatory gap," Ann. N.Y. Acad. Sci. 1313:35-36.
Trynda-Lemiesz, L. (2004). "Paclitaxel-HSA Interaction. Binding Sites on HSA Molecule," Bioorg. Med. Chem. 12:3269-3275.
U.S. Department of Health and Human Services. (Feb. 2012). "Guidance for Industry Quality Considerations in Demonstrating Biosimilarity to a Reference Protein Product," 20 pages.
Venkataramanan, R. et al. (1986). "Leaching of Diethylhexyl phthalate From Polyvinyl chloride Bags Into Intravenous Cyclosporine Solution," Am J Hosp Pharm, 43:2800-2802.
Vllegenthart, G.A. et al. (Apr. 28, 2011). "Compression, Crumpling and Collapse of Spherical Shells and Capsules," New Journal of Physics 13:1-24.
Von Hoff, D.D. et al. (2013). "Randomized Phase III Study of Weekly nab-Paclitaxel Plus Gemcitabine Versus Gemcitabine Alone in Patients With Metastatic Adenocarcinoma of the Pancreas (MPACT)," J. Clin. Oncol. 31(4): Abstract LBA148, 4 pages.
Von Hoff, D.D. et al. (Dec. 1, 2011, e-pub: Oct. 3, 2011). "Gemcitabine Plus nab-Paclitaxel Is An Active Regimen In Patients With Advanced Pancreatic Cancer: A Phase I/II Trial," J. Clin. Oncol. 29(34):4548-4554.
Weiss, R. B. et al. (Jul. 1990). "Hypersensitivity Reactions from Taxol," J. Clin. Oncol. 8(7):1263-1268.
Whitehead, R.P. et al. (Jun. 1997). "Phase II Trial of Paclitaxel and Granulocyte Colony-Stimulating Factor in Patients With Pancreatic Carcinoma: A Southwest Oncology Group Study," J. Clin. Oncol. 15(6):2414-2419.
Woodcock, J. (Feb. 4, 2013). Letter to FDA Sandra Rattray Concerning Docket No. FDA-2009-P-0216, 16 pages.
Written Opinion dated Mar. 18, 2014, for PCT Application No. PCT/US2013/076630, filed on Dec. 19, 2013, 4 pages.
Zavodovskaya, M. et al. (Apr. 2015). "Abstract 5469: Dexamethasone Interrupts Paclitaxel-Induced Apoptosis in Solid Tumor Cells," Proceedings AACR 106 the Annual Meeting 2015, Apr. 18-22, 2015, Philadelphia, PA, 4 pages.
U.S. Appl. No. 15/062,046, filed Mar. 5, 2016, for Peykov et al. U.S. Patent Application is not submitted herewith pursuant to the waiver of 37 C.F.R. § 1.98(a)(2)(iii) issued by the Office on Sep. 21, 2004.).
U.S. Appl. No. 15/062,048, filed Mar. 5, 2016, for Peykov et al. U.S. Patent Application is not submitted herewith pursuant to the waiver of 37 C.F.R. § 1.98(a)(2)(iii) issued by the Office on Sep. 21, 2004.).
U.S. Appl. No. 15/062,049, filed Mar. 5, 2016, for Peykov et al. (U.S. Patent Application is not submitted herewith pursuant to the waiver of 37 C.F.R. § 1.98(a)(2)(iii) issued by the Office on Sep. 21, 2004.).
U.S. Appl. No. 15/399,366, filed Jan. 5, 2017, for Pierce et al. U.S. Patent Application is not submitted herewith pursuant to the waiver of 37 C.F.R. § 1.98(a)(2)(iii) issued by the Office on Sep. 21, 2004.).
U.S. Appl. No. 15/462,361, filed Mar. 17, 2017, for Tao et al. (U.S. Patent Application is not submitted herewith pursuant to the waiver of 37 C.F.R. § 1.98(a)(2)(iii) issued by the Office on Sep. 21, 2004.).
U.S. Appl. No. 15/663,351, filed Jul. 28, 2017, for Desai et al. (U.S. Patent Application is not submitted herewith pursuant to the waiver of 37 C.F.R. § 1.98(a)(2)(iii) issued by the Office on Sep. 21, 2004.).

(56) References Cited

OTHER PUBLICATIONS

U.S. Appl. No. 15/796,578, filed Oct. 27, 2017, for Desai et al. (U.S. Patent Application is not submitted herewith pursuant to the waiver of 37 C.F.R. § 1.98(a)(2)(iii) issued by the Office on Sep. 21, 2004.).

U.S. Appl. No. 15/936,124, filed Mar. 26, 2018, for Peykov et al. (U.S. Patent Application is not submitted herewith pursuant to the waiver of 37 C.F.R. § 1.98(a)(2)(iii) issued by the Office on Sep. 21, 2004.).

U.S. Food & Drug Administration. (2017). "Questions and Answers Regarding Methylphenidate Hydrochloride Extended Release Tablets (Generic Concerta) Made by Mallinckrodt and UCB/Kremers Urban (Formerly Kudco)," Retrieved from the Internet at <https://www.fda.gov/Drugs/DrugSafety/ucm422569.htm>, retrieved on Jul. 24, 2017, 5 pages.

U.S. Food & Drug Administration. (Jun. 2014). "Considering Whether an FDA-Regulated Product Involves the Application of Nanotechnology. Guidance for Industry," Retrieved from the Internet at <https://www.fda.gov/regulatoryinformation/guidances/ucm257698.htm>, retrieved on Jul. 24, 2017, 13 pages.

National Cancer Institute. (2017). "Impacts on Cancer," Retrieved from the Internet at <http://www.nano.cancer.gov/learn/impact>, retrieved on Jul. 24, 2017, 1 page.

National Cancer Institute. (2017). "Learn About Nanotechnology in Cancer," Retrieved from the Internet at <http://www.nano.cancer.gov/learn/understanding/>, retrieved on Jul. 24, 2017, 2 pages.

National Cancer Institute. (2017). "Nanotechnology Animation: Cantilevers," Retrieved from the Internet at <http://www.nano.cancer.gov/learn/understanding/nanotech_cantilevers.asp>, retrieved on Jul. 24, 2017, 2 pages.

National Cancer Institute. (2017). "Nanotechnology Animations: Nanoshells," Retrieved from the Internet at <http://www.nano.cancer.gov/learn/understanding/nanotech_nanoshells.asp>, retrieved on Jul. 24, 2017, 2 pages.

National Cancer Institute. (2017). "Nanotechnology Animations: Nanowires," Retrieved from the Internet at <http://www.nano.cancer.gov/learn/understanding/nanotech_nanowires.asp>, retrieved on Jul. 24, 2017, 1 page.

National Cancer Institute. (2017). "Nanotechnology Glossary," Retrieved from the Internet at <http://www.nano.cancer.gov/learn/understanding/nanotech_glossary.asp>, retrieved on Jul. 24, 2017, 5 pages.

National Cancer Institute. (2017). "Tools for Education," Retrieved from the Internet at <http://www.nano.cancer.gov/learn/understanding/tools.asp>, retrieved on Jul. 24, 2017, 2 pages.

National Cancer Institute. (2017). "Understanding Nanotechnology" Retrieved from the Internet at <http://www.nano.cancer.gov/learn/understanding/>, retrieved on Jul. 24, 2017, 2 pages.

National Cancer Institute. (2017). "Video Journey Into Nanotechnology," Retrieved from the Internet at <http://www.nano.cancer.gov/learn/understanding/video_journey.asp>, retrieved on Jul. 24, 2017, 1 page.

National Cancer Institute. (2017). "Where it Stands Now," Retrieved from the Internet at <http://www.nano.cancer.gov/learn/now/>, retrieved on Jul. 24, 2017, 1 page.

National Cancer Institute. (Nov. 2013). "Frequently Asked Questions," Retrieved from the Internet at <http://www.nano.cancer.gov/learn/understanding/faq.asp>, retrieved on Jul. 24, 2017, 5 pages.

OSHA. (2017). "Section VI: Chapter 2: Controlling Occupational Exposure To Hazardous Drugs," Retrieved from the Internet at <https://www.osha.gov/dts/osta/otm/otm_vi/otm_vi_2.html>, retrieved on Jul. 25, 2017, 20 pages.

Sorrento Therapeutics, Inc. (Mar. 31, 2014). "Sorrento Announces First Patient Dosed in Registration to Evaluate Bioequivalence Between Cynviloq and Abraxane," Retrieved from the Internet at http://sorrentotherapeutics.com/sorrento-announces-firstpatient-dosed-in-registration-trial-to-evaluate-bioequivalence-between-cynviloq-and-abraxane/, retrieved on Aug. 8, 2017, 4 pages.

Final Office Action dated May 20, 2014, for U.S. Appl. No. 13/073,824, filed Mar. 28, 2011, 12 pages.

Non-Final Office Action dated Nov. 1, 2017, for U.S. Appl. No. 15/062,046, filed Mar. 5, 2016, 16 pages.

U.S. Appl. No. 15/928,702, filed Mar. 22, 2018, for Peykov et al. (U.S. Patent Application is not submitted herewith pursuant to the waiver of 37 C.F.R. § 1.98(a)(2)(iii) issued by the Office on Sep. 21, 2004.).

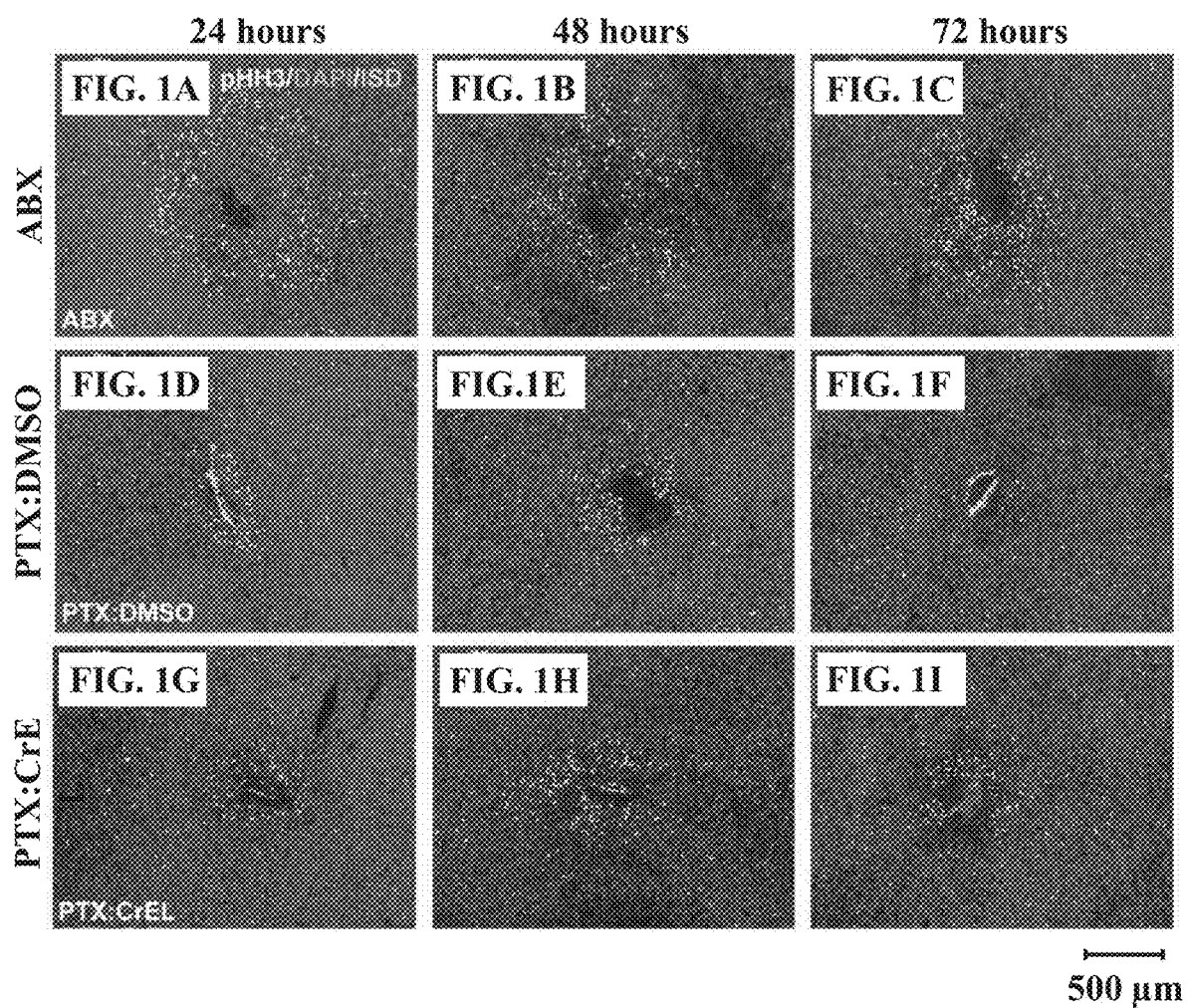

US 10,900,951 B1

METHODS OF ASSESSING SUITABILITY OF USE OF PHARMACEUTICAL COMPOSITIONS OF ALBUMIN AND PACLITAXEL

CROSS REFERENCE TO RELATED APPLICATIONS

This application is a continuation of U.S. patent application Ser. No. 15/062,050, filed Mar. 5, 2016, which claims priority of U.S. Provisional Application No. 62/129,012, filed Mar. 5, 2015, each of which is incorporated herein by reference in its entirety for all purposes.

TECHNICAL FIELD

The present invention relates to methods of assessing suitability of use of a pharmaceutical composition of albumin and paclitaxel.

BACKGROUND

Albumin-based pharmaceutical compositions have been developed as a drug delivery system for delivering substantially water insoluble drugs such as a taxane. See, for example, U.S. Pat. Nos. 5,916,596, 6,506,405, 6,749,868, 6,537,579, 7,820,788, and 7,923,536. ABRAXANE®, an albumin-stabilized nanoparticle formulation of paclitaxel ("nab-paclitaxel"), is a prescription drug approved to treat life-threatening cancers that affect hundreds of thousands of patients in the United States. It is indicated for the treatment of metastatic breast cancer, locally advanced or metastatic non-small cell lung cancer ("NSCLC"), as well as metastatic adenocarcinoma of the pancreas.

It is generally believed that albumin-based nanoparticles, such as those in nab-paclitaxel sold under the trademark ABRAXANE®, when introduced into the blood stream, would dissolve into albumin-drug complexes. Such albumin-drug complexes utilize the natural properties of albumin to transport and deliver substantially water insoluble drugs to the site of disease, such as tumor sites. In addition, the albumin-based nanoparticle technology offers the ability to improve a drug's solubility without the need for toxic solvents in the administration process, thus potentially improving safety through the elimination of solvent-related side effects.

The disclosures of all publications, patents, patent applications, and published patent applications referred to herein are hereby incorporated herein by reference in their entireties.

BRIEF SUMMARY DESCRIBED HEREIN

The present application in some embodiment provides methods of assessing suitability of a composition (such as a pharmaceutical composition) for medical use, wherein the composition (such as a pharmaceutical composition) comprises nanoparticles comprising paclitaxel coated with albumin and a non-nanoparticle portion comprising albumin and paclitaxel.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) is indicative of suitability of the pharmaceutical composition for medical use. In some embodiments, the method further comprises determining the percentage of albumin monomers among the albumin on the nanoparticles, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) is indicative of suitability of the pharmaceutical composition for medical use. In some embodiments, a percentage of albumin monomers among the albumin on the nanoparticles being less than about 52% is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers and oligomers among the albumin on the nanoparticles, wherein a percentage of albumin polymers and oligomers among the albumin on the nanoparticles being more than about 35% is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers and monomers among the albumin on the nanoparticles, wherein a percentage of albumin polymers among the albumin on the nanoparticles being more than about 11% and a percentage of albumin monomers among the albumin on the nanoparticles being less than about 54% is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers and monomers among the albumin on the nanoparticles, wherein a percentage of albumin polymers among the albumin on the nanoparticles being more than about 18% and a percentage of albumin monomers among the albumin on the nanoparticles being less than about 55% is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers, oligomers, and monomers among the albumin on the nanoparticles, wherein the ratio of albumin on the nanoparticles in the forms of polymers and oligomers to the albumin on the nanoparticles in the form of monomers being more than about 62% indicative of suitability of the pharmaceutical composition for medical use.

In some embodiments according to any of the methods described above, the method further comprises determining the weight percentage of the albumin in the nanoparticles, wherein a weight percentage of the albumin in the nanoparticles being about 15% to about 30% (such as about 20% to about 25%, about 15% to about 24%, or about 15% to about 20%) is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, wherein a weight percentage of the albumin in the nanoparticles being about 15% to about 30% (such as about 20% to about 25%, about 15% to about 24%, or about 15% to about 20%) is indicative of suitability of the pharmaceutical composition for medical use.

In some embodiments according to any of the methods described above, the method further comprises determining the weight ratio of albumin to paclitaxel in the nanoparticles, wherein an albumin to paclitaxel ratio of about 1:2 to about 1:6 in the nanoparticles is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles, wherein an albumin to paclitaxel ratio of about 1:2 to about 1:6 in the nanoparticles is indicative of suitability of the pharmaceutical composition for medical use.

In some embodiments according to any of the methods described above, the method further comprises determining the morphology of the nanoparticles under cryo-TEM, wherein an irregular shape of the nanoparticles is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the morphology of the nanoparticles under cryo-TEM, wherein an irregular shape of the nanoparticles is indicative of suitability of the pharmaceutical composition for medical use.

In some embodiments according to any of the methods described above, the method further comprises determining the thickness of the albumin coating of the nanoparticles under cryo-TEM, wherein a thickness of about 5-7 nm (such as about 6 nm) is indicative of suitability of the pharmaceutical composition for medical use.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the thickness of the albumin coating of the nanoparticles under cryo-TEM, wherein a thickness of about 5-7 nm (such as about 6 nm) is indicative of suitability of the pharmaceutical composition for medical use.

In some embodiments according to any of the methods described above, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the distribution of paclitaxel in a tumor tissue upon injection of the pharmaceutical composition directly into the tumor tissue; wherein an enhanced paclitaxel tumor distribution is indicative of suitability of the pharmaceutical composition for medical use.

In some embodiments according to any of the methods described above, the method further comprises determining the distribution of paclitaxel in a tumor tissue upon injection of the pharmaceutical composition directly into the tumor; wherein an enhanced paclitaxel tumor distribution is indicative of suitability of the pharmaceutical composition for medical use.

In some embodiments according to any of the methods described above, the method further comprises determining the solubility of the pharmaceutical composition, wherein a solubility of about 50 µg/ml to about 80 µg/ml in a 5% human albumin solution is indicative of suitability of the pharmaceutical composition for medical use. In some embodiments, the determination of solubility is carried out after storage.

In some embodiments according to any of the methods described above, the method further comprises determining the paclitaxel crystallinity of the pharmaceutical composition, wherein a non-crystalline state of the paclitaxel is indicative of suitability of the pharmaceutical composition for medical use. In some embodiments, the determination of paclitaxel crystalline state is carried out after storage. In some embodiments, the paclitaxel crystallinity is determined by X-ray diffraction, polarized light microscopy, or both.

In some embodiments according to any of the methods described above, the method further comprises determining the paclitaxel recovery following a 0.2 micron filtration of the pharmaceutical composition, wherein a paclitaxel recovery of at least about 80% is indicative of suitability of the pharmaceutical composition for medical use. In some embodiments, the determination of paclitaxel recovery is carried out after storage.

One aspect of the present application provides a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the solubility, paclitaxel crystallinity, and a paclitaxel recovery following a 0.2 micron filtration of the pharmaceutical composition, wherein a solubility of about 50 µg/ml to about 80 µg/ml in a 5% human albumin solution, a non-crystalline state of the paclitaxel, and a paclitaxel recovery date of at least about 80% is indicative of suitability of the pharmaceutical composition for medical use. In some embodiments, the method is carried out after storage.

In some embodiments according to any of the methods described above, the method further comprises determining the binding affinity of albumin to paclitaxel in the pharmaceutical composition. In some embodiments, the binding affinity is determined by equilibrium dialysis, FTIR, NMR, or a combination thereof.

In some embodiments according to any of the methods described above, the method further comprises determining the surface-to-volume ratio of the nanoparticles in the pharmaceutical composition.

In some embodiments according to any of the methods described above, the method further comprises determining the percentage of albumin dimers among the albumin on the nanoparticles, wherein a percentage of about 15% to about 30% of albumin dimers among the albumin on the nanoparticles is indicative of the pharmaceutical composition for medical use.

In some embodiments according to any of the methods described above, the method further comprises determining the percentage of albumin oligomers among the albumin on the nanoparticles, wherein a percentage of about 7% to about 15% of albumin oligomers among the albumin on the nanoparticles is indicative of the pharmaceutical composition for medical use.

In some embodiments according to any of the methods described above, the method further comprises determining the percentage of albumin monomers, dimers, oligomers, or polymers among the total albumin in the pharmaceutical composition. In some embodiments, the percentage of albumin monomers, dimers, oligomers, or polymers is carried out by size-exclusion chromatography.

In some embodiments according to any of the methods described above, the method further comprises determining the particle size of the nanoparticles. In some embodiments, the particle size of the nanoparticles is determined by dynamic light scattering.

In some embodiments according to any of the methods described above, the method further comprises determining the polydispersity index of the nanoparticles in the pharmaceutical composition.

In some embodiments according to any of the methods described above, the method further comprises determining the span of size distribution (($Dv_{90}$–$Dv_{10}$)/$Dv_{50}$) of the nanoparticles in the pharmaceutical composition. $Dv_{50}$ refers to the volume-weighted median particle diameter. $Dv_{90}$ refers to the particle diameter where 90% of the volume of all nanoparticles is contained in nanoparticles with smaller diameters. $Dv_{10}$ refers to the particle diameter where 10% of the volume of all nanoparticles is contained in nanoparticles with smaller diameters.

In some embodiments according to any of the methods described above, the method further comprises determining the surface potential of the nanoparticles.

In some embodiments according to any of the methods described above, the method further comprises determining the percentage of the paclitaxel in the nanoparticles among the total paclitaxel in the pharmaceutical composition. In some embodiments, the percentage of the paclitaxel in the nanoparticles is determined by reversed-phase HPLC.

In some embodiments according to any of the methods described above, the method further comprises determining the percentage of the albumin that is in the non-nanoparticle portion among the total albumin in the pharmaceutical composition. In some embodiments, the percentage of the albumin is determined by size-exclusion chromatography.

In some embodiments according to any of the methods described above, the method further comprises determining the stability of the pharmaceutical composition. In some embodiments, the stability is determined after storage.

In some embodiments according to any of the methods described above, the method further comprises determining tumor distribution of paclitaxel upon administration in vivo.

In some embodiments, the method comprises determining tumor distribution of paclitaxel upon injection of the pharmaceutical composition directly into the tumor tissue.

In some embodiments according to any of the methods described above, the weight ratio of the total albumin to the total paclitaxel in the pharmaceutical composition is about 3:1 to about 7.9:1 or about 10:1 to about 17:1.

In some embodiments according to any of the methods described above, the albumin is human albumin.

In some embodiments according to any of the methods described above, the average particle size of the nanoparticles is less than about 200 nm (such as about 120 nm to about 140 nm, for example about 130 nm).

In a further aspect of the present application, there is provided a method of validating a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, and wherein the method comprises 1) obtaining a sample from the commercial batch, and 2) assessing suitability of the sample for medical use according to any one of the methods of assessing as described above.

In a further aspect of the present application, there is provided a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, and wherein the commercial batch is validated by assessment of suitability for medical use according to any one of the methods of assessing as described above.

Also provided are kits, medicines, and articles of manufacture comprising any one of the compositions (such as pharmaceutical compositions) described above.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE FIGURES

FIGS. 1A-1C show representative imaging of pancreatic MIA PaCa-2 xenograft tumors 24 hours (FIG. 1A), 48 hours (FIG. 1B), and 72 hours (FIG. 1C) post-injection with the nab-paclitaxel sold under the trademark ABRAXANE® (ABX). Mitotically-arrested cells were stained with an anti-pHH3 antibody (white).

FIGS. 1D-1F show representative imaging of pancreatic MIA PaCa-2 xenograft tumors 24 hours (FIG. 1D), 48 hours (FIG. 1E), and 72 hours (FIG. 1F) post-injection with a DMSO formulation of paclitaxel (PTX:DMSO). Mitotically-arrested cells were stained with an anti-pHH3 antibody (white).

FIGS. 1G-1I show representative imaging of pancreatic MIA PaCa-2 xenograft tumors 24 hours (FIG. 1G), 48 hours (FIG. 1H), and 72 hours (FIG. 1I) post-injection with a Cremophor EL formulation of paclitaxel (PTX:CrEL). Mitotically-arrested cells were stained with an anti-pHH3 antibody (white).

DETAILED DESCRIPTION

Figure 2A:
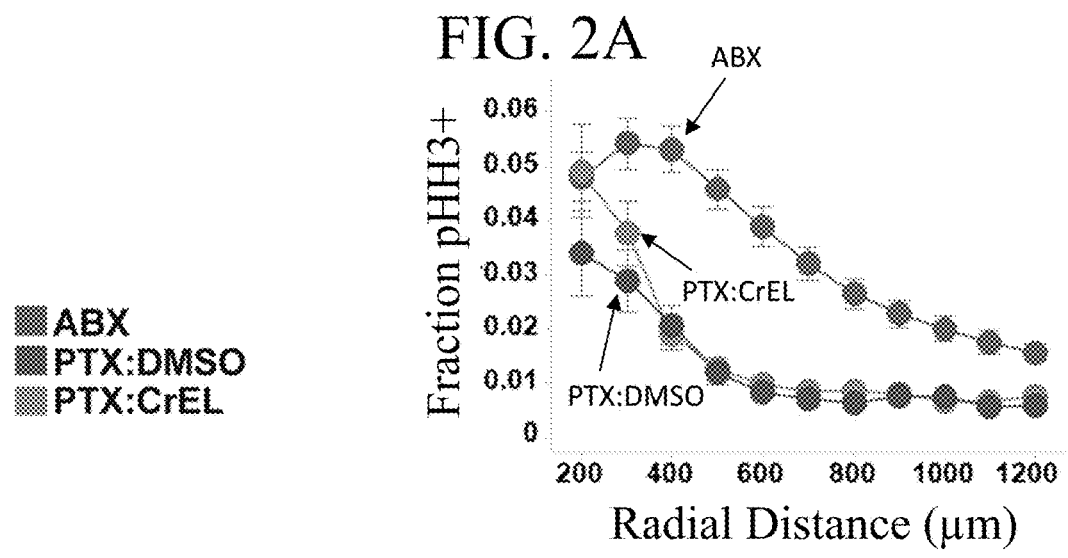
FIGS. 2A-2C show the fraction of pHH3 positive cells (fraction pHH3+) versus the radial distance ($\mu$m) as measured from the injection site for pancreatic MIA PaCa-2 xenograft tumors 24 hours (FIG. 2A), 48 hours (FIG. 2B), and 72 hours (FIG. 2C) post-injection with either ABX, PTX:DMSO, or PTX:CrEL.

The present application provides methods of assessing suitability for medical use (for example, medical use in a human individual) of an albumin-based nanoparticle composition (for example a pharmaceutical composition) by determining one or a number of physicochemical characteristics and functional attributes of the composition. The pharmaceutical compositions comprise: a) nanoparticles comprising paclitaxel coated with albumin, and b) a non-nanoparticle portion comprising albumin and paclitaxel. The methods comprise determination of at least one (such as at least any of 2, 3, 4, 5, 6, 7, or 8) of the following characteristics or attributes: i) the oligomeric status of the albumin on the nanoparticles, including percentage of albumin polymers and/or monomers on the nanoparticles; ii) the percent by weight of the albumin in the nanoparticles; iii) the weight ratio of the albumin to the paclitaxel in the nanoparticles; iv) particle morphology, including shape, thickness of the coating, or surface-to-volume ratio; v) distribution of paclitaxel in a tumor tissue upon administration of the composition; vi) particle solubility; vii) paclitaxel crystallinity; and viii) paclitaxel recovery following a 0.2 micron filtration. The methods may further comprise determination of at least one (such as at least any of 2, 3, 4, 5, 6, 7, 8, or 9) of the following characteristics or attributes: 1) binding affinity of albumin to paclitaxel in the composition (for example by equilibrium dialysis, FTIR, NMR, or a combination thereof); 2) surface-to-volume ratio; 3) percentage of albumin dimers and/or oligomers among the albumin on the nanoparticles; 4) distribution of the total paclitaxel and/or the total albumin between the nanoparticles and the non-nanoparticle portion; 5) oligomeric status of the total albumin in the composition; 6) particle size of the nanoparticles, including average particle size, polydispersity, and/or size distribution; 7) surface potential; 8) in vitro release kinetics; and 9) physical stability.

The methods provided herein are useful, for example, for validating and/or releasing a commercial batch of an albumin-based paclitaxel nanoparticle composition.

The compositions (such as pharmaceutical compositions) described herein, once determined to be suitable for medical use in a human individual, can be useful for treating various diseases, such as cancer. The present application thus also provides compositions (such as pharmaceutical compositions, including for example commercial batches) determined to be suitable for medical use, as well as methods of using such compositions (such as pharmaceutical compositions) for the treatment of diseases, including cancer. Also provided herein are kits, medicines, and dosage forms comprising the compositions (such as pharmaceutical compositions) described herein and for use in methods described herein.

The exemplary embodiments provided herein disclose pharmaceutical compositions. It is to be understood that these are exemplary compositions and that these descriptions apply equally to and describe other compositions of the invention as provided herein, such as compositions having any of the characteristics defined in these exemplary embodiments.

Definitions

The term "individual" refers to a mammal and includes, but is not limited to, human, bovine, horse, feline, canine, rodent, or primate.

It is understood that aspects and embodiments described herein include "consisting" and/or "consisting essentially of" aspects and embodiments.

Reference to "about" a value or parameter herein includes (and describes) variations that are directed to that value or parameter per se. For example, description referring to "about X" includes description of "X."

The term "about X-Y" used herein has the same meaning as "about X to about Y."

As used herein and in the appended claims, the singular forms "a," "or," and "the" include plural referents unless the context clearly dictates otherwise.

"Monomers" used herein refers to a single albumin molecule without intermolecular disulfide bonds.

"RRT" used herein refers to the retention time relative to the albumin monomers retention time on a size-exclusion HPLC chromatography.

"Dimers" used herein refers to albumin species having an RRT of about 0.86 to about 0.97.

"Oligomers" used herein refers to albumin species having an RRT of about 0.70 to about 0.85.

"Polymers" used herein refers to albumin species having an RRT of about 0.57 to about 0.69.

"The total albumin" in a composition (such as a pharmaceutical composition) comprises the albumin on the nanoparticles and the albumin in the non-nanoparticle portion of the composition. "The albumin on the nanoparticles" or "the albumin in the nanoparticles" refers to the albumin coated on the paclitaxel in the nanoparticles, or the albumin coating of the nanoparticles. "The total paclitaxel" in a composition (such as a pharmaceutical composition) comprises the paclitaxel in the nanoparticles and the paclitaxel in the non-nanoparticle portion of the composition.

"Weight percentage of albumin in the nanoparticles" used herein refers to the weight percentage of albumin in the total weight of the nanoparticles.

"Weight ratio of albumin to paclitaxel in the nanoparticles" used herein refers to the weight ratio of albumin on the nanoparticles to the paclitaxel on the nanoparticles.

Methods of Assessing Suitability of Albumin-Based Paclitaxel Nanoparticle Compositions for Medical Use The present application provides a method of assessing suitability of a composition (also referred to as "albumin-based paclitaxel nanoparticle composition") for medical use in an individual, wherein the composition comprises nanoparticles comprising paclitaxel coated with albumin and a non-nanoparticle portion comprising albumin and paclitaxel. The methods comprise determination of at least one (such as at least any of 2, 3, 4, 5, 6, 7, or 8) of the following characteristics or attributes: i) the oligomeric status of the albumin on the nanoparticles (i.e. the albumin coating), including percentage of albumin polymers and/or monomers in the nanoparticles; ii) the percent by weight of the albumin in the nanoparticles; iii) the weight ratio of the albumin to the paclitaxel in the nanoparticles; iv) particle morphology, including shape, thickness of the coating, and surface-to-volume ratio; v) distribution of paclitaxel in a tumor tissue upon administration of the composition (for example upon direct injection of the composition directly into the tumor tissue); vi) particle solubility; vii) paclitaxel crystallinity; and viii) paclitaxel recovery following a 0.2 micron filtration. The methods may further comprise determination of at least one (such as at least any of 2, 3, 4, 5, 6, 7, 8, 9, or 10) of the following characteristics or attributes: 1) binding affinity of albumin to paclitaxel in the composition (for example by equilibrium dialysis, FTIR, NMR, or a combination thereof); 2) surface-to-volume ratio; 3) percentage of albumin dimers and/or oligomers among the albumin on the nanoparticles; 4) distribution of the total paclitaxel and/or the total albumin between the nanoparticles and the non-nanoparticle portion; 5) oligomeric status of the total albumin in the composition; 6) particle size of the nanoparticles, including average particle size, polydispersity, and/or size distribution; 7) surface potential; 8) in vitro release kinetics; 9) physical stability; and, in some embodiments, 10) paclitaxel tumor distribution in vivo.

Unless otherwise indicated, discussion of a certain parameter as being indicative of suitability for medical use suggest that such parameter may be determined in the method described herein. The method thus, in some embodiments, encompasses a step of determining such a parameter.

The compositions (such as pharmaceutical compositions) described herein can be in liquid or powder forms. For example, in some embodiments, the composition is a liquid nanoparticle suspension (for example prior to lyophilization). In some embodiments, the composition is a reconstituted suspension (e.g., in an aqueous solution such as a saline solution). In some embodiments, the paclitaxel concentration in the suspension is about any of 2 mg/ml, 3 mg/ml, 4 mg/ml, 5 mg/ml, 6 mg/ml, 7 mg/ml, 8 mg/ml, 9 mg/ml, or 10 mg/ml. In some embodiments, the paclitaxel in the suspension is about 5 mg/ml. In some embodiments, the composition is lyophilized. In some embodiments, the composition is sterile. In some embodiments, the composition is contained in a sealed vial.

Thus, in some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$-$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) (such as any of about 15% to about 20%, about 20% to about 24.5%, about 24.5% to about 30%, about 30% to about 35%, or about 35% to about 40%), and a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%) is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$-$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, wherein a weight percentage of the albumin in the nanoparticles being about 15% to about 30% (such as about 20% to about 25%, about 15% to about 24%, or about 15% to about 20%) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles and determining the weight percentage of the albumin in the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) and a weight percentage of the albumin in the nanoparticles being about 15% to about 30% (such as about 20% to about 25%, about 15% to about 24%, or about 15% to about 20%) is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$-$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles and determining the weight percentage of the albumin in the nanoparticles, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) and a weight percentage of the albumin in the nanoparticles being about 15% to about 30% (such as about 20% to about 25%, about 15% to about 24%, or about 15% to about 20%) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$-$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles and determining the weight percentage of the albumin in the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), and a weight percentage of the albumin in the nanoparticles being about 15% to about 30% (such as about 20% to about 25%, about 15% to about 24%, or about 15% to about 20%) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles, wherein an albumin to paclitaxel ratio of about 1:2 to about 1:6 in the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles and determining the weight ratio of albumin to paclitaxel in the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) and an albumin to paclitaxel ratio of about 1:2 to about 1:6 in the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles and determining the weight ratio of albumin to paclitaxel in the nanoparticles, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), and an albumin to paclitaxel ratio of about 1:2 to about 1:6 in the nanoparticles is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles and determining the weight ratio of albumin to paclitaxel in the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), and a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), and an albumin to paclitaxel ratio of about 1:2 to about 1:6 in the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, and determining the weight ratio of albumin to paclitaxel in the nanoparticles, wherein a weight percentage of the albumin in the nanoparticles being about 15% to about 30% (such as about 20% to about 25%, about 15% to about 24%, or about 15% to about 20%) and an albumin to paclitaxel ratio of about 1:2 to about 1:6 in the nanoparticles is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, and determining the weight ratio of albumin to paclitaxel in the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%) and an albumin to paclitaxel ratio of about 1:2 to about 1:6 in the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, and determining the weight ratio of albumin to paclitaxel in the nanoparticles, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%) and an albumin to paclitaxel ratio of about 1:2 to about 1:6 in the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, and determining the weight ratio of albumin to paclitaxel in the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), and an albumin to paclitaxel ratio of about 1:2 to about 1:6 in the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition).

In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the morphology of the nanoparticles under cryo-TEM, wherein an irregular shape of the nanoparticles is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles and determining the morphology of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) and an irregular shape of the nanoparticles is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles and determining the morphology of the nanoparticles under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) and about 40% to about 60% (such as about 40% to about 55%, about 40% to about 54%, about 40% to about 53%, about 40% to about 52%, about 40% to about 50%, about 40% to about 48%, or about 40% to about 46%) and an irregular shape of the nanoparticles is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles and determining the morphology of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), and an irregular shape of the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, and determining the morphology of the nanoparticles under cryo-TEM, wherein a weight percentage of the albumin in the nanoparticles being about 15% to about 30% (such as about 20% to about 25%, about 15% to about 24%, or about 15% to about 20%) and an irregular shape of the nanoparticles is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, and determining the morphology of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), and an irregular shape of the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, and determining the morphology of the nanoparticles under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), and an irregular shape of the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, and determining the morphology of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), and an irregular shape of the nanoparticles is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles and determining the morphology of the nanoparticles under cryo-TEM, wherein an albumin to paclitaxel ratio of about 1:2 to about 1:6 in the nanoparticles and an irregular shape of the nanoparticles is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight ratio of albumin to paclitaxel in the nanoparticles, and determining the morphology of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an albumin to paclitaxel ratio of about 1:2 to about 1:6 in the nanoparticles, and an irregular shape of the nanoparticles is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight ratio of albumin to paclitaxel in the nanoparticles, and determining the morphology of the nanoparticles under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles and an irregular shape of the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight ratio of albumin to paclitaxel in the nanoparticles, and determining the morphology of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, and an irregular shape of the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the weight ratio of albumin to paclitaxel in the nanoparticles, and determining the morphology of the nanoparticles under cryo-TEM, wherein a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and an irregular shape of the nanoparticles is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising:

determining the percentage of albumin polymers among the albumin on the nanoparticles, determining the weight percentage of the albumin in the nanoparticles, determining the weight ratio of albumin to paclitaxel in the nanoparticles, and determining the morphology of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and an irregular shape of the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the weight ratio of albumin to paclitaxel in the nanoparticles, and determining the morphology of the nanoparticles under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and an irregular shape of the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the weight ratio of albumin to paclitaxel in the nanoparticles, and determining the morphology of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and an irregular shape of the nanoparticles is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the thickness of the albumin coating of the nanoparticles under cryo-TEM, wherein a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles and determining the thickness of the albumin coating of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles and determining the thickness of the albumin coating of the nanoparticles under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles and determining the thickness of the albumin coating of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, and determining the thickness of the albumin coating of the nanoparticles under cryo-TEM, wherein a weight percentage of the albumin in the nanoparticles being about 15% to about 30% (such as about 20% to about 25%, about 15% to about 24%, or about 15% to about 20%) and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$-$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, and determining the thickness of the albumin coating of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, and determining the thickness of the albumin coating of the nanoparticles under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, and determining the thickness of the albumin coating of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles.

In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles, and determining the thickness of the albumin coating of the nanoparticles under cryo-TEM, wherein an albumin to paclitaxel ratio of about 1:2 to about 1:6 in the nanoparticles, and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight ratio of albumin to paclitaxel in the nanoparticles, and determining the thickness of the albumin coating of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an albumin to paclitaxel ratio of about 1:2 to about 1:6 in the nanoparticles, and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight ratio of albumin to paclitaxel in the nanoparticles, and determining the thickness of the albumin coating of the nanoparticles under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight ratio of albumin to paclitaxel in the nanoparticles and determining the thickness of the albumin coating of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), and a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the weight ratio of albumin to paclitaxel in the nanoparticles, and determining the thickness of the albumin coating of the nanoparticles under cryo-TEM, wherein a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the weight ratio of albumin to paclitaxel in the nanoparticles, and determining the thickness of the albumin coating of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the weight ratio of albumin to paclitaxel in the nanoparticles, and determining the thickness of the albumin coating of the nanoparticles under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the weight ratio of albumin to paclitaxel in the nanoparticles, and determining the thickness of the albumin coating of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), and a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the morphology and thickness of the albumin coating of the nanoparticles under cryo-TEM, wherein an irregular shape of the nanoparticles and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles and determining the morphology of the nanoparticles and thickness of the albumin coating under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), and an irregular shape of the nanoparticles and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles and determining the morphology of the nanoparticles and thickness of the albumin coating under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an irregular shape of the nanoparticles, and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles and determining the morphology of the nanoparticles and thickness of the nanoparticles under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, and determining the morphology of the nanoparticles and thickness of the nanoparticles under cryo-TEM, wherein a weight percentage of the albumin in the nanoparticles being about 15% to about 30% (such as about 20% to about 25%, about 15% to about 24%, or about 15% to about 20%), an irregular shape of the nanoparticles, and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, and determining the morphology of the nanoparticles and thickness of the albumin coating under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, and determining the morphology of the nanoparticles and thickness of the albumin coating under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, and determining the morphology of the nanoparticles and thickness of the albumin coating under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles, determining the morphology of the nanoparticles and thickness of the albumin coating under cryo-TEM, wherein an albumin to paclitaxel ratio of about 1:2 to about 1:6 in the nanoparticles, an irregular shape of the nanoparticles, and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight ratio of albumin to paclitaxel in the nanoparticles, and determining the morphology of the nanoparticles and thickness of the albumin coating under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an albumin to paclitaxel ratio of about 1:2 to about 1:6 in the nanoparticles, an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight ratio of albumin to paclitaxel in the nanoparticles, and determining the morphology of the nanoparticles and thickness of the albumin coating under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight ratio of albumin to paclitaxel in the nanoparticles, and determining the morphology of the nanoparticles and thickness of the albumin coating under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the weight ratio of albumin to paclitaxel in the nanoparticles, and determining the morphology of the nanoparticles and thickness of the albumin coating under cryo-TEM, wherein a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, and a thickness of about 5-7 nm (such as about 6 nm) is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the weight ratio of albumin to paclitaxel in the nanoparticles, and determining the morphology of the nanoparticles and thickness of the albumin coating under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the weight ratio of albumin to paclitaxel in the nanoparticles, and determining the morphology of the nanoparticles and thickness of the albumin coating under cryo-TEM, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the weight ratio of albumin to paclitaxel in the nanoparticles, and determining the morphology of the nanoparticles and thickness of the albumin coating under cryo-TEM, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, and a thickness of about 5-7 nm (such as about 6 nm) is indicative of suitability of the pharmaceutical composition for medical use. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the distribution of paclitaxel in a tumor tissue upon injection of the pharmaceutical composition directly into the tumor tissue; wherein an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700, 800, 900, 1000, 1100 or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, and determining the distribution of paclitaxel in a tumor tissue upon injection of the pharmaceutical composition directly into the tumor tissue, wherein a weight percentage of the albumin in the nanoparticles being about 15% to about 30% (such as about 20% to about 25%, about 15% to about 24%, or about 15% to about 20%) and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%) and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles and determining the distribution of paclitaxel in a tumor tissue upon injection of the pharmaceutical composition directly into the tumor tissue, wherein an albumin to paclitaxel ratio of about 1:2 to about 1:6 in the nanoparticles and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight ratio of albumin to paclitaxel in the nanoparticles, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an albumin to paclitaxel ratio of about 1:2 to about 1:6 in the nanoparticles and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight ratio of albumin to paclitaxel in the nanoparticles, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight ratio of albumin to paclitaxel in the nanoparticles, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700, 800, 900, 1000, 1100 or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the weight ratio of albumin to paclitaxel in the nanoparticles, and determining the distribution of paclitaxel in a tumor tissue upon injection of the pharmaceutical composition directly into the tumor tissue, wherein a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the weight ratio of albumin to paclitaxel in the nanoparticles, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the weight ratio of albumin to paclitaxel in the nanoparticles, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the weight ratio of albumin to paclitaxel in the nanoparticles, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, and an enhanced paclitaxel tumor distribution is indicative of suitability of the pharmaceutical composition for medical use. In some embodiments, the method further comprises determining the solubility of the pharmaceutical composition (including determining solubility after storage). In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the morphology of the nanoparticles under cryo-TEM and determining the distribution of paclitaxel in a tumor tissue upon injection of the pharmaceutical composition directly into the tumor tissue, wherein an irregular shape of the nanoparticles and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$−$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the morphology of the nanoparticles under cryo-TEM, and determining the distribution of paclitaxel in a tumor tissue upon injection of the pharmaceutical composition directly into the tumor tissue, wherein a weight percentage of the albumin in the nanoparticles being about 15% to about 30% (such as about 20% to about 25%, about 15% to about 24%, or about 15% to about 20%), an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles, determining the morphology of the nanoparticles under cryo-TEM, and determining the distribution of paclitaxel in a tumor tissue upon injection of the pharmaceutical composition directly into the tumor tissue, wherein an albumin to paclitaxel ratio of about 1:2 to about 1:6 in the nanoparticles, an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight ratio of albumin to paclitaxel in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an albumin to paclitaxel ratio of about 1:2 to about 1:6 in the nanoparticles, an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight ratio of albumin to paclitaxel in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight ratio of albumin to paclitaxel in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the weight ratio of albumin to paclitaxel in the nanoparticles, determining the morphology of the nanoparticles under cryo-TEM, and determining the distribution of paclitaxel in a tumor tissue upon injection of the pharmaceutical composition directly into the tumor tissue, wherein a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the weight ratio of albumin to paclitaxel in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the weight ratio of albumin to paclitaxel in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the weight ratio of albumin to paclitaxel in the nanoparticles, determining the morphology of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the thickness of the albumin coating of the nanoparticles under cryo-TEM and determining the distribution of paclitaxel in a tumor tissue upon injection of the pharmaceutical composition directly into the tumor tissue, wherein a thickness of about 5-7 nm (such as about 6 nm) and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a weight percentage of the albumin in the nanoparticles being about 15% to about 30% (such as about 20% to about 25%, about 15% to about 24%, or about 15% to about 20%), a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein an albumin to paclitaxel ratio of about 1:2 to about 1:6 in the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight ratio of albumin to paclitaxel in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an albumin to paclitaxel ratio of about 1:2 to about 1:6 in the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight ratio of albumin to paclitaxel in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight ratio of albumin to paclitaxel in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), and a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$−$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the weight ratio of albumin to paclitaxel in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$−$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the weight ratio of albumin to paclitaxel in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the weight ratio of albumin to paclitaxel in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the weight ratio of albumin to paclitaxel in the nanoparticles, determining the thickness of the albumin coating of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the morphology and thickness of the albumin coating of the nanoparticles under cryo-TEM, and determining the distribution of paclitaxel in a tumor tissue upon injection of the pharmaceutical composition directly into the tumor tissue, wherein an irregular shape of the nanoparticles and a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the morphology of the nanoparticles and thickness of the nanoparticles under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the morphology of the nanoparticles and thickness of the nanoparticles under cryo-TEM, and determining the distribution of paclitaxel in a tumor tissue upon injection of the pharmaceutical composition directly into the tumor tissue, wherein a weight percentage of the albumin in the nanoparticles being about 15% to about 30% (such as about 20% to about 25%, about 15% to about 24%, or about 15% to about 20%), an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an irregular shape of the nanoparticles, a thickness of about 5-7 nm (such as about 6 nm) and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution $((Dv_{90}-Dv_{10})/Dv_{50})$ of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein an albumin to paclitaxel ratio of about 1:2 to about 1:6 in the nanoparticles, an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight ratio of albumin to paclitaxel in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), an albumin to paclitaxel ratio of about 1:2 to about 1:6 in the nanoparticles, an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight ratio of albumin to paclitaxel in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight ratio of albumin to paclitaxel in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), an albumin to paclitaxel ratio of about 1:2 to about 1:6 in the nanoparticles, an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}-Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the weight ratio of albumin to paclitaxel in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, determining the weight percentage of the albumin in the nanoparticles, determining the weight ratio of albumin to paclitaxel in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 µm (such as more than about any of 700 µm, 800 µm, 900 µm, 1000 µm, 1100 µm or 1200 µm) within about 24 hours after the composition (such as a pharmaceutical composition) is injected into a tumor tissue (for example injected at the paclitaxel amount of about 12 µg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, determining the weight percentage of the albumin in the nanoparticles, determining the weight ratio of albumin to paclitaxel in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radically for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution (($Dv_{90}$–$Dv_{10}$)/$Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the weight ratio of albumin to paclitaxel in the nanoparticles, determining the morphology of the nanoparticles and thickness of the albumin coating under cryo-TEM, and determining the distribution of paclitaxel in a tumor tissue upon injection of the pharmaceutical composition directly into the tumor tissue, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%), a percentage of albumin monomer among the albumin on the nanoparticles being at least about 40% to about 60% (such as about 40% to about 55%, about 40% to about 54%, about 40% to about 53%, about 40% to about 52%, about 40% to about 50%, about 40% to about 48%, or about 40% to about 46%), a weight percentage of the albumin in the nanoparticles being about 15% to about 30% (such as about 20% to about 25%, about 15% to about 24%, or about 15% to about 20%), an albumin to paclitaxel ratio of about 1:2 to about 1:6 in the nanoparticles, an irregular shape of the nanoparticles, a thickness of about 5-7 nm (such as about 6 nm), and an enhanced paclitaxel tumor distribution is indicative of suitability of the pharmaceutical composition for medical use. In some embodiments, the composition (such as a pharmaceutical composition) is suitable for medical use if upon tumor injection it allows paclitaxel to spread radially for a distance that is greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions. In some embodiments, the composition (such as a pharmaceutical composition) is suitable for medical use if upon tumor injection it allows paclitaxel to spread radially for more than about 700 μm (such as more than about any of 700 μm, 800 μm, 900 μm, 1000 μm, 1100 μm or 1200 μm) within about 24 hours after the composition (such as a pharmaceutical composition) is injected into a tumor tissue (for example injected at the paclitaxel amount of about 12 μg (such as at about 4 mg/ml) into a pancreatic MIA PaCa-2 xenograft tumor). In some embodiments, a percentage of albumin monomer among the albumin on the nanoparticles being less than about 51% is indicative of suitability of the pharmaceutical composition for medical use. In some embodiments, a percentage of albumin polymers and oligomers among the albumin on the nanoparticles being more than about 35% is indicative of suitability of the pharmaceutical composition for medical use. In some embodiments, a percentage of albumin polymers among the albumin on the nanoparticles being more than about 17% and a percentage of albumin monomer among the albumin on the nanoparticles being less than about 54% is indicative of suitability of the pharmaceutical composition for medical use. In some embodiments, a percentage of albumin polymers among the albumin on the nanoparticles being more than about 18% and a percentage of albumin monomer among the albumin on the nanoparticles being less than about 55% is indicative of suitability of the pharmaceutical composition for medical use. In some embodiments, a ratio of albumin on the nanoparticles in the forms of polymers and oligomers to the albumin on the nanoparticles in the form of monomers being more than about 65% is indicative of suitability of the pharmaceutical composition for medical use. In some embodiments, the method further comprises determining the solubility of the pharmaceutical composition (including determining solubility after storage). In some embodiments, the method further comprises determining the paclitaxel crystallinity of the pharmaceutical composition (for example by X-ray diffraction and/or polarized light microscopy, including determining crystallinity after storage). In some embodiments, the method further comprises determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the solubility, paclitaxel crystallinity, and paclitaxel recovery following a 0.2 micron filtration of the pharmaceutical composition, wherein a solubility of about 50 µg/ml to about 80 µg/ml in a 5% human albumin solution, a non-crystalline state, and a recovery of at least about 80% is indicative of suitability of the pharmaceutical composition for medical use. In some embodiments, the solubility, paclitaxel crystallinity, and/or paclitaxel recovery are determined after storage (for example after storage for at least about 6 hours, 12 hours, 18 hours, 24 hours, 36 hours, 48 hours, or 72 hours, such as at room temperature, under refrigerated condition, or at 40° C.). In some embodiments, the paclitaxel crystallinity is determined by X-ray diffraction and/or polarized light microscopy. In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the surface-to-volume ratio of the nanoparticles in the pharmaceutical composition. In some embodiments, the method further comprises determining the percentage of albumin monomers among the albumin on the nanoparticles. In some embodiments, the method further comprises determining the percentage of albumin dimers among the albumin on the nanoparticles. In some embodiments, the method further comprises determining the percentage of albumin oligomers among the albumin on the nanoparticles. In some embodiments, the method further comprises determining the percentage of albumin polymers among the albumin on the nanoparticles. In some embodiments, the method further comprises determining the percentage of albumin monomers, dimers, oligomers, or polymers among the total albumin in the pharmaceutical composition. In some embodiments, the method further comprises determining the particle size of the nanoparticles (for example by dynamic light scattering). In some embodiments, the method further comprises determining the polydispersity index of the nanoparticles in the pharmaceutical composition. In some embodiments, the method further comprises determining the span of size distribution ($(Dv_{90}-Dv_{10})/Dv_{50}$) of the nanoparticles in the pharmaceutical composition. In some embodiments, the method further comprises determining the surface potential of the nanoparticles. In some embodiments, the method further comprises determining the percentage of the paclitaxel in the nanoparticles among the total paclitaxel in the pharmaceutical composition (for example by reversed-phase HPLC). In some embodiments, the method further comprises determining the percentage of the albumin that is in the non-nanoparticle portion among the total albumin in the pharmaceutical composition (for example by size-exclusion chromatography). In some embodiments, the method further comprises determining the in vitro release kinetics of the composition (such as a pharmaceutical composition). In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

The different determination steps described above may be carried out in various combinations in a given method.

For example, in some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight percentage of the albumin in the nanoparticles, determining the solubility of the pharmaceutical composition (including determining solubility after storage), determining the paclitaxel crystallinity of the pharmaceutical composition (for example by X-ray diffraction and/or polarized light microscopy, including determining crystallinity after storage), and determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the size of the nanoparticles (for example by dynamic light scattering) and/or size distribution of the nanoparticles. In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers and polymers among the albumin on the nanoparticles, determining the weight ratio of albumin to paclitaxel in the nanoparticles, determining the morphology of the nanoparticles and thickness of the albumin coating under cryo-TEM, determining the solubility of the pharmaceutical composition (including determining solubility after storage), determining the paclitaxel crystallinity of the pharmaceutical composition (for example by X-ray diffraction and/or polarized light microscopy, including determining crystallinity after storage), and determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the particle size of the nanoparticles (for example by dynamic light scattering) and/or size distribution of the nanoparticles. In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, determining the morphology of the nanoparticles and thickness of the albumin coating under cryo-TEM, determining the solubility of the pharmaceutical composition (including determining solubility after storage), determining the paclitaxel crystallinity of the pharmaceutical composition (for example by X-ray diffraction and/or polarized light microscopy, including determining crystallinity after storage), and determining the paclitaxel recovery following a 0.2 micron filtration (including determining recovery after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the size of the nanoparticles (for example by dynamic light scattering) and/or size distribution of the nanoparticles. In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers, dimers, oligomers, and polymers among the albumin on the nanoparticles, determining the weight percentage of the albumin in the nanoparticles, determining the morphology of the nanoparticles and thickness of the albumin coating under cryo-TEM, determining the surface-to-volume ratio of the nanoparticles in the pharmaceutical composition, and determining the percentage of albumin monomers, dimers, oligomers, or polymers among the total albumin in the pharmaceutical composition. In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the particle size of the nanoparticles (for example by dynamic light scattering) and/or size distribution of the nanoparticles. In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers, dimers, oligomers, and polymers among the albumin on the nanoparticles, determining the weight percentage of the albumin in the nanoparticles, determining the paclitaxel crystallinity of the pharmaceutical composition (for example by X-ray diffraction and/or polarized light microscopy, including determining crystallinity after storage), determining the paclitaxel recovery following a 0.2 micron filtration (including determining recovery after storage), determining the percentage of albumin monomers, dimers, oligomers, or polymers among the total albumin in the pharmaceutical composition, determining the percentage of the paclitaxel in the nanoparticles among the total paclitaxel in the pharmaceutical composition (for example by reversed-phase HPLC), and determining the percentage of the albumin that is in the non-nanoparticle portion among the total albumin in the pharmaceutical composition (for example by size-exclusion chromatography). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the particle size of the nanoparticles (for example by dynamic light scattering) and/or size distribution of the nanoparticles. In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers, dimers, oligomers, and polymers among the albumin on the nanoparticles, determining the weight percentage of the albumin in the nanoparticles, determining the weight ratio of albumin to paclitaxel in the nanoparticles, determining the morphology of the nanoparticles and thickness of the albumin coating under cryo-TEM, determining the solubility of the pharmaceutical composition (including determining solubility after storage), determining the paclitaxel crystallinity of the pharmaceutical composition (for example by X-ray diffraction and/or polarized light microscopy, including determining crystallinity after storage), determining the paclitaxel recovery following a 0.2 micron filtration (including determining recovery after storage), determining the percentage of albumin monomers, dimers, oligomers, or polymers among the total albumin in the pharmaceutical composition, determining the percentage of the paclitaxel in the nanoparticles among the total paclitaxel in the pharmaceutical composition (for example by reversed-phase HPLC), and determining the percentage of the albumin that is in the non-nanoparticle portion among the total albumin in the pharmaceutical composition (for example by size-exclusion chromatography). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the particle size of the nanoparticles (for example by dynamic light scattering) and/or size distribution of the nanoparticles. In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers, dimers, oligomers, and polymers among the albumin on the nanoparticles, determining the weight percentage of the albumin in the nanoparticles, determining the weight ratio of albumin to paclitaxel in the nanoparticles, determining the morphology of the nanoparticles and thickness of the albumin coating under cryo-TEM, determining the solubility of the pharmaceutical composition (including determining solubility after storage), determining the paclitaxel crystallinity of the pharmaceutical composition (for example by X-ray diffraction and/or polarized light microscopy, including determining crystallinity after storage), determining the paclitaxel recovery following a 0.2 micron filtration (including determining recovery after storage), determining the percentage of albumin monomers, dimers, oligomers, or polymers among the total albumin in the pharmaceutical composition, determining the percentage of the paclitaxel in the nanoparticles among the total paclitaxel in the pharmaceutical composition (for example by reversed-phase HPLC), determining the percentage of the albumin that is in the non-nanoparticle portion among the total albumin in the pharmaceutical composition (for example by size-exclusion chromatography), determining the particle size of the nanoparticles (for example by dynamic light scattering) and/or size distribution of the nanoparticles, and determining the stability of the pharmaceutical composition (including determining stability after storage). In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the solubility, paclitaxel crystallinity, and paclitaxel recovery following a 0.2 micron filtration of the pharmaceutical composition, determining the percentage of albumin monomers, dimers, oligomers, or polymers among the total albumin in the pharmaceutical composition, determining the percentage of the paclitaxel in the nanoparticles among the total paclitaxel in the pharmaceutical composition (for example by reversed-phase HPLC), and determining the percentage of the albumin that is in the non-nanoparticle portion among the total albumin in the pharmaceutical composition (for example by size-exclusion chromatography). In some embodiments, the solubility, paclitaxel crystallinity, and/or paclitaxel recovery are determined after storage (for example after storage for at least about 6 hours, 12 hours, 18 hours, 24 hours, 36 hours, 48 hours, or 72 hours, such as at room temperature, under refrigerated condition, or at 40° C.). In some embodiments, the paclitaxel crystallinity is determined by X-ray diffraction and/or polarized light microscopy. In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining the particle size of the nanoparticles (for example by dynamic light scattering) and/or size distribution of the nanoparticles. In some embodiments, the method further comprises determining the stability of the pharmaceutical composition (including determining stability after storage). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the solubility, paclitaxel crystallinity, and paclitaxel recovery following a 0.2 micron filtration of the pharmaceutical composition, determining the percentage of albumin monomers, dimers, oligomers, or polymers among the total albumin in the pharmaceutical composition, determining the percentage of the paclitaxel in the nanoparticles among the total paclitaxel in the pharmaceutical composition (for example by reversed-phase HPLC), determining the percentage of the albumin that is in the non-nanoparticle portion among the total albumin in the pharmaceutical composition (for example by size-exclusion chromatography), determining the particle size of the nanoparticles (for example by dynamic light scattering) and/or size distribution of the nanoparticles, and determining the stability of the pharmaceutical composition (including determining stability after storage). In some embodiments, the solubility, paclitaxel crystallinity, and/or paclitaxel recovery are determined after storage (for example after storage for at least about any of 6 hours, 12 hours, 18 hours, 24 v, 36 hours, 48 hours, or 72 hours, such as at room temperature, under refrigerated condition, or at about 40° C.). In some embodiments, the paclitaxel crystallinity is determined by X-ray diffraction and/or polarized light microscopy. In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining tumor distribution of paclitaxel upon administration in vivo (for example by determining tumor distribution of paclitaxel upon injection of the pharmaceutical composition directly into the tumor tissue).

Determination of Albumin Oligomeric Status on Nanoparticles

The methods of the present application in some embodiments require determination of oligomeric status (e.g., polymers, monomers, dimers, and/or oligomers) of the albumin on the nanoparticles. The oligomeric status of the albumin on the nanoparticles may impact the particle stability, solubility, dissolution rate, and in vivo distribution. Further, because albumin-paclitaxel binding is greater for cross-linked albumin (namely, albumin polymers, oligomers, and dimers) than albumin monomers, the oligomeric status of the albumin on the nanoparticles may also affect in vivo behavior of the albumin-based paclitaxel nanoparticle composition.

In some embodiments, the oligomeric status of the albumin is determined by size-exclusion chromatography, such as gel permeation chromatography or HPLC size-exclusion methods, or polyacrylamide gel electrophoresis (such as sodium dodecyl sulfate polyacrylamide gel electrophoresis, SDS-PAGE). In some embodiments, the oligomeric status is determined by isolating the albumin on the nanoparticles in the pharmaceutical composition by, for example, ultracentrifugation or gel filtration chromatography, and further analyzing the albumin on the nanoparticles by, for example, size-exclusion chromatography. The different classes of albumins can be determined based on differing retention times of albumins when subject to a chromatography (such as size-exclusion chromatography, e.g., gel permeation chromatography). In some embodiments, the different classes of albumins can be determined based on RRT. In some embodiments, the oligomeric status is determined upon reconstitution of the pharmaceutical composition. In some embodiments, the oligomeric status is determined upon storage of the pharmaceutical composition.

In some embodiments, the size-exclusion chromatography method used is capable of separating monomeric albumin from dimeric albumin, oligomeric albumin, and polymeric albumin. In some embodiments, the size-exclusion chromatography method used is capable of separating dimeric albumin from monomeric albumin, oligomeric albumin, and polymeric albumin. In some embodiments, the size-exclusion chromatography method used is capable of separating oligomeric albumin from monomeric albumin, dimeric albumin, and polymeric albumin. In some embodiments, the size-exclusion chromatography method used is capable of separating polymeric albumin from monomeric albumin, dimeric albumin, and polymeric albumin. In some embodiments, the size-exclusion chromatography method used is capable of separating all four categories of albumin on the nanoparticles (e.g., monomeric, dimeric, oligomeric, polymeric).

In some embodiments, when determining the oligomeric status of the albumin, the separation range for the size-exclusion chromatography is about 10,000 daltons to about 500,000 daltons. In some embodiments, the size-exclusion chromatography is run with a TSKgel G3000 SWXL column. In some embodiments, the size-exclusion chromatography is run with a column of TOSOH TSKgel G3000 SWXL, 7.8×300 mm, 5 μm or equivalent. In some embodiments, the size-exclusion chromatography is run with a flow rate of about 1 mL/min. In some embodiments, the size-exclusion chromatography is run at ambient temperature. In some embodiments, the size-exclusion chromatography is run with a column of TOSOH TSKgel G3000 SWXL, 7.8×300 mm, 5 μm or equivalent, at a flow rate of about 1 mL/min at room temperature.

The percentage of the albumin on the nanoparticles that is in the form of a monomer, polymer, dimer, and/or oligomer can be determined by comparing the amount of monomeric, polymeric, dimeric, and/or oligomeric albumin on the nanoparticles with the total amount of the albumin on the nanoparticles.

In some embodiments, the composition (such as a pharmaceutical composition) is suitable for medical use if the percentage of monomeric albumin among the albumin on the nanoparticles is about 40% to about 60%. In some embodiments, the composition (such as a pharmaceutical composition) is suitable for medical use if the percentage of monomeric albumin among the albumin on the nanoparticles is about any one of 30%, 35%, 40%, 45%, 50%, 55%, 60%, 65%, or 70%. In some embodiments, the composition (such as a pharmaceutical composition) is suitable for medical use if the percentage of monomeric albumin among the albumin on the nanoparticles is about any one of 20-30%, 30-40%, 40-50%, 50-60%, 60-70%, 70-80%, 20-40%, 40-60%, 60-80%, 20-50%, 50-80%, 35-40%, 40-45%, 45-50%, 50-55%, 55-60%, 60-65%, 35-45%, 45-55%, 55-65%, 40-55%, or 45-60%.

In some embodiments, the composition (such as a pharmaceutical composition) is suitable for medical use if the percentage of dimeric albumin among the albumin on the nanoparticles is about 15% to about 30% (such as about 20% to about 25%, about 15% to about 24%, or about 15% to about 20%). In some embodiments, the composition (such as a pharmaceutical composition) is suitable for medical use if the percentage of dimeric albumin among the albumin on the nanoparticles is about any one of 10%, 11%, 12%, 13%, 14%, 15%, 16%, 17%, 18%, 19%, 20%, 21%, 22%, 23%, 24%, 25%, or 30%. In some embodiments, the composition (such as a pharmaceutical composition) is suitable for medical use if the percentage of dimeric albumin among the albumin on the nanoparticles is about any of 10-12%, 12-14%, 14-15%, 15-16%, 16-17%, 17-18%, 18-19%, 19-20%, 20-21%, 21-23%, 23-25%, 10-15%, 15-20%, 20-25%, 15-17%, 17-19%, 15-15.5%, 15.5-16%, 16-16.5%, 16.5-17%, 17-17.5%, 17.5-18%, 18-18.5%, 18.5-19%, 19-19.5%, 19.5-20%, 15.5-16.5%, 16.5-17.5%, 17.5-18.5%, 18.5-19.5%, 15-16.5%, 16-17.5%, 17-18.5%, 18-19.5%, 16.5-19%, or 17.5-20%.

In some embodiments, the composition (such as a pharmaceutical composition) is suitable for medical use if the percentage of oligomeric albumin among the albumin on the nanoparticles is about 7% to about 15%. In some embodiments, the composition (such as a pharmaceutical composition) is suitable for medical use if the percentage of oligomeric albumin among the albumin on the nanoparticles is about any one of 5%, 6%, 7%, 8%, 9%, 10%, 11%, 12%, 13%, 14%, 15%, 16%, 17%, 18%, 19%, 20%, or 25%. In some embodiments, the composition (such as a pharmaceutical composition) is suitable for medical use if the percentage of oligomeric albumin among the albumin on the nanoparticles is about any one of about any one of 5-6%, 6-7%, 7-8%, 8-9%, 9-10%, 10-11%, 11-12%, 12-13%, 13-14%, 14-15%, 15-16%, 16-17%, 17-20%, 20-25%, 5-7%, 7-9%, 9-11%, 11-13%, 13-15%, 7-10%, 10-13%, 7-12%, 12-15%, 10-15%, or 15-20%.

In some embodiments, the composition (such as a pharmaceutical composition) is suitable for medical use if the percentage of polymeric albumin among the albumin on the nanoparticles is about 15% to about 40% (such as about 15% to about 20%, about 20% to about 24.5%, about 24.5% to about 30%, about 30% to about 35%, or about 35% to about 40%). In some embodiments, the composition (such as a pharmaceutical composition) is suitable for medical use if the percentage of polymeric albumin among the albumin on the nanoparticles is about any one of 15%, 16%, 17%, 18%, 19%, 20%, 22%, 23%, 24%, 25%, 26%, 27%, 28%, 29%, 30%, 35%, or 40%. In some embodiments, the composition (such as a pharmaceutical composition) is suitable for medical use if the percentage of polymeric albumin among the albumin on the nanoparticles is any of about 15% to about 16%, about 16% to about 17%, about 17% to about 18%, about 18% to about 19%, about 19% to about 20%, about 20% to about 21%, about 21% to about 22%, about 22% to about 23%, about 23% to about 24%, about 24% to about 25%, about 25% to about 26%, about 26% to about 27%, about 27% to about 28%, about 28% to about 29%, about 29% to about 30%, about 30% to about 35%, about 35% to about 40%, about 15% to about 18%, about 18% to about 20%, about 20% to about 23%, about 23% to about 25%, about 25% to about 30%, about 30% to about 40%, about 15% to about 20%, about 20% to about 24.5%, about 24.5% to about 30%, about 15% to about 24.5%, about 15% to about 18.5%, or about 15% to about 40% (such as about 15% to about 20%, about 20% to about 24.5%, about 24.5% to about 30%, about 30% to about 35%, or about 35% to about 40%). In some embodiments, the composition (such as a pharmaceutical composition) is suitable for medical use if the percentage of polymeric albumin among the albumin on the nanoparticles is about 23.6-24.7%, or more than about 29.7%. In some embodiments, the composition (such as a pharmaceutical composition) is suitable for medical use if the percentage of polymeric albumin among the albumin on the nanoparticles is about 23.6-24.7%. In some embodiments, the composition (such as a pharmaceutical composition) is suitable for medical use if the percentage of oligomeric albumin among the albumin on the nanoparticles is about any one of 10-20%, 20-30%, 30-40%, 15-25%, 25-35%, 35-40%, 21-22%, 22-23%, 23-24%, 24-25%, 25-26%, 26-28%, 28-30%, 20-23%, 23-25%, 25-30%, 23-23.2%, 23.2-23.4%, 23.4-23.6%, 23.6-23.8%, 23.8-24%, 24-24.2%, 24.2-24.4%, 24.4-24.6%, 24.6-24.8%, 24.8-25%, 23-23.4%, 23.4-23.8%, 23.8-24.2%, 24.2-24.6%, 24.6%-25%, 23-23.5%, 23.5-24%, 24-24.5%, 24.5-25%, 23-23.6%, 23.6-24.2%, 24.2-24.7%, or 23.6-24.7%.

In some embodiments, the composition (such as a pharmaceutical composition) is suitable for medical use if the percentage of polymeric albumin among the albumin on the nanoparticles is more than about 29.7%. In some embodiments, the composition (such as a pharmaceutical composition) is suitable for medical use if the percentage of polymeric albumin among the albumin on the nanoparticles is about 30% to about 32%, about 32% to about 34%, about 34% to about 36%, about 36% to about 38%, or about 38% to about 40%.

In some embodiments, the composition (such as a pharmaceutical composition) is suitable for medical use if about 15% to about 40% (such as about 15% to about 20%, about 20% to about 24.5%, about 24.5% to about 30%, about 30% to about 35%, or about 35% to about 40%) of the albumin on the nanoparticles is in the form of polymers, and about 40% to about 60% of the albumin on the nanoparticles is in the form of monomers. In some embodiments, the composition (such as a pharmaceutical composition) is suitable for medical use if at least about any one of 10%, 12%, 13%, 14%, 15%, 16%, 17%, 18%, 19%, 20%, 22%, 23%, 24%, 25%, of the albumin on the nanoparticles is in the form of polymers, and about any one of 30%, 35%, 40%, 45%, 50%, 55%, 60%, or 65% of the albumin on the nanoparticles is in the form of monomers. In some embodiments, the composition (such as a pharmaceutical composition) is suitable for medical use if about any one of 10-20%, 20-30%, 30-40%, 15-25%, 25-35%, 35-40%, 21-22%, 22-23%, 23-24%, 24-25%, 25-26%, 26-28%, 28-30%, 20-23%, 23-25%, 25-30%, 23-23.2%, 23.2-23.4%, 23.4-23.6%, 23.6-23.8%, 23.8-24%, 24-24.2%, 24.2-24.4%, 24.4-24.6%, 24.6-24.8%, 24.8-25%, 23-23.4%, 23.4-23.8%, 23.8-24.2%, 24.2-24.6%, 24.6%-25%, 23-23.5%, 23.5-24%, 24-24.5%, 24.5-25%, 23-23.6%, 23.6-24.2%, 24.2-24.7%, or 23.6-24.7% of the albumin on the nanoparticles is in the form of polymers, and about any one of 20-30%, 30-40%, 40-50%, 50-60%, 60-70%, 70-80%, 20-40%, 40-60%, 60-80%, 20-50%, 50-80%, 35-40%, 40-45%, 45-50%, 50-55%, 55-60%, 60-65%, 35-45%, 45-55%, 55-65%, 40-55%, or 45-60% of the albumin on the nanoparticles is in the form of monomers. In some embodiments, the composition (such as a pharmaceutical composition) is suitable for medical use if about 30% to about 32%, about 32% to about 34%, about 34% to about 36%, about 36% to about 38%, or about 38% to about 40% of the albumin on the nanoparticles is in the form of polymers, and about any one of 20-30%, 30-40%, 40-50%, 50-60%, 60-70%, 70-80%, 20-40%, 40-60%, 60-80%, 20-50%, 50-80%, 35-40%, 40-45%, 45-50%, 50-55%, 55-60%, 60-65%, 35-45%, 45-55%, 55-65%, 40-55%, or 45-60% of the albumin on the nanoparticles is in the form of monomers.

In some embodiments, the composition (such as a pharmaceutical composition) is suitable for medical use if about 40% to about 60% (such as about 40% to about 55%, about 40% to about 54%, about 40% to about 53%, or about 40% to about 52%, about 40% to about 50%, about 40% to about 48%, or about 40% to about 46%) of the albumin on the nanoparticles is in the form of monomers. In some embodiments, the composition (such as a pharmaceutical composition) is suitable for medical use if about any one of 30%, 35%, 40%, 45%, 50%, 55%, 60%, 65%, or 70% of the albumin on the nanoparticles is in the form of monomers. In some embodiments, the composition (such as a pharmaceutical composition) is suitable for medical use if about any one of 20-30%, 30-40%, 40-50%, 50-60%, 60-70%, 70-80%, 20-40%, 40-60%, 60-80%, 20-50%, 50-80%, 35-40%, 40-45%, 45-50%, 50-55%, 55-60%, 60-65%, 35-45%, 45-55%, 55-65%, 40-55%, or 45-60% of the albumin on the nanoparticles is in the form of monomers. In some embodiments, the composition (such as a pharmaceutical composition) is suitable for medical use if less than about 51% of the albumin on the nanoparticles are in the form of monomers.

In some embodiments, the composition (such as a pharmaceutical composition) is suitable for medical use if about 7% to about 15% of the albumin on the nanoparticles is in the form of oligomers. In some embodiments, the composition (such as a pharmaceutical composition) is suitable for medical use if about any one of 5%, 6%, 7%, 8%, 9%, 10%, 11%, 12%, 13%, 14%, 15%, 16%, 17%, 18%, 19%, 20%, or 25% of the albumin on the nanoparticles is in the form of oligomers. In some embodiments, the composition (such as a pharmaceutical composition) is suitable for medical use if about any one of 5-6%, 6-7%, 7-8%, 8-9%, 9-10%, 10-11%, 11-12%, 12-13%, 13-14%, 14-15%, 15-16%, 16-17%, 17-20%, 20-25%, 5-7%, 7-9%, 9-11%, 11-13%, 13-15%, 7-10%, 10-13%, 7-12%, 12-15%, 10-15%, or 15-20% of the albumin on the nanoparticles is in the form of oligomers.

In some embodiments, the composition (such as a pharmaceutical composition) is suitable for medical use if about 15% to about 40% (such as any of about 15% to about 20%, about 20% to about 24.5%, about 24.5% to about 30%, about 30% to about 35%, or about 35% to about 40%) of the albumin on the nanoparticles is in the form of polymers, and about 40% to about 60% of the albumin on the nanoparticles is in the form of monomers. In some embodiments, the composition (such as a pharmaceutical composition) is suitable for medical use if about any one of 15%, 16%, 17%, 18%, 19%, 20%, 22%, 23%, 24%, 25%, 26%, 27%, 28%, 29%, 30%, 35%, or 40% of the albumin on the nanoparticles is in the form of polymers, and about any one of 30%, 35%, 40%, 45%, 50%, 55%, 60%, or 65% of the albumin on the nanoparticles is in the form of monomers. In some embodiments, the composition (such as a pharmaceutical composition) is suitable for medical use if about any one of 10-20%, 20-30%, 30-40%, 15-25%, 25-35%, 35-40%, 21-22%, 22-23%, 23-24%, 24-25%, 25-26%, 26-28%, 28-30%, 20-23%, 23-25%, 25-30%, 23-23.2%, 23.2-23.4%, 23.4-23.6%, 23.6-23.8%, 23.8-24%, 24-24.2%, 24.2-24.4%, 24.4-24.6%, 24.6-24.8%, 24.8-25%, 23-23.4%, 23.4-23.8%, 23.8-24.2%, 24.2-24.6%, 24.6%-25%, 23-23.5%, 23.5-24%, 24-24.5%, 24.5-25%, 23-23.6%, 23.6-24.2%, 24.2-24.7%, or 23.6-24.7% of the albumin on the nanoparticles is in the form of polymers, and about any one of 20-30%, 30-40%, 40-50%, 50-60%, 60-70%, 70-80%, 20-40%, 40-60%, 60-80%, 20-50%, 50-80%, 35-40%, 40-45%, 45-50%, 50-55%, 55-60%, 60-65%, 35-45%, 45-55%, 55-65%, 40-55%, or 45-60% of the albumin on the nanoparticles is in the form of monomers. In some embodiments, the composition (such as a pharmaceutical composition) is suitable for medical use if about 30% to about 32%, about 32% to about 34%, about 34% to about 36%, about 36% to about 38%, or about 38% to about 40% of the albumin on the nanoparticles is in the form of polymers, and about any one of 20-30%, 30-40%, 40-50%, 50-60%, 60-70%, 70-80%, 20-40%, 40-60%, 60-80%, 20-50%, 50-80%, 35-40%, 40-45%, 45-50%, 50-55%, 55-60%, 60-65%, 35-45%, 45-55%, 55-65%, 40-55%, or 45-60% of the albumin on the nanoparticles is in the form of monomers. In some embodiments, the composition (such as a pharmaceutical composition) is suitable for medical use if more than about 35% of albumin on the nanoparticles are in the forms of polymers and oligomers. In some embodiments, the composition (such as a pharmaceutical composition) is suitable for medical use if less than about 54% monomers. In some embodiments, the composition (such as a pharmaceutical composition) is suitable for medical use if more than about 35% of albumin on the nanoparticles are in the forms of polymers and oligomers. In some embodiments, the composition (such as a pharmaceutical composition) is suitable for medical use if less than about 54% of the albumin on the nanoparticles are in the form of monomers, and more than about 11% of the albumin in the nanoparticles are in the form of polymers. In some embodiments, the composition (such as a pharmaceutical composition) is suitable for medical use if less than about 55% of the albumin on the nanoparticles are in the form of monomers, and more than about 18% of the albumin in the nanoparticles are in the form of polymers. In some embodiments, the composition (such as a pharmaceutical composition) is suitable for medical use if the ratio of albumin on the nanoparticles in the forms of polymers and oligomers to the albumin on the nanoparticles in the form of monomers is more than about 62%.

In some embodiments, the composition (such as a pharmaceutical composition) is suitable for medical use if less than about 51% including for example less than about any of 51%, 50%, 49%, 48%, 47%, 46%, 45%, 44%, 43%, or 42% albumin on the nanoparticles are in the form of monomers. In some embodiments, the composition (such as a pharmaceutical composition) is suitable for medical use if more than about 30% including for example more than about any of 30%, 31%, 32%, 33%, 34%, 35%, 36%, 37%, 38%, 39%, or 40% of the albumin on the nanoparticles are in the forms of polymers and oligomers. In some embodiments, the composition (such as a pharmaceutical composition) is suitable for medical use if less than about 51% of the albumin on the nanoparticles are in the form of monomers, and more than about 30% (such as more than about 35%) of the albumin on the nanoparticles are in the form of polymers and oligomers. In some embodiments, the composition (such as a pharmaceutical composition) is suitable for medical use if less than about 54% of the albumin on the nanoparticles are in the form of monomers, and more than about 17% of the albumin in the nanoparticles are in the form of polymers. In some embodiments, the composition (such as a pharmaceutical composition) is suitable for medical use if less than about 55% of the albumin on the nanoparticles are in the form of monomers, and more than about 18% of the albumin in the nanoparticles are in the form of polymers. In some embodiments, the composition (such as a pharmaceutical composition) is suitable for medical use if the ratio of albumin on the nanoparticles in the forms of polymers and oligomers to the albumin on the nanoparticles in the form of monomers is more than about 65% including for example more than about any of 65%, 66%, 67%, 68%, 69%, 70%, 71%, 72%, 73%, 74%, 75%, or 76%.

In some embodiments, the composition (such as a pharmaceutical composition) is suitable for medical use if the percentage of albumin on the nanoparticles in the form of monomers minus the percentage of albumin on the nanoparticles in the form of dimers is less than about 30%. In some embodiments, the composition (such as a pharmaceutical composition) is suitable for medical use if the percentage of albumin on the nanoparticles in the form of monomers minus the percentage of albumin on the nanoparticles in the form of dimers is less than about any of 30%, 31%, 32%, 33%, 34%, 35%, 36%, 37%, 38%, 39%, 40%, 41%, 42%, 43%, 44%, 45%, 46%, 47%, 48%, 49%, or 50%. In some embodiments, the composition (such as a pharmaceutical composition) is suitable for medical use if the percentage of albumin on the nanoparticles in the form of monomers plus the percentage of albumin on the nanoparticles in the form of oligomers is less than about 56% to about 58%. In some embodiments, the composition (such as a pharmaceutical composition) is suitable for medical use if the percentage of albumin on the nanoparticles in the form of monomers plus the percentage of albumin on the nanoparticles in the form of oligomers is less than about any of 56%, 57, 58, 59%, 60%. 61%. 62%. 63%, 64%, or 65%. In some embodiments, the composition (such as a pharmaceutical composition) is suitable for medical use if the percentage of albumin on the nanoparticles in the form of monomers minus the percentage of albumin on the nanoparticles in the form of polymers is less than about 20% to about 22%. In some embodiments, the composition (such as a pharmaceutical composition) is suitable for medical use if the percentage of albumin on the nanoparticles in the form of monomers minus the percentage of albumin on the nanoparticles in the form of polymers is less than about any of 20%, 21%, 22%, 23%, 24%, 25%, 26%, 27% or 28%. In some embodiments, the composition (such as a pharmaceutical composition) is suitable for medical use if the percentage of albumin on the nanoparticles in the form of dimers plus the percentage of albumin on the nanoparticles in the form of polymers is greater than about 42%. In some embodiments, the composition (such as a pharmaceutical composition) is suitable for medical use if the percentage of albumin on the nanoparticles in the form of dimers plus the percentage of albumin on the nanoparticles in the form of polymers is greater than about any of 42%, 43%, 44%, 45%, 46%, 47%, 48%, 49%, or 50%. In some embodiments, the composition (such as a pharmaceutical composition) is suitable for medical use if the ratio of albumin on the nanoparticles in the forms of polymers and oligomers to the albumin on the nanoparticles in the form of monomers minus dimers is more than about 88%. In some embodiments, the composition (such as a pharmaceutical composition) is suitable for medical use if the ratio of albumin on the nanoparticles in the forms of polymers and oligomers to the albumin on the nanoparticles in the form of monomers minus dimers is more than about any of 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 05%, 106%, 107%, 108%, 109%, 110%, 111%, 112%, 113%, 114%, 115%, 116%, 117%, 118%, 119%, or 120%.

In some embodiments, the composition (such as a pharmaceutical composition) is suitable for medical use if the weight ratio of albumin on the nanoparticles in the forms of polymers and oligomers to the albumin on the nanoparticles in the form of monomers is more than about 6:10 including for example more than about any of 6:10, 6.2:10, 6.4:10; 6.6:10, 6.8:10, 7.0:10, 7.2:10; 7.4:10; 7.6:10; or 7.8:10. In some embodiments, the composition (such as a pharmaceutical composition) is suitable for medical use if the weight ratio of albumin dimers to albumin monomers on the nanoparticles is more than any of 1.6:10, 2.0:10, 2.5:10, 3.0:10, or 3.5:10. In some embodiments, the composition (such as a pharmaceutical composition) is suitable for medical use if the weight ratio of albumin oligomers to albumin monomers on the nanoparticles is more than any of 0.5:10; 1:10, 1.2:10, 1.4:10, or 1.6:10. In some embodiments, the weight ratio of albumin polymers to albumin monomers on the nanoparticles is less than 5.8:10, or 5.7:10. In some embodiments, the composition (such as a pharmaceutical composition) is suitable for medical use if the weight ratio of albumin polymers to albumin dimers on the nanoparticles is less than 40:10, 30:10, or 20:10. In some embodiments, the composition (such as a pharmaceutical composition) is suitable for medical use if the weight ratio of albumin oligomers to albumin dimers on the nanoparticles is more than any of 3.3:10, 3.5:10, 3.6:10, 3.8:10, 4.0:10, 4.2:10, or 4.4:10. In some embodiments, the composition (such as a pharmaceutical composition) is suitable for medical use if the weight ratio of albumin polymers to albumin oligomers on the nanoparticles is less than any of 120:10, 100:10, 80:10, 60:10, or 40:10.

Determination of Weight Percentage of Albumin in the Nanoparticles

The methods of the present application in some embodiments require determination of the weight percentage of the albumin in the nanoparticles.

Generally, to determine the weight percentage of the albumin in the nanoparticles, the amount of the albumin on the nanoparticles and the total weight of the nanoparticles can be determined. The amount of the albumin on the nanoparticles can be determined by, for example, chromatography, such as reversed-phase chromatography, size-exclusion chromatography and/or HPLC size-exclusion chromatography methods, spectrophotometric measurements, or mass spectrometric measurements. In some embodiments, the method comprises separating the nanoparticles from the non-nanoparticle portion by ultracentrifugation or gel filtration chromatography, followed by analyzing the amount of the albumin on the nanoparticles by, for example, size-exclusion chromatography. Spectrophotometric measurements can be used to determine the amount of the albumin on the nanoparticles. In some embodiments, the weight percentage of the albumin in the nanoparticles is determined upon reconstitution of the pharmaceutical composition. In some embodiments, the weight percentage of the albumin in the nanoparticles is determined upon storage of the pharmaceutical composition.

In some embodiments, the total weight of the nanoparticles is determined by addition of the amount of the albumin on the nanoparticles and the amount of paclitaxel in the nanoparticle. Amount of the paclitaxel in the nanoparticles can be determined by, for example, chromatography, such as reversed-phase high performance liquid chromatography (RP-HPLC), spectrophotometric measurements, or mass spectrometric measurements. In some embodiments, the method comprises determining the amount of the paclitaxel in the nanoparticles, for example, by reversed-phase HPLC.

In some embodiments, the amount of the albumin on the nanoparticles and the amount of the paclitaxel in the nanoparticles are used to determine the total weight of the nanoparticles. The weight percentage of the albumin in the nanoparticles can be calculated from the amount of the albumin on the nanoparticles and the total weight of the nanoparticles.

In some embodiments, the composition (such as a pharmaceutical composition) is suitable for medical use if the weight percentage of the albumin in the nanoparticles is about 15% to about 30% (such as about 20% to about 25%, about 15% to about 24%, or about 15% to about 20%). In some embodiments, the composition (such as a pharmaceutical composition) is suitable for medical use if the weight percentage of the albumin in the nanoparticles is about any one of 10%, 12%, 15%, 15.5%, 16%, 16.5%, 17%, 17.5%, 18%, 18.5%, 19%, 19.5%, 20%, 22%, 25%, 30%, 35%, or 40%. In some embodiments, the composition (such as a pharmaceutical composition) is suitable for medical use if the weight percentage of the albumin in the nanoparticles is about any one of 10-12%, 12-14%, 14-15%, 15-16%, 16-17%, 17-18%, 18-19%, 19-20%, 20-22%, 22-25%, 10-15%, 15-20%, 20-25%, 25-30%, 15-17%, 17-19%, 15-15.5%, 15.5-16%, 16-16.5%, 16.5-17%, 17-17.5%, 17.5-18%, 18-18.5%, 18.5-19%, 19-19.5%, 19.5-20%, 15.5-16.5%, 16.5-17.5%, 17.5-18.5%, 18.5-19.5%, 15-16.5%, 16-17.5%, 17-18.5%, 18-19.5%, 16.5-19%, 17.5-20%, 15-17.5%, 17.5-20%, 20-22.5%, or 22.5-24%.

Determination of Weight Ratio of Albumin to Paclitaxel on the Nanoparticles

The methods of the present application in some embodiments require determination of the weight ratio of the albumin on the nanoparticles to the paclitaxel in the nanoparticles.

Exemplary means for determining the amount of the albumin on the nanoparticles and the amount of the paclitaxel in the nanoparticles are discussed above. In some embodiments, the weight ratio of albumin to paclitaxel in the nanoparticles is determined by the amount of the albumin on the nanoparticles over the amount of the paclitaxel in the nanoparticles. In some embodiment, the weight ratio of albumin to paclitaxel in the nanoparticles is determined upon storage of the pharmaceutical composition.

In some embodiments, the composition (such as a pharmaceutical composition) is suitable for medical use if the weight ratio of albumin to paclitaxel in the nanoparticles is about 1:2 to about 1:6. In some embodiments, the composition (such as a pharmaceutical composition) is suitable for medical use if the weight ratio of albumin to paclitaxel in the nanoparticles is about any of 1:1, 1:2, 1:3, 1:3.5, 1:4, 1:4.5, 1:5, 1:5.5, 1:6, 1:6.5, 1:7, 1:8, 1:9, or 1:10. In some embodiments, the composition (such as a pharmaceutical composition) is suitable for medical use if the weight ratio of albumin to paclitaxel in the nanoparticles is any of about 1:1 to about 1:2, about 1:2 to about 1:3, about 1:3 to about 1:3.5, about 1:3.5 to about 1:4, about 1:4 to about 1:4.5, about 1:4.5 to about 1:5, about 1:5 to about 1:5.5, about 1:5.5 to about 1:6, about 1:6 to about 1:6.5, about 1:6.5 to about 1:7, about 1:7 to about 1:8, about 1:8 to about 1:9, about 1:9 to about 1:10, about 1:1 to about 1:4, about 1:4 to about 1:6, about 1:6 to about 1:10, about 1:3 to about 1:4, about 1:4 to about 1:5, about 1:5 to about 1:6, about 1:6 to about 1:7, about 1:3.5 to about 1:4.5, about 1:4.5 to about 1:5.5, about 1:5.5 to about 1:6.5, or about 1:2 to about 1:6.

Determination of Paclitaxel Concentration

The methods of present application in some embodiments require determination of the concentration of paclitaxel in the nanoparticle portion of the composition.

The concentration of paclitaxel in the nanoparticle portion of the composition (such as a pharmaceutical composition) can be determined by a variety of techniques including an HPLC assay using UV absorbance. Briefly, for example, the nanoparticle portion of composition (such as a pharmaceutical composition) is separated from the non-nanoparticle portion of the composition by ultracentrifugation, for example, at 50,000 rpm for 41 minutes at 25° C. The supernatant is removed and the pellet is gently washed with water twice. The pellet is then dispersed in a volume of 50:50 acetonitrile:water solution, for example 3.0 ml, by sonication. The sample is further diluted to ensure a homogenous solution is formed. The sample is analyzed on an HPLC system equipped with, for example, a Phenomenex, Curosil PFP guard column (4.6 mm×30 mm, 5 µm particle size) and a Phenomenex, Curosil PFP analytical column (4.6 mm×250 mm, 5 µm particle size), UV absorbance detector, and data acquisition system. Chromatograms are generated with the UV absorbance detector set at 228 nm. Comparison to analysis of paclitaxel standards is used to determine the concentration of paclitaxel in the nanoparticle portion of the composition. In some embodiments, the paclitaxel concentration in the nanoparticles is determined by the amount of paclitaxel in the nanoparticle portion of the composition in the same volume of the original sample.

In some embodiments, the composition (such as a pharmaceutical composition) is suitable for medical use if the paclitaxel concentration in the composition (such as a pharmaceutical composition) is about any of about 2 mg/ml, 3 mg/ml, 4 mg/ml, 5 mg/ml, 6 mg/ml, 7 mg/ml, 8 mg/ml, 9 mg/ml, or 10 mg/ml.

In some embodiments, the composition (such as a pharmaceutical composition) is suitable for medical use if the paclitaxel concentration in the composition (such as a pharmaceutical composition) is any of about 2 mg/ml, 3 mg/ml, 4 mg/ml, 5 mg/ml, 6 mg/ml, 7 mg/ml, 8 mg/ml, 9 mg/ml, or 10 mg/ml. In some embodiments, the composition (such as a pharmaceutical composition) is suitable for medical use if the paclitaxel concentration in the composition (such as a pharmaceutical composition) is about 4.4-4.5 mg/ml, 4.5-4.6 mg/ml, 4.6-4.7 mg/ml, 4.7-4.8 mg/ml, 4.8-4.9 mg/ml, or 4.9-5.0 mg/ml. In some embodiments, the composition (such as a pharmaceutical composition) is suitable for medical use if the paclitaxel in the suspension is about 5 mg/ml. In some embodiments, the composition (such as a pharmaceutical composition) is suitable for medical use if the paclitaxel in the composition (such as a pharmaceutical composition) is about 5 mg/ml.

In some embodiments, the composition (such as a pharmaceutical composition) is suitable for medical use if the paclitaxel in the nanoparticle portion of the composition (such as a pharmaceutical composition) is any of about 2 mg/ml, 3 mg/ml, 4 mg/ml, 5 mg/ml, 6 mg/ml, 7 mg/ml, 8 mg/ml, 9 mg/ml, or 10 mg/ml. In some embodiments, the composition (such as a pharmaceutical composition) is suitable for medical use if the paclitaxel in the nanoparticle portion of the composition (such as a pharmaceutical composition) is about 4.2-4.3 mg/ml, 4.3-4.4 mg/ml, 4.4-4.5 mg/ml, 4.5-4.6 mg/ml, 4.6-4.7 mg/ml, 4.7-4.8 mg/ml, 4.9-5.0 mg/ml.

Determination of Nanoparticle Morphology

The methods of the present application in some embodiments require determination of the nanoparticle morphology. The morphology of paclitaxel nanoparticles in an albumin-based paclitaxel nanoparticle composition can affect particle solubility, dissolution rate, and disintegration kinetics.

In some embodiments, the methods comprise determining the shape of the nanoparticles, for example by microscopic methods such as cryo-TEM. In some embodiments, the methods comprise determining the thickness of the albumin coating on the nanoparticles, for example by microscopic methods such as cryo-TEM. In some embodiments, the methods comprise determining both the shape of the nanoparticles and the thickness of the albumin coating on the nanoparticles by microscopic methods, such as cryo-TEM. In some embodiments, the shape of the nanoparticles is determined upon reconstitution of the pharmaceutical composition. In some embodiments, the shape of the nanoparticles is determined upon storage of the pharmaceutical composition.

For example, the composition (such as a pharmaceutical composition) can be rapidly cooled to cryogenic temperatures following reconstitution of the composition (such as a pharmaceutical composition) to form a vitreous form of the reconstituted composition which can then be analyzed. The nanoparticles of the composition (such as a pharmaceutical composition) remain in their native structure during cryo-TEM sample preparation and image recording. In some embodiments, cryo-TEM records the native structure of the nanoparticles of the composition (such as a pharmaceutical composition).

In some embodiments, the thickness of the albumin coating on the nanoparticles is calculated based on measured parameters of the nanoparticles, including for example the albumin-to-paclitaxel ratio of the nanoparticles. In some embodiments, the thickness of the albumin coating on the nanoparticles is determined upon reconstitution of the pharmaceutical composition. In some embodiments, the thickness of the albumin coating on the nanoparticles is determined upon storage of the pharmaceutical composition.

In some embodiments, the composition (such as a pharmaceutical composition) is suitable for medical use if the nanoparticles are of irregular shape. In some embodiments, the composition (such as a pharmaceutical composition) is suitable for medical use if the nanoparticles have a non-smooth surface. In some embodiments, the composition (such as a pharmaceutical composition) is suitable for medical use if the nanoparticles are of irregular shape and have a non-smooth surface. In some embodiments, the composition (such as a pharmaceutical composition) is suitable for medical use if the nanoparticles have a high degree of rugosity. In some embodiments, the composition (such as a pharmaceutical composition) is suitable for medical use of the nanoparticles are of irregular shape and have a high degree of rugosity.

In some embodiments, the composition (such as a pharmaceutical composition) is suitable for medical use if the thickness of the albumin coating on the nanoparticles is about 5 nanometers to about 7 nanometers as measured by cryo-TEM. In some embodiments, the composition (such as a pharmaceutical composition) is suitable for medical use if the nanoparticles are of irregular shape and have an albumin coating with a thickness of about 5 nanometers to about 7 nanometers as measured by cryo-TEM. In some embodiments, the composition (such as a pharmaceutical composition) is suitable for medical use if the albumin coating has a thickness of about any of 3 nanometers, 4 nanometers, 5 nanometers, 5.5 nanometers, 6 nanometers, 6.5 nanometers, 7 nanometers, 8 nanometers, or 9 nanometers as measured by cryo-TEM. In some embodiments, the composition (such as a pharmaceutical composition) is suitable for medical use if the albumin coating has a thickness of about any of 3-4 nanometers, 4-5 nanometers, 5-6 nanometers, 6-7 nanometers, 7-8 nanometers, 8-9 nanometers, 3-5 nanometers, 5-7 nanometers, 7-9 nanometers, 5-5.5 nanometers, 5.5-6 nanometers, 6-6.5 nanometers, 6.5-7 nanometers, 4.5-5.5 nanometers, 5.5-6.5 nanometers, 6.5-7.5 nanometers, 5-6.5 nanometers, or 5.5-7 nanometers as measured by cryo-TEM.

In some embodiments, the methods described herein further comprise determining the surface-to-volume ratio of the nanoparticles. Surface-to-volume ratios of the nanoparticles can be determined, for example, by microscopy methods, such as, cryo-TEM, atomic force microscopy, or Fourier transform infrared spectroscopy. In some embodiments, the surface-to-volume ratio of the nanoparticles is determined upon reconstitution of the pharmaceutical composition. In some embodiments, the surface-to-volume ratio of the nanoparticles is determined upon storage of the pharmaceutical composition.

In some embodiments, the composition (such as a pharmaceutical composition) is suitable for medical use if the surface-to-volume ratio of the nanoparticles is more than about 46.2:1 $\mu m^{-1}$, or the surface-to-volume ratio of a perfect sphere having the same particle size as the nanoparticles. In some embodiments, the composition (such as a pharmaceutical composition) is suitable for medical use if the surface-to-volume ratio of the nanoparticles is more than about any of 30:1 $\mu m^{-1}$, 35:1 $\mu m^{-1}$, 40:1 $\mu m^{-1}$, 45:1 $\mu m^{-1}$, 46.2:1 $\mu m^{-1}$, 47:1 $\mu m^{-1}$, 48:1 $\mu m^{-1}$, 49:1 $\mu m^{-1}$, 50:1 $\mu m^{-1}$, 52:1 $\mu m^{-1}$, 55:1 $\mu m^{-1}$, 58:1 $\mu m^{-1}$, 60:1 $\mu m^{-1}$, 65:1 $\mu m^{-1}$, 70:1 $\mu m^{-1}$, 75:1 $\mu m^{-1}$, 80:1 $\mu m^{-1}$, 90:1 $\mu m^{-1}$, 100:1 $\mu m^{-1}$, 110:1 $\mu m^{-1}$, 120:1 $\mu m^{-1}$, 130:1 $\mu m^{-1}$, 140:1 $\mu m^{-1}$, 150:1 $\mu m^{-1}$, 160:1 $\mu m^{-1}$, 170:1 $\mu m^{-1}$, 180:1 $\mu m^{-1}$, 190:1 $\mu m^{-1}$, 200:1 $\mu m^{-1}$, 210:1 $\mu m^{-1}$, 220:1 $\mu m^{-1}$, 250:1 $\mu m^{-1}$, 300:1 $\mu m^{-1}$, or 400:1 $\mu m^{-1}$. In some embodiments, the composition (such as a pharmaceutical composition) is suitable for medical use if the surface-to-volume ratio of the nanoparticles is more than any of about 30:1 $\mu m^{-1}$ to about 35:1 $\mu m^{-1}$, about 35:1 $\mu m^{-1}$ to about 40:1 $\mu m^{-1}$, about 40:1 $\mu m^{-1}$ to about 45:1 $\mu m^{-1}$, about 46.2:1 $\mu m^{-1}$ to about 47:1 $\mu m^{-1}$, about 47:1 $\mu m^{-1}$ to about 48:1 $\mu m^{-1}$, about 48:1 $\mu m^{-1}$ to about 49:1 $\mu m^{-1}$, about 49:1 $\mu m^{-1}$ to about 50:1 $\mu m^{-1}$, about 50:1 $\mu m^{-1}$ to about 52:1 $\mu m^{-1}$, about 52:1 $\mu m^{-1}$ to about 55:1 $\mu m^{-1}$, about 55:1 $\mu m^{-1}$ to about 58:1 $\mu m^{-1}$, about 58:1 $\mu m^{-1}$ to about 60:1 $\mu m^{-1}$, about 60:1 $\mu m^{-1}$ to about 65:1 $\mu m^{-1}$, about 65:1 $\mu m^{-1}$ to about 70:1 $\mu m^{-1}$, about 70:1 $\mu m^{-1}$ to about 75:1 $\mu m^{-1}$, about 75:1 $\mu m^{-1}$ to about 80:1 $\mu m^{-1}$, about 46.2:1 $\mu m^{-1}$ to about 50:1 $\mu m^{-1}$, about 50:1 $\mu m^{-1}$ to about 60:1 $\mu m^{-1}$, about 60:1 $\mu m^{-1}$ to about 70:1 $\mu m^{-1}$, about 70:1 $\mu m^{-1}$ to about 80:1 $\mu m^{-1}$, about 46.2:1 $\mu m^{-1}$ to about 60:1 $\mu m^{-1}$, about 60:1 $\mu m^{-1}$ to about 80:1 $\mu m^{-1}$, about 50:1 $\mu m^{-1}$ to about 70:1 $\mu m^{-1}$, about 48:1 $\mu m^{-1}$ to about 52:1 $\mu m^{-1}$, about 52:1 $\mu m^{-1}$ to about 65:1 $\mu m^{-1}$, about 65:1 $\mu m^{-1}$ to about 80:1 $\mu m^{-1}$, about 80:1 $\mu m^{-1}$ to about 90:1 $\mu m^{-1}$, about 100:1 $\mu m^{-1}$ to about 120:1 $\mu m^{-1}$, about 120:1 $\mu m^{-1}$ to about 140:1 $\mu m^{-1}$, about 140:1 $\mu m^{-1}$ to about 160:1 $\mu m^{-1}$, about 160:1 $\mu m^{-1}$ to about 180:1 $\mu m^{-1}$, about 180:1 $\mu m^{-1}$ to about 200:1 $\mu m^{-1}$, about 200:1 $\mu m^{-1}$ to about 220:1 $\mu m^{-1}$, about 220:1 $\mu m^{-1}$ to about 250:1 $\mu m^{-1}$, about 250:1 $\mu m^{-1}$ to about 300:1 $\mu m^{-1}$, about 300:1 $\mu m^{-1}$ to about 400:1 $\mu m^{-1}$, about 30:1 $\mu m^{-1}$ to about 40:1 $\mu m^{-1}$, about 30:1 $\mu m^{-1}$ to about 45:1 $\mu m^{-1}$, about 80:1 $\mu m^{-1}$ to about 120:1 $\mu m^{-1}$, about 120:1 $\mu m^{-1}$ to about 150:1 $\mu m^{-1}$, or about 150:1 $\mu m^{-1}$ to about 200:1 $\mu m^{-1}$.

In some embodiments, the composition (such as a pharmaceutical composition) is suitable for medical use if the surface-to-volume ratio of the nanoparticles is more than about 6/d, wherein d is the average diameter of the nanoparticles (i.e. the surface-to-volume ratio of a perfect sphere having the same particle size as the nanoparticles). In some embodiments, the composition (such as a pharmaceutical composition) is suitable for medical use if the surface-to-volume ratio of the nanoparticles is more than about any of 1, 1.1, 1.2, 1.3, 1.4, 1.5, 1.6, 1.7, 1.8, 1.9, 2, 2.1, 2.2, 2.3, 2.4, 2.5, 3, 4, 5, or more than 5 times of 6/d, wherein d is the average diameter of the nanoparticles.

The surface-to-volume ratio of the nanoparticles is related to the average diameter of the nanoparticles. As used herein, "diameter of the nanoparticle" refers to the diameter of the sphere that has the same volume or weight as the nanoparticle. "Average diameter of the nanoparticles" is the average of the diameters of all nanoparticles in the composition (such as a pharmaceutical composition). For example, in some embodiments, when the average diameter of the nanoparticles is no more than about 130 nm, the composition (such as a pharmaceutical composition) is suitable for medical use if the surface-to-volume ratio of the nanoparticles is more than about 46.2:1 $\mu m^{-1}$. In some embodiments, when the average diameter of the nanoparticles is no more than about 130 nm, the composition (such as a pharmaceutical composition) is suitable for medical use if the surface-to-volume ratio of the nanoparticles is more than about any of 46.2:1 $\mu m^{-1}$, 47:1 $\mu m^{-1}$, 48:1 $\mu m^{-1}$, 49:1 $\mu m^{-1}$, 50:1 $\mu m^{-1}$, 52:1 $\mu m^{-1}$, 55:1 $\mu m^{-1}$, 58:1 $\mu m^{-1}$, 60:1 $\mu m^{-1}$, 65:1 $\mu m^{-1}$, 70:1 $\mu m^{-1}$, 75:1 $\mu m^{-1}$, 80:1 $\mu m^{-1}$, 90:1 $\mu m^{-1}$, 100:1 $\mu m^{-1}$, 110:1 $\mu m^{-1}$, 120:1 $\mu m^{-1}$, or 140:1 $\mu m^{-1}$. In some embodiments, when the average diameter of the nanoparticles is no more than about 130 nm, the composition (such as a pharmaceutical composition) is suitable for medical use if the surface-to-volume ratio of the nanoparticles is more than any of about 46.2:1 $\mu m^{-1}$ to about 47:1 $\mu m^{-1}$, about 47:1 $\mu m^{-1}$ to about 48:1 $\mu m^{-1}$, about 48:1 $\mu m^{-1}$ to about 49:1 $\mu m^{-1}$, about 49:1 $\mu m^{-1}$ to about 50:1 $\mu m^{-1}$, about 50:1 $\mu m^{-1}$ to about 52:1 $\mu m^{-1}$, about 52:1 $\mu m^{-1}$ to about 55:1 $\mu m^{-1}$, about 55:1 $\mu m^{-1}$ to about 58:1 $\mu m^{-1}$, about 58:1 $\mu m^{-1}$ to about 60:1 $\mu m^{-1}$, about 60:1 $\mu m^{-1}$ to about 65:1 $\mu m^{-1}$, about 65:1 $\mu m^{-1}$ to about 70:1 $\mu m^{-1}$, about 70:1 $\mu m^{-1}$ to about 75:1 $\mu m^{-1}$, about 75:1 $\mu m^{-1}$ to about 80:1 $\mu m^{-1}$, about 46.2:1 $\mu m^{-1}$ to about 50:1 $\mu m^{-1}$, about 50:1 $\mu m^{-1}$ to about 60:1 $\mu m^{-1}$, about 60:1 $\mu m^{-1}$ to about 70:1 $\mu m^{-1}$, about 70:1 $\mu m^{-1}$ to about 80:1 $\mu m^{-1}$, about 80:1 $\mu m^{-1}$ to about 90:1 $\mu m^{-1}$, about 90:1 $\mu m^{-1}$ to about 120:1 $\mu m^{-1}$, about 120:1 $\mu m^{-1}$ to about 140:1 $\mu m^{-1}$, about 46.1:1 $\mu m^{-1}$ to about 60:1 $\mu m^{-1}$, about 60:1 $\mu m^{-1}$ to about 80:1 $\mu m^{-1}$, about 50:1 $\mu m^{-1}$ to about 70:1 $\mu m^{-1}$, about 48:1 $\mu m^{-1}$ to about 52:1 $\mu m^{-1}$, about 52:1 $\mu m^{-1}$ to about 65:1 $\mu m^{-1}$, or about 65:1 $\mu m^{-1}$ to about 80:1 $\mu m^{-1}$. In some embodiments, when the average diameter of the nanoparticles is about 60 nm to about 190 nm, the composition (such as a pharmaceutical composition) is suitable for medical use if the surface-to-volume ratio of the nanoparticles is more than about any of 31.5:1 $\mu m^{-1}$, 35:1 $\mu m^{-1}$, 40:1 $\mu m^{-1}$, 45:1 $\mu m^{-1}$, 50:1 $\mu m^{-1}$, 55:1 $\mu m^{-1}$, 60:1 $\mu m^{-1}$, 65:1 $\mu m^{-1}$, 70:1 $\mu m^{-1}$, 80:1 $\mu m^{-1}$, 90:1 $\mu m^{-1}$, 100:1 $\mu m^{-1}$, 110:1 $\mu m^{-1}$, 120:1 $\mu m^{-1}$, 130:1 $\mu m^{-1}$, 140:1 $\mu m^{-1}$, 150:1 $\mu m^{-1}$, 160:1 $\mu m^{-1}$, 170:1 $\mu m^{-1}$, 180:1 $\mu m^{-1}$, 190:1 $\mu m^{-1}$, 200:1 $\mu m^{-1}$, or more than 200:1 $\mu m^{-1}$. In some embodiments, when the average diameter of the nanoparticles is about 120 nm to about 140 nm, the composition (such as a pharmaceutical composition) is suitable for medical use if the surface-to-volume ratio of the nanoparticles is more than about any of 42.9:1 $\mu m^{-1}$, 45:1 $\mu m^{-1}$, 50:1 $\mu m^{-1}$, 55:1 $\mu m^{-1}$, 60:1 $\mu m^{-1}$, 65:1 $\mu m^{-1}$, 70:1 $\mu m^{-1}$, 75:1 $\mu m^{-1}$, 80:1 $\mu m^{-1}$, 85:1 $\mu m^{-1}$, 90:1 $\mu m^{-1}$, 95:1 $\mu m^{-1}$, 100:1 $\mu m^{-1}$ or more than 100:1 $\mu m^{-1}$.

Determination of Particle Size and Polydispersity

The methods of the present application in some embodiments require determination of the size of nanoparticles in the composition (such as a pharmaceutical composition). Particle size impacts the dissolution rate of nanoparticles, controls the solubility of nanoparticles, and contributes to the functional behavior of the nanoparticles.

In some embodiments, the methods comprise determining the size of the nanoparticles in the pharmaceutical composition. In some embodiments, the methods comprise determining the polydispersity index of the nanoparticles in the pharmaceutical composition. In some embodiments, the methods comprise determining the size distribution of the nanoparticles in the pharmaceutical composition. In some embodiments, the polydispersity index of the nanoparticles is determined upon reconstitution of the pharmaceutical composition. In some embodiments, the polydispersity index of the nanoparticles is determined upon storage of the pharmaceutical composition.

In some embodiments, the particle size is determined by laser diffraction techniques, such as dynamic light scattering. In some embodiments, the size is determined by volume weighted arithmetic mean particle diameter (D4,3) using a laser diffraction technique. In some embodiments, the particle size is determined by disc centrifugation methods. In some embodiments, the particle size is determined by tunable resistive pulse sensing (TRPS). In some embodiments, the particle size is determined by laser diffraction polarization intensity differential scattering (PIDS-LD). In some embodiments, the particle size is determined by sucrose gradient centrifugation. In some embodiments, the particle size is determined by analytical centrifugation.

In some embodiments, the polydispersity index is determined by, for example, dynamic light scattering. $Dv_{50}$ is the volume-weighted median particle diameter.

In some embodiments, the composition (such as a pharmaceutical composition) is suitable for medical use if the average particle size of the nanoparticles in the pharmaceutical composition is less than about 200 nm. In some embodiments, the composition (such as a pharmaceutical composition) is suitable for medical use if the average particle size of the nanoparticles in the pharmaceutical composition is less than about any of 260 nm, 240 nm, 220 nm, 200 nm, 180 nm, 160 nm, 140 nm, 120 nm, 100 nm, 80 nm, or 60 nm. In some embodiments, the composition (such as a pharmaceutical composition) is suitable for medical use if the average particle size of the nanoparticles in the pharmaceutical composition is about any of 60-80 nm, 80-100 nm, 100-120 nm, 120-140 nm, 140-160 nm, 160-180 nm, 180-200 nm, 200-220 nm, 220-240 nm, 240-260 nm, 80-120 nm, 120-160 nm, 160-200 nm, 200-240 nm, 50-100 nm, 100-150 nm, 150-200 nm, 200-250 nm, 100-105 nm, 105-115 nm, 115-125 nm, 125-135 nm, 135-145 nm, 145-155 nm, 155-160 nm, 100-110 nm, 110-120 nm, 120-130 nm, 130-140 nm, 140-150 nm, 150-160 nm, 105-125 nm, 125-145 nm, 145-160 nm, 100-130 nm, 130-160 nm, 105-135 nm, 135-160 nm, 100-140 nm, 120-160 nm, 110-150 nm, 100-150 nm, 105-155 nm, or 100-160 nm. In some embodiments, the composition (such as a pharmaceutical composition) is suitable for medical use if the average particle size of the nanoparticles in the pharmaceutical composition is about 130 nm.

The parameter $((Dv_{90}-Dv_{10})/Dv_{50})$ describes the span of distribution of the particle sizes of the nanoparticles. $Dv_{50}$ refers to the volume-weighted median particle diameter. $Dv_{90}$ refers to the particle diameter where 90% of the volume of all nanoparticles is contained in nanoparticles with smaller diameters. $Dv_{10}$ refers to the particle diameter where 10% of the volume of all nanoparticles is contained in nanoparticles with smaller diameters. In some embodiments, the composition (such as a pharmaceutical composition) is suitable for medical use if the nanoparticles in the pharmaceutical composition have a span of size distribution $((Dv_{90}-Dv_{10})/Dv_{50})$ of about 0.8 to about 1.5. In some embodiments, the composition (such as a pharmaceutical composition) is suitable for medical use if the nanoparticles in the pharmaceutical composition have a span of size distribution $((Dv_{90}-Dv_{10})/Dv_{50})$ of about any of 0.5, 0.6, 0.7, 0.8, 0.9, 1, 1.1, 1.2, 1.3, 1.4, 1.5, 1.6, 1.7, or 1.8. In some embodiments, the composition (such as a pharmaceutical composition) is suitable for medical use if the nanoparticles in the pharmaceutical composition have a size distribution (($DV_{90}$–$DV_{10}$/$DV_{50}$)) of about any of 0.5-0.6, 0.6-0.7, 0.7-0.8, 0.8-0.9, 0.9-1, 1-1.1, 1.1-1.2, 1.2-1.3, 1.3-1.4, 1.4-1.5, 1.5-1.6, 1.6-1.7, 1.7-1.8, 0.9-1.1, 1.1-1.3, 1.3-1.5, 1.5-1.7, 0.6-0.8, 0.8-1, 1-1.2, 1.2-1.4, 1.4-1.6, 1.6-1.8, 0.5-0.8, 0.8-1.1, 1.1-1.4, 1.4-1.8, 0.8-1.1, 1.1-1.4, 0.9-1.2, 1.2-1.5, 0.8-1.2, 0.9-1.3, 1-1.4, 1.1-1.5, 0.8-1.3, 0.9-1.4, 1-1.5, 0.8-1.4, 0.9-1.5, or 0.8-1.5.

In some embodiments, the composition (such as a pharmaceutical composition) is suitable for medical use if the nanoparticles in the pharmaceutical composition have a polydispersity index of less than about 0.3. In some embodiments, the nanoparticles in the pharmaceutical composition have a polydispersity index of less than about any of 0.3, 0.25, 0.2, 0.15, 0.1, or 0.05. In some embodiments, the composition (such as a pharmaceutical composition) is suitable for medical use if the nanoparticles in the pharmaceutical composition have a polydispersity index of about any of 0.05-0.07, 0.07-0.09, 0.09-0.11, 0.11-0.13, 0.13-0.15, 0.15-0.17, 0.17-0.2, 0.2-0.25, 0.25-0.3, 0.05-0.09, 0.09-0.13, 0.13-0.17, 0.17-0.25, 0.06-0.08, 0.08-0.12, 0.12-0.16, 0.16-0.18, 0.18-0.22, 0.22-0.28, 0.28-0.3, 0.06-0.12, 0.12-0.18, 0.18-0.3, 0.05-0.1, 0.1-0.15, 0.15-0.2, or 0.2-0.3.

In some embodiments, the composition (such as a pharmaceutical composition) is suitable for medical use if the composition (such as a pharmaceutical composition) has a size distribution curve similar to that of nab-paclitaxel sold under the trademark ABRAXANE®.

Determination of Surface Potential

The methods of the present application in some embodiments comprise determining the surface potential, such as zeta-potential, of the nanoparticles. Particle surface potential, such as zeta-potential, can play an important role in preventing the particles from aggregating.

Zeta-potential of the nanoparticles can be determined by techniques, such as, microelectrophoresis, electrophoretic light scattering, or dynamic electrophoretic mobility. In some embodiments, the zeta-potential of the nanoparticles can be determined by tunable resistive pulse sensing (TRPS). In some embodiments, the zeta-potential of the nanoparticles is determined upon reconstitution of the pharmaceutical composition. In some embodiments, the zeta-potential of the nanoparticles is determined upon storage of the pharmaceutical composition.

In some embodiments, the composition (such as a pharmaceutical composition) is suitable for medical use if the nanoparticles in the pharmaceutical composition have a zeta-potential of about –20 mV to about –35 mV. In some embodiments, the composition (such as a pharmaceutical composition) is suitable for medical use if the nanoparticles in the pharmaceutical composition have a zeta-potential of about –25 mV. In some embodiments, the composition (such as a pharmaceutical composition) is suitable for medical use if the nanoparticles in the pharmaceutical composition have a zeta-potential of about any of –40 mV, –35 mV, –30 mV, –29 mV, –28 mV, –27 mV, –26 mV, –25 mV, –24 mV, –23 mV, –22 mV, –21 mV, –20 mV, –15 mV, –10 mV. In some embodiments, the composition (such as a pharmaceutical composition) is suitable for medical use if the nanoparticles in the pharmaceutical composition have a zeta-potential of any of about –40 mV to about –35 mV, about –35 mV to about –30 mV, about –30 mV to about –25 mV, about –25 mV to about –20 mV, about –20 mV to about –15 mV, about –15 mV to about –10 mV, about –30 mV to about –28 mV, about –28 mV to about –26 mV, about –26 mV to about –24 mV, about –24 mV to about –22 mV, about –22 mV to about –20 mV, about –29 mV to about –27 mV, about –27 mV to about –25 mV, about –25 mV to about –23 mV, about –23 mV to about –21 mV, about –30 mV to about –26 mV, about –26 mV to about –22 mV, about –28 mV to about –24 mV, about –24 mV to about –20 mV, about –30 mV to about –25 mV, about –25 mV to about –20 mV, or about 30 mV to about –20 mV.

Determination of Paclitaxel Crystallinity

The methods of the present application in some embodiments comprise determining the crystalline state of paclitaxel in the composition (such as a pharmaceutical composition). In some embodiments, the method comprises determining the crystalline state of paclitaxel by X-ray diffraction. In some embodiments, the method comprises determining the crystallinity of paclitaxel by light microscopy, such as polarized light microscopy. In some embodiments, the method comprises determining the crystallinity of paclitaxel by both X-ray diffraction and a polarized light microscopy method. In some embodiments, the method comprises determining the crystallinity of paclitaxel by Raman spectroscopy. In some embodiments, the method comprises determining the crystallinity of paclitaxel by second harmonic generation microscopy. In some embodiments, the method comprises determining the crystallinity of paclitaxel by X-ray powder diffraction. In some embodiments, the method comprises determining the crystallinity of paclitaxel by differential scanning calorimetry. In some embodiments, the method comprises determining the crystallinity of paclitaxel by thermal gravimetric analysis. In some embodiments, the method comprises determining the crystallinity of paclitaxel using one or more technique selected from the group consisting of X-ray diffraction, X-ray powder diffraction, light microscopy, polarized light microscopy, Raman spectroscopy, second harmonic generation microscopy, differential scanning calorimetry, and thermal gravimetric analysis.

In some embodiments, the method comprises determining the crystallinity of paclitaxel by qualitatively determining one or more crystalline forms of paclitaxel. In some embodiments, the method comprises determining the crystallinity of paclitaxel by qualitatively determining two crystalline forms of paclitaxel. In some embodiments, the method comprises determining the crystallinity of paclitaxel by quantitatively determining one or more crystalline forms of paclitaxel. In some embodiments, the method comprises determining the crystallinity of paclitaxel by quantitatively determining two crystalline forms of paclitaxel. In some embodiments, the method comprises determining the crystallinity of paclitaxel by qualitatively and quantitatively determining one or more crystalline forms of paclitaxel. In some embodiments, the method comprises determining the crystallinity of paclitaxel by qualitatively and quantitatively determining two crystalline forms of paclitaxel.

In some embodiments, the determination of paclitaxel crystallinity is determined immediately after reconstitution. In some embodiments, the determination of paclitaxel crystallinity is determined after storage, for example after storage for at least about any of 6 hours, 12 hours, 18 hours, 24 hours, 36 hours, 40 hours, 44 hours, 48 hours, 52 hours, 56 hours, 60 hours, 64 hours, or 72 hours (for example at room temperature, under refrigerated condition, or at about 40° C.).

In some embodiments, nanoparticles are isolated by, for example, ultracentrifugation or gel permeation chromatography. In some embodiments, following ultracentrifugation, the supernatant is decanted and the pellet is washed with water. The isolated nanoparticles are then dried by, for example, lyophilization.

In some embodiments, subsequent analysis of the nanoparticles by X-ray diffraction can determine the physical state of paclitaxel in the nanoparticles. Non-crystalline paclitaxel in the nanoparticles will exhibit broad scattering halos, indicative of an amorphous material (e.g., non-crystalline). Crystalline paclitaxel in the nanoparticles will exhibit numerous well-defined scattering peaks.

In some embodiments, X-ray powder diffraction of the dried sample is used (alone or in addition to any other method described herein) to determine the physical state of the paclitaxel in the nanoparticles. Non-crystalline paclitaxel in the nanoparticles will exhibit broad scattering halos, indicative of an amorphous material (e.g., non-crystalline). Crystalline paclitaxel in the nanoparticles will exhibit numerous well-defined scattering peaks such as sharp scattering peaks.

In some embodiments, polarized light microscopy of a reconstituted suspension of nanoparticles is used (alone or in addition to any other method described herein) to determine the physical state of paclitaxel in the nanoparticles. A birefringence test can be performed with an optical microscope to determine if the paclitaxel in the nanoparticles is crystalline or non-crystalline. Absence of birefringence indicates that the paclitaxel remained amorphous.

In some embodiments, Raman spectroscopy can be used (alone or in addition to any other method described herein) to determine the physical state of the paclitaxel in the nanoparticles. Crystalline paclitaxel, such as crystalline paclitaxel hydrate, has peaks at 945-947 $cm^{-1}$, 1320 $cm^{-1}$, 1349 $cm^{-1}$, 1360 $cm^{-1}$, 1631-1647 $cm^{-1}$ and a shoulder on the peak at 1715 $cm^{-1}$.

In some embodiments, differential scanning calorimetry can be used (alone or in addition to any other method described herein) to determine the physical state of the paclitaxel in the nanoparticles. The temperature of thermal transition, e.g., glass transition, can be used to determine the presence of crystalline paclitaxel in the nanoparticles. For example, amorphous paclitaxel in the nanoparticles has a thermal transition of 150° C., the crystalline melt of the anhydrous crystal is 213° C., and the solid-state transition in the crystal hydrate is 166° C.

In some embodiments, the composition (such as a pharmaceutical composition) is suitable for medical use if the paclitaxel in the pharmaceutical composition is non-crystalline. In some embodiments, the composition (such as a pharmaceutical composition) is suitable for medical use if the paclitaxel in the reconstituted pharmaceutical composition is non-crystalline for at least about any of 6 hours, 12 hours, 18 hours, 24 hours, 36 hours, 40 hours, 44 hours, 48 hours, 52 hours, 56 hours, 60 hours, 64 hours, or 72 hours. In some embodiments, the composition (such as a pharmaceutical composition) is suitable for medical use if the paclitaxel in the lyophilized pharmaceutical composition is non-crystalline upon storage at about 40° C. for at least about any of 1 month, 2 months, 3 months, 4 months, 5 months, 6 months, 12 months, 24 months, or more months. In some embodiments, the composition (such as a pharmaceutical composition) is suitable for medical use if the paclitaxel in the pharmaceutical composition is non-crystalline upon storage of the composition (such as a pharmaceutical composition) at about 4° C. for at least about 24 hours. In some embodiments, the composition (such as a pharmaceutical composition) is suitable for medical use if the paclitaxel in the pharmaceutical composition is non-crystalline upon storage of the composition (such as a pharmaceutical composition) for at least about any of 6 hours, 12 hours, 18 hours, 24 hours, 36 hours, 40 hours, 44 hours, 48 hours, 52 hours, 56 hours, 60 hours, 64 hours, or 72 hours at, for example at room temperature, under refrigerated condition, or at about 40° C. In some embodiments, the composition (such as a pharmaceutical composition) is suitable for medical use if no crystalline form of paclitaxel can be detected in the pharmaceutical composition. In some embodiments, the composition (such as a pharmaceutical composition) is suitable for medical use if no crystalline form of paclitaxel can be detected at a limit of 2% of the total paclitaxel mass in the pharmaceutical composition. In some embodiments, the composition (such as a pharmaceutical composition) is suitable for medical use if less than about 0.01%, 0.008%, 0.005%, or 0.003% of the paclitaxel in the pharmaceutical composition is in a crystalline form. In some embodiments, the composition (such as a pharmaceutical composition) is suitable for medical use if no crystalline form of paclitaxel can be detected in the pharmaceutical composition in solution. In some embodiments, the composition (such as a pharmaceutical composition) is suitable for medical use if no crystalline form of paclitaxel can be detected at a limit of 2% of the total paclitaxel mass in the pharmaceutical composition in solution. In some embodiments, the composition (such as a pharmaceutical composition) is suitable for medical use if less than 0.01%, 0.008%, 0.005%, or 0.003% of the paclitaxel in the pharmaceutical composition in solution is in a crystalline form.

Determination of Distribution of the Total Albumin and the Total Paclitaxel Between Nanoparticles and the Non-Nanoparticle Portion The methods of the present application in some embodiments comprise determining the distribution of the total albumin and the total paclitaxel between nanoparticles and the non-nanoparticle portion of the composition (such as a pharmaceutical composition). In some embodiments, the method comprises determining the distribution of the total albumin between the nanoparticles and the non-nanoparticle portion of the composition (such as a pharmaceutical composition). In some embodiments, the method comprises determining the distribution of the total paclitaxel between the nanoparticles and the non-nanoparticle portion of the composition (such as a pharmaceutical composition). In some embodiments, the distribution of the total paclitaxel between the nanoparticles and the non-nanoparticle portion is determined upon reconstitution of the pharmaceutical composition. In some embodiments, the distribution of the total paclitaxel between the nanoparticles and the non-nanoparticle portion is determined upon storage of the pharmaceutical composition.

The distribution of the total albumin between the nanoparticles and the non-nanoparticle portion of the composition (such as a pharmaceutical composition) can be determined by measuring the amount of the albumin on the nanoparticles of the composition (such as a pharmaceutical composition) and/or the amount of the albumin in the non-nanoparticle portion of the composition (such as a pharmaceutical composition). Exemplary methods for measuring the amount albumin in the nanoparticles and the non-nanoparticle portion are discussed above. In some embodiments, the distribution of the total albumin is determined as a percentage of the total albumin in the composition (such as a pharmaceutical composition) in the non-nanoparticle portion of the composition (such as a pharmaceutical composition).

In some embodiments, the distribution of the total paclitaxel in the nanoparticles and/or the non-nanoparticle portion of the composition (such as a pharmaceutical composition) can be determined by measuring the amount of the paclitaxel in the nanoparticles of the composition (such as a pharmaceutical composition) and the amount of the paclitaxel in the non-nanoparticle portion of the composition (such as a pharmaceutical composition). Exemplary methods for measuring the amount of the paclitaxel in the nanoparticles and the non-nanoparticle portion are discussed above. In some embodiments, the distribution of the total paclitaxel is determined as a percentage of the total paclitaxel in the composition (such as a pharmaceutical composition) in the nanoparticle portion of the composition (such as a pharmaceutical composition).

The amount of the total paclitaxel in the composition (such as a pharmaceutical composition) associated with nanoparticles can be determined by reversed-phase high performance liquid chromatography (RP-HPLC). For example, the nanoparticles can first be isolated by ultracentrifugation or gel filtration chromatography. Subsequently, the amount of the paclitaxel in the nanoparticles can then be determined by assaying with quantitative RP-HPLC methods or mass spectrometric methods. The amount of the paclitaxel measured from the isolated nanoparticles can then be compared with the amount of the total paclitaxel in the composition (such as a pharmaceutical composition) to calculate the percentage of the total paclitaxel in the composition (such as a pharmaceutical composition) that is associated with the nanoparticles. In some embodiments, the amount of the total paclitaxel in the composition (such as a pharmaceutical composition) associated with the nanoparticles can be determined by measuring the amount of the paclitaxel not associated with the nanoparticles. For example, following ultracentrifugation to pellet the nanoparticles, the amount of paclitaxel in the resulting supernatant can be assayed by RP-HPLC methods to determine the amount of paclitaxel in solution (i.e., not associated with nanoparticles). The amount of the paclitaxel measured from the supernatant and the amount of the total paclitaxel in the composition (such as a pharmaceutical composition) can be used to calculate the percentage of the total paclitaxel in the composition (such as a pharmaceutical composition) that is associated with the nanoparticles.

The quantity of the albumin in the nanoparticles can be determined from isolated nanoparticles assayed for albumin content by size-exclusion chromatography or HPLC size-exclusion chromatography methods. The albumin in the non-nanoparticle portion can be determined by assaying the supernatant using a similar size-exclusion chromatography method.

In some embodiments, the composition (such as a pharmaceutical composition) is suitable for medical use if at least about 95% of the total paclitaxel in the composition (such as a pharmaceutical composition) are associated with the nanoparticles. In some embodiments, the composition (such as a pharmaceutical composition) is suitable for medical use if at least about any of 99.5%, 99%, 98.5%, 98%, 97.5%. 97%, 96.5%, 96%, 95%, 94%, 93%, 92%, 91%, 90%, 85%, or 80% of the total paclitaxel in the composition (such as a pharmaceutical composition) are associated with the nanoparticles. In some embodiments, the composition (such as a pharmaceutical composition) is suitable for medical use if about any of 80-85%, 85-90%, 90-95%, 95-97%, 97-97.5%, 97.5-98%, 98-98.5%, 98.5-99%, 99-99.5%, 97-98%, 98-99%, 97.5-98.5%, 98.5-99.5%, 97-98.5%, 97-99%, 97-99.5% of the total paclitaxel in the composition (such as a pharmaceutical composition) are associated with the nanoparticles.

In some embodiments, the composition (such as a pharmaceutical composition) is suitable for medical use if at least about 95% of the total albumins in the composition (such as a pharmaceutical composition) are in the non-nanoparticle portion of the composition (such as a pharmaceutical composition). In some embodiments, the composition (such as a pharmaceutical composition) is suitable for medical use if at least about any of 99.5%, 99%, 98.5%, 98%, 97.5%, 97%, 96.5%, 96%, 95.5%, 95%, 94%, 93%, 92%, 91%, 90%, 85%, or 80% of the total albumin in the composition (such as a pharmaceutical composition) are in the non-nanoparticle portion of the composition (such as a pharmaceutical composition). In some embodiments, the composition (such as a pharmaceutical composition) is suitable for medical use if about any of 80-85%, 85-90%, 90-95%, 95-96%, 96-96.5%, 96.5-97%, 97-97.5%, 97.5-98%, 98-98.5%, 98.5-99%, 99-99.5%, 96-97%, 97-98%, 98-99%, 96.5-97.5%, 97.5-98.5%, 98.5-99.5%, 96-98%, 98-99.5%, 96-98.5%, 97-99.5%, or 96-99.5% of the total albumin in the composition (such as a pharmaceutical composition) are in the non-nanoparticle portion of the composition (such as a pharmaceutical composition).

Determination of Albumin Oligomeric Status in the Composition

The methods of the present application in some embodiments comprise determining the oligomeric status (e.g., polymers, monomers, dimers, and/or oligomers) of the total albumin in the composition (such as a pharmaceutical composition).

The oligomeric forms of the total albumin in the composition (such as a pharmaceutical composition) (e.g., monomeric, dimeric, oligomeric, polymeric) can be determined by, for example, size-exclusion chromatography, such as gel permeation chromatography or HPLC size-exclusion chromatography methods, or polyacrylamide gel electrophoresis. For example, the oligomeric status can be determined by analysis of the total albumin in the composition (such as a pharmaceutical composition) by size-exclusion chromatography. The different classes of albumins can be determined based on differing retention time of albumin when subject to a chromatography (such as size-exclusion chromatography). The distribution of the components can be confirmed by permeation chromatography. In some embodiments, the oligomeric status of the total albumin in the pharmaceutical composition is determined upon reconstitution of the pharmaceutical composition. In some embodiments, the oligomeric status of the total albumin in the pharmaceutical composition is determined upon storage of the pharmaceutical composition.

The amount of monomeric albumin in the composition (such as a pharmaceutical composition) can be compared with the amount of the total albumin in the composition (such as a pharmaceutical composition) to calculate the percentage of the total albumin in the composition (such as a pharmaceutical composition) in the form of monomers. The amount of dimeric albumin in the composition (such as a pharmaceutical composition) can be compared with the amount of the total albumin in the composition (such as a pharmaceutical composition) to calculate the percentage of the total albumin in the composition (such as a pharmaceutical composition) in the form of dimers. The amount of oligomeric albumin in the composition (such as a pharmaceutical composition) can be compared with the amount of the total albumin in the composition (such as a pharmaceutical composition) to calculate the percentage of the total albumin in the composition (such as a pharmaceutical composition) in the form of oligomers. The amount of polymeric albumin in the composition (such as a pharmaceutical composition) can be compared with the amount of the total albumin in the composition (such as a pharmaceutical composition) to calculate the percentage of the total albumin in the composition (such as a pharmaceutical composition) in the form of polymers.

In some embodiments, the separation range for the size-exclusion chromatography is about 10,000 daltons to about 500,000 daltons. In some embodiments, the size-exclusion chromatography is run with a TSKgel G3000 SWXL column. In some embodiments, the size-exclusion chromatography is run with a column of TOSOH TSKgel G3000 SWXL, 7.8×300 mm, 5 μm or equivalent. In some embodiments, the size-exclusion chromatography is run with a flow rate of about 1 mL/min. In some embodiments, the size-exclusion chromatography is run at ambient temperature. In some embodiments, the size-exclusion chromatography is run with a column of TOSOH TSKgel G3000 SWXL, 7.8×300 mm, 5 μm or equivalent, at a flow rate of about 1 mL/min at room temperature.

In some embodiments, the composition (such as a pharmaceutical composition) is suitable for medical use if at least about 2% of the total albumin in the composition (such as a pharmaceutical composition) is in the form of polymers. In some embodiments, the composition (such as a pharmaceutical composition) is suitable for medical use if about 2% to about 5% of the total albumin in the composition (such as a pharmaceutical composition) is in the form of polymers. In some embodiments, the composition (such as a pharmaceutical composition) is suitable for medical use if at least about any of 1%, 2%, 2.5%, 3%, 3.5%, 4%, 4.5%, 5%, 6%, or 8% of the total albumin in the composition (such as a pharmaceutical composition) is in the form of polymers. In some embodiments, the composition (such as a pharmaceutical composition) is suitable for medical use if the percentage of polymeric albumin among the total albumin in the pharmaceutical composition is about any of 1-2%, 2-2.5%, 2.5-3%, 3-3.5%, 3.5-4%, 4-4.5%, 4.5-5%, 5-6%, 6-8%, 2-3%, 3-4%, 4-5%, 5-6%, 2.5-3.5%, 3.5-4.5%, 4.5-5.5%, 2-4%, 4-6%, 3-5%, 2.5-4.5%, 4.5-6%, 2-3.5%, or 2-5%.

The present application in some embodiments provides albumin-based paclitaxel compositions (such as pharmaceutical compositions) suitable for medical use in which about 75% to about 87% of the total albumin in the composition (such as a pharmaceutical composition) is in the form of monomers. In some embodiments, the composition (such as a pharmaceutical composition) is suitable for medical use if about any of 70%, 75%, 76%, 77%, 78%, 79%, 80%, 81%, 82%, 83%, 84%, 85%, 86%, 87%, or 90% of the total albumin in the composition (such as a pharmaceutical composition) is in the form of monomers. In some embodiments, the composition (such as a pharmaceutical composition) is suitable for medical use if about any of 70-75%, 75-76%, 76-77%, 77-78%, 78-79%, 79-80%, 80-81%, 81-82%, 82-83%, 83-84%, 84-85%, 85-86%, 86-87%, 87-90%, 75-77%, 77-79%, 79-81%, 81-83%, 83-85%, 85-87%, 76-78%, 78-80%, 80-82%, 82-84%, 84-86%, 75-78%, 78-81%, 81-84%, 84-87%, 75-80%, 80-87%, 78-84%, 84-87%, 75-85%, 77-87%, or 75-87% of the total albumin in the composition (such as a pharmaceutical composition) is in the form of monomers.

In some embodiments, the composition (such as a pharmaceutical composition) is suitable for medical use if about 1% to about 4% of the total albumin in the composition (such as a pharmaceutical composition) is in the form of oligomers. In some embodiments, the composition (such as a pharmaceutical composition) is suitable for medical use if about any of 0.5%, 1%, 1.2%, 1.4%, 1.6%, 1.8%, 2%, 2.2%, 2.4%, 2.6%, 2.8%, 3%, 3.2%, 3.4%, 3.7%, 4%, or 4.5% of the total albumin in the composition (such as a pharmaceutical composition) is in the form of oligomers. In some embodiments, the composition (such as a pharmaceutical composition) is suitable for medical use if about any of 0.5-1%, 1-1.2%, 1.2-1.4%, 1.4-1.6%, 1.6-1.8%, 1.8-2%, 2-2.2%, 2.2-2.4%, 2.4-2.6%, 2.6-2.8%, 2.8-3%, 3-3.2%, 3.2-3.4%, 3.4-3.7%, 3.7-4%, 4-4.5%, 1-1.4%, 1.4-1.8%, 1.8-2.2%, 2.2-2.6%, 2.6-3%, 3-3.4%, 3.4-4%, 1.2-1.6%, 1.6-2%, 2-2.4%, 2.4-2.8%, 2.8-3.2%, 3.2-3.7%, 1-1.8%, 1.8%-2.4%, 2.4-3%, 3-3.7%, 1.4-2%, 2-2.6%, 2.6-3.2%, 3.2-4%, 1-2%, 2-3%, 3-4%, 1.5-2.5%, 2.5-3.5%, 3.5-4%, 1-2.5%, 2.5-4%, or 1-4% of the total albumin in the composition (such as a pharmaceutical composition) is in the form of oligomers.

In some embodiments, the composition (such as a pharmaceutical composition) is suitable for medical use if about 6% to about 13% of the total albumin in the composition (such as a pharmaceutical composition) is in the form of dimers. In some embodiments, the composition (such as a pharmaceutical composition) is suitable for medical use if about any of 3%, 4%, 5%, 6%, 7%, 8%, 9%, 10%, 11%, 12%, 13%, 14%, or 15% of the total albumin in the composition (such as a pharmaceutical composition) is in the form of dimers. In some embodiments, the composition (such as a pharmaceutical composition) is suitable for medical use if about any of 3-4%, 4-5%, 5-6%, 6-7%, 7-8%, 8-9%, 9-10%, 10-11%, 11-12%, 12-13%, 13-14%, 14-15%, 5.5-6.5%, 6.5-7.5%, 7.5-8.5%, 8.5-9.5%, 9.5-10.5%, 10.5-11.5%, 6-8%, 8-10%, 10-12%, 7-9%, 9-11%, 6.5-8.5%, 8.5-10.5%, 10.5-13%, 6-9%, 9-13%, 6-10%, 8-13%, or 6-13% of the total albumin in the composition (such as a pharmaceutical composition) is in the form of dimers.

In some embodiments, the composition (such as a pharmaceutical composition) is suitable for medical use if about 2% to about 5% of the total albumin in the composition (such as a pharmaceutical composition) is in the form of polymers, and about 75% to about 85% of the total albumin in the composition (such as a pharmaceutical composition) in the form of monomers. In some embodiments, the composition (such as a pharmaceutical composition) is suitable for medical use if about any of 1%, 2%, 2.5%, 3%, 3.5%, 4%, 4.5%, 5%, 6%, or 8% of the total albumin in the composition (such as a pharmaceutical composition) is in the form of polymers, and about any of 70%, 75%, 76%, 77%, 78%, 79%, 80%, 81%, 82%, 83%, 84%, 85%, 86%, 87%, or 90% of the total albumin in the composition (such as a pharmaceutical composition) is in the form of monomers. In some embodiments, the composition (such as a pharmaceutical composition) is suitable for medical use if about any of 1-2%, 2-2.5%, 2.5-3%, 3-3.5%, 3.5-4%, 4-4.5%, 4.5-5%, 5-6%, 6-8%, 2-3%, 3-4%, 4-5%, 5-6%, 2.5-3.5%, 3.5-4.5%, 4.5-5.5%, 2-4%, 4-6%, 3-5%, 2.5-4.5%, 4.5-6%, 2-3.5%, or 2-5% of the total albumin in the composition (such as a pharmaceutical composition) is in the form of polymers, and about any of 70-75%, 75-76%, 76-77%, 77-78%, 78-79%, 79-80%, 80-81%, 81-82%, 82-83%, 83-84%, 84-85%, 85-86%, 86-87%, 87-90%, 75-77%, 77-79%, 79-81%, 81-83%, 83-85%, 85-87%, 76-78%, 78-80%, 80-82%, 82-84%, 84-86%, 75-78%, 78-81%, 81-84%, 84-87%, 75-80%, 80-87%, 78-84%, 84-87%, 75-85%, 77-87%, or 75-87% of the total albumin in the composition (such as a pharmaceutical composition) is in the form of monomers.

In some embodiments, the composition (such as a pharmaceutical composition) is suitable for medical use if the oligomeric status of the total albumin in the composition (such as a pharmaceutical composition) do not change significantly upon storage (such as at about 25° C. for about any of 3 months, 6 months, 9 months, 12 months, 18 months, 24 months, or 36 months). In some embodiments, the composition (such as a pharmaceutical composition) is suitable for medical use if the percentage of albumin polymers in the total albumin in the composition (such as a pharmaceutical composition) does not increase by any of 5%, 10%, 20%, 30%, 40%, 50%, or more than 50% upon storage (such as at about 25° C. for 18 months). In some embodiments, the composition (such as a pharmaceutical composition) is suitable for medical use if the percentage of albumin polymers in the total albumin in the composition (such as a pharmaceutical composition) does not decrease by any of 5%, 10%, 20%, 30%, 40%, 50%, or more than 50% upon storage (such as at about 25° C. for 18 months). In some embodiments, the composition (such as a pharmaceutical composition) is suitable for medical use if the percentage of albumin monomers in the total albumin in the composition (such as a pharmaceutical composition) does not increase by any of 5%, 10%, 15%, 20%, 30%, 40%, 50%, or more than 50% upon storage (such as at about 25° C. for 18 months). In some embodiments, the composition (such as a pharmaceutical composition) is suitable for medical use if the percentage of albumin monomers in the total albumin in the composition (such as a pharmaceutical composition) does not decrease by any of 5%, 10%, 15%, 20%, 30%, 40%, 50%, or more than 50% upon storage (such as at about 25° C. for 18 months).

Determination of Recovery of Paclitaxel Following Filtration

The methods of the present application in some embodiments comprise determining the recovery of paclitaxel following filtration. Loss of paclitaxel following 0.2 micron filtration is a measure of the faction of paclitaxel mass associated with particles large than 200 nm. This measure can be more sensitive to the large particle fraction than particle sizing techniques.

In some embodiments, the methods comprise determining the recovery of paclitaxel following filtration with a 0.2 micron filter immediately after reconstitution. In some embodiments, the method comprises determining the recovery of paclitaxel following filtration with a 0.2 micron filter upon storage (after storage for at least about any of 6 hours, 12 hours, 24 hours, 36 hours, 48 hours, 72 hours or more hours (for example under storage at room temperature, under refrigerated conditions, or under accelerated storage condition (for example at 40° C.)).

The recovery of the paclitaxel in the composition (such as a pharmaceutical composition) following 0.2 micron filtration can be determined by measuring the amount, such as weight, of paclitaxel in the composition (such as a pharmaceutical composition) that passes through the 0.2 micron filter. As discussed above, the amount of paclitaxel can be measured by RP-HPLC techniques. In some embodiments, to determine the recovery, the amount of paclitaxel that remains in the composition (such as a pharmaceutical composition) following 0.2 micron filtration is compared with the amount of the total paclitaxel in the composition (such as a pharmaceutical composition) prior to filtration. In some embodiments, the recovery is assessed following storage of the composition (such as a pharmaceutical composition) at elevated temperatures, for example, about 40° C. for about 24 hours.

In some embodiments, the composition (such as a pharmaceutical composition) is suitable for medical use if the composition (such as a pharmaceutical composition) has a paclitaxel recovery of at least about any of 80%, 85%, 90%, 95%, 98%, 99%, 99.5% or more following a 0.2 micron filtration (for example immediately after reconstitution). In some embodiments, the composition (such as a pharmaceutical composition) is suitable for medical use if the composition (such as a pharmaceutical composition) has a paclitaxel recovery of about any of 80-85%, 85-90%, 90-95%, 95-98%, 80-90%, 90-98%, 85-95%, 85-98%, 80-95%, 80-98%, 98%-99%, 99%-99.5%, or 99.5%-100% following a 0.2 micron filtration (for example immediately after reconstitution).

In some embodiments, the composition (such as a pharmaceutical composition) is suitable for medical use if the composition (such as a pharmaceutical composition) has a paclitaxel recovery of at least about any of 80%, 85%, 90%, 95%, 98%, 99%, 99.5%, or more following a 0.2 micron filtration after storage for at least about any of 6 hours, 12 hours, 24 hours, 36 hours, 48 hours, 72 hours or more hours (for example under storage at room temperature, under refrigerated conditions, or under accelerated storage condition (for example at about 40° C.)). In some embodiments, the composition (such as a pharmaceutical composition) is suitable for medical use if the composition (such as a pharmaceutical composition) has a paclitaxel recovery of about any of 80-85%, 85-90%, 90-95%, 95-98%, 80-90%, 90-98%, 85-95%, 85-98%, 80-95%, 80-98%, 98%-99%, 99%-99.5%, or 99.5%-100% following a 0.2 micron filtration after storage for at least about any of 6 hours, 12 hours, 24 hours, 36 hours, 48 hours, 72 hours or more hours (for example under storage at room temperature, under refrigerated conditions, or under accelerated storage condition (for example at about 40° C.)).

Determination of Particle Solubility

The methods of the present application in some embodiments comprise determining particle solubility of the albumin-based paclitaxel nanoparticle composition. In some embodiments, the solubility is determined immediately after reconstitution. In some embodiments, the solubility is determined upon storage, for example after storage for at least about any of 6 hours, 12 hours, 24 hours, 36 hours, 48 hours, 72 hours or more hours (for example under storage at room temperature, under refrigerated conditions, or under accelerated storage condition (for example at 40° C.)).

In some embodiments, the solubility of the pharmaceutical composition is determined by performing dynamic light scattering measurements for a series of concentrations of the composition (such as a pharmaceutical composition). The proportion of intact particles to free paclitaxel is a function of the solubility of the particles. Thus, as measured by this method, the solubility is determined as the concentration below which particles are no longer detectable by dynamic light scattering. In some embodiments, the solubility is determined in a 5% human serum albumin solution. In some embodiments, the solubility is determined in saline. In some embodiments, the solubility is determined in plasma.

In some embodiments, the composition (such as a pharmaceutical composition) is suitable for medical use if the composition (such as a pharmaceutical composition) has a solubility of about 50 to about 80 µg/ml when reconstituted in a 5% human albumin solution (for example immediately after reconstitution). In some embodiments, the composition (such as a pharmaceutical composition) has a solubility of about any of 40 µg/ml, 45 µg/ml, 50 µg/ml, 55 µg/ml, 60 µg/ml, 65 µg/ml, 70 µg/ml, 75 µg/ml, 80 µg/ml, 85 µg/ml, 90 µg/ml, or 100 µg/ml when diluted in a 5% human albumin solution (for example immediately after reconstitution). In some embodiments, the composition (such as a pharmaceutical composition) is suitable for medical use if the composition (such as a pharmaceutical composition) has a solubility of about any of 40-45 µg/ml, 45-50 µg/ml, 50-55 µg/ml, 55-60 µg/ml, 60-65 µg/ml, 65-70 µg/ml, 70-75 µg/ml, 75-80 µg/ml, 80-85 µg/ml, 85-90 µg/ml, 40-50 µg/ml, 50-60 µg/ml, 60-70 µg/ml, 70-80 µg/ml, 80-90 µg/ml, 40-50 µg/ml, 45-55 µg/ml, 55-65 µg/ml, 65-75 µg/ml, 40-55 µg/ml, 55-70 µg/ml, 65-80 µg/ml, 50-70 µg/ml, 60-80 µg/ml, 50-80 µg/ml, 65-90 µg/ml, 65-85 µg/ml, 65-95 µg/ml, 65-100 µg/ml, 70-85 µg/ml, 70-90 µg/ml, 75-95 µg/ml, or 75-100 µg/ml when reconstituted in a 5% human albumin solution (for example immediately after reconstitution).

In some embodiments, the composition (such as a pharmaceutical composition) is suitable for medical use if the composition (such as a pharmaceutical composition) has a solubility of about 50 to about 100 µg/ml when reconstituted in a 5% human albumin solution after storage for at least about any of 6 hours, 12 hours, 24 hours, 36 hours, 48 hours, 72 hours or more hours (for example under storage at room temperature, under refrigerated conditions, or under accelerated storage condition (for example at about 40° C.)). In some embodiments, the composition (such as a pharmaceutical composition) has a solubility of about any of 40 µg/ml, 45 µg/ml, 50 µg/ml, 55 µg/ml, 60 µg/ml, 65 µg/ml, 70 µg/ml, 75 µg/ml, 80 µg/ml, 85 µg/ml, 90 µg/ml, 100 µg/ml when reconstituted in a 5% human albumin solution after storage for at least about any of 6 hours, 12 hours, 24 hours, 36 hours, 48 hours, 72 hours or more hours (for example under storage at room temperature, under refrigerated conditions, or under accelerated storage condition (for example at about 40° C.)). In some embodiments, the composition (such as a pharmaceutical composition) is suitable for medical use if the composition (such as a pharmaceutical composition) has a solubility of about any of 40-45 µg/ml, 45-50 µg/ml, 50-55 µg/ml, 55-60 µg/ml, 60-65 µg/ml, 65-70 µg/ml, 70-75 µg/ml, 75-80 µg/ml, 80-85 µg/ml, 85-90 µg/ml, 40-50 µg/ml, 50-60 µg/ml, 60-70 µg/ml, 70-80 µg/ml, 80-90 µg/ml, 45-55 µg/ml, 55-65 µg/ml, 65-75 µg/ml, 40-55 µg/ml, 55-70 µg/ml, 65-80 µg/ml, 50-70 µg/ml, 60-80 µg/ml, 50-80 µg/ml, 65-90 µg/ml, 65-85 µg/ml, 65-95 µg/ml, 65-100 µg/ml, 70-85 µg/ml, 70-90 µg/ml, 75-95 µg/ml, or 75-100 µg/ml when reconstituted in a 5% human albumin solution after storage for at least about any of 6 hours, 12 hours, 24 hours, 36 hours, 48 hours, 72 hours or more hours (for example under storage at room temperature, under refrigerated conditions, or under accelerated storage condition (for example at about 40° C.)).

Determination of Albumin Binding Affinity

The methods of the present application in some embodiments comprise determining albumin binding affinity to paclitaxel. In some embodiments, the binding affinity is determined by an equilibrium dialysis test. In some embodiments, the binding affinity is determined by Fourier transform infrared spectroscopy (FTIR) and/or nuclear magnetic resonance (NMR) analysis. In some embodiments, the binding affinity is determined by an equilibrium dialysis test and FTIR. In some embodiments, the binding affinity is determined by an equilibrium dialysis test and NMR. In some embodiments, the binding affinity is determined by an equilibrium dialysis test, FTIR, and NMR. In some embodiments, the albumin binding affinity to paclitaxel is determined upon reconstitution of the pharmaceutical composition. In some embodiments, the albumin binding affinity to paclitaxel is determined upon storage of the pharmaceutical composition.

In some embodiments, the albumin binding affinity to paclitaxel is determined by an equilibrium dialysis test. For example, the composition (such as a pharmaceutical composition) is reconstituted with 0.9% saline solution to create solutions containing 1 mg/mL, 75 µg/mL and 50 µg/mL paclitaxel. Additionally, a 10% albumin solution is prepared by diluting Albumin (Human) USP with 0.9% sodium chloride solution. 200 µL samples, with replicates, are prepared at various paclitaxel concentrations using an equilibrium dialysis plate with 12 kD molecular weight cutoff insert. In some embodiments, replicate wells of buffer were also included. Subsequently, the plate is sealed and processed on an orbital shaker, heated to 37° C., for 2 hours at 800 rpm. Then, 50 µL is transferred from each sample and buffer well to an empty well on a 386-well plate for the paclitaxel assay. Matrix matching was performed by adding 50 µL of 0.9% sodium chloride solution to the wells containing samples on the 386-well plate, and by adding 50 µL of albumin solution to the wells containing buffer. 100 µL of an internal paclitaxel standard is added to all wells and the plate is then processed on a plate shaker. Contents of the plate are then transferred to a filter plate and vacuum filtered. Subsequently, the filtrate was assayed to determine paclitaxel concentration using reversed-phase liquid chromatography mass spectrometry. Briefly, 10 µL of the filtrate was injected from an autosampler onto a reversed-phase C18 column. Elution is performed using a gradient method at a flow rate of 0.5 mL/min. Mobile phase compositions are as follows: A, water with 0.1% formic acid and B, acetonitrile with 0.1% formic acid. Effluent is introduced into MS system through heated electrospray ionization.

In some embodiments, the albumin binding affinity to paclitaxel is determined by an equilibrium dialysis test after dialysis for at least 12 hours, 24 hours, 36 hours, 48 hours, 72 hours, or more hours.

In some embodiments, the composition (such as a pharmaceutical composition) is suitable for medical use if the binding affinity of the albumin in the composition (such as a pharmaceutical composition) for paclitaxel is about the same as the binding affinity of albumin in the nab-paclitaxel sold under the trademark ABRANXANE®. In some embodiments, the composition (such as a pharmaceutical composition) is suitable for medical use if the equilibrium binding (or dissociation) constant of the albumin in the composition (such as a pharmaceutical composition) for paclitaxel is less than about any of 130 µM, 110 µM, 90 µM, 70 µM, 60 µM, 55 µM, 50 µM or 45 µM. In some embodiments, the composition (such as a pharmaceutical composition) is suitable for medical use if the binding affinity of the albumin in the composition (such as a pharmaceutical composition) for paclitaxel is about 42 µM.

Determination of In Vitro Release Kinetics

The methods of the present application in some embodiments further comprise determining the in vitro release kinetics of the albumin-based paclitaxel nanoparticle composition. In some embodiments, the determination is carried out immediately after reconstitution. In some embodiments, the determination is carried out upon storage, for example upon storage for least about any of 6 hours, 12 hours, 24 hours, 36 hours, 48 hours, 72 hours, or more hours (for example under storage at room temperature, under refrigerated conditions, or under accelerated storage condition (for example at about 40° C.)). In some embodiments, the determination is carried out upon storage, for example upon storage for least about any of 1 month, 2 months, 3 months, 4 months, 5 months, 6 months, 7 months, 8 months, 9 months, or more months (for example under storage at room temperature, under refrigerated conditions, or under accelerated storage condition (for example at about 40° C.)). In some embodiments, the determination is carried out immediately after dilution of the composition. In some embodiments, the determination is carried out after, for example, at least 1 hour, 2 hours, 3 hours, 4 hours, 5 hours, 6 hours, or more hours after dilution of the composition.

In vitro release kinetics may be assayed using different techniques. In one example, an in vitro release kinetics assay measures the particle size and intensity of light scattered by the particles using, for example, dynamic light scattering over a period of time immediately following a reduction in particle concentration. In some embodiments, the release kinetics are determined by diluting the composition (such as a pharmaceutical composition) in a 0.9% saline solution. In some embodiments, the release kinetics is determined by diluting the composition (such as a pharmaceutical composition) in a 5% human serum albumin solution. In a second example, an in vitro release kinetics assay measures the absorbance of the composition over a period of time immediately following a reduction in particle concentration. In some embodiments, the absorbance of the composition is measured using a UV-Vis spectrophotometer. In some embodiments, the absorbance of the composition is measured using a UV-Vis spectrophotometer equipped with a 295 nm cut-off filter. In some embodiments, the absorbance of the composition is measured at, for example, 340 nm. In some embodiments, the composition is diluted to, for example, 100 µg/ml, as measured by the concentration of paclitaxel.

In some embodiments, the composition (such as a pharmaceutical composition) is suitable for medical use if the dissolution profile of the composition (such as a pharmaceutical composition), as measured by an in vitro release kinetics assay, matches the dissolution profile of nab-paclitaxel sold under the trademark ABRAXANE®. In some embodiments, the composition (such as a pharmaceutical composition) is suitable for medical use if the dissolution profile of the composition (such as a pharmaceutical composition) following an accelerated aging process matches the dissolution profile of the nab-paclitaxel sold under the trademark ABRAXANE®. In some embodiments, the composition (such as a pharmaceutical composition) is suitable for medical use if the dissolution profile of the composition (such as a pharmaceutical composition) following an accelerated aging process matches the dissolution profile of nab-paclitaxel sold under the trademark ABRAXANE® following the same accelerated aging process. In some embodiments, the composition (such as a pharmaceutical composition) is suitable for medical use if the composition (such as a pharmaceutical composition) has an in vitro release kinetic behavior that is similar to that of the nab-paclitaxel sold under the trademark ABRAXANE® under the same assay conditions upon storage for at least about any of 6 hours, 12 hours, 24 hours, 36 hours, 48 hours, 72 hours, or more hours (for example under storage at room temperature, under refrigerated conditions, or under accelerated storage condition (for example at about 40° C.)).

In some embodiments, the in vitro release is determined using the dynamic light scattering method. In some embodiments, the in vitro release kinetics assay measures the intensity of light scattered by the composition over a period of time immediately following a reduction in particle concentration. In some embodiments, the light scattering intensity of the composition is measured using a dynamic light scattering apparatus, where the concentration of paclitaxel released from the nanoparticles is calculated from the intensity of scattered light. In some embodiments, the intensity of light scattered is measured at a scattering angle of 173°. In some embodiments, the composition is diluted to 20 µg/ml, as measured by the concentration of paclitaxel, and in some embodiments the composition is diluted to 37.5 µg/ml. In some embodiments, the composition (such as a pharmaceutical composition) is suitable for medical use if the mean value of percent released paclitaxel from a nanoparticle composition (such as a pharmaceutical composition) at 20 µg/ml in 10 mM sodium chloride, as measured by the paclitaxel concentration, after 120 minutes is about 100%. In some embodiments, the composition (such as a pharmaceutical composition) is suitable for medical use if the mean value of percent released paclitaxel from a nanoparticle composition (such as a pharmaceutical composition) at 37.5 µg/ml in 10 mM sodium chloride, as measured by the paclitaxel concentration, after 120 minutes is about 85%.

Determination of Physical Stability

The methods of the present application in some embodiments comprise determining the physical stability of particles in the composition (such as a pharmaceutical composition). In some embodiments, the stability is determined immediately after reconstitution. In some embodiments, the stability is measured upon storage, for example upon storage for at least about any of 6 hours, 12 hours, 24 hours, 36 hours, 48 hours, 72 hours, or more hours (for example under storage at room temperature, under refrigerated conditions, or under accelerated storage condition (for example at about 40° C.)). In some embodiments, the stability is measured after storage, for example, for 8 hours at about 5° C. followed by storage for 8 hours at about 25° C., or after for storage for 24 hours at about 25° C.

Stability of nanoparticles in the pharmaceutical composition can be assayed by a number of techniques, including, but not limited to, visual inspection (such as visual appearance, visual color, visible particulate matter), microscopy imaging, and loss of potency. In some embodiments, the stability of the composition (such as a pharmaceutical composition) is determined based on sedimentation. Sedimentation can be assessed by visual inspection and/or microscopy (such as cross-polarization microscopy). Microscopy can be used to determine the size of aggregated sediment particles. In some embodiments, the stability of the composition (such as a pharmaceutical composition) is determined based on the crystalline state of the nanoparticles, for example by increased presence of nanoparticles with crystalline paclitaxel. In some embodiments, the stability of the composition (such as a pharmaceutical composition) is determined based on a loss of potency following a 0.2 micron filtration of the composition (such as a pharmaceutical composition). In some embodiments, the loss of potency is in vitro potency. In some embodiments, the loss of potency is in vivo potency.

In some embodiments, the composition (such as a pharmaceutical composition) is suitable for medical use if the nanoparticles are physically stable (for example immediately after reconstitution). In some embodiments, the composition (such as a pharmaceutical composition) is suitable for medical use if the nanoparticles are physically stable for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)). In some embodiments, the composition (such as a pharmaceutical composition) is suitable for medical use if the nanoparticles are physically stable after storage for 8 hours at about 5° C. followed by storage for 8 hours at about 25° C., or after for storage for 24 hours at about 25° C.

In some embodiments, the composition (such as a pharmaceutical composition) is suitable for medical use if the composition (such as a pharmaceutical composition) shows no visible particulate matter (for example immediately after reconstitution). In some embodiments, the composition (such as a pharmaceutical composition) is suitable for medical use if the composition (such as a pharmaceutical composition) shows no visible particulate matter for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)).

In some embodiments, the composition (such as a pharmaceutical composition) is suitable for medical use if the composition (such as a pharmaceutical composition) shows no visible particulate matter after storage for 8 hours at about 5° C. followed by storage for 8 hours at about 25° C., or after for storage for 24 hours at about 25° C.

In some embodiments, the composition (such as a pharmaceutical composition) is suitable for medical use if the composition (such as a pharmaceutical composition) shows no sedimentation (for example immediately after reconstitution). In some embodiments, the composition (such as a pharmaceutical composition) is suitable for medical use if the composition (such as a pharmaceutical composition) shows no sedimentation for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)). In some embodiments, the composition (such as a pharmaceutical composition) is suitable for medical use if the composition (such as a pharmaceutical composition) shows no sedimentation after storage for 8 hours at about 5° C. followed by storage for 8 hours at about 25° C., or after for storage for 24 hours at about 25° C.

In some embodiments, the composition (such as a pharmaceutical composition) is suitable for medical use if the paclitaxel in the composition (such as a pharmaceutical composition) shows no crystallinity (e.g., by polarized light microscopy) (for example immediately after reconstitution). In some embodiments, the composition (such as a pharmaceutical composition) is suitable for medical use if the paclitaxel in the composition (such as a pharmaceutical composition) shows no crystallinity (e.g., by polarized light microscopy) for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)). In some embodiments, the composition (such as a pharmaceutical composition) is suitable for medical use if the paclitaxel in the composition (such as a pharmaceutical composition) shows no crystallinity (e.g., by polarized light microscopy) after storage for 8 hours at about 5° C. followed by storage for 8 hours at about 25° C., or after for storage for 24 hours at about 25° C.

In some embodiments, the composition (such as a pharmaceutical composition) is suitable for medical use if the composition (such as a pharmaceutical composition) shows no loss of potency (e.g., by in vitro or in vivo testing) following a 0.2 micron filtration (for example immediately after reconstitution). In some embodiments, the composition (such as a pharmaceutical composition) is suitable for medical use if the composition (such as a pharmaceutical composition) shows no loss of potency (e.g., by in vitro or in vivo testing) for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)). In some embodiments, the composition (such as a pharmaceutical composition) is suitable for medical use if the composition (such as a pharmaceutical composition) shows no loss of potency (e.g., by in vitro or in vivo testing) after storage for 8 hours at about 5° C. followed by storage for 8 hours at about 25° C., or after for storage for 24 hours at about 25° C.

Determination of Osmolality

The methods described herein in some embodiments comprise determining the osmolality of a reconstituted composition (such as a pharmaceutical composition). In some embodiments, the osmolality is determined immediately after reconstitution. In some embodiments, the osmolality is measured upon storage, for example upon storage for at least about any of 1 month, 2 months, 3 months, 4 months, 5 months, or 6 months, at a temperature of, for example, about 25° C. or about 40° C. In some embodiments, the osmolality is measured after storage for 6 months at about 25° C. and a relative humidity of about 60% at an inverted position. In some embodiments, the osmolality is measured after storage for 6 months at about 40° C. and a relative humidity of about 75% at an inverted position.

Osmolality of a composition (such as a pharmaceutical composition) can be assayed by a number of methods, including, comprising use of a vapor pressure depression osmometer, a membrane osmometer, or a freezing point depression osmometer.

In some embodiments, the composition (such as a pharmaceutical composition) has an osmolality of between about 320 mOsm/kg to about 360 mOsm/kg. In some embodiments, the composition (such as a pharmaceutical composition) has an osmolality of between about 325 mOsm/kg to about 355 mOsm/kg. In some embodiments, the composition (such as a pharmaceutical composition) has an osmolality of between about 330 mOsm/kg to about 350 mOsm/kg. In some embodiments, the composition (such as a pharmaceutical composition) has an osmolality of about 330 mOsm/kg, 331 mOsm/kg, 332 mOsm/kg, 333 mOsm/kg, 334 mOsm/kg, 335 mOsm/kg, 336 mOsm/kg, 337 mOsm/kg, 338 mOsm/kg, 339 mOsm/kg, 340 mOsm/kg, 341 mOsm/kg, 342 mOsm/kg, 343 mOsm/kg, 344 mOsm/kg, 345 mOsm/kg, 346 mOsm/kg, 347 mOsm/kg or 348 mOsm/kg.

In some embodiments, the composition (such as a pharmaceutical composition) is suitable for medical use if the composition (such as a pharmaceutical composition) shows no significant change in osmolality after storage. In some embodiments, the composition (such as a pharmaceutical composition) is suitable for medical use if the composition (such as a pharmaceutical composition) shows no significant change in osmolality after storage at elevated temperatures, such as 40° C. In some embodiments, the composition (such as a pharmaceutical composition) is suitable for medical use if the composition (such as a pharmaceutical composition) shows no significant change in osmolality for at least about any of 1 month, 2 months, 3 months, 4 months, 5 months, 6 months or more months upon storage (for example under storage at room temperature, under refrigerated conditions, or under accelerated storage condition (for example at about 40° C.)).

Determination of Viscosity

The methods described herein in some embodiments comprise determining the viscosity (such as dynamic viscosity) of a reconstituted composition (such as a pharmaceutical composition). In some embodiments, the viscosity is determined immediately after reconstitution. In some embodiments, the viscosity is measured upon storage, for example upon storage for at least about any of 1 month, 2 months, 3 months, 4 months, 5 months, or 6 months, at a temperature of, for example, about 25° C. or about 40° C. In some embodiments, the viscosity is measured after storage for 6 months at about 25° C. and a relative humidity of about 60% at an inverted position. In some embodiments, the viscosity is measured after storage for 6 months at about 40° C. and a relative humidity of about 75% at an inverted position.

Viscosity (such as dynamic viscosity) of a composition (such as a pharmaceutical composition) can be assayed by a number of methods, including, comprising use of a viscometers and rheometers.

In some embodiments, the composition (such as a pharmaceutical composition) has a viscosity of between about 1.20 centipoise to about 1.50 centipoise. In some embodiments, the composition (such as a pharmaceutical composition) has a viscosity of between about 1.25 centipoise to about 1.45 centipoise. In some embodiments, the composition (such as a pharmaceutical composition) has a viscosity of about 1.25 centipoise, 1.26 centipoise, 1.27 centipoise, 1.28 centipoise, 1.29 centipoise, 1.30 centipoise, 1.31 centipoise, 1.32 centipoise, 1.33 centipoise, 1.34 centipoise, 1.35 centipoise, 1.36 centipoise, 1.37 centipoise, 1.38 centipoise, 1.39 centipoise, 1.40 centipoise, 1.41 centipoise, 1.42 centipoise, 1.43 centipoise, 1.44 centipoise, or 1.45 centipoise.

In some embodiments, the composition (such as a pharmaceutical composition) is suitable for medical use if the composition (such as a pharmaceutical composition) shows no significant change in viscosity after storage. In some embodiments, the composition (such as a pharmaceutical composition) is suitable for medical use if the composition (such as a pharmaceutical composition) shows no significant change in viscosity after storage at elevated temperatures, such as 40° C. In some embodiments, the composition (such as a pharmaceutical composition) is suitable for medical use if the composition (such as a pharmaceutical composition) shows no significant change in viscosity for at least about any of 1 month, 2 months, 3 months, 4 months, 5 months, 6 months or more months upon storage (for example under storage at room temperature, under refrigerated conditions, or under accelerated storage condition (for example at about 40° C.)).

Determination of Tumor Distribution of Paclitaxel In Vivo

The methods described herein in some embodiments comprise determining tumor distribution of paclitaxel upon administration of the albumin-based paclitaxel nanoparticle composition in vivo. Variations in albumin-based paclitaxel nanoparticle compositions, and their formulations, can affect in vivo distribution of paclitaxel within tumor tissue. In some embodiments, tumor penetration of a composition (such as a pharmaceutical composition) is determined. In some embodiments, tumor cell uptake of a composition (such as a pharmaceutical composition) is determined. In some embodiments, tumor penetration and tumor cell update of a composition (such as a pharmaceutical composition) are determined.

In some embodiments, the method comprises administering the composition (such as a pharmaceutical composition) to an animal having a tumor and measuring the level of paclitaxel in the tumor tissue. The level of paclitaxel can be measured, for example, by imaging, immunohistochemistry or quantitative mass spectrometry methods. In some embodiments, the paclitaxel in the composition (such as a pharmaceutical composition) that is administered into the animal is radio-labeled, thus allowing sensitive determination of tumor distribution of the paclitaxel.

In some embodiments, methods for determining the distribution of paclitaxel within tumor tissue comprise use of a tumor model. In some embodiments, the methods are performed on a naturally occurring tumor in an individual. In some embodiments, the methods are performed on a xenograft tumor in an individual. In some embodiments, the tumor model is a MIA PaCa-2 xenograft, A2058 xenograft, or H2122 xenograft. In some embodiments, the distribution of paclitaxel within tumor tissue is determined upon reconstitution of the pharmaceutical composition. In some embodiments, the distribution of paclitaxel within tumor tissue is determined upon storage of the pharmaceutical composition.

In some embodiments, the composition (such as a pharmaceutical composition) is administered to the animal by systemic administration. In some embodiments, the composition (such as a pharmaceutical composition) is delivered to the tumor by direct injection. In some embodiments, the composition (such as a pharmaceutical composition) is delivered to the tumor by direct microinjection, for example, via a CIVO™ arrayed microinjection device (Presage Biosciences, Seattle, Wash.). In some embodiments, the composition (such as a pharmaceutical composition) is delivered into flank tumor xenografts. For methods comprising the use of direct injection, in some embodiments, an imaging agent is injected with the composition (such as a pharmaceutical composition) to locate the injection site. In some embodiments, the composition (such as a pharmaceutical composition) is co-injected with an imaging agent, such as a fluorescent compound, for example, VivoTag680-S. In some embodiments, a labeled-paclitaxel is used in the composition (such as a pharmaceutical composition).

In some embodiments, methods for determining the distribution of paclitaxel within tumor tissue comprise measuring spatial distribution of paclitaxel within the tumor and/or tumor-associated tissue. In some embodiments, spatial distribution of paclitaxel is measured from sections (e.g., slices) of tumor tissue. In some embodiments, the sections of tumor tissue are perpendicular to the injection path. In some embodiments, spatial distribution of paclitaxel is measured by imaging, such as immunohistochemical imaging, fluorescent imaging, or any combinations thereof, of the tumor tissue. In some embodiments, spatial distribution of paclitaxel is measured by immunohistochemical staining of cells in mitotic arrest. In some embodiments, cells in mitotic arrest are detected by phospho-histone H3 (pHH3) staining, such as immunohistochemical staining of pHH3 using an anti-pHH3 antibody. Generally, a cell stained by a pHH3 detection agent is indicative of a cell in mitotic arrest. In some embodiments, tumor tissue is stained with a cell imaging agent, such as an agent for imaging a cell nucleus, for example, 4',6-diamindino-2-phenylindole (DAPI). In some embodiments, spatial distribution of paclitaxel comprises use of software, such as CIVOanalyzer™ (Presage Biosciences, Seattle, Wash.). In some embodiments, spatial distribution of paclitaxel is measured by performing mass spectrometry-based imaging (e.g., MALDI-MS-based imaging). In some embodiments, spatial distribution of paclitaxel is measured by detecting labeled-paclitaxel.

In some embodiments, spatial distribution of paclitaxel in a tumor tissue is performed on more than one tumor sections (e.g., slices) from a tumor. In some embodiments, spatial distribution of paclitaxel in tumor tissue is performed on more than one adjacent tumor sections from a tumor, thereby allowing for the recreation of a 3-dimensional tumor distribution of paclitaxel. In some embodiments, the more than one adjacent tumor sections are in spatial proximity to a microinjection site.

In some embodiments, distribution of paclitaxel within tumor tissue is determined by measuring spatial distribution of paclitaxel over a time-course following administration of the composition (such as a pharmaceutical composition). In some embodiments, distribution of paclitaxel within tumor tissue is measured at about 24 hours, about 48 hours, and/or about 72 hours following administration. In some embodiments, distribution of paclitaxel within tumor tissue is measured at least about 12 hours, at least about 24 hours, at least about 48 hours, and/or at least about 72 hours following administration. In some embodiments, distribution of paclitaxel within tumor tissue is determined by direct microinjection of a pharmaceutical composition into flank human tumor xenografts and analyzed, for example, at about 24 hours, about 48 hours, and/or about 72 hours following direct microinjection.

In some embodiments, the distribution of paclitaxel within tumor tissue is determined based on detection of paclitaxel in an area of the tumor tissue. In some embodiments, the distribution of paclitaxel within tumor tissue is determined based on detection of paclitaxel within a cell. Generally, methods comprising identification of cells in mitotic arrest comprise assessing the number of cells in mitotic arrest and/or the number of cells not in mitotic arrest. In some embodiments, the distribution of paclitaxel is determined based on the percentage of cells in mitotic arrest. In some embodiments, the percentage of mitotic arrest is reported as the fraction of pHH3 positive cells (i.e., number of pHH3 positive cells over the number of total cells in the sample area). In some embodiments, mitotic arrest is measured at one or more defined radial distances extending from the site of injection, for example, at about 100 µm, about 200 µm, about 300 µm, about 400 µm, about 500 µm, about 600 µm, about 700 µm, about 800 µm, about 900 µm, about 1000 µm, about 1100 µm, about 1200 µm, and/or about 1300 µm from the site of the injection. In some embodiments, mitotic arrest is measured at one or more defined radial distances extending from the site of injection, for example, at least about 100 µm, at least about 200 µm, at least about 300 µm, at least about 400 µm, at least about 500 µm, at least about 600 µm, at least about 700 µm, at least about 800 µm, at least about 900 µm, at least about 1000 µm, at least about 1100 µm, at least about 1200 µm, and/or at least about 1300 µm from the site of the injection.

In some embodiments, the distribution of paclitaxel within tumor tissue comprises determining an area of response (e.g., an area of tumor tissue wherein paclitaxel is detected).

In some embodiments, the distribution profile of paclitaxel within tumor tissue for a composition (such as a pharmaceutical composition) is compared to the distribution profile of paclitaxel for another composition. Generally, the amount (e.g., concentration) of paclitaxel in each composition is measured, for example by mass spectrometry, to allow for normalization of paclitaxel concentrations between compositions (such as pharmaceutical compositions).

In some embodiments, the composition (such as a pharmaceutical composition) is suitable for medical use if it allows an enhanced paclitaxel tumor distribution. A composition allows "enhanced paclitaxel tumor distribution" if, upon tumor injection, it allows a distribution of paclitaxel within the tumor tissue that is more extensive than that of a solvent-based paclitaxel formulation (such as the solvent-based paclitaxel formulation sold under the trademark TAXOL®). In some embodiments, the radial distance of paclitaxel spread (penetration and/or tumor cell uptake of paclitaxel) in a tumor tissue extending from the site of injection of the composition (such as a pharmaceutical composition) is greater than (for example more than about 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions.

In some embodiments, the composition (such as a pharmaceutical composition) is suitable for medical use if upon tumor injection it allows a distribution of paclitaxel within the tumor tissue that is similar to that of nab-paclitaxel sold under the trademark ABRAXANE® under the same assay conditions. For example, in some embodiments, the radial distance of paclitaxel penetration (or tumor cell uptake of paclitaxel) in a tumor tissue extending from the site of injection of the composition (such as a pharmaceutical composition) is greater than or equal to that of nab-paclitaxel sold under the trademark ABRAXANE® under the same assay conditions. In some embodiments, the radial distance of paclitaxel penetration (or tumor cell uptake of paclitaxel) in a tumor tissue extending from the site of injection of the composition (such as a pharmaceutical composition) is at least about 90% (including for example at least about any of 90%, 95%, 98% or 99%) of that of nab-paclitaxel sold under the trademark ABRAXANE® under the same assay conditions.

In some embodiments, the composition (such as a pharmaceutical composition) is suitable for medical use if it allows paclitaxel to spread radially for more than about 700 µm (such as more than about 1200 µm) within about 24 hours when the composition (such as a pharmaceutical composition) is injected into a tumor tissue (for example when injected at the paclitaxel amount of about 12 µg (or 4 mg/ml) into a pancreatic MIA PaCa-2 xenograft tumor). In some embodiments, the composition (such as a pharmaceutical composition) is suitable for medical use if it allows paclitaxel to spread radially for more than about 700 µm within about any one of 12 hours, 24 hours, 36 hours, 48 hours, or 72 hours when the composition (such as a pharmaceutical composition) is injected into a tumor tissue. In some embodiments, the composition (such as a pharmaceutical composition) is suitable for medical use if it allows paclitaxel to spread radially for more than about 1200 µm within about any one of 12 hours, 24 hours, 36 hours, 48 hours, or 72 hours when the composition (such as a pharmaceutical composition) is injected into a tumor tissue. In some embodiments, the composition (such as a pharmaceutical composition) is suitable for medical use if it allows paclitaxel to spread radially for more than about any of 200 µm, 300 µm, 400 µm, 500 µm, 600 µm, 700 µm, 750 µm, 800 µm, 850 µm, 900 µm, 950 µm, 1000 µm, 1100 µm, 1200 µm, 1300 µm, 1400 µm, 1500 µm or 2000 µm within about 12 hours when the composition (such as a pharmaceutical composition) is injected into a tumor tissue. In some embodiments, the composition (such as a pharmaceutical composition) is suitable for medical use if it allows paclitaxel to spread radially for more than about any of 200 µm, 300 µm, 400 µm, 500 µm, 600 µm, 700 µm, 750 µm, 800 µm, 850 µm, 900 µm, 950 µm, 1000 µm, 1100 µm, 1200 µm, 1300 µm, 1400 µm, 1500 µm or 2000 µm within about 24 hours when the composition (such as a pharmaceutical composition) is injected into a tumor tissue. In some embodiments, the composition (such as a pharmaceutical composition) is suitable for medical use if it allows paclitaxel to spread radially for more than about any of 200 μm, 300 μm, 400 μm, 500 μm, 600 μm, 700 μm, 750 μm, 800 μm, 850 μm, 900 μm, 950 μm, 1000 μm, 1100 μm, 1200 μm, 1300 μm, 1400 μm, 1500 μm or 2000 μm within about 36 hours when the composition (such as a pharmaceutical composition) is injected into a tumor tissue. In some embodiments, the composition (such as a pharmaceutical composition) is suitable for medical use if it allows paclitaxel to spread radially for more than about any of 200 μm, 300 μm, 400 μm, 500 μm, 600 μm, 700 μm, 750 μm, 800 μm, 850 μm, 900 μm, 950 μm, 1000 μm, 1100 μm, 1200 μm, 1300 μm, 1400 μm, 1500 μm or 2000 μm within about 48 hours when the composition (such as a pharmaceutical composition) is injected into a tumor tissue. In some embodiments, the composition (such as a pharmaceutical composition) is suitable for medical use if it allows paclitaxel to spread radially for more than about any of 200 μm, 300 μm, 400 μm, 500 μm, 600 μm, 700 μm, 750 μm, 800 μm, 850 μm, 900 μm, 950 μm, 1000 μm, 1100 μm, 1200 μm, 1300 μm, 1400 μm, 1500 μm or 2000 μm within about 72 hours when the composition (such as a pharmaceutical composition) is injected into a tumor tissue. In some embodiments, the composition (such as a pharmaceutical composition) meets two or more of the above-described functional attributes.

Determination of the radial distance of paclitaxel penetration (or tumor cell uptake) extending from the injection site in a tumor tissue requires setting a baseline percentage (or fraction) of mitotically arrested cells among all cells in the tumor tissue. The radial distance of paclitaxel penetration (or tumor cell uptake) extending from the injection site is the radial distance extending from the injection site, beyond which the percentage of mitotically arrested cells among all cells at the radial distance is no more than the baseline percentage. In some embodiments, the baseline percentage is set to be about 0.6%. In some embodiments, the baseline percentage is set to be about any of 0.1%, 0.3%, 0.5%, 0.6%, 0.7%, 0.8%, 0.9%, 1%, 1.5%, 2%, 2.5%, 3%, 3.5%, 4%, 5%, 10%, or more. The radial distance of paclitaxel penetration (or tumor cell uptake) extending from the injection site of the composition (such as a pharmaceutical composition), and that of nab-paclitaxel sold under the trademark ABRAXANE® are compared to determine whether tumor distribution of the composition (such as a pharmaceutical composition) in vivo is similar to that of nab-paclitaxel sold under the trademark ABRAXANE®. Similarly, the radial distance of paclitaxel penetration (or tumor cell uptake) extending from the injection site of the composition (such as a pharmaceutical composition), and that of a solvent-based paclitaxel (such as the solvent-based paclitaxel formulation sold under the trademark TAXOL®) are compared to determine whether tumor distribution of the composition (such as a pharmaceutical composition) in vivo is greater than that of a solvent-based paclitaxel (such as the solvent-based paclitaxel formulation sold under the trademark TAXOL®).

In some embodiments, tumor distribution of paclitaxel is determined based on the percentage of mitotically arrested cells (such as pHH3+ cells) at a defined radial distance extending from the site of injection. The percentages (or fractions) of mitotically arrested cells (such as pHH3+ cells) at defined radial distances extending from the site of injection of the compositions (such as pharmaceutical compositions) vary according to the volume and dose of the paclitaxel in the composition (such as a pharmaceutical composition) being injected, the time at which the tumor tissue is harvested, the cell type of the tumor tissue or xenograft (such as cell lines or source of tumor tissue), the animal model, or other assay conditions.

In some embodiments, the composition (such as a pharmaceutical composition) is suitable for medical use if, upon injection of the pharmaceutical composition, the percentage (or fraction) of mitotically arrested cells (such as pHH3+ cells) at a radial distance extending from the site of injection (such as at any of 200 μm, 400 μm, 500 μm, 600 μm, 700 μm, 800 μm, 900 μm, 1000 μm, 1100 μm, 1200 μm, 1500 μm, or 2000 μm) of the composition (such as a pharmaceutical composition) is similar to that of nab-paclitaxel sold under the trademark ABRAXANE® within about 24 hours of injection. In some embodiments, the composition (such as a pharmaceutical composition) is suitable for medical use if, upon injection of the pharmaceutical composition, the percentages (or fractions) of mitotically arrested cells (such as pHH3+ cells) at a plurality of radial distances extending from the site of injection (such as at any combination of 200 μm, 400 μm, 500 μm, 600 μm, 700 μm, 800 μm, 900 μm, 1000 μm, 1100 μm, 1200 μm, 1500 μm, or 2000 μm) of the composition (such as a pharmaceutical composition) is similar to those of nab-paclitaxel sold under the trademark ABRAXANE® within about 24 hours of injection. In some embodiments, the composition (such as a pharmaceutical composition) is suitable for medical use if, upon injection of the pharmaceutical composition, the percentage (or fraction) of mitotically arrested cells (such as pHH3+ cells) at a radial distance extending from the site of injection (such as at any of 200 μm, 400 μm, 500 μm, 600 μm, 700 μm, 800 μm, 900 μm, 1000 μm, 1100 μm, 1200 μm, 1500 μm, or 2000 μm) of the composition (such as a pharmaceutical composition) is greater than that of a solvent-based paclitaxel (such as the solvent-based paclitaxel formulation sold under the trademark TAXOL®) within about 24 hours of injection. In some embodiments, the composition (such as a pharmaceutical composition) is suitable for medical use if, upon injection of the pharmaceutical composition, the percentages (or fractions) of mitotically arrested cells (such as pHH3+ cells) at a plurality of radial distances extending from the site of injection (such as at any combination of 200 μm, 400 μm, 500 μm, 600 μm, 700 μm, 800 μm, 900 μm, 1000 μm, 1100 μm, 1200 μm, 1500 μm, or 2000 μm) of the composition (such as a pharmaceutical composition) are greater than those of a solvent-based paclitaxel (such as the solvent-based paclitaxel formulation sold under the trademark TAXOL®) within about 24 hours of injection.

In some embodiments, the composition (such as a pharmaceutical composition) is suitable for medical use if it allows more than about 5% (such as more than about any of 4%, 4.5%, 5%, 5.5%, 6%, 6.5%, or 7% or more) of all cells at a radial distance of about 400 μm extending from a site of injection to be mitotically arrested cells within about 24 hours of the injection when the composition (such as a pharmaceutical composition) is injected into a tumor tissue (for example when injected at the paclitaxel amount of about 12 μg (or 4 mg/ml) into a pancreatic MIA PaCa-2 xenograft tumor). In some embodiments, the composition (such as a pharmaceutical composition) is suitable for medical use if it allows more than about 3.5% (such as more than about any one of 2%, 2.5%, 3%, 3.5%, 4%, 4.5%, 5%, 5.5% or more) of all cells at a radial distance of about 400 μm extending from a site of injection to be mitotically arrested cells within about 24 hours of the injection when the composition (such as a pharmaceutical composition) is injected into a tumor tissue (for example when injected at the paclitaxel amount of about 12 μg (or 4 mg/ml) into a pancreatic MIA PaCa-2 xenograft tumor). In some embodiments, the composition (such as a pharmaceutical composition) is suitable for medical use if it allows more than about 2.5% (such as more than about any one of 1%, 1.5%, 2%, 2.5%, 3%, 3.5%, 4%, 4.5% or more) of all cells at a radial distance of about 400 μm extending from a site of injection to be mitotically arrested cells within about 24 hours of the injection when the composition (such as a pharmaceutical composition) is injected into a tumor tissue (for example when injected at the paclitaxel amount of about 12 (or 4 mg/ml) into a pancreatic MIA PaCa-2 xenograft tumor). In some embodiments, the composition (such as a pharmaceutical composition) is suitable for medical use if it allows more than about 1.5% (such as more than about any one of 0.5%, 0.8%, 1%, 1.5%, 2%, 2.5%, 3% or more) of all cells at a radial distance of about 400 μm extending from a site of injection to be mitotically arrested cells within about 24 hours of the injection when the composition (such as a pharmaceutical composition) is injected into a tumor tissue (for example when injected at the paclitaxel amount of about 12 μg (or 4 mg/ml) into a pancreatic MIA PaCa-2 xenograft tumor). In some embodiments, the composition (such as a pharmaceutical composition) is suitable for medical use if it allows more than about 1% (such as more than about any one of 0.4%, 0.6%, 0.8%, 1%, 1.5%, 2% or more) of all cells at a radial distance of about 400 μm extending from a site of injection to be mitotically arrested cells within about 24 hours of the injection when the composition (such as a pharmaceutical composition) is injected into a tumor tissue (for example when injected at the paclitaxel amount of about 12 μg (or 4 mg/ml) into a pancreatic MIA PaCa-2 xenograft tumor). In some embodiments, suitability of medical use is determined based on two or more of the above-described functional attributes.

Thus, the present application in one aspect also provides methods of determining distribution of paclitaxel in a tumor tissue. For example, in some embodiments there is provided a method of determining distribution of paclitaxel in a tumor tissue upon administration of an albumin-based paclitaxel nanoparticle composition to the tumor tissue, comprising 1) injecting the composition (such as a pharmaceutical composition) directly to the tumor tissue; and 2) assessing the spatial distribution of paclitaxel within the tumor tissue. In some embodiments, there is provided a method of determining distribution of paclitaxel in a tumor tissue upon administration of an albumin-based paclitaxel nanoparticle composition to the tumor tissue, comprising 1) microinjecting (for example by using a CIVO™ arrayed microinjection device (Presage Biosciences, Seattle, Wash.) the composition (such as a pharmaceutical composition) directly to the tumor tissue; and 2) assessing the spatial distribution of paclitaxel within the tumor tissue. In some further embodiments, the injection further comprises injection of an imaging agent. In some embodiments, the composition (such as a pharmaceutical composition) is co-injected with an imaging agent to determine the location of the injection site. In some embodiments, the composition (such as a pharmaceutical composition) is co-injected with VivoTag680-S to determine the location of the injection site.

In some embodiments, there is provided a method of determining distribution of paclitaxel in a tumor tissue upon administration of an albumin-based paclitaxel nanoparticle composition to the tumor tissue, comprising 1) microinjecting (for example by using a CIVO™ arrayed microinjection device (Presage Biosciences, Seattle, Wash.) the composition (such as a pharmaceutical composition) directly to the tumor tissue; and 2) staining the tissue with an agent that indicate the presence of paclitaxel; and 3) determining the radial distance of paclitaxel distribution extending from the site of injection. In some embodiments, the agent that indicates the presence of paclitaxel is an indicator of mitotic arrest such as an anti-pHH3 detection agent (for example an antibody).

In some embodiments, there is provided a method of determining distribution of paclitaxel in a tumor tissue upon administration of an albumin-based paclitaxel nanoparticle composition to the tumor tissue, comprising 1) microinjecting (for example by using a CIVO™ arrayed microinjection device (Presage Biosciences, Seattle, Wash.) the composition (such as a pharmaceutical composition) directly to the tumor tissue; and 2) staining the tissue with an agent that indicate mitotic arrest of a cell; and 3) determining the radial distance of paclitaxel distribution extending from the site of injection.

In some embodiments, there is provided a method of determining distribution of paclitaxel in a tumor tissue upon administration of an albumin-based paclitaxel nanoparticle composition to the tumor tissue, comprising 1) microinjecting (for example by using a CIVO™ arrayed microinjection device (Presage Biosciences, Seattle, Wash.) the composition (such as a pharmaceutical composition) directly to the tumor tissue; and 2) staining the tissue with an agent that indicate the mitotic arrest of the cell; and 3) determining the fraction of stained cells a given radial distance extending from the injection site. In some embodiments, the agent that indicates mitotic arrest of a cell is an anti-pHH3 detection agent (for example an antibody).

In some embodiments, there is provided a method of determining distribution of paclitaxel in a tumor tissue upon administration of an albumin-based paclitaxel nanoparticle composition to the tumor tissue, comprising 1) microinjecting (for example by using a CIVO™ arrayed microinjection device (Presage Biosciences, Seattle, Wash.) the composition (such as a pharmaceutical composition) directly to the tumor tissue; and 2) staining the tissue with an agent that indicate the mitotic arrest of the cell; and 3) determining the fraction of cells in mitotic arrest at a given radial distance extending from the injection site. In some embodiments, the agent that indicates mitotic arrest of a cell is an anti-pHH3 detection agent (for example an antibody).

Weight Ratio of the Total Albumin to the Total Paclitaxel in the Composition

The albumin-based paclitaxel nanoparticle compositions assessed by methods descried herein in some embodiments have a specific albumin to paclitaxel ratio. For example, in some embodiments, the weight ratio of the total albumin to the total paclitaxel in the composition (such as a pharmaceutical composition) is about 3:1 to about 7.9:1 or about 10:1 to about 17:1. In some embodiments, the weight ratio of the total albumin to the total paclitaxel in the composition (such as a pharmaceutical composition) is about 3:1 to about 7.9:1, which including for example about 4:1 to about 7:1, about 5:1 to about 7:1, about 6:1 to about 7:1, about 7:1 to about 7.5:1, and about 7.5:1 to about 7.9:1. In some embodiments, the weight ratio of the total albumin to the total paclitaxel in the composition (such as a pharmaceutical composition) is about 10:1 to about 17:1, which include for example, about 10:1 to about 15:1, about 10:1 to about 12:1, about 10:1 to about 11:1, or about 10:1 to about 10.5:1.

In some embodiments, the weight ratio of the total albumin to the total paclitaxel in the composition (such as a pharmaceutical composition) is about 8:1 to about 10:1. In some embodiments, the weight ratio of the total albumin to the total paclitaxel in the composition (such as a pharmaceutical composition) is about 9:1.

In some embodiments, the weight ratio of the total albumin to the total paclitaxel in the composition (such as a pharmaceutical composition) is about any of 1:1, 2:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, 10.5:1, 11:1, 12:1, 13:1, 14:1, 15:1, 16:1, 17:1, 18:1, 19:1, or 20:1. In some embodiments, the weight ratio of the total albumin to the total paclitaxel in the composition (such as a pharmaceutical composition) is any of about 1:1 to about 2:1, about 2:1 to about 3:1, about 3:1 to about 3.5:1, about 3.5:1 to about 4:1, about 4:1 to about 4.5:1, about 4.5:1 to about 5:1, about 5:1 to about 5.5:1, about 5.5:1 to about 6:1, about 6:1 to about 6.5:1, about 6.5:1 to about 7:1, about 7:1 to about 7.5:1, about 7.5:1 to about 8:1, about 8:1 to about 8.5:1, about 8.5:1 to about 9:1, about 9:1 to about 9.5:1, about 9.5:1 to about 10:1, about 10:1 to about 10.5:1, about 10.5:1 to about 11:1, about 11:1 to about 12:1, about 12:1 to about 13:1, about 13:1 to about 14:1, about 14:1 to about 15:1, about 15:1 to about 16:1, about 16:1 to about 17:1, about 17:1 to about 18:1, about 18:1 to about 19:1, about 19:1 to about 20:1, about 1:1 to about 3:1, about 3:1 to about 4:1, about 4:1 to about 5:1, about 5:1 to about 6:1, about 6:1 to about 7:1, about 7:1 to about 8:1, about 8:1 to about 9:1, about 9:1 to about 10:1, about 10:1 to about 11:1, about 11:1 to about 13:1, about 13:1 to about 15:1, about 15:1 to about 17:1, about 17:1 to about 19:1, about 3:1 to about 5:1, about 5:1 to about 7:1, about 7:1 to about 9:1, about 9:1 to about 11:1, about 2:1 to about 4:1, about 4:1 to about 6:1, about 6:1 to about 8:1, about 8:1 to about 12:1, about 12:1 to about 14:1, about 14:1 to about 16:1, about 16:1 to about 18:1, about 3:1 to about 7:1, about 7:1 to about 11:1, about 11:1 to about 15:1, about 15:1 to about 19:1, about 4:1 to about 8:1, about 8:1 to about 12:1, about 12:1 to about 16:1, or about 16:1 to about 20:1.

In some embodiments, to determine the weight ratio of the total albumin to the total paclitaxel in the composition (such as a pharmaceutical composition), the amount of the albumin on the nanoparticle, the amount of the albumin not on the nanoparticle (e.g., in the non-nanoparticle portion, or free in solution in the composition (such as a pharmaceutical composition)), the amount of the paclitaxel in the nanoparticle, and the amount of the paclitaxel not associated with the nanoparticle (e.g., in the non-nanoparticle portion, or free in solution in the composition (such as a pharmaceutical composition)) are needed. As discussed previously, the amount of the albumin on the nanoparticles can be determined by, for example, chromatography, such as size-exclusion chromatography, or spectrophotometric measurements following isolation of the nanoparticles in the pharmaceutical composition. In some embodiments, for example, following ultracentrifugation to pellet the nanoparticles, the amount of albumin in the resulting supernatant can be determined by similar methods discussed above for determining the amount of the albumin on the nanoparticles. As discussed previously, the amount of the paclitaxel in the nanoparticles can be determined by, for example, chromatography, such as RP-HPLC, spectrophotometric measurements, or mass spectrometric measurements. In some embodiments, for example, following ultracentrifugation to pellet the nanoparticles, the amount of paclitaxel in the resulting supernatant can be determined by similar methods discussed above for determining the amount of paclitaxel not on the nanoparticles.

In some embodiments, to determine the weight ratio of the total albumin to the total paclitaxel in the composition (such as a pharmaceutical composition), the amount of the total albumin in the composition (such as a pharmaceutical composition) and the amount of the total paclitaxel in the composition (such as a pharmaceutical composition) are needed. The amount of the total albumin, for example, can be measured using the methods discussed above using a sample that contains all albumins from the composition (such as a pharmaceutical composition). The amount of the total paclitaxel, for example, can be measured using the methods discussed above using a sample that contains all paclitaxel from the composition (such as a pharmaceutical composition).

The weight ratio of the total albumin to the total paclitaxel in the composition (such as a pharmaceutical composition) can be determined, for example, by calculating the ratio of the amount of the total albumin in the composition (such as a pharmaceutical composition) and the amount of the total paclitaxel in the composition (such as a pharmaceutical composition).

Other Components in the Albumin-Based Paclitaxel Nanoparticle Composition

The compositions (such as pharmaceutical compositions) described herein may also include an antimicrobial agent (e.g., an agent in addition to the paclitaxel) in an amount sufficient to significantly inhibit (e.g., delay, reduce, slow, and/or prevent) microbial growth in the composition (such as a pharmaceutical composition) for use in the methods of treatment, methods of administration, and dosage regimens described herein. Exemplary microbial agents and variations for the use of microbial agents are disclosed in US 2007/0117744A1 (such as those described in paragraphs [0036] to [0058] therein), the content of which is hereby incorporated by reference in its entirety. In some embodiments, the antimicrobial agent is a chelating agent, such as EDTA, edetate, citrate, pentetate, tromethamine, sorbate, ascorbate, derivatives thereof, or mixtures thereof. In some embodiments, the antimicrobial agent is a polydentate chelating agent. In some embodiments, the antimicrobial agent is a non-chelating agent, such as any of sulfites, benzoic acid, benzyl alcohol, chlorobutanol, and paraben. In some embodiments, an antimicrobial other than the taxane discussed above is not contained or used in the methods of treatment, methods of administration, and dosage regimens described herein.

In some embodiments, the compositions (such as pharmaceutical compositions) described herein include a sugar. Exemplary sugars and variations for the use of sugars are disclosed in US 2007/0117744A1 (such as those described in paragraphs [0084] to [0090] therein), the content of which is hereby incorporated by reference in its entirety. In some embodiments, the sugar serves as a reconstitution enhancer which causes a lyophilized composition to dissolve or suspend in water and/or aqueous solution more quickly than the lyophilized composition would dissolve without the sugar. In some embodiments, the composition (such as a pharmaceutical composition) is a liquid (e.g., aqueous) composition obtained by reconstituting or resuspending a dry composition. In some embodiments, the concentration of sugar in the composition (such as a pharmaceutical composition) is greater than about 50 mg/ml. In some embodiments, the sugar is in an amount that is effective to increase the stability of the paclitaxel in the composition (such as a pharmaceutical composition) as compared to a composition (such as a pharmaceutical composition) without the sugar. In some embodiments, the sugar is in an amount that is effective to improve filterability of the composition (such as a pharmaceutical composition) as compared to a composition (such as a pharmaceutical composition) without the sugar.

The sugar-containing compositions (such as pharmaceutical compositions) described herein may further comprise one or more antimicrobial agents, such as the antimicrobial agents described herein or in US 2007/0117744A1. In addition to one or more sugars, other reconstitution enhancers (such as those described in US 2005/0152979A1, which is hereby incorporated by reference in its entirety) can also be added to the compositions (such as pharmaceutical compositions).

The compositions (such as pharmaceutical compositions) described herein may be used in pharmaceutical compositions or formulations, by combining the pharmaceutical composition(s) described with a pharmaceutically acceptable carrier, excipients, stabilizing agents and/or other agents, which are known in the art, for use in the methods of treatment, methods of administration, and dosage regimens described herein.

To increase stability by increasing the negative zeta-potential of nanoparticles, certain negatively charged components may be added. Such negatively charged components include, but are not limited to bile salts, bile acids, glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid, and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine, stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), di stearoylphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

The pharmaceutical compositions described herein may include other agents, excipients, or stabilizers to improve properties of the composition (such as a pharmaceutical composition). Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. Examples of emulsifying agents include tocopherol esters such as tocopheryl polyethylene glycol succinate and the like, Pluronic®, emulsifiers based on polyoxy ethylene compounds, Span 80 and related compounds and other emulsifiers known in the art and approved for use in animals or human dosage forms. The compositions (such as pharmaceutical compositions) can be formulated so as to provide rapid, sustained or delayed release of the active ingredient after administration to the patient by employing procedures well known in the art.

In some embodiments, the composition (such as a pharmaceutical composition) is formulated to have a pH in the range of about 4.5 to about 9.0, including for example pH ranges of any one of about 5.0 to about 8.0, about 6.5 to about 7.5, or about 6.5 to about 7.0. In some embodiments, the pH of the composition (such as a pharmaceutical composition) is formulated to no less than about 6, including for example no less than about any one of 6.5, 7, or 8 (e.g., about 8). The composition (such as a pharmaceutical composition) can also be made to be isotonic with blood by the addition of a suitable tonicity modifier, such as glycerol.

In some embodiments, the composition (such as a pharmaceutical composition) is suitable for administration to a human. In some embodiments, the composition (such as a pharmaceutical composition) is suitable for administration to a human by parenteral administration. Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a freeze-dried (lyophilized) condition requiring only the addition of the sterile liquid excipient methods of treatment, methods of administration, and dosage regimens described herein (e.g., water) for injection, immediately prior to use. Extemporaneous injection solutions and suspensions can be prepared from sterile powders, granules, and tablets of the kind previously described. Injectable formulations are preferred. In some embodiments, the composition (such as a pharmaceutical composition) is contained in a single-use vial, such as a single-use sealed vial. In some embodiments, each single-use vial contains about 100 mg paclitaxel. In some embodiments, the single-use vial contains about 900 mg albumin. In some embodiments, the composition (such as a pharmaceutical composition) is contained in a multi-use vial. In some embodiments, the composition (such as a pharmaceutical composition) is contained in bulk in a container.

Also provided are unit dosage forms comprising the compositions (such as pharmaceutical compositions) and formulations described herein. These unit dosage forms can be stored in a suitable packaging in single or multiple unit dosages and may also be further sterilized and sealed. In some embodiments, the composition (such as a pharmaceutical composition) (such as a pharmaceutical composition)

also includes one or more other compounds (or pharmaceutically acceptable salts thereof) that are useful for treating cancer. In various variations, the amount of paclitaxel in the composition (such as a pharmaceutical composition) is included in any one of the following ranges: about 5 mg to about 50 mg, about 20 mg to about 50 mg, about 50 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 300 mg, about 300 mg to about 350 mg, about 350 mg to about 400 mg, about 400 mg to about 450 mg, or about 450 mg to about 500 mg. In some embodiments, the amount of paclitaxel in the composition (such as a pharmaceutical composition) (e.g., a dosage or unit dosage form) is in the range of about 5 mg to about 500 mg, such as about 30 mg to about 300 mg or about 50 mg to about 200 mg. In some embodiments, the carrier is suitable for parental administration (e.g., intravenous administration). In some embodiments, the paclitaxel is the only pharmaceutically active agent for the treatment of cancer that is contained in the composition (such as a pharmaceutical composition).

In some embodiments, there is provided a dosage form (e.g., a unit dosage form) for the treatment of cancer comprising any one of the compositions (such as pharmaceutical compositions) described herein. In some embodiments, there are provided articles of manufacture comprising the compositions (such as pharmaceutical compositions), formulations, and unit dosages described herein in suitable packaging for use in the methods of treatment, methods of administration, and dosage regimens described herein. Suitable packaging for compositions (such as pharmaceutical compositions) described herein are known in the art, and include, for example, vials (such as sealed vials), vessels (such as sealed vessels), ampules, bottles, jars, flexible packaging (e.g., sealed Mylar or plastic bags), and the like. These articles of manufacture may further be sterilized and/or sealed.

Methods of Validating and/or Releasing a Commercial Batch of Albumin-Based Paclitaxel Nanoparticle Compositions The methods described herein may be carried out when validating and/or releasing a commercial batch of an albumin-based paclitaxel nanoparticle composition. "Commercial batch" used herein refers to a batch size that is at least about 20 grams (by amount of paclitaxel). In some embodiments, the batch size is at least about 30 grams, 40 grams, 50 grams, 60 grams, 70 grams, 80 grams, 90 grams, 100 grams, 150 grams, 200 grams, 250 grams, 300 grams, 350 grams, 400 grams, 450 grams, 500 grams, 550 grams, 600 grams, 650 grams, 700 grams, 750 grams, 800 grams, 850 grams, 900 grams, 1000 grams, 1500 grams, 2000 grams, 2500 grams, 3000 grams, 3500 grams, 4000 grams, 4500 grams, 5000 grams, or 10,000 grams (by amount of paclitaxel). In some embodiments, the commercial batch comprises a plurality of vials comprising any of the compositions (such as pharmaceutical compositions) described herein. In some embodiments, the commercial batch comprises at least about any of 100 vials, 150 vials, 200 vials, 100 vials, 150 vials, 200 vials, 250 vials, 300 vials, 350 vials, 400 vials, 450 vials, 500 vials, 550 vials, 600 vials, 650 vials, 700 vials, 750 vials, 800 vials, 850 vials, 900 vials, 1000 vials, 1500 vials, 2000 vials, 2500 vials, 3000 vials, 3500 vials, 4000 vials, 4500 vials, 5000 vials, 10000 vials, 12000 vials, 14000 vials, 16000 vials, 18000 vials, 20000 vials, 22000 vials, 24000 vials, 26000 vials, 28000 vials, 30000 vials, 32000 vials, 34000 vials, 36000 vials, 38000 vials, 40000 vials, 42000 vials, 44000 vials, 46000 vials, 48000 vials, or 50000 vials. For example, each vial contains about any of 100 mg, 200 mg, 300 mg, 400 mg, 500 mg, 600 mg, 700 mg, 800 mg, 900 mg, or 1000 mg of the composition (such as a pharmaceutical composition). In some embodiments, the pharmaceutical composition in the commercial batch is a liquid suspension. In some embodiments, the pharmaceutical composition in the commercial batch is a lyophilized powder.

The present application thus in some embodiments provides a method of validating and/or releasing a commercial batch of a pharmaceutical composition for medical use in a human individual, wherein the pharmaceutical composition comprise nanoparticles comprising paclitaxel coated with albumin and a non-nanoparticle portion comprising albumin and paclitaxel, the method comprises a) obtaining a sample from the commercial batch; and 2) assessing suitability of the pharmaceutical composition for medical use according to any one of the methods described herein. In some embodiments, at least about 2 samples, 3 samples, 4 samples, 5 samples, 6 samples, 10 samples, 20 samples, 30 samples, 40 samples, 50 samples, 60 samples, 70 samples, 80 samples, 90 samples, 100 samples, or more samples are obtained from the commercial batch and subject to assessment. In some embodiments, the amount of the sample (i.e., the amount of the pharmaceutical composition taken from the commercial batch) is about any of 10-20 µg, 20-50 µg, 50-100 µg, 100-200 µg, 200-500 µg, 500-1000 µg, 1000 µg, 2000 µg, 3000 µg, 4000 µg, 5000 µg, or greater than 5000 µg. In some embodiments, the sample is the pharmaceutical composition in a vial. In some embodiments, the sample is obtained from the commercial batch prior to lyophilization of the composition (such as a pharmaceutical composition). In some embodiments, the sample is obtained from the commercial batch after lyophilization of the composition (such as a pharmaceutical composition). In some embodiments, the sample is obtained from the commercial batch after reconstitution.

Thus, for example, the present application in some embodiments provides a method of validating and/or releasing a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: a) obtaining a sample from the commercial batch; and b) determining the percentage of albumin polymers among the albumin on the nanoparticles in the sample, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) is indicative of suitability of the commercial batch for medical use and/or release.

In some embodiments, there is provided a method of validating and/or releasing a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: a) obtaining a sample from the commercial batch; and b) determining the percentage of albumin monomers among the albumin on the nanoparticles in the sample, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) is indicative of suitability of the commercial batch for medical use and/or release.

In some embodiments, there is provided a method of validating and/or releasing a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: a) obtaining a sample from the commercial batch; and b) determining the weight percentage of the albumin in the nanoparticles, wherein a weight percentage of the albumin in the nanoparticles being about 15% to about 30% (such as about 20% to about 25%, about 15% to about 24%, or about 15% to about 20%) is indicative of suitability of the commercial batch for medical use and/or release.

In some embodiments, there is provided a method of validating and/or releasing a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: a) obtaining a sample from the commercial batch; and b) determining the weight ratio of albumin to paclitaxel in the nanoparticles, wherein an albumin to paclitaxel ratio of about 1:2 to about 1:6 in the nanoparticles is indicative of suitability of the commercial batch for medical use and/or release.

In some embodiments, there is provided a method of validating and/or releasing a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: a) obtaining a sample from the commercial batch; and b) determining the morphology of the nanoparticles under cryo-TEM, wherein an irregular shape of the nanoparticles is indicative of suitability of the commercial batch for medical use and/or release.

In some embodiments, there is provided a method of validating and/or releasing a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: a) obtaining a sample from the commercial batch; and b) determining the thickness of the albumin coating of the nanoparticles under cryo-TEM, wherein a thickness of about 5-7 nm (such as about 6 nm) is indicative of suitability of the commercial batch for medical use and/or release.

In some embodiments, there is provided a method of validating and/or release a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: a) obtaining a sample from the commercial batch; and b) determining the distribution of paclitaxel in a tumor tissue upon injection of the pharmaceutical composition directly into the tumor tissue; wherein an enhanced paclitaxel tumor distribution is indicative of suitability of the commercial batch for medical use and/or release.

In some embodiments, there is provided a method of validating and/or releasing a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: a) obtaining a sample from the commercial batch; and b) determining the solubility, paclitaxel crystallinity, and a recovery following a 0.2 micron filtration of the pharmaceutical composition, wherein a solubility of about 50 µg/ml to about 100 µg/ml in a 5% human albumin solution, a non-crystalline state of the paclitaxel, and a recovery date of at least about 80% is indicative of suitability of the commercial batch for medical use and/or release.

In some embodiments, the method comprises various combinations of the determination steps described above. In some embodiments, the method comprises at least 2, 3, 4, 5, 6, 7, or 8 determination steps described above. In some embodiments, the method further comprises determining at least one (such as at least any of 2, 3, 4, 5, 6, 7, 8, 9, or 10) of the following characteristics of the sample: 1) binding affinity of albumin to paclitaxel in the composition (such as a pharmaceutical composition) (for example by equilibrium dialysis, FTIR, NMR, or a combination thereof); 2) surface-to-volume ratio; 3) percentage of albumin dimers and/or oligomers among the albumin on the nanoparticles; 4) distribution of the total paclitaxel and/or the total albumin between the nanoparticles and the non-nanoparticle portion; 5) oligomeric status of the total albumin in the composition (such as a pharmaceutical composition); 6) particle size of the nanoparticles, including average particle size, polydispersity, and/or size distribution; 7) surface potential; 8) in vitro release kinetics; 9) physical stability; and 10) paclitaxel tumor distribution in vivo. In some embodiments, at least one (such as at least any of 2, 3, 4, 5, 6, 7, 8, or 9) of the determination steps are carried out upon reconstitution of the sample. In some embodiments, at least one (such as at least any of 2, 3, 4, 5, 6, 7, 8, or 9) of the determination steps are carried out upon storage of the sample. In some embodiments, at least one of the determination steps are carried out after storage of the sample for at least about any of 6 hours, 12 hours, 24 hours, 36 hours, 48 hours, or 72 hours. In some embodiments, at least one of the determination steps are carried out after storage of the sample at room temperature, under refrigerated condition, or at about 40° C.

In some embodiments, there is provided a method of validating and/or releasing a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the solubility, paclitaxel crystallinity, and paclitaxel recovery following a 0.2 micron filtration of the pharmaceutical composition, determining the percentage of albumin monomers, dimers, oligomers, or polymers among the total albumin in the pharmaceutical composition, determining the percentage of the paclitaxel in the nanoparticles among the total paclitaxel in the pharmaceutical composition (for example by reversed-phase HPLC), determining the percentage of the albumin that is in the non-nanoparticle portion among the total albumin in the pharmaceutical composition (for example by size-exclusion chromatography), determining the particle size of the nanoparticles (for example by dynamic light scattering) and/or size distribution of the nanoparticles, and determining the stability of the pharmaceutical composition (including determining stability after storage). In some embodiments, the solubility, paclitaxel crystallinity, and/or paclitaxel recovery are determined after storage (for example after storage for at least about any of 6 hours, 12 hours, 18 hours, 24 hours, 36 hours, 48 hours, or 72 hours, such as at room temperature, under refrigerated condition, or at about 40° C.). In some embodiments, the paclitaxel crystallinity is determined by X-ray diffraction and/or polarized light microscopy. In some embodiments, the method further comprises determining binding affinity of albumin to paclitaxel in the composition (such as a pharmaceutical composition) (for example by equilibrium dialysis, FTIR, NMR, or a combination thereof). In some embodiments, the method further comprises determining tumor distribution of paclitaxel upon administration in vivo (for example by determining tumor distribution of paclitaxel upon injection of the pharmaceutical composition directly into the tumor tissue).

In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles having less than about 52% of the albumin on the nanoparticles in the form of monomers is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles having more than about 35% of albumin on the nanoparticles in the forms of polymers and oligomers is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles having less than about 54% of the albumin on the nanoparticles in the form of monomers, and more than about 11% of the albumin in the nanoparticles in the form of polymers is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles having less than about 55% of the albumin on the nanoparticles in the form of monomers, and more than about 18% of the albumin in the nanoparticles in the form of polymers is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles having a ratio of albumin on the nanoparticles in the form of polymers and oligomers divided by the albumin on the nanoparticles in the form of monomers of more than about 62% is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles having a weight percentage of the albumin in the nanoparticles of about 15% to about 30% (such as about 20% to about 25%, about 15% to about 24%, or about 15% to about 20%) is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles having a weight ratio of the albumin to the paclitaxel in the nanoparticles of about 1:2 to about 1:6 is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles in the pharmaceutical composition having an irregular shape is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein a thickness of the albumin coating on the nanoparticles of about 5-7 nm as measured by cryo-TEM is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein a weight ratio of the total albumin to the total paclitaxel in the pharmaceutical composition of about 3:1 to about 7.9:1 or about 10:1 to about 17:1 is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein a solubility of about 50 µg/ml to about 100 µg/ml (including for example any of about 50 µg/ml to about 60 µg/ml, about 60 µg/ml to about 70 µg/ml, about 70 µg/ml to about 75 µg/ml, about 75 µg/ml to about 80 µg/ml, about 80 µg/ml to about 90 µg/ml, or about 90 µg/ml to about 100 µg/ml) when diluted in a 5% human albumin solution is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein a paclitaxel recovery of at least about 80% (including for example at least about any of 85%, 90%, 95%, 98%, or 99%) following a 0.2 micron filtration is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein an average particle size of the nanoparticles in the pharmaceutical composition of less than about 200 nm (including for example about 100 to about 160 nm) is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles in the pharmaceutical composition having a zeta-potential of about −20 mV to about −35 mV is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles in the pharmaceutical composition having a polydispersity index of less than about 0.3 (including for example less than about 0.06 or about any of 0.05-0.09, 0.09-0.13, 0.13-0.15, 0.15-0.2, or 0.2-0.3) is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the nanoparticles in the pharmaceutical composition having a span of size distribution (($Dv_{90}$−$Dv_{10}$)/$Dv_{50}$) of about 0.8 to about 1.5 (including for example about any of 0.8-0.9, 0.9-1, 1-1.1, 1.1-1.2, 1.2-1.3, 1.3-1.4, or 1.4-1.5) is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the paclitaxel in the pharmaceutical composition being non-crystalline (including for example non-crystalline after storage for about 24 hours at about 4° C.) is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the pharmaceutical composition upon tumor injection allowing paclitaxel to spread radially for a distance of greater than (for example more than about any of 1.1×, 1.2×, 1.3×, 1.4×, 1.5×, 1.6×, 1.7×, 1.8×, 2×, 3×, 4×, 5×, 6×, 7×, 8×, or more of) that of a solvent-based paclitaxel formulation (such as the solvent-based paclitaxel formulation sold under the trademark TAXOL®) under the same assay conditions is indicative of suitability of the commercial batch for medical use and/or release. In some embodiments, there is provided a method of validating and/or releasing a commercial batch of a pharmaceutical composition for medical use in a human individual, wherein the commercial batch of a pharmaceutical composition comprising a pharmaceutical composition comprising: a) nanoparticles comprising paclitaxel coated with albumin, and b) a non-nanoparticle portion comprising albumin and paclitaxel, wherein the pharmaceutical composition upon tumor injection allowing paclitaxel to spread radially for more than about 700 µm (such as more than about any of 700 µm, 800 µm, 900 µm, 1000 µm, 1100 µm or 1200 µm) within about 24 hours after the pharmaceutical composition is injected into a tumor tissue (for example injected at the paclitaxel amount of about 12 µg (such as at about 4 mg/ml) into a pancreatic MIA PaCa-2 xenograft tumor) is indicative of suitability of the commercial batch for medical use and/or release.

Also provided are commercial batches released by following any one of the methods described herein.

Further provided are kits for use in any one of the methods of assessment and commercial batch release described herein.

Kits Comprising the Albumin-Based Paclitaxel Nanoparticle Compositions

Once determined to be suitable for medical use, the pharmaceutical compositions can be included in kits comprising the compositions (such as pharmaceutical compositions), formulations, unit dosages, and articles of manufacture for use in the methods of treatment, methods of administration, and dosage regimens described herein. Kits described herein include one or more containers comprising the paclitaxel pharmaceutical compositions (formulations or unit dosage forms and/or articles of manufacture), and in some embodiments, further comprise instructions for accessing and/or using in accordance with any of the methods of treatment described herein. In various embodiments, the amount of paclitaxel in the kit is included in any one of the following ranges: about 5 mg to about 20 mg, about 20 mg to about 50 mg, about 50 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 300 mg, about 300 mg to about 350 mg, about 350 mg to about 400 mg, about 400 mg to about 450 mg, or about 450 mg to about 500 mg. In some embodiments, the amount of paclitaxel in the kit is in the range of about 5 mg to about 500 mg, such as about 30 mg to about 300 mg or about 50 mg to about 200 mg. In some embodiments, the kit includes one or more other compounds (e.g., one or more compounds other than paclitaxel that are useful for cancer).

Instructions supplied in the kits described herein are typically written instructions on a label or package (e.g., a paper sheet included in the kit), but machine-readable instructions (e.g., instructions carried on a magnetic or optical storage disk) are also acceptable. The instructions relating to the use of the pharmaceutical compositions generally include information as to dosage, dosing schedule, and route of administration for the intended treatment. The kit may further comprise a description of selecting an individual suitable or treatment.

The present application also provides kits comprising compositions (such as pharmaceutical compositions) (or unit dosages forms and/or articles of manufacture) described herein and may further comprise instruction(s) on methods of assessing and/or using the composition (such as a pharmaceutical composition), such as uses further described herein. In some embodiments, the kit described herein comprises the packaging described above. In other variations, the kit described herein comprises the packaging described above and a second packaging comprising a buffer. It may further include other materials desirable from a commercial and user standpoint, including other buffers, diluents, filters, needles, syringes, and packages with instructions for performing any methods described herein.

For combination therapies described herein, the kit may contain instructions for administering the first and second therapies simultaneously and/or sequentially for the effective treatment of cancer. The first and second therapies can be present in separate containers or in a single container. It is understood that the kit may comprise one distinct composition or two or more compositions (such as pharmaceutical compositions) wherein one composition comprises a first therapy and one composition comprises a second therapy.

Kits may also be provided that contain sufficient dosages of the paclitaxel as disclosed herein to provide effective treatment for an individual for an extended period, such as any one of a week, 2 weeks, 3 weeks, 4 weeks, 6 weeks, 8 weeks, 3 months, 4 months, 5 months, 6 months, 7 months, 8 months, 9 months or more. Kits may also include multiple unit doses of the paclitaxel, compositions (such as pharmaceutical compositions), and formulations described herein and instructions for use and packaged in quantities sufficient for storage and use in pharmacies, for example, hospital pharmacies and compounding pharmacies. In some embodiments, the kit comprises a dry (e.g., lyophilized) composition that can be reconstituted, resuspended, or rehydrated to form generally a stable aqueous suspension of nanoparticles comprising paclitaxel and albumin.

The kits described herein are in suitable packaging. Suitable packaging include, but is not limited to, vials, bottles, jars, flexible packaging (e.g., sealed Mylar or plastic bags), and the like. Kits may optionally provide additional components such as buffers and interpretative information.

Methods of Making the Pharmaceutical Compositions

The present application also provides methods of making the paclitaxel pharmaceutical compositions described herein. Nanoparticles containing poorly water soluble pharmaceutical agents and carrier proteins (e.g., albumin) can be prepared under conditions of high shear forces (e.g., sonication, high pressure homogenization, or the like). These methods are disclosed in, for example, U.S. Pat. Nos. 5,916,596; 6,096,331; 6,749,868; 6,537,579; and PCT Application Pub. Nos. WO98/14174; WO99/00113; WO07/027941; and WO07/027819. The contents of these publications, particularly with respect to the method of making compositions (such as pharmaceutical compositions) containing carrier proteins, are hereby incorporated by reference in their entireties.

Generally, to make the paclitaxel pharmaceutical compositions described herein, paclitaxel is dissolved in an organic solvent. Suitable organic solvents include, for example, ketones, esters, ethers, chlorinated solvents, and other solvents known in the art. For example, the organic solvent can be methylene chloride/ethanol, chloroform/ethanol, or chloroform/t-butanol (for example with a ratio of about any one of 1:9, 1:8, 1:7, 1:6, 1:5, 1:4, 1:3, 1:2, 1:1, 2:1, 3:1, 4:1, 5:1, 6:1, 7:1, 8:1, or 9:1 or with a ratio of about any one of 3:7, 5:7, 4:6, 5:5, 6:5, 8:5, 9:5, 9.5:5, 5:3, 7:3, 6:4, or 9.5:0.5). Albumin (such as recombinant albumin, for example recombinant albumin sold under the trademark NOVOZYME™ or recombinant albumin sold under the trademark INTRIVIA™ recombinant albumin disclosed herein) is dissolved in water and combined with the paclitaxel solution. The mixture is subjected to high pressure homogenization (e.g., using a high pressure homogenizer sold by Avestin, APV Gaulin, or Stansted, or a high pressure homogenizer sold under the trademark MICROFLUIDIZER™ such as the high pressure homogenizer sold under the trademark MICROFLUIDIZER™ Processor M-110EH sold by Microfluidics, or the high pressure homogenizer sold under the trademark ULTRA-TURRAX®). The emulsion may be cycled through the high pressure homogenizer for between about 2 to about 100 cycles, such as about 5 to about 50 cycles or about 8 to about 20 cycles (e.g., about any one of 8, 10, 12, 14, 16, 18 or 20 cycles). The organic solvent can then be removed by evaporation utilizing suitable equipment known for this purpose, including, but not limited to, rotary evaporators, falling film evaporators, wiped film evaporators, spray driers, and the like that can be operated in batch mode or in continuous operation. The solvent may be removed at reduced pressure (such as at about any one of 25 mm Hg, 30 mm Hg, 40 mm Hg, 50 mm Hg, 100 mm Hg, 200 mm Hg, or 300 mm Hg). The amount of time used to remove the solvent under reduced pressure may be adjusted based on the volume of the formulation. For example, for a formulation produced on a 300 mL scale, the solvent can be removed at about 1 to about 300 mm Hg (e.g., about any one of 5-100 mm Hg, 10-50 mm Hg, 20-40 mm Hg, or 25 mm Hg) for about 5 minutes to about 60 minutes (e.g., about any one of 7 minutes, 8 minutes, 9 minutes, 10 minutes, 11 minutes, 12 minutes, 13 minutes, 14 minutes, 15 minutes, 16 minutes, 18 minutes, 20 minutes, 25 minutes, or 30 minutes). The dispersion obtained can be further lyophilized.

If desired, additional albumin solution may be added to the dispersion to adjust the albumin to paclitaxel ratio, or to adjust the concentration of paclitaxel in the dispersion. For example, albumin solution (e.g., 25% w/v) can be added to adjust the albumin to paclitaxel ratio to about any one of 18:1, 15:1 14:1, 13:1, 12:1, 11:1, 10:1, 9:1, 8:1, 7.5:1, 7:1, 6:1, 5:1, 4:1, or 3:1. In another example, albumin solution (e.g., 25% w/v) or another solution is added to adjust the concentration of paclitaxel in the dispersion to about any one of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml. The dispersion may be serially filtered through multiple filters, such as a combination of 1.2 µm and 0.8/0.2 µm filters; the combination of 1.2 µm, 0.8 µm, 0.45 µm, and 0.22 µm filters; or the combination of any other filters known in the art. The dispersion obtained can be further lyophilized. The pharmaceutical compositions may be made using a batch process or a continuous process (e.g., the production of a composition (such as a pharmaceutical composition) on a large scale).

If desired, a second therapy (e.g., one or more compounds useful for treating cancer), an antimicrobial agent, sugar, and/or stabilizing agent can also be included in the composition (such as a pharmaceutical composition). For example, this additional agent can either be admixed with paclitaxel and/or the albumin during the preparation of the paclitaxel pharmaceutical composition, or added after the paclitaxel pharmaceutical composition is prepared. In some embodiments, the agent is admixed with the paclitaxel pharmaceutical composition prior to lyophilization. In some embodiments, the agent is added to the lyophilized paclitaxel pharmaceutical composition. In some embodiments when the addition of the agent changes the pH of the composition (such as a pharmaceutical composition), the pH in the composition (such as a pharmaceutical composition) are generally (but not necessarily) adjusted to a desired pH. Exemplary pH values of the compositions (such as pharmaceutical compositions) include, for example, in the range of about 5 to about 8.5. In some embodiments, the pH of the composition (such as a pharmaceutical composition) is adjusted to no less than about 6, including for example no less than any one of about 6.5, 7, or 8 (e.g., about 8).

Methods of Treating Diseases

Once determined suitable for medical use by following the methods described herein, the pharmaceutical compositions may be used to treat diseases associated with cellular proliferation or hyperproliferation, such as cancers.

Examples of cancers that may be treated by the methods described herein include, but are not limited to, breast cancer (such as metastatic breast cancer), lung cancer (such as non-small cell lung cancer), pancreatic cancer (such as metastatic pancreatic cancer or locally advanced unresectable pancreatic cancer), multiple myeloma, renal cell carcinoma, prostate cancer, melanoma (such as metastatic melanoma), colon cancer, colorectal cancer, ovarian cancer, liver cancer, renal cancer, and gastric cancer. In some embodiments, the cancer is breast cancer after failure of combination chemotherapy for metastatic disease or relapse within 6 months of adjuvant chemotherapy. In some embodiments, the prior therapy includes an anthracycline treatment.

Cancers to be treated by compositions (such as pharmaceutical compositions) described herein include, but are not limited to, carcinoma, lymphoma, blastoma, sarcoma, and leukemia. Examples of cancers that can be treated by compositions (such as pharmaceutical compositions) described herein include, but are not limited to, squamous cell cancer, lung cancer (including small cell lung cancer, non-small cell lung cancer, adenocarcinoma of the lung, and squamous carcinoma of the lung, including squamous NSCLC), cancer of the peritoneum, hepatocellular cancer, gastric or stomach cancer (including gastrointestinal cancer), pancreatic cancer (such as advanced pancreatic cancer), glioblastoma, cervical cancer, ovarian cancer, liver cancer (such as hepatocellular carcinoma), bladder cancer, hepatoma, breast cancer, colon cancer, melanoma, endometrial or uterine carcinoma, salivary gland carcinoma, kidney or renal cancer, prostate cancer (such as advanced prostate cancer), vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome. In some embodiments, there is provided a method of treating metastatic cancer (that is, cancer that has metastasized from the primary tumor). In some embodiments, there is provided a method of reducing cell proliferation and/or cell migration. In some embodiments, there is provided a method of treating hyperplasia, for example hyperplasia in the vascular system that can result in restenosis or hyperplasia that can result in arterial or venous hypertension.

In some embodiments, there are provided methods of treating cancer at advanced stage(s). In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the cancer is lung cancer, including, for example, non-small cell lung cancer (NSCLC, such as advanced NSCLC), small cell lung cancer (SCLC, such as advanced SCLC), and advanced solid tumor malignancy in the lung. In some embodiments, the cancer is ovarian cancer, head and neck cancer, gastric malignancies, melanoma (including metastatic melanoma), colorectal cancer, pancreatic cancer, and solid tumors (such as advanced solid tumors). In some embodiments, the cancer is any of (and in some embodiments selected from the group consisting of) breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, gliomas, glioblastomas, neuroblastomas, and multiple myeloma. In some embodiments, the cancer is a solid tumor.

In some embodiments, the cancer to be treated is breast cancer, such as metastatic breast cancer. In some embodiments, the cancer to be treated is lung cancer, such as non-small cell lung cancer, including advanced stage non-small cell lung cancer. In some embodiments, the cancer to be treated is pancreatic cancer, such as early stage pancreatic cancer or advanced or metastatic pancreatic cancer. In some embodiments, the cancer to be treated is melanoma, such as stage III or IV melanoma.

In some embodiments, the individual being treated for a proliferative disease has been identified as having one or more of the conditions described herein. Identification of the conditions as described herein by a skilled physician is routine in the art (e.g., via blood tests, X-rays, CT scans, endoscopy, biopsy, angiography, CT-angiography, etc.) and may also be suspected by the individual or others, for example, due to tumor growth, hemorrhage, ulceration, pain, enlarged lymph nodes, cough, jaundice, swelling, weight loss, cachexia, sweating, anemia, paraneoplastic phenomena, thrombosis, etc. In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

In some embodiments, the methods and/or compositions (such as pharmaceutical compositions) used herein reduce the severity of one or more symptoms associated with proliferative disease (e.g., cancer) by at least about any one of 10%, 20%, 30%, 40%, 50%, 60%, 70%, 80%, 90%, 95%, or 100% compared to the corresponding symptom in the same individual prior to treatment or compared to the corresponding symptom in other individuals not receiving the methods and/or compositions (such as pharmaceutical compositions).

In some embodiments, the composition (such as a pharmaceutical composition) (such as a pharmaceutical composition) described herein is used in combination with another administration modality or treatment. For example, in some embodiments, the composition (such as a pharmaceutical composition) is used in combination with gemcitabine (for example for treating pancreatic cancer). In some embodiments, the composition (such as a pharmaceutical composition) is used in combination with carboplatin (for example for treating lung cancer).

Dosing and Method of Administration

The amount of the pharmaceutical composition administered to an individual (such as a human) may vary with the particular composition, the method of administration, and the particular type of recurrent cancer being treated. The amount should be sufficient to produce a desirable beneficial effect. For example, in some embodiments, the amount of the composition (such as a pharmaceutical composition) is effective to result in an objective response (such as a partial response or a complete response). In some embodiments, the amount of pharmaceutical composition is sufficient to result in a complete response in the individual. In some embodiments, the amount of the composition (such as a pharmaceutical composition) is sufficient to result in a partial response in the individual. In some embodiments, the amount of the composition (such as a pharmaceutical composition) administered alone is sufficient to produce an overall response rate of more than about any one of 40%, 50%, 60%, or 64% among a population of individuals treated with the composition (such as a pharmaceutical composition). Responses of an individual to the treatment of the methods described herein can be determined, for example, based on RECIST or CA-125 level. For example, when CA-125 is used, a complete response can be defined as a return to a normal range value of at least 28 days from the pretreatment value. A particle response can be defined as a sustained over 50% reduction from the pretreatment value.

In some embodiments, the amount of pharmaceutical composition is sufficient to prolong progress-free survival of the individual (for example as measured by RECIST or CA-125 changes). In some embodiments, the amount of the pharmaceutical composition is sufficient to prolong overall survival of the individual. In some embodiments, the amount of the composition (such as a pharmaceutical composition) is sufficient to produce clinical benefit of more than about any one of 50%, 60%, 70%, or 77% among a population of individuals treated with the composition (such as a pharmaceutical composition).

In some embodiments, the amount of paclitaxel in the composition (such as a pharmaceutical composition) is below the level that induces a toxicological effect (i.e., an effect above a clinically acceptable level of toxicity) or is at a level where a potential side effect can be controlled or tolerated when the composition (such as a pharmaceutical composition) is administered to the individual. In some embodiments, the amount of the composition (such as a pharmaceutical composition) is close to a maximum tolerated dose (MTD) of the composition (such as a pharmaceutical composition) following the same dosing regimen. In some embodiments, the amount of the composition (such as a pharmaceutical composition) is more than about any one of 80%, 90%, 95%, or 98% of the MTD.

In some embodiments, the amount of paclitaxel and/or composition is an amount sufficient to decrease the size of a tumor, decrease the number of cancer cells, or decrease the growth rate of a tumor by at least about any one of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of paclitaxel in the composition (such as a pharmaceutical composition) is included in any one of the following ranges: about 0.5 mg to about 5 mg, about 5 mg to about 10 mg, about 10 mg to about 15 mg, about 15 mg to about 20 mg, about 20 mg to about 25 mg, about 20 mg to about 50 mg, about 25 mg to about 50 mg, about 50 mg to about 75 mg, about 50 mg to about 100 mg, about 75 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 300 mg, about 300 mg to about 350 mg, about 350 mg to about 400 mg, about 400 mg to about 450 mg, or about 450 mg to about 500 mg. In some embodiments, the amount of paclitaxel in the composition (such as a pharmaceutical composition) (e.g., a unit dosage form) is in the range of about 5 mg to about 500 mg, such as about 30 mg to about 300 mg or about 50 mg to about 200 mg. In some embodiments, the concentration of the paclitaxel in the composition (such as a pharmaceutical composition) is dilute (about 0.1 mg/ml) or concentrated (about 100 mg/ml), including for example any one of about 0.1 mg/ml to about 50 mg/ml, about 0.1 mg/ml to about 20 mg/ml, about 1 mg/ml to about 10 mg/ml, about 2 mg/ml to about 8 mg/ml, about 4 mg/ml to about 6 mg/ml, or about 5 mg/ml. In some embodiments, the concentration of the paclitaxel is at least about any one of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary doses of paclitaxel in the pharmaceutical composition include, but are not limited to, about any one of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m² of paclitaxel. In various embodiments, the composition (such as a pharmaceutical composition) includes less than about any one of 350 mg/m², 300 mg/m², 250 mg/m², 200 mg/m², 150 mg/m², 120 mg/m², 100 mg/m², 90 mg/m², 50 mg/m², or 30 mg/m² of paclitaxel. In some embodiments, the amount of paclitaxel per administration is less than about any one of 25 mg/m², 22 mg/m², 20 mg/m², 18 mg/m², 15 mg/m², 14 mg/m², 13 mg/m², 12 mg/m², 11 mg/m², 10 mg/m², 9 mg/m², 8 mg/m², 7 mg/m², 6 mg/m², 5 mg/m², 4 mg/m², 3 mg/m², 2 mg/m², or 1 mg/m². In some embodiments, the dose of paclitaxel in the composition (such as a pharmaceutical composition) is included in any one of the following ranges: about 1 mg/m² to about 5 mg/m², about 5 mg/m² to about 10 mg/m², about 10 mg/m² to about 25 mg/m², about 25 mg/m² to about 50 mg/m², about 50 mg/m² to about 75 mg/m², about 75 mg/m² to about 100 mg/m², about 100 mg/m² to about 125 mg/m², about 125 mg/m² to about 150 mg/m², about 150 mg/m² to about 175 mg/m², about 175 mg/m² to about 200 mg/m², about 200 mg/m² to about 225 mg/m², about 225 mg/m² to about 250 mg/m², about 250 mg/m² to about 300 mg/m², about 300 mg/m² to about 350 mg/m², or about 350 mg/m² to about 400 mg/m². Preferably, the dose of paclitaxel in the composition (such as a pharmaceutical composition) is about 5 mg/m² to about 300 mg/m², such as about 100 mg/m² to about 150 mg/m², about 120 mg/m², about 130 mg/m², or about 140 mg/m².

In some embodiments of any of the above aspects, the dose of paclitaxel in the composition (such as a pharmaceutical composition) includes at least about any one of 1 mg/kg, 2.5 mg/kg, 3.5 mg/kg, 5 mg/kg, 6.5 mg/kg, 7.5 mg/kg, 10 mg/kg, 15 mg/kg, or 20 mg/kg. In various variations, the dose of paclitaxel in the composition (such as a pharmaceutical composition) includes less than about any one of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, 2 mg/kg, 1.5 mg/kg, or 1 mg/kg of paclitaxel. In some embodiments, the dose of paclitaxel in the composition (such as a pharmaceutical composition) includes less than about any one of 500 µg/kg, 350 µg/kg, 300 µg/kg, 250 µg/kg, 200 µg/kg, 150 µg/kg, 100 µg/kg, 50 µg/kg, 25 µg/kg, 20 µg/kg, 10 µg/kg, 7.5 µg/kg, 6.5 µg/kg, 5 µg/kg, 3.5 µg/kg, 2.5 µg/kg, 2 µg/kg, 1.5 µg/kg, 1 µg/kg, or 0.5 µg/kg of paclitaxel.

Exemplary dosing frequencies include, but are not limited to, any one of weekly without break; weekly, three out of four weeks; once every three weeks; once every two weeks; weekly, two out of three weeks. In some embodiments, the composition (such as a pharmaceutical composition) is administered about once every 2 weeks, once every 3 weeks, once every 4 weeks, once every 6 weeks, or once every 8 weeks. In some embodiments, the composition (such as a pharmaceutical composition) is administered at least about any one of 1×, 2×, 3×, 4×, 5×, 6×, or 7× (i.e., daily) a week. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the composition (such as a pharmaceutical composition) can be over an extended period of time, such as from about a month up to about seven years. In some embodiments, the composition (such as a pharmaceutical composition) is administered over a period of at least about any one of 2 months, 3 months, 4 months, 5 months, 6 months, 7 months, 8 months, 9 months, 10 months, 11 months, 12 months, 18 months, 24 months, 30 months, 36 months, 48 months, 60 months, 72 months, or 84 months. In some embodiments, the composition (such as a pharmaceutical composition) is administered over a period of at least one month, wherein the interval between each administration is no more than about a week, and wherein the dose of paclitaxel at each administration is about 0.25 mg/m² to about 75 mg/m², such as about 0.25 mg/m² to about 25 mg/m² or about 25 mg/m² to about 50 mg/m².

In some embodiments, the dosage of paclitaxel in a pharmaceutical composition can be in the range of 5 mg/m² to 400 mg/m² when given on a 3 week schedule, or 5 mg/m² to 250 mg/m² when given on a weekly schedule. For example, the amount of a paclitaxel is about 60 mg/m² to about 300 mg/m² (e.g., about 260 mg/m²).

Other exemplary dosing schedules for the administration of the pharmaceutical composition include, but are not limited to, any one of 100 mg/m², weekly, without break; 75 mg/m² weekly, 3 out of four weeks; 100 mg/m², weekly, 3 out of 4 weeks; 125 mg/m², weekly, 3 out of 4 weeks; 125 mg/m², weekly, 2 out of 3 weeks; 130 mg/m², weekly, without break; 175 mg/m², once every 2 weeks; 260 mg/m², once every 2 weeks; 260 mg/m², once every 3 weeks; 180-300 mg/m², every three weeks; 60-175 mg/m², weekly, without break; 20-150 mg/m² twice a week; and 150-250 mg/m² twice a week. The dosing frequency of the composition (such as a pharmaceutical composition) may be adjusted over the course of the treatment based on the judgment of the administering physician.

In some embodiments, the composition (such as a pharmaceutical composition) is administered (e.g., intravenously) at 260 mg/m² every three weeks. In some embodiments, the composition (such as a pharmaceutical composition) is administered (e.g., intravenously) at 220 mg/m², every three weeks. In some embodiments, the composition (such as a pharmaceutical composition) is administered (e.g., intravenously) at 180 mg/m², every three weeks. In some embodiments, the composition (such as a pharmaceutical composition) is administered (e.g., intravenously) at 200 mg/m², every three weeks. In some embodiments, the composition (such as a pharmaceutical composition) is administered (e.g., intravenously) at 130 mg/m², every three weeks.

In some embodiments, the composition (such as a pharmaceutical composition) is administered (e.g., intravenously) at 150 mg/m² on days 1, 8, and 15 every 4 weeks. In some embodiments, the composition (such as a pharmaceutical composition) is administered (e.g., intravenously) at 125 mg/m2 on days 1, 8, and 15 every 4 weeks. In some embodiments, the composition (such as a pharmaceutical composition) is administered (e.g., intravenously) at 100 mg/m² on days 1, 8, and 15 every 4 weeks. In some embodiments, the composition (such as a pharmaceutical composition) is administered (e.g., intravenously) at 75 mg/m2 on days 1, 8, and 15 every 4 weeks. In some embodiments, the composition (such as a pharmaceutical composition) is administered (e.g., intravenously) at 50 mg/m² on days 1, 8, and 15 every 4 weeks.

The compositions (such as pharmaceutical compositions) described herein allow infusion of the composition (such as a pharmaceutical composition) to an individual over an infusion time that is shorter than about 24 hours. For example, in some embodiments, the composition (such as a pharmaceutical composition) is administered over an infusion period of less than about any one of 24 hours, 12 hours, 8 hours, 5 hours, 3 hours, 2 hours, 1 hour, 30 minutes, 20 minutes, or 10 minutes. In some embodiments, the composition (such as a pharmaceutical composition) is administered over an infusion period of about 30 minutes. In some embodiments, the composition (such as a pharmaceutical composition) is administered over an infusion period between about 30 minutes to about 40 minutes.

In some embodiments, the present application provides a method of treating cancer in an individual by parenterally administering to the individual (e.g., a human) an effective amount of a composition (such as a pharmaceutical composition) described herein. The present application also provides a method of treating cancer in an individual by intravenous, intra-arterial, intramuscular, subcutaneous, inhalation, oral, intraperitoneal, nasally, or intra-tracheal administering to the individual (e.g., a human) an effective amount of a paclitaxel pharmaceutical composition. In some embodiments, the route of administration is intraperitoneal. In some embodiments, the route of administration is intravenous, intra-arterial, intramuscular, or subcutaneous. In various variations, about 5 mg to about 500 mg, such as about 30 mg to about 300 mg or about 50 mg to about 500 mg, of the paclitaxel is administered per dose. In some embodiments, the paclitaxel is the only pharmaceutically active agent for the treatment of cancer that is contained in the composition (such as a pharmaceutical composition).

Any of the compositions (such as pharmaceutical compositions) described herein can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, transdermal, intratumoral, direct injection into the blood vessel wall, intracranial, or intra-cavity. In some embodiments, sustained continuous release formulation of the composition (such as a pharmaceutical composition) may be used. In one variation described herein, nanoparticles (such as albumin nanoparticles) of the inventive compositions (such as pharmaceutical compositions) can be administered by any acceptable route including, but not limited to, orally, intramuscularly, transdermally, intravenously, through an inhaler or other air borne delivery systems and the like.

In some embodiments, the albumin-based paclitaxel-containing pharmaceutical compositions may be administered with a second therapeutic compound and/or a second therapy. The dosing frequency of the composition (such as a pharmaceutical composition) and the second compound may be adjusted over the course of the treatment based on the judgment of the administering physician. In some embodiments, the first and second therapies are administered simultaneously, sequentially, or concurrently. When administered separately, the pharmaceutical composition and the second compound can be administered at different dosing frequency or intervals. For example, the composition (such as a pharmaceutical composition) can be administered weekly, while a second compound can be administered more or less frequently. In some embodiments, sustained continuous release formulation of paclitaxel-containing nanoparticle and/or second compound may be used. Various formulations and devices for achieving sustained release are known in the art. A combination of the administration configurations described herein can be used.

In some embodiments, the cancer is breast cancer (for example metastatic breast cancer), and the composition (such as a pharmaceutical composition) is administered at 260 mg/m$^2$ once every three weeks.

In some embodiments, the cancer is pancreatic cancer (for example advanced pancreatic cancer, or adenocarcinoma of the pancreas), and the composition (such as a pharmaceutical composition) is administered at 125 mg/m$^2$ weekly, three out of four weeks. In some embodiments, the cancer is pancreatic cancer (for example advanced pancreatic cancer), and the composition (such as a pharmaceutical composition) is administered at 125 mg/m$^2$ weekly, three out of four weeks in combination with gemcitabine at 1000 mg/m$^2$.

In some embodiments, the cancer is lung cancer (for example non-small cell lung cancer), and the composition (such as a pharmaceutical composition) is administered at 100 mg/m$^2$ weekly. In some embodiments, the cancer is lung cancer (for example non-small cell lung cancer), and the composition (such as a pharmaceutical composition) is administered at 100 mg/m$^2$ weekly, such as on Days 1, 8, 15 of each three weeks cycle, in combination with carboplatin at AUC=6 mg·min/mL once every three weeks, such as on Day 1 of each three weeks cycle.

Metronomic Therapy Regimens

The present invention also provides metronomic therapy regimens for any of the methods of treatment and methods of administration described herein. Exemplary metronomic therapy regimens and variations for the use of metronomic therapy regimens are discussed below and disclosed in U.S. application Ser. No. 11/359,286, filed Feb. 21, 2006, published as US 2006/0263434A1 (such as those described in paragraphs [0138] to [0157] therein), which is hereby incorporated by reference in its entirety. In some embodiments, the pharmaceutical composition is administered over a period of at least one month, wherein the interval between each administration is no more than about a week, and wherein the dose of the paclitaxel at each administration is about 0.25% to about 25% of its maximum tolerated dose following a traditional dosing regimen. In some embodiments, the pharmaceutical composition is administered over a period of at least two months, wherein the interval between each administration is no more than about a week, and wherein the dose of the paclitaxel at each administration is about 1% to about 20% of its maximum tolerated dose following a traditional dosing regimen. In some embodiments, the dose of paclitaxel per administration is less than about any one of 25%, 24%, 23%, 22%, 20%, 18%, 15%, 14%, 13%, 12%, 11%, 10%, 9%, 8%, 7%, 6%, 5%, 4%, 3%, 2%, or 1% of the maximum tolerated dose. In some embodiments, any pharmaceutical composition is administered at least about any one of 1×, 2×, 3×, 4×, 5×, 6×, or 7× (i.e., daily) a week. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, the composition (such as a pharmaceutical composition) is administered over a period of at least about any one of 2 months, 3 months, 4 months, 5 months, 6 months, 7 months, 8 months, 9 months, 10 months, 11 months, 12 months, 18 months, 24 months, 30 months, 36 months, 48 months, 60 months, 72 months, or 84 months.

EXEMPLARY EMBODIMENTS

Embodiment 1

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin polymers among the albumin on the nanoparticles, wherein a percentage of albumin polymer among the albumin on the nanoparticles being about 15% to about 40% (such as about 15% to about 20%, about 20% to about 24.5%, about 24.5% to about 30%, about 30% to about 35%, or about 35% to about 40%) is indicative of suitability of the pharmaceutical composition for medical use.

Embodiment 2

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the percentage of albumin monomers among the albumin on the nanoparticles, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) is indicative of suitability of the pharmaceutical composition for medical use.

Embodiment 3

In some further embodiments of embodiment 1, the method further comprises determining the percentage of albumin monomers among the albumin on the nanoparticles, wherein a percentage of albumin monomers among the albumin on the nanoparticles being about 40% to about 60% (such as about 40% to about 55%, about 40% to about 54%, about 40% to about 53%, about 40% to about 52%, about 40% to about 50%, about 40% to about 48%, or about 40% to about 46%) is indicative of suitability of the pharmaceutical composition for medical use.

Embodiment 4

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight percentage of the albumin in the nanoparticles, wherein a weight percentage of the albumin in the nanoparticles being about 15% to about 30% is indicative of suitability of the pharmaceutical composition for medical use.

Embodiment 5

In some further embodiments of any one of embodiments 1-3, the method further comprises determining the weight percentage of the albumin in the nanoparticles, wherein a weight percentage of the albumin in the nanoparticles being about 15% to about 30% is indicative of suitability of the pharmaceutical composition for medical use.

Embodiment 6

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the weight ratio of albumin to paclitaxel in the nanoparticles, wherein an albumin to paclitaxel ratio of about 1:2 to about 1:6 in the nanoparticles is indicative of suitability of the pharmaceutical composition for medical use.

Embodiment 7

In some further embodiments of any one of embodiments 1-5, the method further comprises determining the weight ratio of albumin to paclitaxel in the nanoparticles, wherein an albumin to paclitaxel ratio of about 1:2 to about 1:6 in the nanoparticles is indicative of suitability of the pharmaceutical composition for medical use.

Embodiment 8

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the morphology of the nanoparticles under cryo-TEM, wherein an irregular shape of the nanoparticles is indicative of suitability of the pharmaceutical composition for medical use.

Embodiment 9

In some further embodiments of any one of embodiments 1-8, the method further comprises determining the morphology of the nanoparticles under cryo-TEM, wherein an irregular shape of the nanoparticles is indicative of suitability of the pharmaceutical composition for medical use.

Embodiment 10

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the thickness of the albumin coating of the nanoparticles under cryo-TEM, wherein a thickness of about 5-7 nm (such as about 6 nm) is indicative of suitability of the pharmaceutical composition for medical use.

Embodiment 11

In some further embodiments of any one of embodiments 1-9, the method further comprises determining the thickness of the albumin coating of the nanoparticles under cryo-

267

TEM, wherein a thickness of about 5-7 nm (such as about 6 nm) is indicative of suitability of the pharmaceutical composition for medical use.

Embodiment 12

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the distribution of paclitaxel in a tumor tissue upon injection of the pharmaceutical composition directly into the tumor tissue; wherein an enhanced paclitaxel tumor distribution is indicative of suitability of the pharmaceutical composition for medical use.

Embodiment 13

In some further embodiments of any one of embodiments 1-11, the method further comprises determining the distribution of paclitaxel in a tumor tissue upon injection of the pharmaceutical composition directly into the tumor; wherein an enhanced paclitaxel tumor distribution is indicative of suitability of the pharmaceutical composition for medical use.

Embodiment 14

In some embodiments, there is provided a method of assessing suitability of a pharmaceutical composition for medical use in a human individual, wherein the pharmaceutical composition comprises nanoparticles comprising paclitaxel coated with albumin and a non-nanoparticle portion comprising albumin and paclitaxel, the method comprising: determining the solubility, paclitaxel crystallinity, and a paclitaxel recovery following a 0.2 micron filtration of the pharmaceutical composition, wherein a solubility of about 50 µg/ml to about 80 µg/ml in a 5% human albumin solution, a non-crystalline state of the paclitaxel, and a paclitaxel recovery date of at least about 80% is indicative of suitability of the pharmaceutical composition for medical use.

Embodiment 15

In some further embodiments of any one of embodiments 1-13, the method further comprises determining the solubility of the pharmaceutical composition, wherein a solubility of about 50 µg/ml to about 80 µg/ml in a 5% human albumin solution is indicative of suitability of the pharmaceutical composition for medical use.

Embodiment 16

In some further embodiments of any one of embodiments 1-13 and 15, the method further comprises determining the paclitaxel crystallinity of the pharmaceutical composition, wherein a non-crystalline state of the paclitaxel is indicative of suitability of the pharmaceutical composition for medical use.

Embodiment 17

In some further embodiments of any one of embodiments 1-13 and 15, the method further comprises determining the paclitaxel recovery following a 0.2 micron filtration of the pharmaceutical composition, wherein a paclitaxel recovery of at least about 80% is indicative of suitability of the pharmaceutical composition for medical use.

268

Embodiment 18

In some further embodiments of any one of embodiments 15-17, the determination of solubility, paclitaxel crystalline state, or paclitaxel recovery is carried out after storage.

Embodiment 19

In some further embodiments of any one of embodiments 14 and 16-18, the paclitaxel crystallinity is determined by X-ray diffraction, polarized light microscopy, or both.

Embodiment 20

In some further embodiments of any one of embodiments 1-19, the method further comprises determining the binding affinity of albumin to paclitaxel in the pharmaceutical composition.

Embodiment 21

In some further embodiments of embodiment 20, the binding affinity is determined by equilibrium dialysis, FTIR, NMR, or a combination thereof.

Embodiment 22

In some further embodiments of any one of embodiments 1-21, the method further comprises determining the surface-to-volume ratio of the nanoparticles in the pharmaceutical composition.

Embodiment 23

In some further embodiments of any one of embodiments 1-22, the method further comprises determining the percentage of albumin dimers among the albumin on the nanoparticles, wherein a percentage of about 15% to about 30% of albumin dimers among the albumin on the nanoparticles is indicative of the pharmaceutical composition for medical use.

Embodiment 24

In some further embodiments of any one of embodiments 1-23, the method further comprises determining the percentage of albumin oligomers among the albumin on the nanoparticles, wherein a percentage of about 7% to about 15% of albumin oligomers among the albumin on the nanoparticles is indicative of the pharmaceutical composition for medical use.

Embodiment 25

In some further embodiments of any one of embodiments 1-24, the method further comprises determining the percentage of albumin monomers, dimers, oligomers, or polymers among the total albumin in the pharmaceutical composition.

Embodiment 26

In some further embodiments of any one of embodiments 1-3, 5, 7, 9, 11, 13, and 15-25, the percentage of albumin monomers, dimers, oligomers, or polymers is carried out by size-exclusion chromatography.

Embodiment 27

In some further embodiments of any one of embodiments 1-26, the method further comprises determining the particle size of the nanoparticles.

Embodiment 28

In some further embodiments of embodiment 27, the particle size of the nanoparticles is determined by dynamic light scattering.

Embodiment 29

In some further embodiments of any one of embodiments 1-28, the method further comprises determining the polydispersity index of the nanoparticles in the pharmaceutical composition.

Embodiment 30

In some further embodiments of any one of embodiments 1-29, the method further comprises determining the span of size distribution (($Dv_{90}$-$Dv_{10}$)/$Dv_{50}$) of the nanoparticles in the pharmaceutical composition.

Embodiment 31

In some further embodiments of any one of embodiments 1-30, the method further comprises determining the surface potential of the nanoparticles.

Embodiment 32

In some further embodiments of any one of embodiments 1-31, the method further comprises determining the percentage of the paclitaxel in the nanoparticles among the total paclitaxel in the pharmaceutical composition.

Embodiment 33

In some further embodiments of embodiment 32, the percentage of the paclitaxel in the nanoparticles is determined by reversed-phase HPLC.

Embodiment 34

In some further embodiments of any one of embodiments 1-33, the method further comprises determining the percentage of the albumin that is in the non-nanoparticle portion among the total albumin in the pharmaceutical composition.

Embodiment 35

In some further embodiments of embodiment 34, the percentage of the albumin is determined by size-exclusion chromatography.

Embodiment 36

In some further embodiments of any one of embodiments 1-35, the method further comprises determining the stability of the pharmaceutical composition.

Embodiment 37

In some further embodiments of embodiment 36, the stability is determined after storage.

Embodiment 38

In some further embodiments of any one of embodiments 1-11 and 14-37, the method further comprises determining tumor distribution of paclitaxel upon administration in vivo.

Embodiment 39

In some further embodiments of embodiment 38, the method comprises determining tumor distribution of paclitaxel upon injection of the pharmaceutical composition directly into the tumor tissue.

Embodiment 40

In some further embodiments of any one of embodiments 1-39, the weight ratio of the total albumin to the total paclitaxel in the pharmaceutical composition is about 3:1 to about 7.9:1 or about 10:1 to about 17:1.

Embodiment 41

In some further embodiments of any one of embodiments 1-40, the albumin is human albumin.

Embodiment 42

In some further embodiments of any one of embodiments 1-41, the average particle size of the nanoparticles is less than about 200 nm.

Embodiment 43

In some embodiments, there is provided a method of validating a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, and wherein the method comprises 1) obtaining a sample from the commercial batch, and 2) assessing suitability of the sample for medical use according to any one of embodiments 1-42.

Embodiment 44

In some embodiments, there is provided a commercial batch of a pharmaceutical composition for medical use in a human individual, wherein the pharmaceutical composition comprises nanoparticles comprising paclitaxel coated with albumin and a non-nanoparticle portion comprising albumin and paclitaxel, and wherein the commercial batch is validated by assessment of suitability for medical use according to any one of embodiments 1-42.

EXAMPLES

The examples below are intended to be purely exemplary of the invention and should therefore not be considered to limit the invention in any way. The following examples and detailed description are offered by way of illustration and not by way of limitation.

Example 1. Determination of the Distribution of Paclitaxel within Tumor Tissue This example demonstrates the measurement of the distribution of paclitaxel in tumor tissue. Distribution of paclitaxel activity was used to monitor drug penetration and tumor cell uptake at defined radial distances extending from a site of microinjection for three formulations of paclitaxel.

To generate xenografts, athymic Nude-Foxn1nu mice (Jackson Laboratories) were injected subcutaneously with $2.5 \times 10^6$ MIA PaCa-2, A2058 melanoma, or H2122 non-small cell lung cancer (NSCLC) cells in a 1:1 ratio with BD Biosciences Matrigel Matrix.

Three formulations of paclitaxel were prepared for this study: paclitaxel (PTX) solubilized in DMSO (PTX: DMSO), paclitaxel solubilized in oil-based solvent Cremophor EL (PTX:CrEL), and a nanoparticle formulation of paclitaxel and albumin sold under the trademark ABRAXANE® (ABX). The concentration of paclitaxel in each formulation was determined by liquid chromatography mass spectrometry (LC-MS).

Microinjections were performed using the CIVO™ arrayed microinjection device (Presage Biosciences, Seattle, Wash.) by inserting the device transcutaneously into flank tumors of anesthetized mice. A minimum of 3 tumors per time point were used with 2-3 replicate injection sites per formulation in each tumor. An average drug volume of 3 µL was delivered via an extrusion method over an injection column length of 6 mm. An equal amount of paclitaxel in each formulation (12 µg) was administered per injection. Inactivated near infrared dye, VivoTag680-S (50 µg/mL), was co-injected with each drug to mark the injection site.

Tumors were analyzed 24, 48, or 72 hours post-drug microinjection for mitotic arrest by immunofluorescent staining of phospho-histone H3 (pHH3). At these post-injection time points, animals were euthanized. Tumors were harvested and resected, fixed in 10% buffered formalin for 48 hours, and scanned on a Xenogen IVIS in the near infrared spectrum (excitation 680 nm, emission 720 nm) to confirm the location of each injection site. Each tumor was cut into 2 mm thick cross sections perpendicular to the plane of injection to enable a three-dimensional assessment of the entire injection column.

Following IVIS imaging, tumors were processed for standard paraffin embedding and histological analysis. 4 micron sections, cut from each 2 mm cross section, were stained with an anti-pHH3 antibody and an Alexa Fluor 488 secondary antibody to assess drug-induced tumor responses (mitotic arrest) using custom software (CIVOanalyzer™; Presage Biosciences, Seattle, Wash.). Tissue sections were stained with 4',6-diamindino-2-phenylindole (DAPI) to visualize nuclei. Mean fraction values of pHH3 positive cells were plotted with standard error bars, as a function of radial distance for each formulation and time point. To assess the statistical significance of the differences between any pair of formulations, a linear mixed model approach was used. In the model, the response to the PTX:CrEL formulation was assumed to be a random effect and the differential response due to the nab-paclitaxel sold under the trademark ABRAXANE® or PTX:DMSO was assumed to be a fixed effect. A p-value of less than 0.05, adjusted for multiple comparisons, indicates statistically significant differences. Data are expressed as mean plus/minus standard error.

Figure 2B:
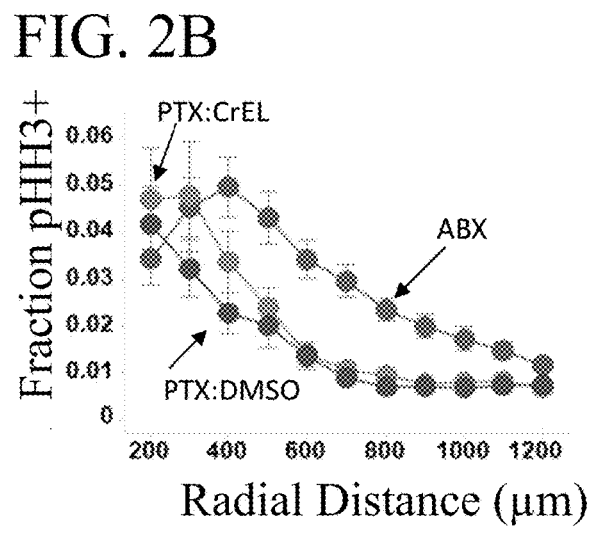
Figure 2C:
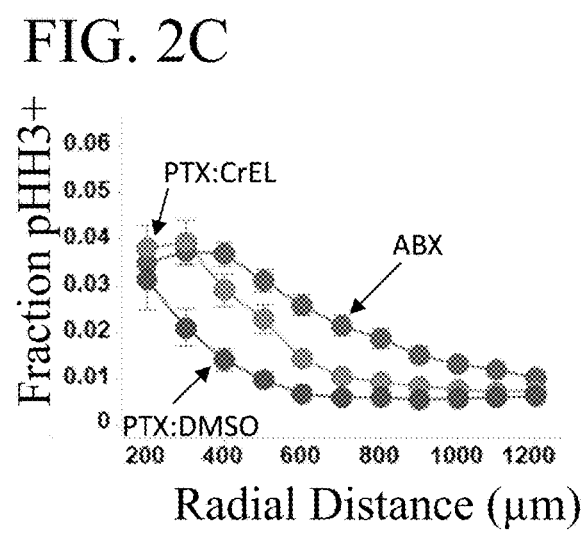

Immunofluorescent staining of pHH3 was used as a pharmacodynamics indicator of paclitaxel activity to monitor drug penetration and tumor cell uptake for MIA PaCa-2 xenografts at defined radial distances extending from the site of injection. FIGS. 1A-1I show representative imaging of pancreatic MIA PaCa-2 at 24, 48, and 72 hours following microinjection with ABX, PTX:DMSO, or PTX:CrEL. At all three time points (24, 48, and 72 hours), the area of response and the total fraction of pHH3 positive cells at a specific radial distance following drug microinjection were significantly greater for the nab-paclitaxel sold under the trademark ABRAXANE® compared with either PTX: DMSO or PTX:CrEL ($p<0.01$)(FIGS. 2A-2C).

Figure 3A:
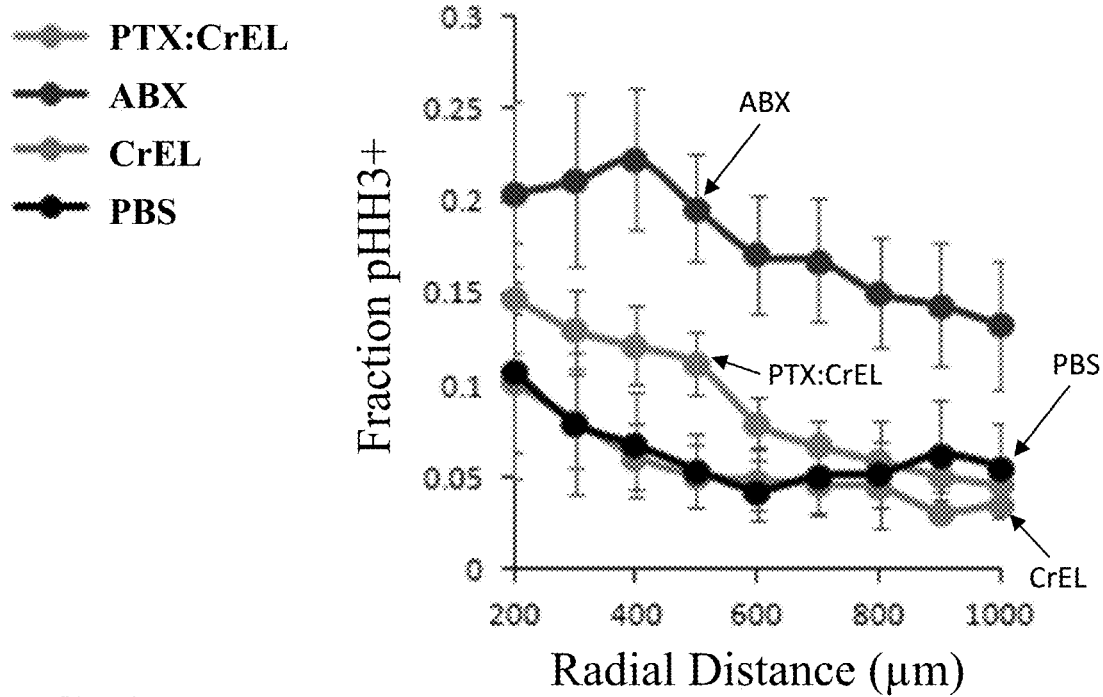
FIG. 3A shows the fraction pHH3+ versus the radial distance ($\mu$m) as measured from the injection site for A2058 tumor xenografts 24 hours post-injection with either ABX, PTX:CrEL, CrEL, or PBS.
Figure 3B:
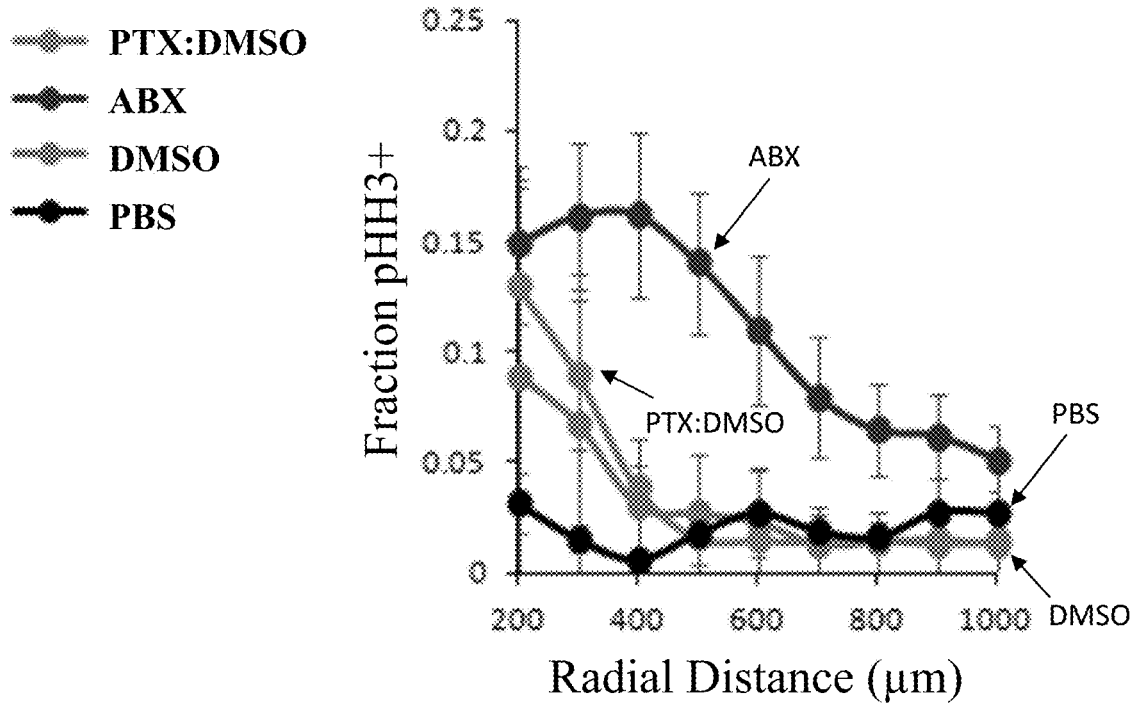
FIG. 3B shows the fraction pHH3+ versus the radial distance ($\mu$m) as measured from the injection site for H2122 tumor xenografts 24 hours post-injection with either ABX, PTX:DMSO, DMSO, or PBS.

Microinjections of paclitaxel formulations were also tested on two additional tumor xenografts, namely, A2058 melanoma and H2122 NSCLC xenografts. Results for microinjection of A2058 xenografts showed that ABX induced a larger increase in both the area of response and total fraction of cells arrested in mitosis at 24 hours post-injection when compared to PTX:CrEL (FIG. 3A)(n=5 tumors; $p<0.001$). Results for microinjection of H2122 xenografts showed that ABX induced a larger increase in both the area of response and total fraction of cells arrested in mitosis at 24 hours post-injection when compared to PTX:DMSO microinjection of (FIG. 3B)(n=3 tumors; $p<0.001$).

Example 2. Determination of the Distribution of Paclitaxel within Tumor Tissue for Increasing Concentrations of Paclitaxel This example demonstrates the measurement of the distribution of paclitaxel in tumor tissue. Distribution of paclitaxel activity was used to monitor drug penetration and tumor cell uptake at defined radial distances extending from a site of microinjection for three formulations of paclitaxel at three paclitaxel concentrations.

MIA PaCa-2 xenografts were generated as discussed in Example 1.

Three paclitaxel formulations were prepared for this study: paclitaxel (PTX) solubilized in DMSO (PTX: DMSO), paclitaxel solubilized in oil-based solvent Cremophor EL (PTX:CrEL), and a nanoparticle formulation of paclitaxel and albumin sold under the trademark ABRAXANE® (ABX). The concentration of paclitaxel in each formulation was determined by liquid chromatography mass spectrometry (LC-MS).

Microinjections were performed using the CIVO™ arrayed microinjection device (Presage Biosciences, Seattle, Wash.) by inserting the device transcutaneously into flank tumors of anesthetized mice. A minimum of 3 tumors per time point were used with 2-3 replicated injection sites per formulation in each tumor. An average drug volume of 3 µL was delivered via an extrusion method over an injection column length of 6 mm. Paclitaxel, as measured in PTX: DMSO, PTX:CrEL, and ABX, was administered at three concentrations: 1.6 mg/mL, 2.5 mg/mL, or 4.75 mg/mL. Inactivated near infrared dye, VivoTag680-S (50 µg/mL), was co-injected with each drug to mark the injection site.

Tumors were analyzed at 24 hours post-drug microinjection for mitotic arrest by immunofluorescent staining of phospho-histone H3 (pHH3). Tumor tissue samples were prepared and analyzed as discussed in Example 1.

Figure 4A:
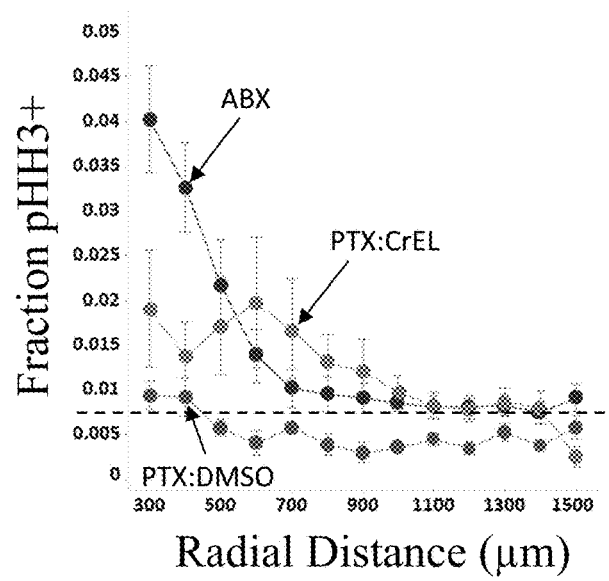
FIGS. 4A-4C show the fraction pHH3+ versus the radial distance ($\mu$m) as measured from the injection site for pancreatic MIA PaCa-2 xenograft tumors at 24 hours post-injection with either 1.6 mg/mL ABX, 1.6 mg/mL PTX:DMSO, or 1.6 mg/mL PTX:CrEL (FIG. 4A); either 2.5 mg/mL ABX, 2.5 mg/mL PTX:DMSO, or 2.5 mg/mL PTX:CrEL (FIG. 4B); and either 4.75 mg/mL ABX, 4.75 mg/mL PTX:DMSO, or 4.75 mg/mL PTX:CrEL (FIG. 4C). The level of background signal is indicated with a dashed line.
Figure 4B:
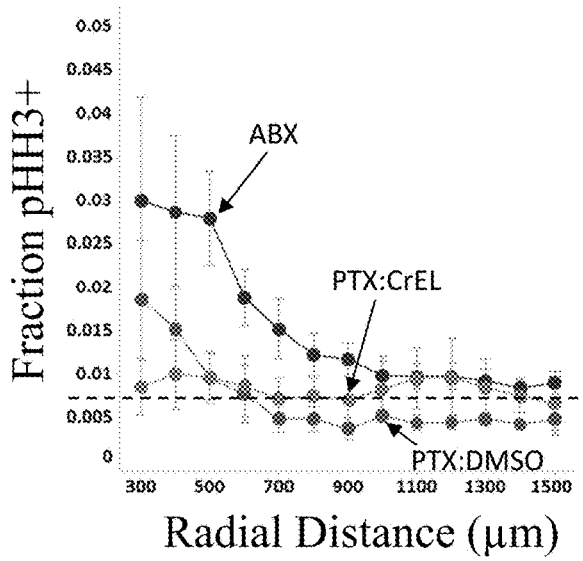
Figure 4C:
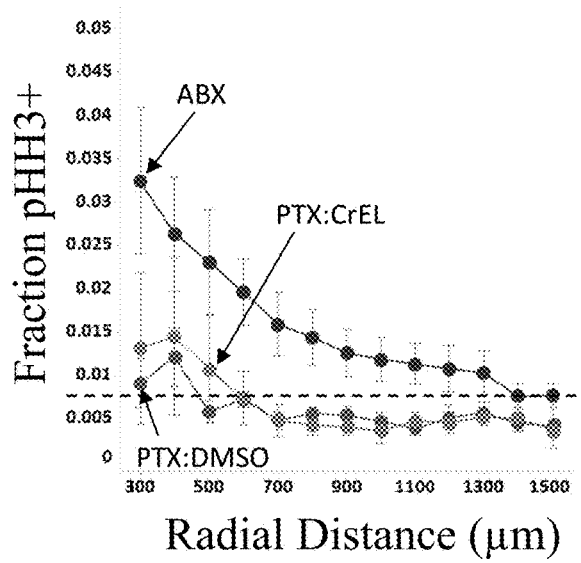

Immunofluorescent staining of pHH3 was used as a pharmacodynamics indicator of paclitaxel activity to monitor drug penetration and tumor cell uptake at defined radial distances extending from the site of injection for 3 concentrations of paclitaxel. At 24 hours, the area of response and the total fraction of pHH3 positive cells at a specific radial distance were greater for the three concentrations of microinjected nab-paclitaxel sold under the trademark ABRAX- ANE® compared with respective concentrations of either PTX:DMSO and PTX:CrEL (FIGS. 4A-4C).

Example 3. Ultracentrifugation of Nanoparticles in the Composition

This example demonstrates a method for separating nanoparticles in the composition (such as a pharmaceutical composition) from a non-nanoparticle portion of a composition (such as paclitaxel and albumin). Ultracentrifugation was performed at speeds and durations that allow the sedimentation of the nanoparticles without significant sedimentation of any albumin and/or paclitaxel not associated with the nanoparticles.

A pharmaceutical composition comprising nanoparticles comprising paclitaxel coated with albumin and a non-nanoparticle portion comprising albumin and paclitaxel was obtained. The composition was reconstituted with 0.9% sodium chloride to yield a 5 mg/mL suspension as measured by paclitaxel. 4.0 mL aliquots of reconstituted suspension were transferred to Beckman Coulter quick seal polyallomer bell-top tubes and submitted to ultracentrifugation at 50,000 rpm for 41 minutes at 25° C. in a Type 00 Ti rotor. After ultracentrifugation, the tubes were removed without disturbing the pelleted nanoparticles. A micropipette was used to remove 3.0 mL of supernatant from each tube. Each supernatant was transferred to a separate test tube and saved for further analysis. The remaining supernatant was poured out of the tube containing the pelleted nanoparticles. The pellet was then gently washed with 2 mL of water. The water was poured out of the tube and the pellet was again gently washed with 2 mL of water.

Example 4. Determining the Concentration of Paclitaxel and Albumin in a Non-Nanoparticle Portion of a Composition This example demonstrates a method for measuring the concentration of paclitaxel and albumin from a non-nanoparticle portion of a composition (such as a pharmaceutical composition).

As demonstrated in Example 3, the non-nanoparticle portion of a pharmaceutical composition was separated from the nanoparticle portion of the pharmaceutical composition by ultracentrifugation. To determine the concentration of albumin in the non-nanoparticle portion of the pharmaceutical composition, 1.0 mL of the supernatant obtained following ultracentrifugation was transferred to a 10-mL volumetric flask. The supernatant was then diluted to 10-mL with 0.9% sodium chloride. This dilute solution was then subjected to HPLC analysis as discussed below.

Briefly, human albumin standards were created with a concentration of 0.4 mg/mL in 0.9% sodium chloride. An HPLC system equipped with a variable wavelength UV/VIS detector and data acquisition system was set up with a TosoHaas TSK Guard Column SWxL (6.0 mm×40 mm, 7 µm particle size) and a TosoHaas Analytical Column G3000 SWxL (7.8 mm×300 mm, 5 µm particle size) kept at ambient temperature. Separate 10 µL injections of the albumin standards or dilute supernatant samples obtained from ultracentrifugation of the pharmaceutical composition were analyzed on the HPLC system at 228 nm using a 60-minute chromatography cycle with a flow rate of 1.0 mL/min using 100 mM $K_2HPO_4$ (pH 7.0) mobile phase. After each chromatographic cycle, the entire line of the HPLC system, including pump and columns, were washed with a 0.05% sodium azide solution. The concentration of albumin in the non-nanoparticle portion of the pharmaceutical composition was calculated using the information obtained from the chromatograms of the human albumin standards and the samples.

To determine the concentration of paclitaxel in the non-nanoparticle portion of the pharmaceutical composition, 1.0 mL of the supernatant obtained following ultracentrifugation was transferred to a 25-mL volumetric flask. The supernatant was then diluted to 25.0 mL with purified water, sonicated for 5 minutes, and then allowed to cool to room temperature. 5.0 mL of this solution was then transferred into a 10-mL volumetric flask, diluted to 10.0 mL with a 50:50 solution of acetonitrile and water, sonicated for 5 minutes, and then allowed to cool to room temperature. This solution was then subjected to HPLC analysis as discussed below.

Briefly, paclitaxel standards were created with a concentration of 1.2 mg/mL in acetonitrile. 2.0 mL of the 1.2 mg/mL paclitaxel solution was transferred to a 100-mL volumetric flask and diluted to volume with acetonitrile to obtain a solution of 24 µg/mL paclitaxel. 2.0 mL of the 24 µg/mL paclitaxel solution was transferred to a 25-mL volumetric flask and diluted to volume with acetonitrile to obtain a solution of 1.9 µg/mL paclitaxel. This standard solution was stored at 4° C. until use. Additionally, a system sensitivity solution of paclitaxel was prepared. 2.0 mL of the 1.9 µg/mL paclitaxel solution was transferred to a 50-mL volumetric flask and diluted to volume with acetonitrile to obtain a solution of 0.08 µg/mL paclitaxel. An HPLC system equipped with a UV absorbance detector and data acquisition system was set up with a Phenomenex, Curosil PFP guard column (4.6 mm×30 mm, 5 µm particle size) and a Phenomenex, Curosil PFP analytical column (4.6 mm×250 mm, 5 µm particle size). The autosampler was maintained at 4° C. Separate 10 µL injections of the paclitaxel system sensitivity solution, paclitaxel standard or dilute supernatant samples obtained from ultracentrifugation of the pharmaceutical composition were analyzed on the HPLC system at 228 nm using a 10-minute chromatography cycle with a flow rate of 1.0 mL/min using a 70:30 acetonitrile:water mobile phase. To check the system suitability for sample injection, the 1.9 µg/mL paclitaxel standard was injected and analyzed, followed by an injection and analysis of 100% acetonitrile, and then an injection and analysis of the system sensitivity solution of paclitaxel. The height of the interference peak in the acetonitrile was confirmed to be not more than one-fourth of the paclitaxel peak height in the analysis of the system sensitivity solution of paclitaxel. Additionally, it was confirmed that the signal-to-noise ratio of the paclitaxel peak in the system sensitivity solution of paclitaxel was not less than 10. The concentration of paclitaxel in the non-nanoparticle portion of the pharmaceutical composition was calculated using the information obtained from the chromatograms of the paclitaxel standard and the samples.

Example 5. Determining the Concentration of Paclitaxel and Albumin in a Nanoparticle Portion of a Composition This example demonstrates a method for measuring the concentration of paclitaxel and albumin from a nanoparticle portion of a composition (such as a pharmaceutical composition).

As demonstrated in Example 3, the nanoparticle portion of a pharmaceutical composition was separated from the non-nanoparticle portion of the pharmaceutical composition by ultracentrifugation. To determine the concentration of albumin in the nanoparticle portion of the pharmaceutical composition, 3.0 mL of ethanol (200 absolute proof) was added to the pellet and sonicated until the pellet was fully dispersed. After the pellet was dispersed, the solution was transferred with a glass pipette to another centrifuge tube. The original tube was rinsed with 2 mL ethanol and transferred to the other centrifuge tube. The sample was then centrifuged at 10,000 rpm for 20 minutes at 25° C. After centrifugation, the ethanol was removed with a long glass pipette. The pellet was then dried in a desiccator under vacuum for about 1-2 hours. 3.0 mL of 0.9% sodium chloride was added to the dried pellet and then sonicated to disperse the pellet into a homogeneous mixture. The mixture was then transferred into a 10-mL volumetric flask, using 5.0 mL of 0.9% sodium chloride to wash and transfer the mixture, and then diluted to volume using 0.9% sodium chloride. The solution was sonicated until dissolved into a homogeneous solution and then allowed to cool to room temperature. This solution was then subjected to HPLC analysis as discussed in Example 4.

As demonstrated in Example 3, the nanoparticle portion of a pharmaceutical composition was separated from the non-nanoparticle portion of the pharmaceutical composition by ultracentrifugation. To determine the concentration of paclitaxel in the nanoparticle portion of the pharmaceutical composition, 3.0 mL of a 50:50 acetonitrile:water solution was added to the pellet and then sonicated until the pellet dispersed into a homogeneous mixture. The mixture was transferred into a 250-mL volumetric flask and additional 50:50 acetonitrile:water solution was used to wash the tube that contained the pellet. The solution was then diluted to volume using the 50:50 acetonitrile:water solution, sonicated until the pellet was completely dissolved, and then allowed to cool to room temperature. 2.0 mL of this solution was transferred into a 100-mL volumetric flask and diluted to volume with the 50:50 acetonitrile:water solution. This solution was then subjected to HPLC analysis as discussed in Example 4.

Example 6. Determining the Percentage of Albumin Monomers, Dimers, Oligomers, and Polymers Among the Albumin on the Nanoparticles in the Composition This example demonstrates the measurement of albumin monomers, dimers, oligomers, and polymers among the total albumin either in the nanoparticle portion of the pharmaceutical composition or in the non-nanoparticle portion of the pharmaceutical composition.

Figure 5:
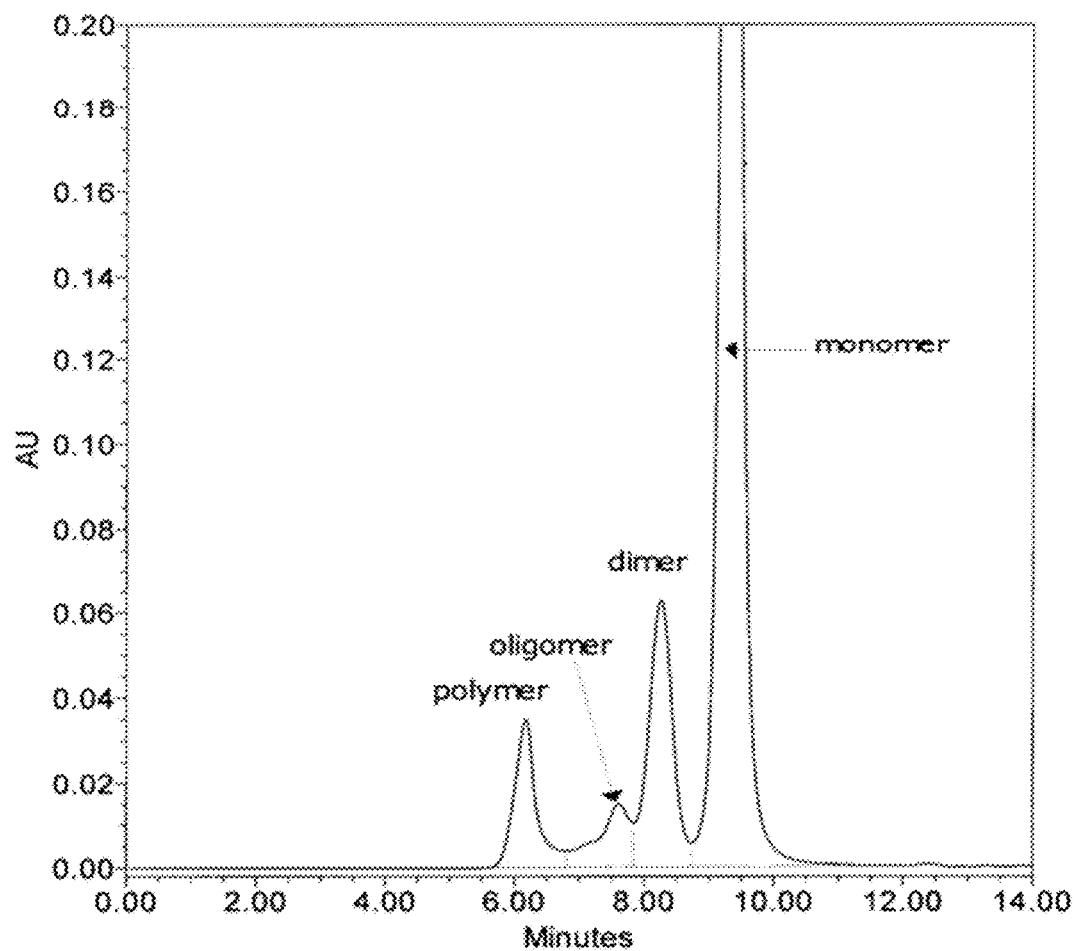
FIG. 5 shows a chromatogram from the separation of polymeric, oligomeric, dimeric, and monomeric albumin on nanoparticles from a pharmaceutical composition using size-exclusion chromatography.

HPLC analysis of albumin in a nanoparticle portion of a composition and albumin in a non-nanoparticle portion of a composition was performed as discussed herein. Chromatograms were generated as discussed above. For example, A chromatogram from the method was generated as shown in FIG. 5. The RRT, as compared to monomeric albumin, for the separated albumin species was determined and used to classify peaks in the chromatographs as monomeric, dimeric, oligomeric, or polymeric albumin. The percentage of albumin monomers, dimers, oligomers, and polymers in the nanoparticle portion of the composition was calculated by comparing the integrated peak areas of each albumin species to the total integrated peak area of the albumin on the nanoparticles.

Example 7. Determining the Weight Percentage of Albumin and Paclitaxel in the Nanoparticles in the Composition This example demonstrates the measurement of weight percentage of albumin on the nanoparticles and paclitaxel in the nanoparticles in the pharmaceutical composition.

A pharmaceutical composition comprising nanoparticles comprising paclitaxel coated with albumin and a non-nanoparticle portion comprising albumin and paclitaxel was obtained. If necessary, the composition was reconstituted. The nanoparticles in the composition were then isolated away from the non-nanoparticle portion of the composition by ultracentrifugation as discussed above.

Isolated nanoparticles were diluted and the amount of albumin and paclitaxel in the nanoparticles was measured. The amount of albumin on the nanoparticle is measured as detailed herein. The amount of paclitaxel was measured by a RP-HPLC method as detailed herein. Paclitaxel was detected at 228 nm.

The weight percentage of albumin on the nanoparticles was determined from the amount of albumin on the nanoparticles and the total weight of the nanoparticles (e.g., the amount of albumin and the amount of paclitaxel). The weight ratio of albumin on the nanoparticles to paclitaxel in the nanoparticles was determined from the amount of albumin on the nanoparticles and the amount of paclitaxel in the nanoparticles.

Example 8. Determining the Morphology and Thickness of the Nanoparticles in the Composition Using Cryo-TEM This example demonstrates a cryo-TEM technique for determining the morphology and thickness of the nanoparticles in the pharmaceutical composition.

A pharmaceutical composition comprising nanoparticles comprising paclitaxel coated with albumin and a non-nanoparticle portion comprising albumin and paclitaxel was obtained. If necessary, the composition was reconstituted. Optionally, the nanoparticles in the composition are then isolated away from the non-nanoparticle portion of the composition by ultracentrifugation as discussed above.

Nanoparticles were prepared for cryo-TEM imaging. In short, the reconstituted nanoparticles were rapidly cooled to cryogenic temperatures to form a vitreous form of the reconstituted composition which was then analyzed. Briefly, the nanoparticles of the composition were analyzed in their native structure at magnifications ranging from 6,500× to 110,000× at different areas in the sample. The morphology of the nanoparticles, such as the irregularity of shape, rugosity, and surface-to-volume ratio, was assessed from the cryo-TEM images. The thickness of the albumin coating on the nanoparticles was also measured from the cryo-TEM image.

Example 9. Determining the Solubility, Paclitaxel Crystallinity, and Paclitaxel Recovery of the Composition Following 0.2 Micron Filtration of the Composition This example demonstrates the measurement of nanoparticle solubility, paclitaxel crystallinity, and paclitaxel recovery of the pharmaceutical composition following 0.2 micron filtration.

A pharmaceutical composition comprising nanoparticles comprising paclitaxel coated with albumin and a non-nanoparticle portion comprising albumin and paclitaxel was obtained. If necessary, the composition was reconstituted. The composition was assessed for nanoparticle solubility, paclitaxel crystallinity, and paclitaxel recovery of the pharmaceutical composition following 0.2 micron filtration immediately after reconstitution and after an accelerated aging process. To age the composition, the reconstituted composition was stored for 24 hours at 40° C. Compositions were filtered by passing the reconstituted composition through a 0.2 micron filter.

Solubility of nanoparticles of the composition was determined by performing dynamic light scattering measurements on a series of concentrations of the composition after reconstitution. The proportion of intact particles to free paclitaxel was a function of the solubility of the particles. Thus, as measured by this method, the solubility was determined as the concentration below which particles were no longer detectable by dynamic light scattering.

Paclitaxel crystallinity of the nanoparticles of the composition was determined by performing an X-ray diffraction method and a polarized light microscopy method after reconstitution. Optionally, X-ray diffraction measurements were made on isolated nanoparticles. Nanoparticles in the composition were optionally isolated away from the non-nanoparticle portion of the composition by ultracentrifugation as discussed herein. The isolated nanoparticles were then optionally dried by lyophilization. Non-crystalline paclitaxel in the nanoparticles will exhibit broad scattering halos, indicative of an amorphous material (e.g., non-crystalline). Crystalline paclitaxel in the nanoparticles will exhibit numerous well-defined scattering peaks. Polarized light microscopy measurements were performed on a suspension of the composition. To determine the crystalline state of the nanoparticles of the composition, a birefringence test was performed with an optical microscope using polarized light.

Paclitaxel recovery following 0.2 micron filtration of the composition was determined by performing RP-HPLC. Following 0.2 micron filtration, nanoparticles in the composition were optionally isolated away from the non-nanoparticle portion of the composition by ultracentrifugation as discussed herein. The amount of paclitaxel in the nanoparticles recovered after the 0.2 micron filtration was measured by a RP-HPLC method as discussed herein. Paclitaxel was detected at 228 nm. The degree of paclitaxel recovery was assessed by comparing the amount of paclitaxel in the composition following 0.2 micron filtration to the amount of paclitaxel in the composition prior to 0.2 micron filtration.

Example 10. Validating a Composition for Medical Use

This example demonstrates the validation of a composition for medical use by assessing particle morphology, particle size, surface potential, paclitaxel crystallinity, fraction of free and bound paclitaxel or albumin, nature of the bond between paclitaxel and albumin, dissolution profile, and oligomeric status of albumin.

A pharmaceutical composition comprising nanoparticles comprising paclitaxel coated with albumin and a non-nanoparticle portion comprising albumin and paclitaxel was obtained. If necessary, the composition was reconstituted. The composition was assessed for sameness, compared to nab-paclitaxel sold under the trademark ABRAXANE®, with respect to particle morphology, particle size (both $Dv_{50}$ and span or polydispersity index), surface potential, paclitaxel crystallinity, fraction of free and bound paclitaxel or albumin, nature of the bond between paclitaxel and albumin, dissolution profile, and oligomeric status of albumin.

To assess for sameness with respect to particle morphology of nanoparticles in the pharmaceutical composition, the morphology of the nanoparticles was assessed.

To assess for sameness with respect to particle size and span or polydispersity index of the nanoparticles in the pharmaceutical composition, the reconstituted composition was subjected to dynamic light scattering measurements. The particle size was measured as the mean particle size ($D_{50}$) of the nanoparticles in the composition. The span or polydispersity index was measured as the span of the size distribution, $(D_{90}-D_{10})/D_{50}$.

To assess for sameness with respect to the surface potential of nanoparticles in the pharmaceutical composition, the zeta potential of the nanoparticles was determined. The zeta potential was measured using techniques such as microelectrophoresis, electrophoretic light scattering, dynamic electrophoretic mobility, or tunable resistive pulse sensing (TRPS).

To assess for sameness with respect to paclitaxel crystallinity of nanoparticles in the pharmaceutical composition, the crystallinity of paclitaxel in the nanoparticles of the composition was assessed as discussed above.

To assess for sameness with respect to the fraction of free and bound paclitaxel or albumin in the pharmaceutical composition, the nanoparticle portion of the composition was separated from the non-nanoparticle portion of the composition. Nanoparticles in the composition are isolated away from the non-nanoparticle portion of the composition by ultracentrifugation as discussed herein. Isolated nanoparticles are diluted and the amount of albumin or paclitaxel in the nanoparticles was measured. The amount of albumin on the nanoparticle was measured by a HPLC size-exclusion chromatography method. Albumin was detected at 228 nm. The amount of paclitaxel was measured by a RP-HPLC method. Paclitaxel was detected at 228 nm. The non-nanoparticle portion of the composition is isolated and if the amount of albumin was determined in the nanoparticles, then the amount of albumin was determined in the non-nanoparticle portion of the composition. The amount of albumin in the non-nanoparticle portion of the composition was measured by a HPLC size-exclusion chromatography method. Albumin was detected at 228 nm. If the amount of paclitaxel was determined in the nanoparticles, then the amount of paclitaxel was determined in the non-nanoparticle portion of the composition. The amount of paclitaxel was measured by a RP-HPLC method. Paclitaxel was detected at 228 nm. The fraction of free (non-nanoparticle portion) and bound paclitaxel (nanoparticle portion) or albumin was calculated from the measured values.

To assess for sameness with respect to the nature of the bond between paclitaxel and albumin, the nature of the bond between albumin and paclitaxel was assessed.

To assess for sameness with respect to the dissolution profile, the reconstituted composition was subjected to an in vitro release kinetics assay. The reconstituted composition was diluted in a 0.9% saline solution and dynamic light scattering was used to monitor particle size over 60 minutes for a range of concentrations of the composition, or the reconstituted composition was diluted in a 5% human albumin solution and dynamic light scattering was used to monitor scattering and particle size over 60 minutes for a range of concentrations of the composition, or the reconstituted composition was diluted in water and a UV-Vis spectrophotometer was used to monitor absorbance over 60 minutes for a range of concentrations of the composition.

To assess for sameness with respect to the oligomeric status of albumin, albumins in the starting material and in the final composition were assessed for oligomeric status. Isolated albumin in the starting material and final composition were analyzed by a HPLC size-exclusion chromatography method. Albumin was detected at 228 nm. A chromatogram of the HPLC-size exclusion chromatography method was generated as shown in FIG. 5. The RRT, as compared to monomeric albumin, for the separated albumin species was determined and used to classify peaks in the chromatographs as monomeric, dimer, oligomeric, or polymeric albumin.

The composition was suitable for medical use if the particle morphology, particle size, surface potential, paclitaxel crystallinity, fraction of free and bound paclitaxel or albumin, nature of the bond between paclitaxel and albumin, dissolution profile, and oligomeric status of albumin were found to exhibit sameness with respect to results obtained from analysis of nab-paclitaxel sold under the trademark ABRAXANE®.

Example 11. Validating a Composition for Medical Use

This example demonstrates the validation of a composition for medical use, both before and after storage, by assessing particle morphology, particle size, surface potential, paclitaxel crystallinity, fraction of free and bound paclitaxel or albumin, nature of the bond between paclitaxel and albumin, dissolution profile, oligomeric status of albumin, oligomeric status of albumin on the nanoparticle, and the recovery of paclitaxel following 0.2 micron filtration.

A pharmaceutical composition comprising nanoparticles comprising paclitaxel coated with albumin and a non-nanoparticle portion comprising albumin and paclitaxel was obtained. If necessary, the composition was reconstituted. The composition was assessed for sameness, in view of nab-paclitaxel sold under the trademark ABRAXANE®, with respect to particle morphology, particle size, surface potential, paclitaxel crystallinity, fraction of free and bound paclitaxel or albumin, nature of the bond between paclitaxel and albumin, dissolution profile, oligomeric status of albumin, oligomeric status of albumin on the nanoparticle, and the recovery of paclitaxel following 0.2 micron filtration. To test the composition following storage conditions, the composition was stored for 24 hours at 40° C. to simulate an accelerated aging process.

To assess for sameness with respect to particle morphology of nanoparticles in the pharmaceutical composition, the nanoparticles in the composition were assessed as discussed herein. The morphology of the nanoparticles, such as the irregularity of shape, was assessed from the cryo-TEM images.

To assess for sameness with respect to particle size and span or polydispersity index of the nanoparticles in the pharmaceutical composition, the reconstituted composition was subjected to dynamic light scattering measurements. The particle size was measured as the volume-weighted mean particle size ($Dv_{50}$) of the nanoparticles in the composition. The span or polydispersity index was measured as the span of the volume-weighted size distribution, ($Dv_{90}$–$Dv_{10}$)/$Dv_{50}$.

To assess for sameness with respect to the surface potential of nanoparticles in the pharmaceutical composition, the zeta potential of the nanoparticles was determined. The zeta potential was measured using techniques such as microelectrophoresis, electrophoretic light scattering, dynamic electrophoretic mobility, or tunable resistive pulse sensing (TRPS).

To assess for sameness with respect to paclitaxel crystallinity of nanoparticles in the pharmaceutical composition, paclitaxel crystallinity of the nanoparticles of the composition was determined by performing an X-ray diffraction method and a polarized light microscopy method as detailed herein.

To assess for sameness with respect to the fraction of free (i.e., not associated with the nanoparticles) and bound (i.e., associated with the nanoparticles) paclitaxel and albumin in the pharmaceutical composition, the composition was assessed as detailed herein.

To assess for sameness with respect to the nature of the bond between paclitaxel and albumin, the composition was assessed via equilibrium dialysis test and FTIR and NMR analysis. The nature of the bond between paclitaxel and albumin was assessed using paclitaxel and processed albumin. The binding affinity between paclitaxel and processed albumin in the composition was measured via an equilibrium dialysis testing apparatus and further by FTIR and NMR analysis.

To assess for sameness with respect to the dissolution profile, the reconstituted composition was subject to an in vitro release kinetics assay. The reconstituted composition was diluted in a 0.9% saline solution and dynamic light scattering is used to monitor particle size over 60 minutes for a range of concentrations of the composition, or the reconstituted composition was diluted in a 5% human albumin solution and dynamic light scattering was used to monitor scattering and particle size over 60 minutes for a range of concentrations of the composition, or the reconstituted composition was diluted in water and a UV-Vis spectrophotometer was used to monitor absorbance over 60 minutes for a range of concentrations of the composition.

To assess for sameness with respect to the oligomeric status of albumin, albumins in the starting material and in the final composition are isolated away from the other components of the composition and their oligomeric status was assessed. Isolated albumins in the starting product of final composition are analyzed by a HPLC size-exclusion chromatography method as detailed herein.

To assess for sameness with respect to the oligomeric status of albumin on the nanoparticle, the nanoparticles in the composition were isolated away from the non-nanoparticle portion of the composition by ultracentrifugation as discussed herein. Isolated nanoparticles are diluted and then analyzed by a HPLC size-exclusion chromatography method as discussed herein.

To assess for sameness with respect to the recovery of paclitaxel following 0.2 micron filtration, the reconstituted composition was filtered with a 0.2 micron filter. Following 0.2 micron filtration, nanoparticles in the composition are isolated away from the non-nanoparticle portion of the composition by ultracentrifugation as discussed herein. The amount of paclitaxel in the recovered nanoparticles from the 0.2 micron filtered composition was measured by a RP-HPLC method as discussed herein. Paclitaxel was detected at 228 nm. The degree of paclitaxel recovery was assessed by comparing the amount of paclitaxel in the composition following 0.2 micron filtration to the amount of paclitaxel in the composition prior to 0.2 micron filtration.

The composition was suitable for medical use if the particle morphology, particle size, surface potential, paclitaxel crystallinity, fraction of free and bound paclitaxel or albumin, nature of the bond between paclitaxel and albumin, dissolution profile, oligomeric status of albumin, status of albumin on the nanoparticle, and the recovery of paclitaxel following 0.2 micron filtration were found to exhibit sameness with respect to results obtained from analysis of nab-paclitaxel sold under the trademark ABRAXANE®.

Example 12. Determining In Vitro Dissolution Kinetics of the Pharmaceutical Composition Using a UV-Vis Spectrophotometer This example demonstrates the measurement of in vitro release kinetics of the pharmaceutical composition after reconstitution, as determined by a UV-Vis spectrophotometer.

Figure 6:
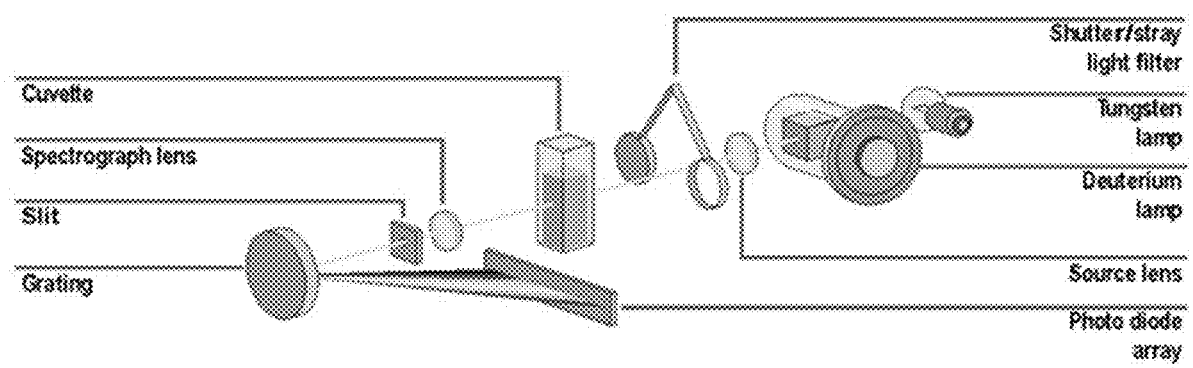
FIG. 6 shows a diagram of a UV-Vis spectrophotometer optical system.

The pharmaceutical composition was reconstituted with a 0.9% sodium chloride solution to produce a 5 mg/ml stock solution of the pharmaceutical composition, as measured by the concentration of paclitaxel. For example, starting from a vial of the lyophilized pharmaceutical composition containing 100 mg, as measured by the amount of paclitaxel, 20 ml of 0.9% sodium chloride was slowly injected into the vial over a minimum of 1 minute using a sterile syringe. The flow of 0.9% sodium chloride was directed onto the inside wall of the vial. Subsequently, the lyophilized pharmaceutical composition was allowed to rest for 5 minutes and then the vial was gently swirled or slowly inverted for at least 2 minutes until complete dissolution of the pharmaceutical composition occurred. The lyophilized pharmaceutical composition was reconstituted in a manner to avoid the formation of foam. The spectrophotometer was set up as shown in FIG. 6. A 295 nm longwave pass filter was placed between the UV light source and the cuvette. A 10-mm quartz cuvette was placed into an Agilent Cary 8454 UV-Vis spectrophotometer pre-equilibrated to 20° C. while stirring at 2000 rpm. An appropriate volume of water was transferred to the cuvette. A magnetic stirrer bar was added to the bottom of cuvette. The spectrophotometer was equilibrated over an hour (or longer) until the 340 nm signal was stabilized. An appropriate volume of the stock reconstituted pharmaceutical composition suspension was then added to the cuvette to achieve a target paclitaxel concentration of 100 µg/ml. The suspension was immediately mixed and the cuvette was capped.

During the preparation of the 100 µg/ml pharmaceutical composition, a series of consecutive intensity measurement was performed. All kinetic measurements were performed at 20° C. with the following settings: path length: 1 cm; wavelength range: 190-1100 nm; integration time: 0.5 seconds; interval: 1 nm; deuterium lamp (UV): On; run time: 3600 seconds; cycle time: 0.5 seconds; wavelength: 340 nm; and stirrer speed: 2000 rpm.

Figure 7:
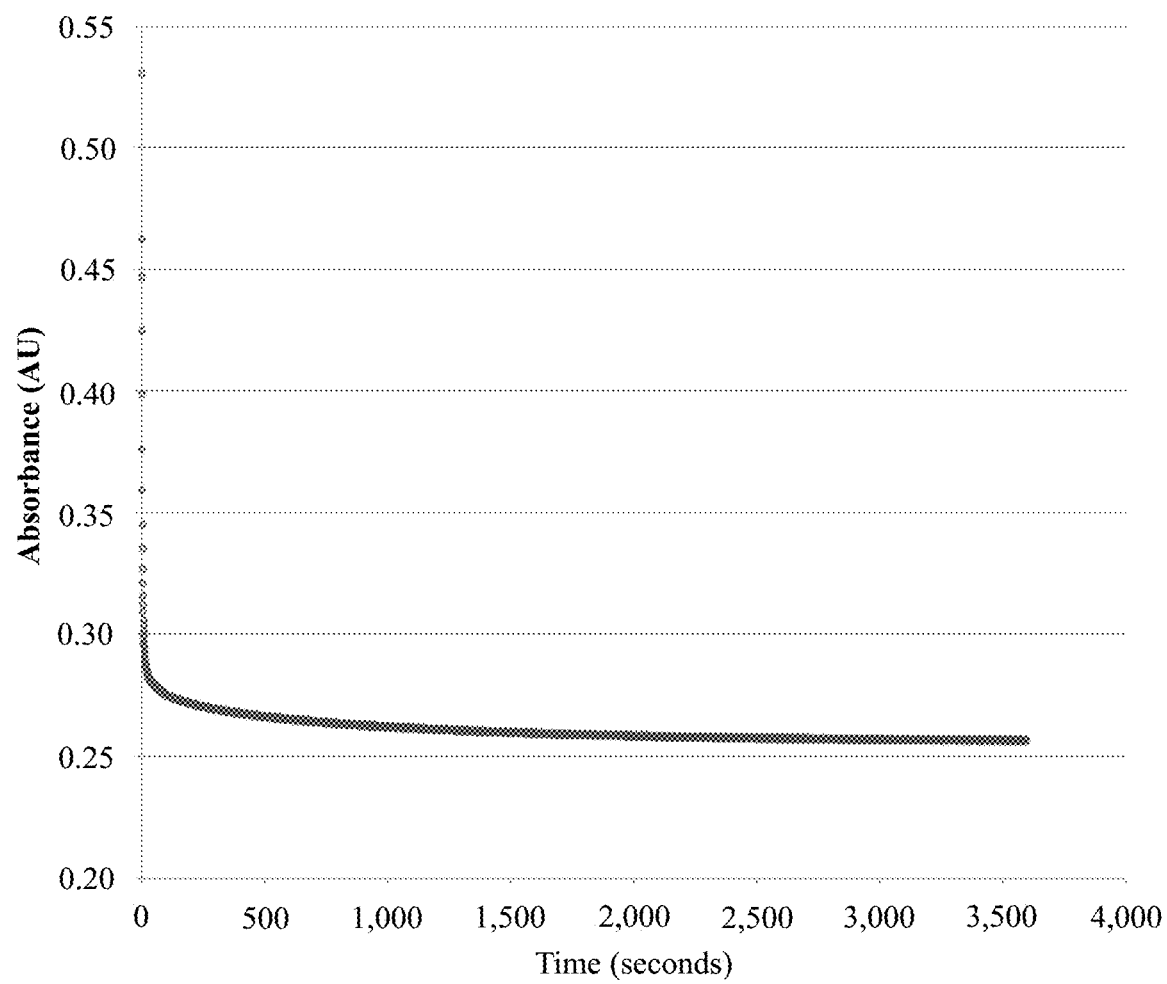
FIG. 7 shows in vitro dissolution kinetics of the nab-paclitaxel sold under the trademark ABRAXANE® in water at 100 $\mu$g/ml paclitaxel concentration, as measured at 340 nm by a UV-Vis spectrophotometer with a 295 nm low wavelength cut-off filter.

As shown in FIG. 7, the majority of particles in the reconstituted pharmaceutical composition suspension diluted to concentrations above the paclitaxel solubility in the release media dissolved and disintegrated rapidly, first over 30 seconds, followed by a long slow transient release over 3600 seconds or longer. The rate of disintegration and dissolution, and the dissolution profile shapes were concentration dependent.

Example 13. Methods of Making a Nanoparticle Composition

This example demonstrates methods of making an albumin/paclitaxel nanoparticle composition (such as a pharmaceutical composition) and variants thereof.

All variants were manufactured using laboratory scale/bench-top equipment.

Variant 5 (V5) was prepared using the following procedure.

5% human albumin (HA) solution and paclitaxel solvent solution containing approximately 200 mg/mL paclitaxel in 90:10 v:v chloroform:ethanol mixture were prepared. 18.4 mL of the 5% HA solution was transferred to a beaker and mixed using a Silverson high-shear mixer. 1.6 mL of the paclitaxel solvent solution was slowly (drop-wise) added to the HA solution and mixed for approximately 5 minutes at 5000-6000 rpm to create a crude emulsion. The crude emulsion was high-pressure homogenized at pressure of approximately 18-20 kpsi using Avestin EmulsiFlex-C5 emulsifier for approximately 12 passes to create a fine emulsion. The fine emulsion was transferred to a 2 L round bottom flask and the solvents were removed using BUCHI rotary evaporator with a water bath temperature set at 40° C. The evaporation was performed using the parameters in Table 1. The evaporation continued until the initial volume was reduced by approximately 45-80%. The whole process was repeated once to generate enough material for in-process (IP) and finished product (FP) testing. The post-evaporated (PE) suspension was combined, mixed and assayed for paclitaxel and HA. Based on the assay values, the PE suspension was diluted with MilliQ water and 20-25% HA solution to paclitaxel concentration of 7 mg/mL and HA concentration of 56 mg/mL. The diluted suspension was filtered through a series of 1.2 µm, 0.8 µm, 0.45 µm and 0.2 µm syringe filters with Supor PES membrane. 1-3 mL aliquots of the filtered suspension were filled in 10 mL, 20 mm glass vials and lyophilized in VirTis Genesis EL25 lyophilizer (SP Industries, Gardiner, N.Y.) using the cycle in Table 2. After lyophilization the vials were stoppered under nitrogen, crimped and stored at −20° C. for future testing.

A total of three lots of Variant 5 were manufactured.

TABLE 1

Evaporation cycle.

| Step # | Pressure set point | Hold time after pressure is achieved |
|---|---|---|
| 1 | 70 mm Hg | 1 min |
| 2 | 60 mm Hg | 1 min |
| 3 | 50 mm Hg | 1 min |
| 4 | 40 mm Hg | 1 min |
| 5 | 30 mm Hg | 1 min |
| 6 | 25 mm Hg | As needed |

TABLE 2

Lyophilization cycle.

| Step | Temp. (° C.) | Time (min) | Vac (mTorr) | Type |
|---|---|---|---|---|
| Loading | | | | |
| 1 | −55 | N/A | N/A | Hold |
| Freezing | | | | |
| 1 | −55 | 240 | N/A | Hold |
| Drying | | | | |
| 1 | −55 | 10 | 350 | Hold |
| 2 | −15 | 200 | 350 | Ramp |
| 3 | −15 | 10 | 350 | Hold |
| 4 | 25 | 400 | 350 | Ramp |
| 5 | 25 | 840 | 350 | Hold |
| 6 | 30 | 50 | 350 | Ramp |
| 7 | 30 | 480 | 350 | Hold |

Variant 1 (V1) was prepared using the procedure for Variant 5 with the following modification. The organic solvent mixture used to prepare the 200 mg/mL paclitaxel solvent solution contained 50% by volume ethanol and 50% by volume chloroform.

A total of three lots of Variant 1 were manufactured.

Variant 2 (V2) was prepared using the procedure for Variant 5 with the following modification. The concentration of the human albumin solution used to prepare the crude emulsion was 10 mg/mL.

A total of three lots of Variant 2 were manufactured.

Variant 3 (V3) was prepared using the procedure for Variant 5 with the following modification. The high-pressure homogenization of the crude emulsion was performed at pressure of approximately 5 kpsi.

A total of three lots of Variant 3 were manufactured.

Variant 4 (V4) was prepared using the procedure for Variant 5 with the following modifications. After the high-pressure homogenization the fine emulsion was transferred to a 500 mL round bottom flask and the solvents were removed using BUCHI rotary evaporator with a water bath temperature set at 30° C. The evaporation was performed using the parameters in Table 3.

TABLE 3

Evaporation cycle for variant 4.

| Step # | Pressure set point | Hold time after pressure is achieved |
|---|---|---|
| 1 | 70 mm Hg | 1 min |
| 2 | 60 mm Hg | 1 min |
| 3 | 50 mm Hg | 1 min |
| 4 | From 40 mm Hg to 25 mm Hg, every 1 mm Hg | 1 min |
| 5 | 15 mm Hg | As needed |

A total of three lots of Variant 4 were manufactured.

Example 14. Assessment of Compositions

This example reports results from the assessment of various albumin/paclitaxel nanoparticle compositions.

The compositions were assessed using the methods described herein. Variants are designated as discussed herein (e.g., FP refers to finished product; IP refers to in-process product). ABRAXANE® is the proprietary albumin/paclitaxel nanoparticle product of Celgene/Abraxis. Paclitaxel NAB, Albupax, and PacliALL are purported copies of the proprietary albumin/paclitaxel nanoparticle product of Celgene/Abraxis sold under the trademark ABRAXANE® made by different companies.

TABLE 4

$D_{V4,3}$ (nm) measured immediately after reconstitution.

| Sample Name | N (number) | Mean | Margin of error | Min | Max |
|---|---|---|---|---|---|
| ABRAXANE® | 22 | 153.8 | 2.8 | 144.1 | 164.4 |
| Paclitax NAB | 3 | 113.7 | 12.7 | 108.5 | 118.7 |
| Albupax | 5 | 140.0 | 12.0 | 129.6 | 151.6 |
| PacliALL | 5 | 426.3 | 864.0 | 221.7 | 827.9 |
| V5 FP | 3 | 159.5 | 19.8 | 153.4 | 168.5 |
| V1 FP | 3 | 177.6 | 74.4 | 158.8 | 212.1 |
| V2 FP | 3 | 179.5 | 27.1 | 167.0 | 186.9 |
| V3 FP | 3 | 178.9 | 17.8 | 171.5 | 185.8 |
| V4 FP | 3 | 147.2 | 9.8 | 142.7 | 150.0 |

TABLE 5

Z average (nm) measured immediately after reconstitution.

| Sample Name | N (number) | Mean | Margin of error | Min | Max |
|---|---|---|---|---|---|
| ABRAXANE® | 22 | 145.9 | 1.9 | 138.5 | 153.0 |
| Paclitax NAB | 3 | 118.7 | 8.5 | 115.2 | 122.0 |
| Albupax | 5 | 138.9 | 1.7 | 137.2 | 140.5 |
| PacliALL | 5 | 178.6 | 13.6 | 165.8 | 190.0 |
| V5 FP | 3 | 149.7 | 12.2 | 146.5 | 155.4 |
| V1 FP | 3 | 164.8 | 55.7 | 149.3 | 190.5 |
| V2 FP | 3 | 161.4 | 12.9 | 155.6 | 165.6 |
| V3 FP | 3 | 162.6 | 6.8 | 159.9 | 165.4 |
| V4 FP | 3 | 142.9 | 6.7 | 139.9 | 145.1 |

TABLE 6

Polydispersity index (PDI) measured immediately after reconstitution.

| Sample Name | N (number) | Mean | Margin of error | Min | Max |
|---|---|---|---|---|---|
| ABRAXANE® | 22 | 0.119 | 0.006 | 0.097 | 0.145 |
| Paclitax NAB | 3 | 0.099 | 0.039 | 0.087 | 0.117 |
| Albupax | 5 | 0.117 | 0.011 | 0.109 | 0.132 |
| PacliALL | 5 | 0.166 | 0.060 | 0.118 | 0.241 |
| V5 FP | 3 | 0.127 | 0.027 | 0.118 | 0.139 |
| V1 FP | 3 | 0.092 | 0.079 | 0.071 | 0.129 |
| V2 FP | 3 | 0.128 | 0.059 | 0.109 | 0.155 |
| V3 FP | 3 | 0.111 | 0.041 | 0.093 | 0.126 |
| V4 FP | 3 | 0.098 | 0.024 | 0.088 | 0.107 |

TABLE 7

$D_{V5}$ (nm) measured immediately after reconstitution.

| Sample Name | N (number) | Mean | Margin of error | Min | Max |
|---|---|---|---|---|---|
| ABRAXANE® | 22 | 75.0 | 2.3 | 68.2 | 88.0 |
| Paclitax NAB | 3 | 62.1 | 12.0 | 59.3 | 67.7 |
| Albupax | 5 | 73.4 | 19.8 | 55.2 | 91.8 |
| PacliALL | 5 | 86.7 | 6.1 | 82.1 | 93.6 |
| V5 FP | 3 | 71.7 | 10.1 | 67.7 | 75.8 |
| V1 FP | 3 | 91.1 | 53.4 | 71.4 | 114.0 |
| V2 FP | 3 | 80.7 | 18.1 | 72.3 | 85.2 |
| V3 FP | 3 | 85.6 | 3.7 | 84.2 | 87.2 |
| V4 FP | 3 | 76.2 | 8.9 | 73.3 | 80.2 |

TABLE 8

$D_{V50}$ (nm) measured immediately after reconstitution.

| Sample Name | N (number) | Mean | Margin of error | Min | Max |
|---|---|---|---|---|---|
| ABRAXANE® | 22 | 137.9 | 2.6 | 129 | 148 |
| Paclitax NAB | 3 | 102.8 | 13.8 | 98.3 | 109 |
| Albupax | 5 | 130.6 | 15.3 | 117 | 146 |
| PacliALL | 5 | 192.0 | 25.6 | 168 | 214 |
| V5 FP | 3 | 140.7 | 22.3 | 135 | 151 |
| V1 FP | 3 | 164.0 | 83.1 | 139 | 202 |
| V2 FP | 3 | 160.7 | 17.4 | 154 | 168 |
| V3 FP | 3 | 163.3 | 10.0 | 159 | 167 |
| V4 FP | 3 | 134.3 | 10.0 | 130 | 138 |

TABLE 9

$D_{V95}$ (nm) measured immediately after reconstitution.

| Sample Name | N (number) | Mean | Margin of error | Min | Max |
|---|---|---|---|---|---|
| ABRAXANE® | 22 | 288.4 | 10.1 | 237 | 341 |
| Paclitax NAB | 3 | 207.3 | 23.6 | 198 | 217 |
| Albupax | 5 | 243.2 | 8.5 | 235 | 251 |

TABLE 9-continued $D_{V95}$ (nm) measured immediately after reconstitution.

| Sample Name | N (number) | Mean | Margin of error | Min | Max |
|---|---|---|---|---|---|
| PacliALL | 5 | 1263.0 | 2393.5 | 333 | 4710 |
| V5 FP | 3 | 314.0 | 33.4 | 299 | 325 |
| V1 FP | 3 | 315.3 | 93.2 | 277 | 352 |
| V2 FP | 3 | 344.0 | 123.0 | 294 | 393 |
| V3 FP | 3 | 328.0 | 66.1 | 300 | 353 |
| V4 FP | 3 | 264.3 | 22.5 | 256 | 274 |

TABLE 10

$(D_{V90} - D_{V10})/D_{V50}$ measured immediately after reconstitution.

| Sample Name | N (number) | Mean | Margin of error | Min | Max |
|---|---|---|---|---|---|
| ABRAXANE® | 22 | 1.21 | 0.06 | 0.82 | 1.53 |
| Paclitax NAB | 3 | 1.08 | 0.25 | 0.98 | 1.18 |
| Albupax | 5 | 1.05 | 0.30 | 0.79 | 1.36 |
| PacliALL | 5 | 4.35 | 8.40 | 1.11 | 16.46 |
| V5 FP | 3 | 1.35 | 0.20 | 1.30 | 1.45 |
| V1 FP | 3 | 1.10 | 0.60 | 0.94 | 1.38 |
| V2 FP | 3 | 1.30 | 0.63 | 1.08 | 1.58 |
| V3 FP | 3 | 1.17 | 0.23 | 1.07 | 1.26 |
| V4 FP | 3 | 1.10 | 0.12 | 1.05 | 1.15 |

TABLE 11

Paclitaxel in solution phase (non-nanoparticle portion) as a fraction of total paclitaxel, expressed as a percentage, immediately after reconstitution.

| Sample Name | N (number) | Mean | Margin of error | Min | Max |
|---|---|---|---|---|---|
| ABRAXANE® | 65 | 1.71 | 0.027 | 1.46 | 2.14 |
| Paclitax NAB | 1 | 2.64 | — | 2.64 | 2.64 |
| Albupax | 1 | 1.42 | — | 1.42 | 1.42 |
| PacliALL | 4 | 2.24 | 0.706 | 1.65 | 2.64 |
| V5 FP | 1 | 1.55 | — | 1.55 | 1.55 |
| V1 FP | 1 | 1.51 | — | 1.51 | 1.51 |
| V2 FP | 1 | 1.63 | — | 1.63 | 1.63 |
| V3 FP | 1 | 1.55 | — | 1.55 | 1.55 |
| V4 FP | 1 | 1.59 | — | 1.59 | 1.59 |
| V5 IP | 1 | 0.85 | — | 0.85 | 0.85 |
| V1 IP | 1 | 0.93 | — | 0.93 | 0.93 |
| V2 IP | 1 | 0.69 | — | 0.69 | 0.69 |
| V3 IP | 1 | 0.71 | — | 0.71 | 0.71 |
| V4 IP | 1 | 1.23 | — | 1.23 | 1.23 |

TABLE 12

Paclitaxel in particles (nanoparticle portion) as a fraction of total paclitaxel, expressed as a percentage, immediately after reconstitution.

| Sample Name | N (number) | Mean | Margin of error | Min | Max |
|---|---|---|---|---|---|
| ABRAXANE® | 65 | 98.290 | 0.025 | 97.860 | 98.540 |
| Paclitax NAB | 1 | 97.351 | — | 97.351 | 97.351 |
| Albupax | 1 | 98.575 | — | 98.575 | 98.575 |
| PacliALL | 4 | 97.760 | 0.705 | 97.360 | 98.350 |
| V5 FP | 1 | 98.441 | — | 98.441 | 98.441 |
| V1 FP | 1 | 98.482 | — | 98.482 | 98.482 |
| V2 FP | 1 | 98.365 | — | 98.365 | 98.365 |
| V3 FP | 1 | 98.442 | — | 98.442 | 98.442 |
| V4 FP | 1 | 98.409 | — | 98.409 | 98.409 |
| V5 IP | 1 | 99.1 | — | 99.1 | 99.1 |
| V1 IP | 1 | 99.1 | — | 99.1 | 99.1 |
| V2 IP | 1 | 99.3 | — | 99.3 | 99.3 |
| V3 IP | 1 | 99.3 | — | 99.3 | 99.3 |
| V4 IP | 1 | 98.8 | — | 98.8 | 98.8 |

TABLE 13

Albumin in solution phase (non-nanoparticle portion) as a fraction of total albumin, expressed as a percentage, immediately after reconstitution.

| Sample Name | N (number) | Mean | Margin of error | Min | Max |
|---|---|---|---|---|---|
| ABRAXANE® | 66 | 96.150 | 0.135 | 95.330 | 97.760 |
| Paclitax NAB | 1 | 98.701 | — | 98.701 | 98.701 |
| Albupax | 1 | 96.648 | — | 96.648 | 96.648 |
| PacliALL | 4 | 98.450 | 0.175 | 98.360 | 98.600 |
| V5 FP | 1 | 97.094 | — | 97.094 | 97.094 |
| V1 FP | 1 | 98.033 | — | 98.033 | 98.033 |
| V2 FP | 1 | 97.961 | — | 97.961 | 97.961 |
| V3 FP | 1 | 96.846 | — | 96.846 | 96.846 |
| V4 FP | 1 | 96.033 | — | 96.033 | 96.033 |
| V5 IP | 1 | 94.1 | — | 94.1 | 94.1 |
| V1 IP | 1 | 96.9 | — | 96.9 | 96.9 |
| V2 IP | 1 | 71.0 | — | 71.0 | 71.0 |
| V3 IP | 1 | 90.8 | — | 90.8 | 90.8 |
| V4 IP | 1 | 95.6 | — | 95.6 | 95.6 |

TABLE 14

Albumin in particles (nanoparticle portion) as a fraction of total albumin, expressed as a percentage, immediately after reconstitution.

| Sample Name | N (number) | Mean | Margin of error | Min | Max |
|---|---|---|---|---|---|
| ABRAXANE® | 66 | 3.846 | 0.134 | 2.240 | 4.670 |
| Paclitax NAB | 1 | 1.299 | — | 1.299 | 1.299 |
| Albupax | 1 | 3.352 | — | 3.352 | 3.352 |
| PacliALL | 4 | 1.555 | 0.173 | 1.400 | 1.640 |
| V5 FP | 1 | 2.906 | — | 2.906 | 2.906 |
| V1 FP | 1 | 1.967 | — | 1.967 | 1.967 |
| V2 FP | 1 | 2.039 | — | 2.039 | 2.039 |
| V3 FP | 1 | 3.154 | — | 3.154 | 3.154 |
| V4 FP | 1 | 3.967 | — | 3.967 | 3.967 |
| V5 IP | 1 | 5.9 | — | 5.9 | 5.9 |
| V1 IP | 1 | 3.1 | — | 3.1 | 3.1 |
| V2 IP | 1 | 29.0 | — | 29.0 | 29.0 |
| V3 IP | 1 | 9.2 | — | 9.2 | 9.2 |
| V4 IP | 1 | 4.4 | — | 4.4 | 4.4 |

TABLE 15

Concentration of free (in solution phase) paclitaxel (μg/ml) in the composition immediately after reconstitution.

| Sample Name | N (number) | Mean | Margin of error | Min | Max |
|---|---|---|---|---|---|
| ABRAXANE® | 65 | 80.6 | 1.2 | 68.4 | 94.2 |
| Paclitax NAB | 1 | 125.0 | — | 125.0 | 125.0 |
| Albupax | 1 | 71.5 | — | 71.5 | 71.5 |
| PacliALL | 4 | 101.1 | 30.6 | 73.9 | 116.1 |
| V5 FP | 1 | 75.0 | — | 75.0 | 75.0 |
| V1 FP | 1 | 70.4 | — | 70.4 | 70.4 |
| V2 FP | 1 | 71.6 | — | 71.6 | 71.6 |
| V3 FP | 1 | 70.6 | — | 70.6 | 70.6 |
| V4 FP | 1 | 77.5 | — | 77.5 | 77.5 |
| V5 IP | 1 | 130.4 | — | 130.4 | 130.4 |
| V1 IP | 1 | 115.8 | — | 115.8 | 115.8 |
| V2 IP | 1 | 71.2 | — | 71.2 | 71.2 |
| V3 IP | 1 | 102.0 | — | 102.0 | 102.0 |
| V4 IP | 1 | 125.0 | — | 125.0 | 125.0 |

TABLE 16

Concentration of bound (in particles/nanoparticle portion) paclitaxel (µg/ml) in the composition immediately after reconstitution.

| Sample Name | N (number) | Mean | Margin of error | Min | Max |
|---|---|---|---|---|---|
| ABRAXANE ® | 66 | 4624 | 45 | 4156 | 5147 |
| Paclitax NAB | 1 | 4594 | — | 4594 | 4594 |
| Albupax | 1 | 4945 | — | 4945 | 4945 |
| PacliALL | 4 | 4405 | 176 | 4281 | 4547 |
| V5 FP | 1 | 4737 | — | 4737 | 4737 |
| V1 FP | 1 | 4568 | — | 4568 | 4568 |
| V2 FP | 1 | 4307 | — | 4307 | 4307 |
| V3 FP | 1 | 4461 | — | 4461 | 4461 |
| V4 FP | 1 | 4795 | — | 4795 | 4795 |
| V5 IP | 1 | 15058.0 | — | 15058.0 | 15058.0 |
| V1 IP | 1 | 12282.4 | — | 12282.4 | 12282.4 |
| V2 IP | 1 | 10164.6 | — | 10164.6 | 10164.6 |
| V3 IP | 1 | 14152.6 | — | 14152.6 | 14152.6 |
| V4 IP | 1 | 9967.2 | — | 9967.2 | 9967.2 |

TABLE 17

Concentration of free (in solution phase) albumin (mg/ml) in the composition immediately after reconstitution.

| Sample Name | N (number) | Mean | Margin of error | Min | Max |
|---|---|---|---|---|---|
| ABRAXANE ® | 66 | 39.0 | 0.485 | 34.9 | 46.4 |
| Paclitax NAB | 1 | 60.8 | — | 60.8 | 60.8 |
| Albupax | 1 | 34.4 | — | 34.4 | 34.4 |
| PacliALL | 4 | 42.7 | 1.005 | 41.8 | 43.3 |
| V5 FP | 1 | 40.1 | — | 40.1 | 40.1 |
| V1 FP | 1 | 36.6 | — | 36.6 | 36.6 |
| V2 FP | 1 | 44.5 | — | 44.5 | 44.5 |
| V3 FP | 1 | 36.9 | — | 36.9 | 36.9 |
| V4 FP | 1 | 37.4 | — | 37.4 | 37.4 |
| V5 IP | 1 | 51.4 | — | 51.4 | 51.4 |
| V1 IP | 1 | 47.8 | — | 47.8 | 47.8 |
| V2 IP | 1 | 7.3 | — | 7.3 | 7.3 |
| V3 IP | 1 | 52.9 | — | 52.9 | 52.9 |
| V4 IP | 1 | 51.5 | — | 51.5 | 51.5 |

TABLE 18

Concentration of bound (in particles/nanoparticle portion) albumin (mg/ml) in the composition immediately after reconstitution.

| Sample Name | N (number) | Mean | Margin of error | Min | Max |
|---|---|---|---|---|---|
| ABRAXANE ® | 66 | 1.555 | 0.052 | 0.800 | 1.900 |
| Paclitax NAB | 1 | 0.800 | — | 0.800 | 0.800 |
| Albupax | 1 | 1.193 | — | 1.193 | 1.193 |
| PacliALL | 4 | 0.676 | 0.087 | 0.595 | 0.715 |
| V5 FP | 1 | 1.199 | — | 1.199 | 1.199 |
| V1 FP | 1 | 0.735 | — | 0.735 | 0.735 |
| V2 FP | 1 | 0.926 | — | 0.926 | 0.926 |
| V3 FP | 1 | 1.201 | — | 1.201 | 1.201 |
| V4 FP | 1 | 1.544 | — | 1.544 | 1.544 |
| V5 IP | 1 | 3.234 | — | 3.234 | 3.234 |
| V1 IP | 1 | 1.520 | — | 1.520 | 1.520 |
| V2 IP | 1 | 2.996 | — | 2.996 | 2.996 |
| V3 IP | 1 | 5.376 | — | 5.376 | 5.376 |
| V4 IP | 1 | 2.382 | — | 2.382 | 2.382 |

TABLE 19

Albumin as a percentage of the nanoparticle mass immediately after reconstitution.

| Sample Name | N (number) | Mean | Margin of error | Min | Max |
|---|---|---|---|---|---|
| ABRAXANE ® | 30 | 24.0 | 1.4 | 13.6 | 29.0 |
| Paclitax NAB | 1 | 14.8 | — | 14.8 | 14.8 |
| Albupax | 1 | 19.4 | — | 19.4 | 19.4 |
| PacliALL | 4 | 13.3 | 1.7 | 11.9 | 14.3 |
| V5 FP | 1 | 20.2 | — | 20.2 | 20.2 |
| V1 FP | 1 | 13.9 | — | 13.9 | 13.9 |
| V2 FP | 1 | 17.7 | — | 17.7 | 17.7 |
| V3 FP | 1 | 21.2 | — | 21.2 | 21.2 |
| V4 FP | 1 | 24.4 | — | 24.4 | 24.4 |
| V5 IP | 1 | 17.7 | — | 17.7 | 17.7 |
| V1 IP | 1 | 11.0 | — | 11.0 | 11.0 |
| V2 IP | 1 | 22.8 | — | 22.8 | 22.8 |
| V3 IP | 1 | 27.5 | — | 27.5 | 27.5 |
| V4 IP | 1 | 19.3 | — | 19.3 | 19.3 |

Figure 8:
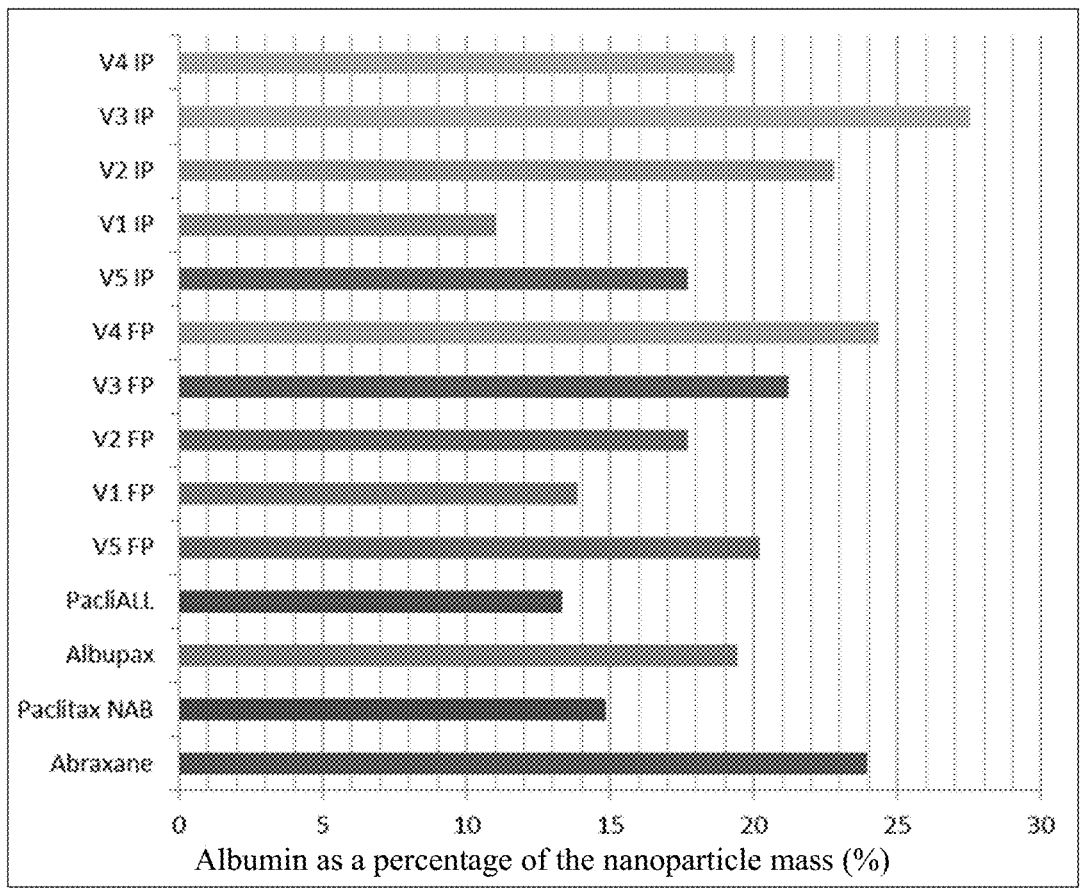
FIG. 8 shows a bar graph of the albumin as a percentage of the nanoparticle mass.

A comparison of the albumin as a percentage of the nanoparticle mass (Table 19) is illustrated in the bar graph of FIG. 8. Amongst all the compositions, ABRAXANE® and Paclitax NAB are most stable.

TABLE 20

Paclitaxel as a percentage of the nanoparticle mass immediately after reconstitution.

| Sample Name | N (number) | Mean | Margin of error | Min | Max |
|---|---|---|---|---|---|
| ABRAXANE ® | 30 | 76.1 | 1.435 | 71.0 | 86.4 |
| Paclitax NAB | 1 | 85.2 | — | 85.2 | 85.2 |
| Albupax | 1 | 80.6 | — | 80.6 | 80.6 |
| PacliALL | 4 | 86.7 | 1.695 | 85.7 | 88.1 |
| V5 FP | 1 | 79.8 | — | 79.8 | 79.8 |
| V1 FP | 1 | 86.1 | — | 86.1 | 86.1 |
| V2 FP | 1 | 82.3 | — | 82.3 | 82.3 |
| V3 FP | 1 | 78.8 | — | 78.8 | 78.8 |
| V4 FP | 1 | 75.6 | — | 75.6 | 75.6 |
| V5 IP | 1 | 82 | — | 82 | 82 |
| V1 IP | 1 | 89 | — | 89 | 89 |
| V2 IP | 1 | 77 | — | 77 | 77 |
| V3 IP | 1 | 72 | — | 72 | 72 |
| V4 IP | 1 | 81 | — | 81 | 81 |

TABLE 21

Percentage of albumin in the form of monomers on the nanoparticles.

| Sample Name | N (number) | Mean | Margin of error | Min | Max |
|---|---|---|---|---|---|
| ABRAXANE ® | 66 | 47.1 | 2.5 | 20.3 | 66.9 |
| Paclitax NAB | 1 | 44.8 | — | 44.8 | 44.8 |
| Albupax | 1 | 55.6 | — | 55.6 | 55.6 |
| PacliALL | 4 | 54.1 | 20.2 | 40.7 | 70.9 |
| V5 FP | 1 | 68.5 | — | 68.5 | 68.5 |
| V1 FP | 1 | 72.8 | — | 72.8 | 72.8 |
| V2 FP | 1 | 61.9 | — | 61.9 | 61.9 |
| V3 FP | 1 | 56.3 | — | 56.3 | 56.3 |
| V4 FP | 1 | 63.5 | — | 63.5 | 63.5 |
| V5 IP | 1 | 66.1 | — | 66.1 | 66.1 |
| V1 IP | 1 | 78.1 | — | 78.1 | 78.1 |
| V2 IP | 1 | 51.9 | — | 51.9 | 51.9 |
| V3 IP | 1 | 55.7 | — | 55.7 | 55.7 |
| V4 IP | 1 | 69.9 | — | 69.9 | 69.9 |

Figure 9:
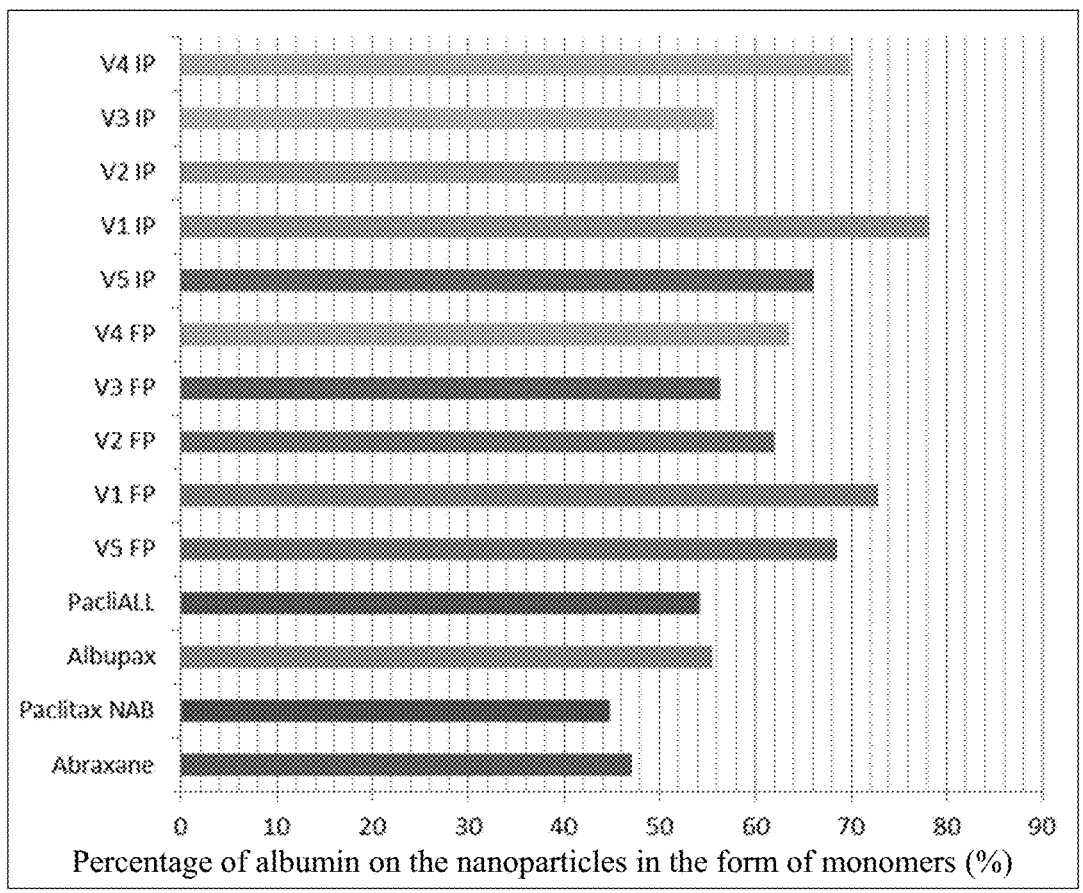
FIG. 9 shows a bar graph of the percentage of albumin on the nanoparticles in the form of monomers.

A comparison of the percentage of albumin on the nanoparticles in the form of monomers (Table 21) is illustrated in the bar graph of FIG. 9. Amongst all the compositions, ABRAXANE® and Paclitax NAB are most stable.

TABLE 22

Percentage of albumin in the form of dimers on the nanoparticles.

| Sample Name | N (number) | Mean | Margin of error | Min | Max |
|---|---|---|---|---|---|
| ABRAXANE ® | 66 | 17.8 | 1.1 | 6.7 | 25.7 |
| Paclitax NAB | 1 | 19.4 | — | 19.4 | 19.4 |
| Albupax | 1 | 16.5 | — | 16.5 | 16.5 |
| PacliALL | 4 | 21.9 | 6.0 | 16.6 | 25.1 |
| V5 FP | 1 | 11.0 | — | 11.0 | 11.0 |
| V1 FP | 1 | 11.3 | — | 11.3 | 11.3 |
| V2 FP | 1 | 12.9 | — | 12.9 | 12.9 |
| V3 FP | 1 | 8.0 | — | 8.0 | 8.0 |
| V4 FP | 1 | 9.8 | — | 9.8 | 9.8 |
| V5 IP | 1 | 13.5 | — | 13.5 | 13.5 |
| V1 IP | 1 | 10.9 | — | 10.9 | 10.9 |
| V2 IP | 1 | 21.0 | — | 21.0 | 21.0 |
| V3 IP | 1 | 11.6 | — | 11.6 | 11.6 |
| V4 IP | 1 | 10.8 | — | 10.8 | 10.8 |

Figure 10:
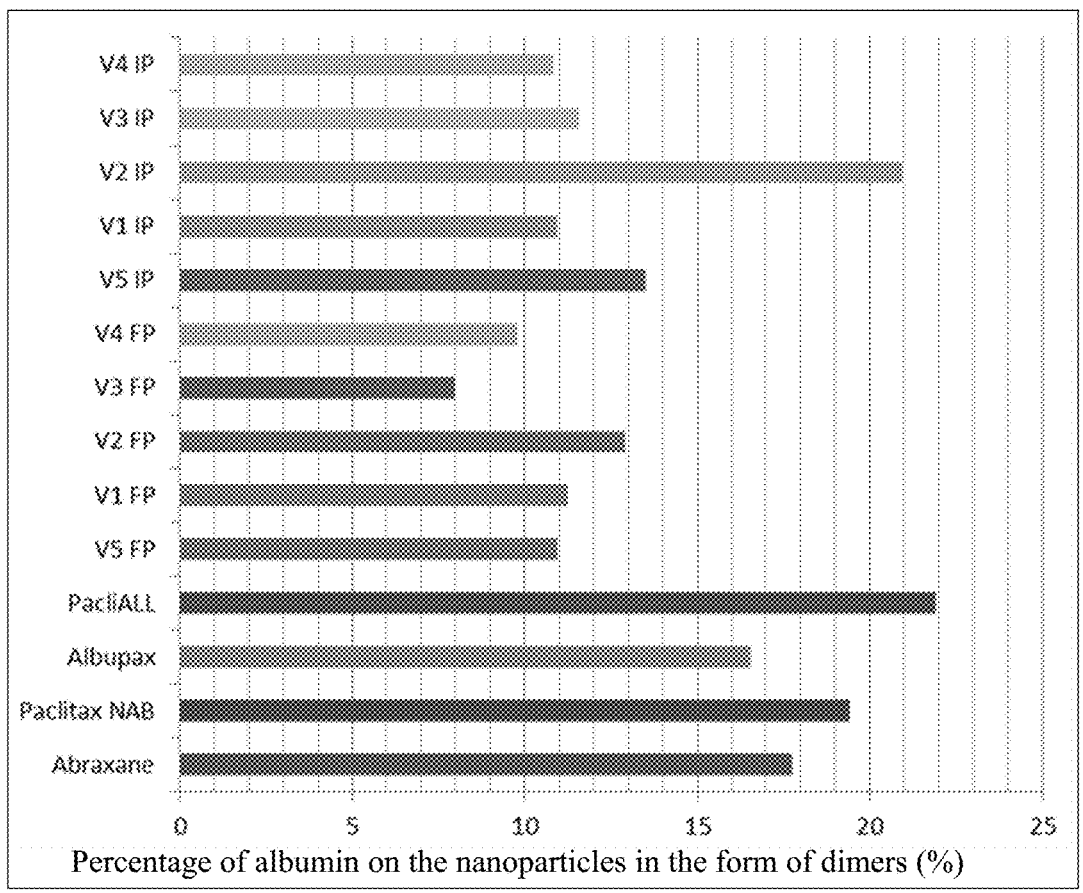
FIG. 10 shows a bar graph of the percentage of albumin on the nanoparticles in the form of dimers.

A comparison of the percentage of albumin on the nanoparticles in the form of dimers (Table 22) is illustrated in the bar graph of FIG. 10. Amongst all the compositions, the nab-paclitaxel sold under the trademark ABRAXANE® and Paclitax NAB are most stable.

TABLE 23

Percentage of albumin in the form of oligomers on the nanoparticles.

| Sample Name | N (number) | Mean | Margin of error | Min | Max |
|---|---|---|---|---|---|
| ABRAXANE ® | 66 | 7.9 | 0.9 | 3.1 | 16.5 |
| Paclitax NAB | 1 | 12.3 | — | 12.3 | 12.3 |
| Albupax | 1 | 9.1 | — | 9.1 | 9.1 |
| PacliALL | 4 | 13.4 | 6.8 | 8.3 | 17.2 |
| V5 FP | 1 | 3.2 | — | 3.2 | 3.2 |
| V1 FP | 1 | 3.3 | — | 3.3 | 3.3 |
| V2 FP | 1 | 4.0 | — | 4.0 | 4.0 |
| V3 FP | 1 | 2.6 | — | 2.6 | 2.6 |
| V4 FP | 1 | 2.7 | — | 2.7 | 2.7 |
| V5 IP | 1 | 5.4 | — | 5.4 | 5.4 |
| V1 IP | 1 | 3.0 | — | 3.0 | 3.0 |
| V2 IP | 1 | 10.4 | — | 10.4 | 10.4 |
| V3 IP | 1 | 2.7 | — | 2.7 | 2.7 |
| V4 IP | 1 | 3.4 | — | 3.4 | 3.4 |

Figure 11:
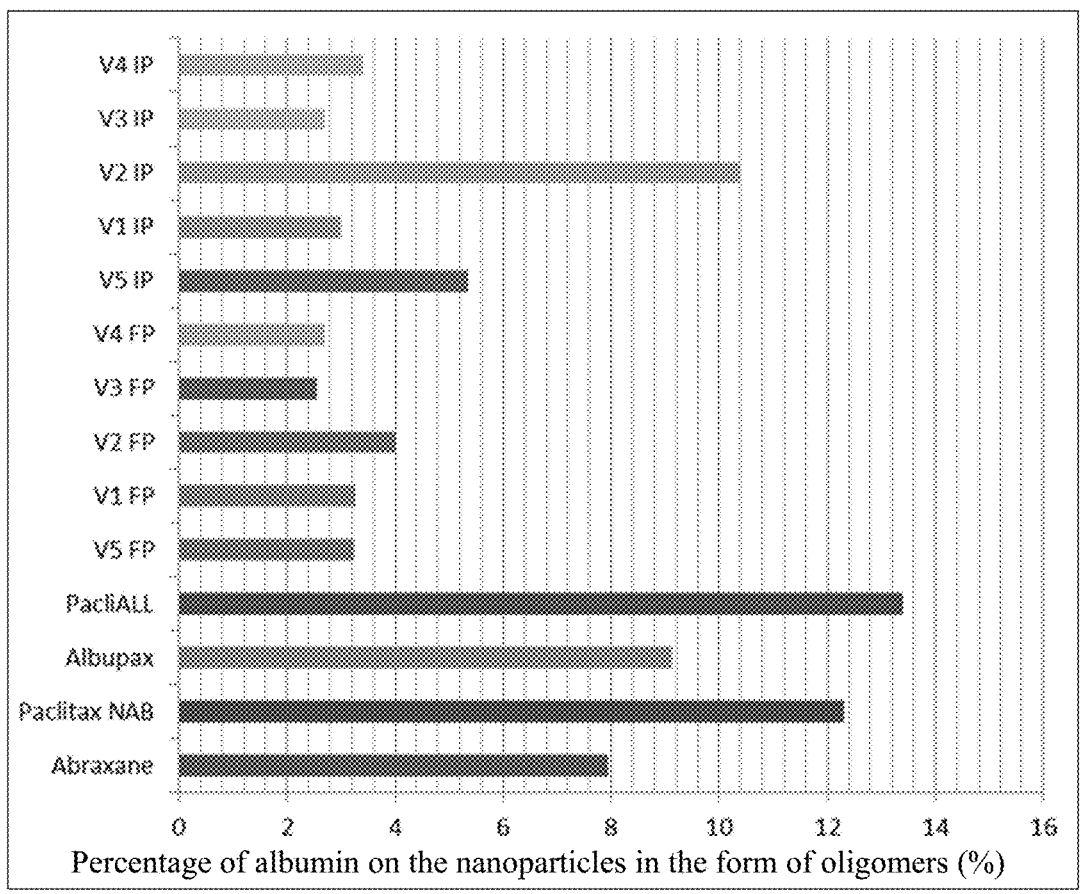
FIG. 11 shows a bar graph of the percentage of albumin on the nanoparticles in the form of oligomers.

A comparison of the percentage of albumin on the nanoparticles in the form of oligomers (Table 23) is illustrated in the bar graph of FIG. 11. Amongst all the compositions, the nab-paclitaxel sold under the trademark ABRAXANE® and Paclitax NAB are most stable.

TABLE 24

Percentage of albumin in the form of polymers on the nanoparticles.

| Sample Name | N (number) | Mean | Margin of error | Min | Max |
|---|---|---|---|---|---|
| ABRAXANE ® | 66 | 27.2 | 2.5 | 10.7 | 69.0 |
| Paclitax NAB | 1 | 23.5 | — | 23.5 | 23.5 |
| Albupax | 1 | 18.8 | — | 18.8 | 18.8 |
| PacliALL | 4 | 10.6 | 9.6 | 4.3 | 18.5 |
| V5 FP | 1 | 17.3 | — | 17.3 | 17.3 |
| V1 FP | 1 | 12.7 | — | 12.7 | 12.7 |
| V2 FP | 1 | 21.1 | — | 21.1 | 21.1 |
| V3 FP | 1 | 33.2 | — | 33.2 | 33.2 |
| V4 FP | 1 | 24.0 | — | 24.0 | 24.0 |
| V5 IP | 1 | 15.0 | — | 15.0 | 15.0 |
| V1 IP | 1 | 8.0 | — | 8.0 | 8.0 |
| V2 IP | 1 | 16.8 | — | 16.8 | 16.8 |
| V3 IP | 1 | 30.1 | — | 30.1 | 30.1 |
| V4 IP | 1 | 15.9 | — | 15.9 | 15.9 |

Figure 12:
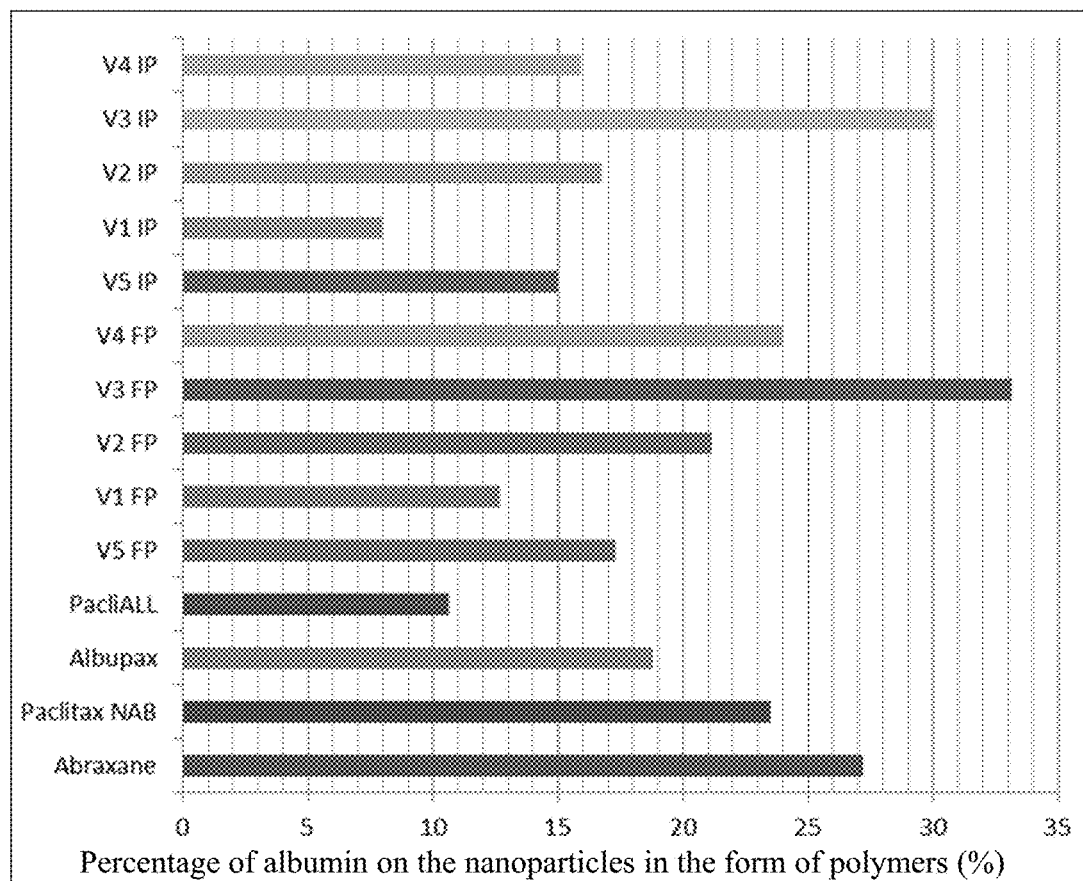
FIG. 12 shows a bar graph of the percentage of albumin on the nanoparticles in the form of polymers.

A comparison of the percentage of albumin on the nanoparticles in the form of polymers (Table 24) is illustrated in the bar graph of FIG. 12. Amongst all the compositions, the nab-paclitaxel sold under the trademark ABRAXANE® and Paclitax NAB are most stable.

Using the measurements of albumin in the form of monomers (M), dimers (D), oligomers (O), and polymers (P) on the nanoparticles, composition attributes were calculated as reported in Table 25.

TABLE 25

Summary of attributes calculated for albumin forms on the nanoparticles in the compositions.

| Sample Name | D/M | O/M | P/M | (P + O)/M | (P + O)/(M − D) | M + D | M − D | M + O | M + P | M − P | D + O | D + P | O + P | P/D | O/D | P/O |
|---|---|---|---|---|---|---|---|---|---|---|---|---|---|---|---|---|
| ABRAXANE ® | 37.7 | 16.8 | 57.7 | 74.6 | 119.7 | 64.9 | 29.4 | 55.1 | 74.3 | 19.9 | 25.7 | 45.0 | 35.1 | 153.3 | 44.7 | 343.0 |
| Paclitax NAB | 43.3 | 27.5 | 52.5 | 79.9 | 140.9 | 64.2 | 25.4 | 57.1 | 68.3 | 21.3 | 31.7 | 42.9 | 35.8 | 121.1 | 63.4 | 191.1 |
| Albupax | 29.8 | 16.4 | 33.8 | 50.2 | 71.5 | 72.1 | 39.0 | 64.7 | 74.3 | 36.8 | 25.7 | 35.3 | 27.9 | 113.5 | 55.1 | 205.9 |
| PacliALL | 40.5 | 24.8 | 19.6 | 44.4 | 74.6 | 76.0 | 32.2 | 67.5 | 64.8 | 43.5 | 35.3 | 32.5 | 24.0 | 48.5 | 61.2 | 79.3 |
| V5 FP | 16.0 | 4.7 | 25.3 | 30.0 | 35.7 | 79.5 | 57.6 | 71.7 | 85.8 | 51.2 | 14.2 | 28.3 | 20.5 | 157.8 | 29.5 | 535.6 |
| V1 FP | 15.5 | 4.5 | 17.4 | 21.9 | 25.9 | 84.0 | 61.5 | 76.0 | 85.5 | 60.1 | 14.5 | 24.0 | 16.0 | 112.7 | 29.0 | 389.3 |
| V2 FP | 20.9 | 6.5 | 34.1 | 40.6 | 51.4 | 74.8 | 49.0 | 65.9 | 83.1 | 40.8 | 17.0 | 34.1 | 25.2 | 163.5 | 31.1 | 525.9 |
| V3 FP | 14.2 | 4.5 | 58.9 | 63.4 | 73.9 | 64.3 | 48.3 | 58.9 | 89.5 | 23.2 | 10.5 | 41.1 | 35.7 | 416.1 | 32.1 | 1295.3 |
| V4 FP | 15.4 | 4.2 | 37.8 | 42.0 | 49.7 | 73.3 | 53.7 | 66.2 | 87.5 | 39.5 | 12.5 | 33.8 | 26.7 | 244.5 | 27.4 | 891.8 |
| V5 IP | 20.4 | 8.1 | 22.7 | 30.8 | 38.7 | 79.6 | 52.7 | 71.5 | 81.2 | 51.1 | 18.9 | 28.5 | 20.4 | 111.3 | 39.7 | 280.0 |
| V1 IP | 14.0 | 3.8 | 10.2 | 14.0 | 16.3 | 89.0 | 67.2 | 81.1 | 86.1 | 70.2 | 13.9 | 18.9 | 11.0 | 72.7 | 27.4 | 265.0 |
| V2 IP | 40.4 | 20.0 | 32.3 | 52.3 | 87.6 | 72.9 | 31.0 | 62.3 | 68.7 | 35.2 | 31.3 | 37.7 | 27.1 | 80.0 | 49.5 | 161.4 |
| V3 IP | 20.8 | 4.8 | 54.0 | 58.8 | 74.3 | 67.2 | 44.1 | 58.4 | 85.8 | 25.6 | 14.3 | 41.6 | 32.8 | 260.1 | 23.3 | 1117.8 |
| V4 IP | 15.5 | 4.9 | 22.7 | 27.6 | 32.7 | 80.7 | 59.0 | 73.3 | 85.8 | 54.0 | 14.2 | 26.7 | 19.3 | 146.7 | 31.5 | 466.0 |

Figure 13:
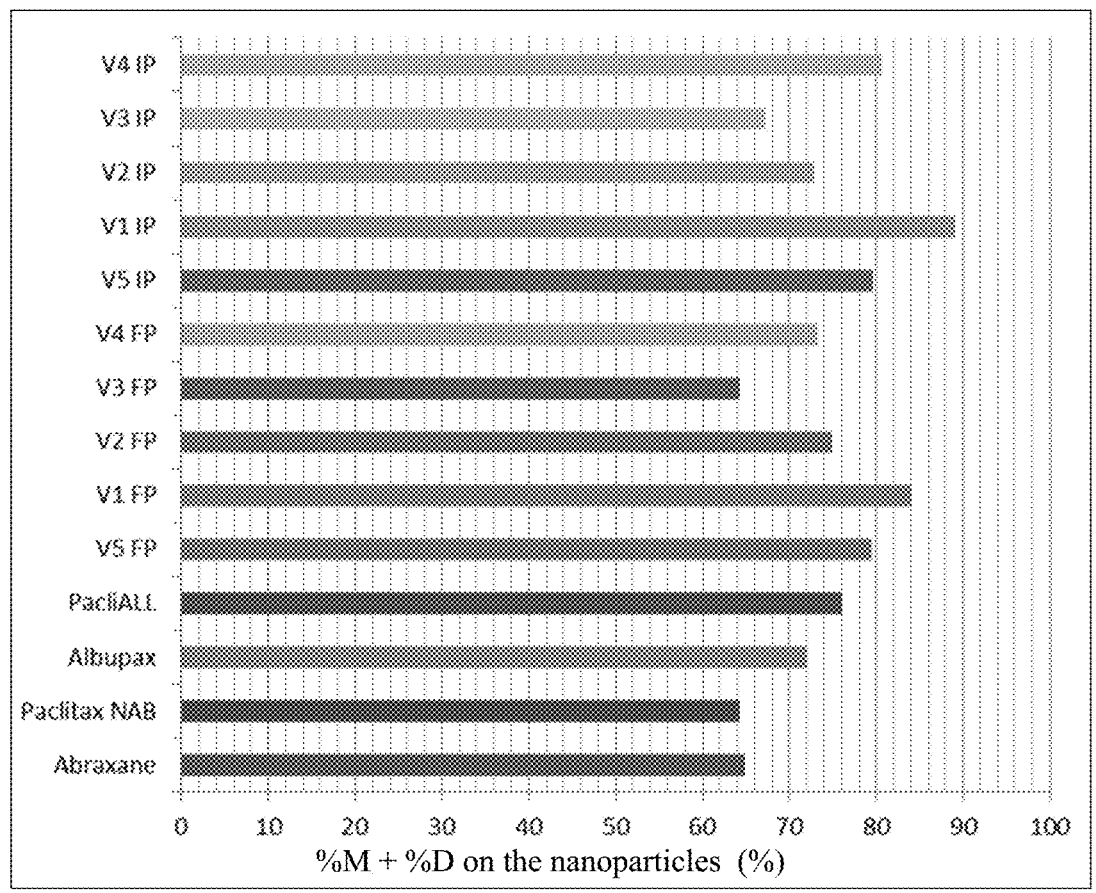
FIG. 13 shows a bar graph of the percentage of albumin on the nanoparticles in the form of monomers (M) and dimers (D).

A comparison of the percentage of albumin on the nanoparticles in the form of monomers (M) and dimers (D) (Table 25) is illustrated in the bar graph of FIG. 13. Amongst all the compositions, the nab-paclitaxel sold under the trademark ABRAXANE® and Paclitax NAB are most stable.

Figure 14:
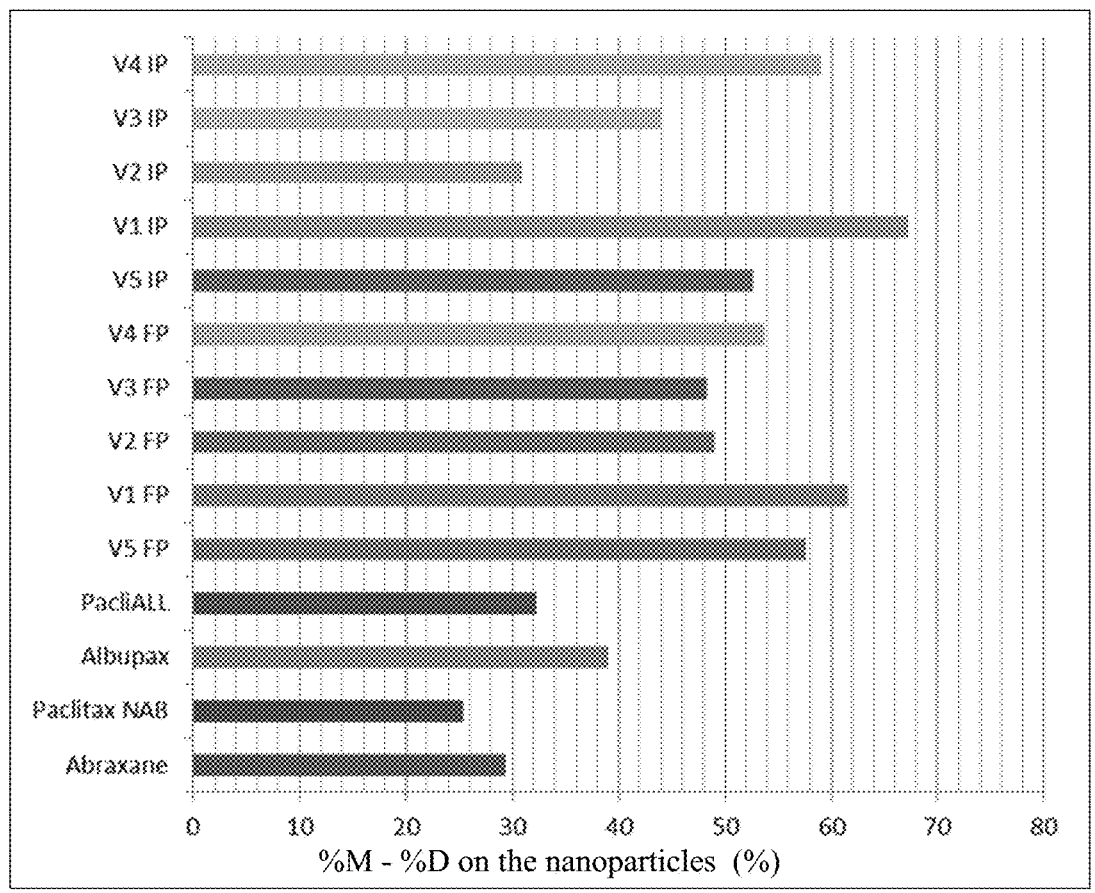
FIG. 14 shows a bar graph of the percentage of albumin on the nanoparticles in the form of monomers (M) minus the percentage of albumin on the nanoparticles in the form of dimers (D).

A comparison of the percentage of albumin on the nanoparticles in the form of monomers (M) minus the percentage of albumin on the nanoparticles in the form of dimers (D) (Table 25) is illustrated in the bar graph of FIG. 14. Amongst all the compositions, the nab-paclitaxel sold under the trademark ABRAXANE® and Paclitax NAB are most stable.

Figure 15:
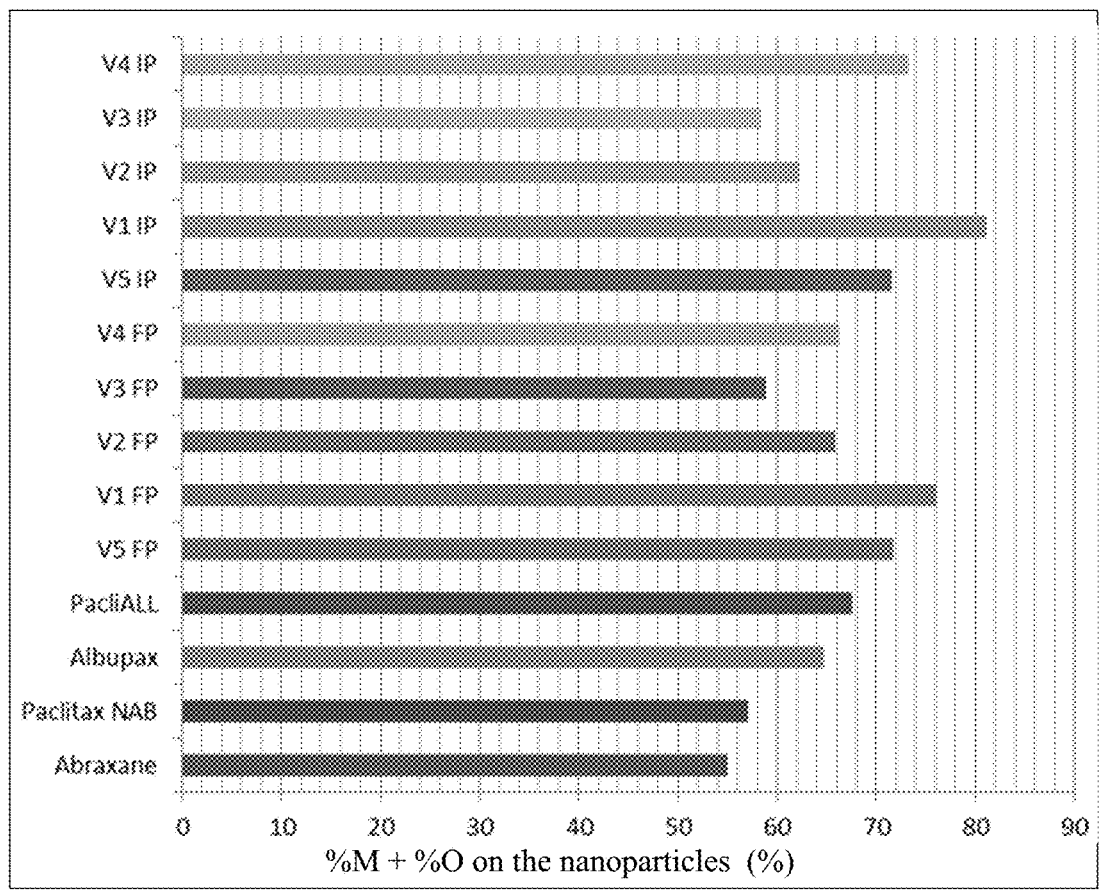
FIG. 15 shows a bar graph of the percentage of albumin on the nanoparticles in the form of monomers (M) and oligomers (O).

A comparison of the percentage of albumin on the nanoparticles in the form of monomers (M) and oligomers (O) (Table 25) is illustrated in the bar graph of FIG. 15. Amongst all the compositions, the nab-paclitaxel sold under the trademark ABRAXANE® and Paclitax NAB are most stable.

Figure 16:
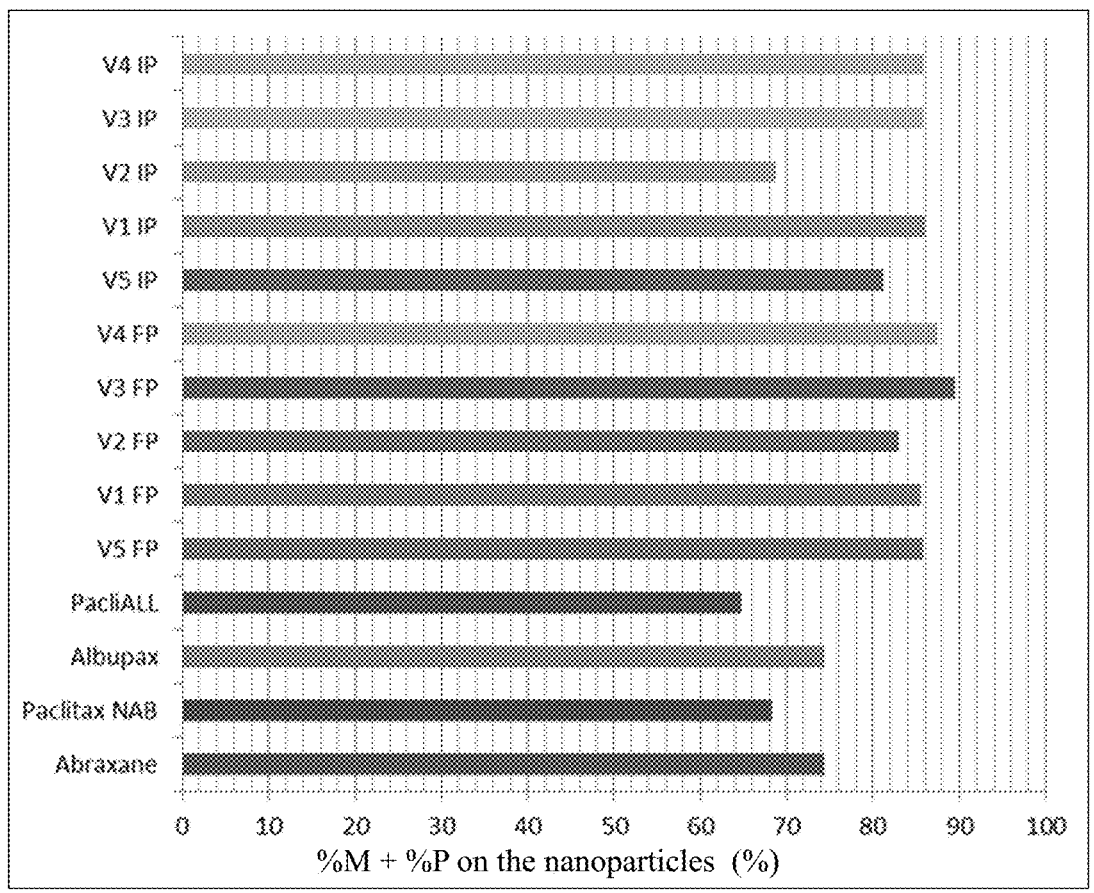
FIG. 16 shows a bar graph of the percentage of albumin on the nanoparticles in the form of monomers (M) and polymers (P).

A comparison of the percentage of albumin on the nanoparticles in the form of monomers (M) and polymers (P) (Table 25) is illustrated in the bar graph of FIG. 16. Amongst all the compositions, the nab-paclitaxel sold under the trademark ABRAXANE® and Paclitax NAB are most stable.

Figure 17:
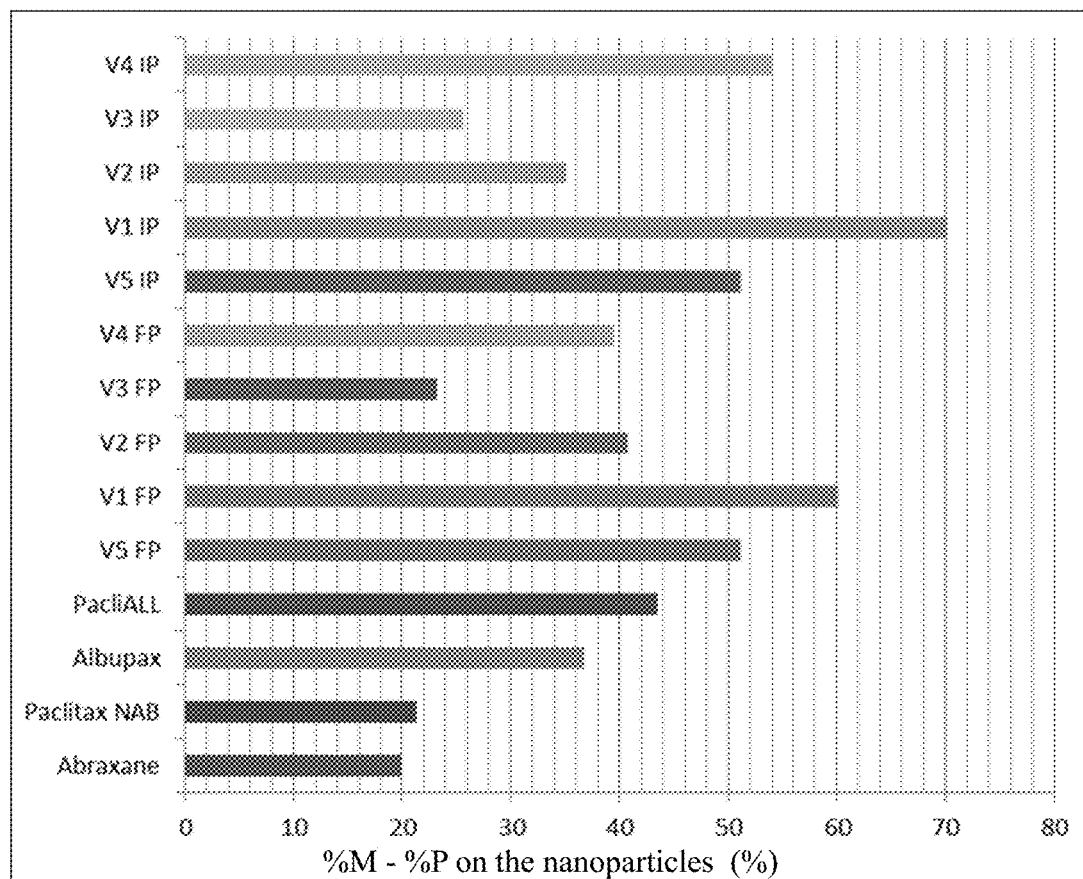
FIG. 17 shows a bar graph of the percentage of albumin on the nanoparticles in the form of monomers (M) minus the percentage of albumin on the nanoparticles in the form of polymers (P).

A comparison of the percentage of albumin on the nanoparticles in the form of monomers (M) minus the percentage of albumin on the nanoparticles in the form of polymers (P) (Table 25) is illustrated in the bar graph of FIG. 17. Amongst all the compositions, the nab-paclitaxel sold under the trademark ABRAXANE® and Paclitax NAB are most stable.

Figure 18:
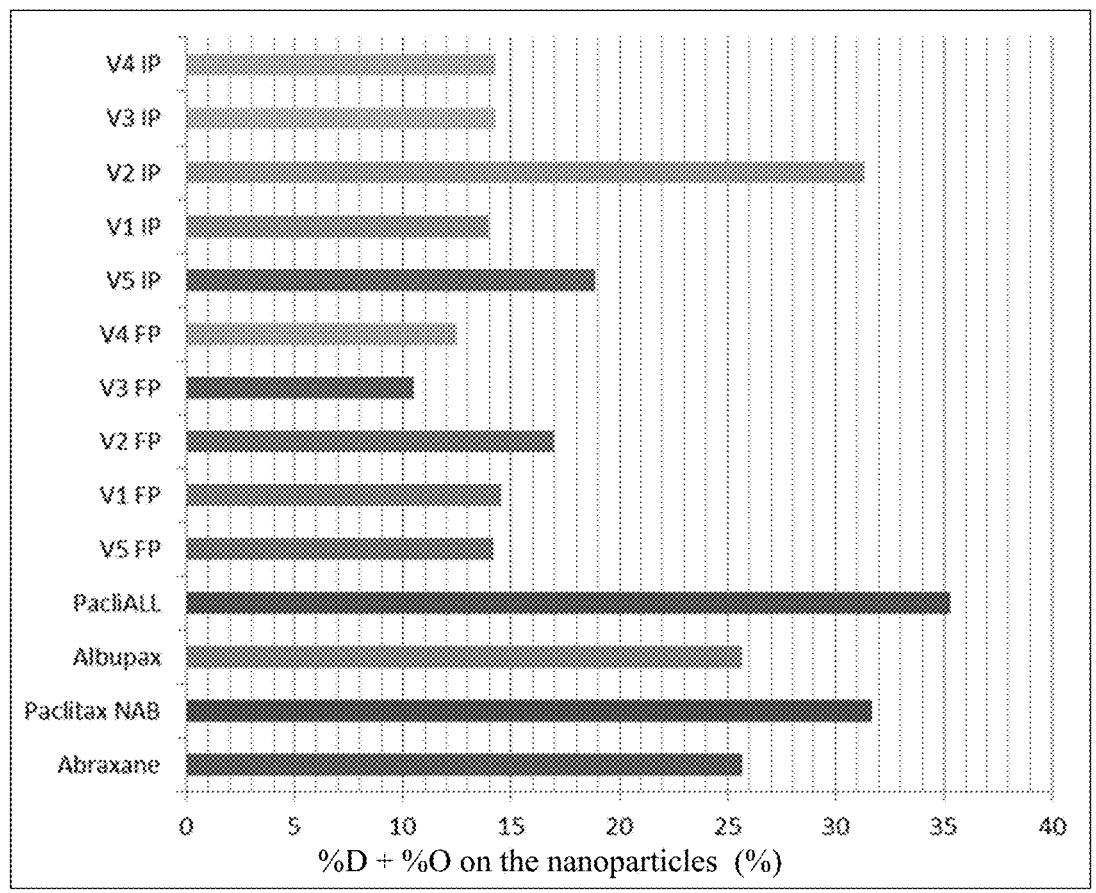
FIG. 18 shows a bar graph of the percentage of albumin on the nanoparticles in the form of dimers (D) and oligomers (O).

A comparison of the percentage of albumin on the nanoparticles in the form of dimers (D) and oligomers (O) (Table 25) is illustrated in the bar graph of FIG. 18. Amongst all the compositions, the nab-paclitaxel sold under the trademark ABRAXANE® and Paclitax NAB are most stable.

Figure 19:
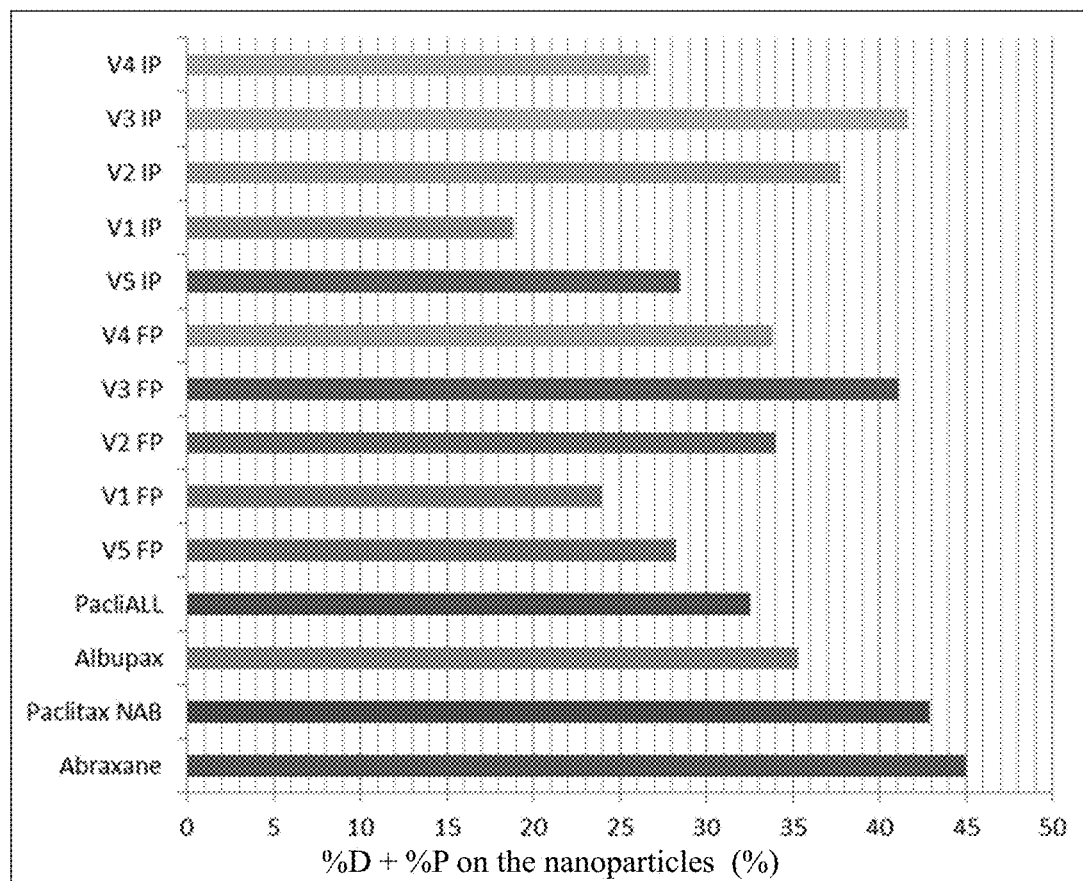
FIG. 19 shows a bar graph of the percentage of albumin on the nanoparticles in the form of dimers (D) and polymers (P).

A comparison of the percentage of albumin on the nanoparticles in the form of dimers (D) and polymers (P) (Table 25) is illustrated in the bar graph of FIG. 19. Amongst all the compositions, the nab-paclitaxel sold under the trademark ABRAXANE® and Paclitax NAB are most stable.

Figure 20:
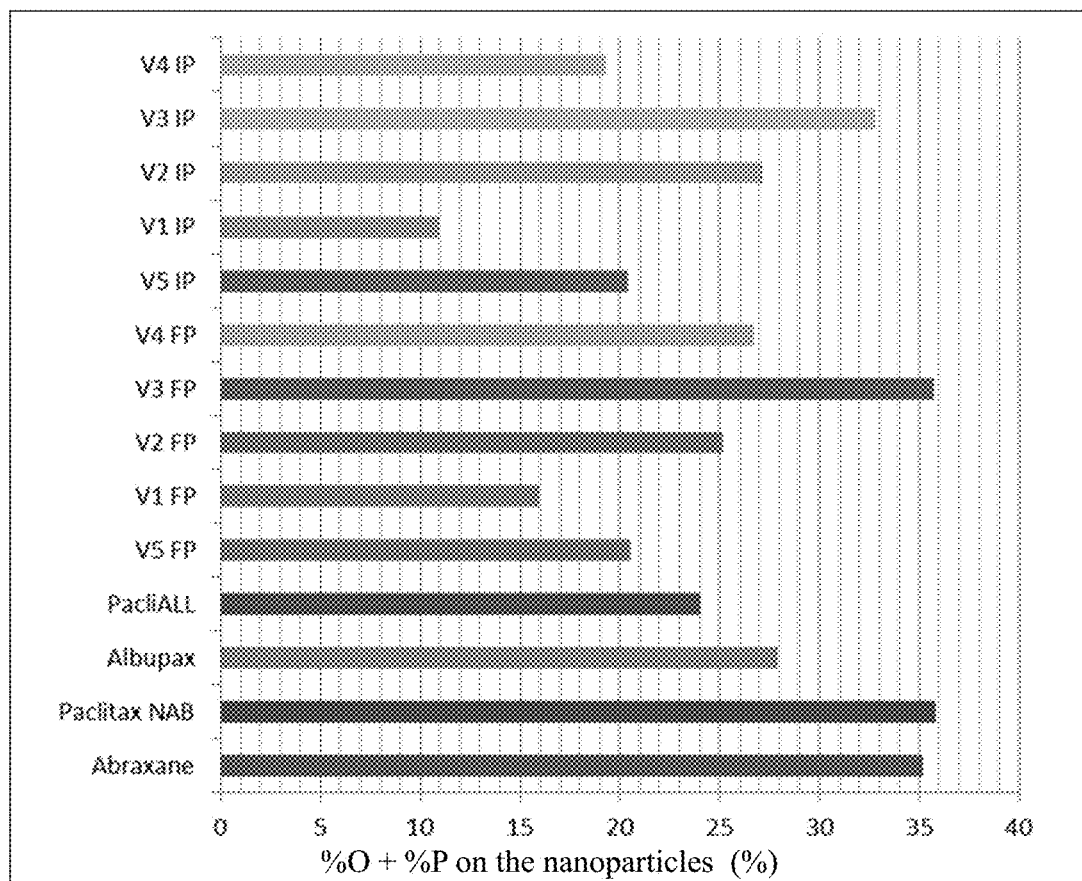
FIG. 20 shows a bar graph of the percentage of albumin on the nanoparticles in the form of oligomers (O) and polymers (P).

A comparison of the percentage of albumin on the nanoparticles in the form of oligomers (O) and polymers (P) (Table 25) is illustrated in the bar graph of FIG. 20. Amongst all the compositions, the nab-paclitaxel sold under the trademark ABRAXANE® and Paclitax NAB are most stable.

Figure 21:
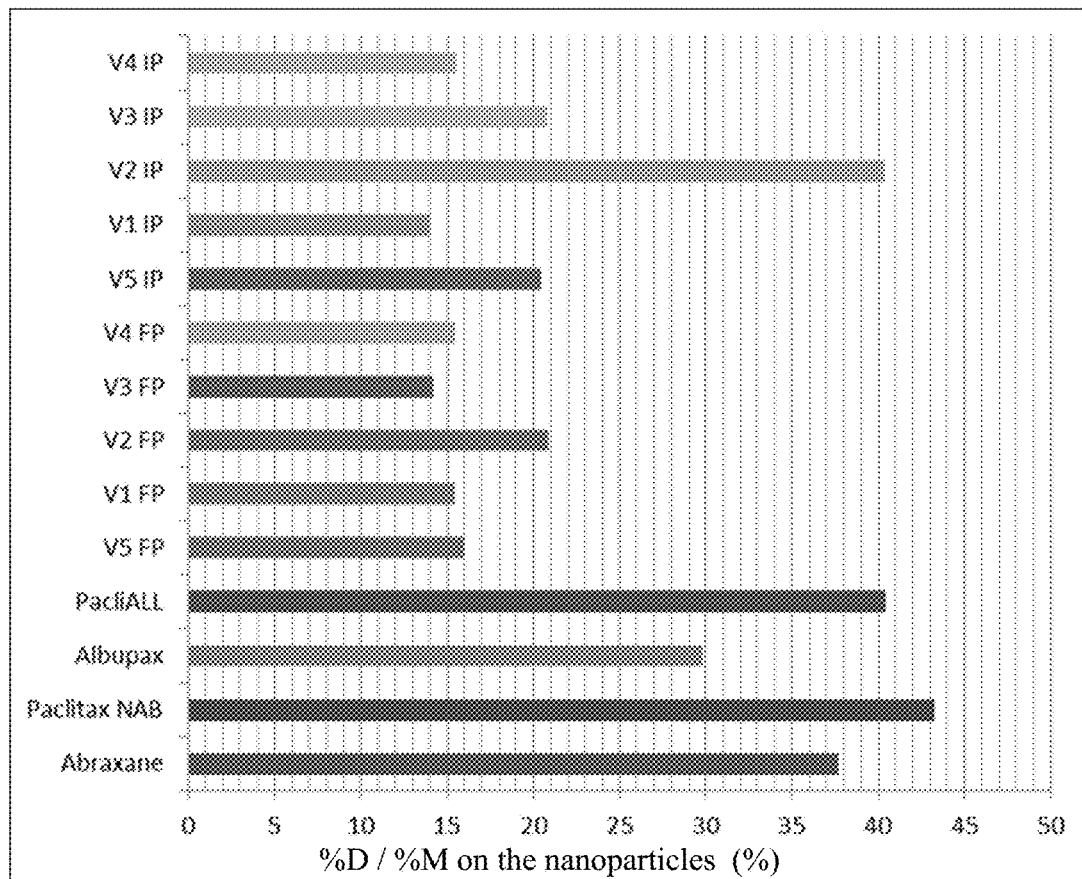
FIG. 21 shows a bar graph of the ratio (reported as a percentage) of the percentage of albumin on the nanoparticles in the form of dimers (D) divided by the percentage of albumin on the nanoparticles in the form of monomers (M).

A comparison of the ratio (as reported as a percentage) of the percentage of albumin on the nanoparticles in the form of dimers (D) divided by the percentage of albumin on the nanoparticles in the form of monomers (M) (Table 25) is illustrated in the bar graph of FIG. 21. Amongst all the compositions, the nab-paclitaxel sold under the trademark ABRAXANE® and Paclitax NAB are most stable.

Figure 22:
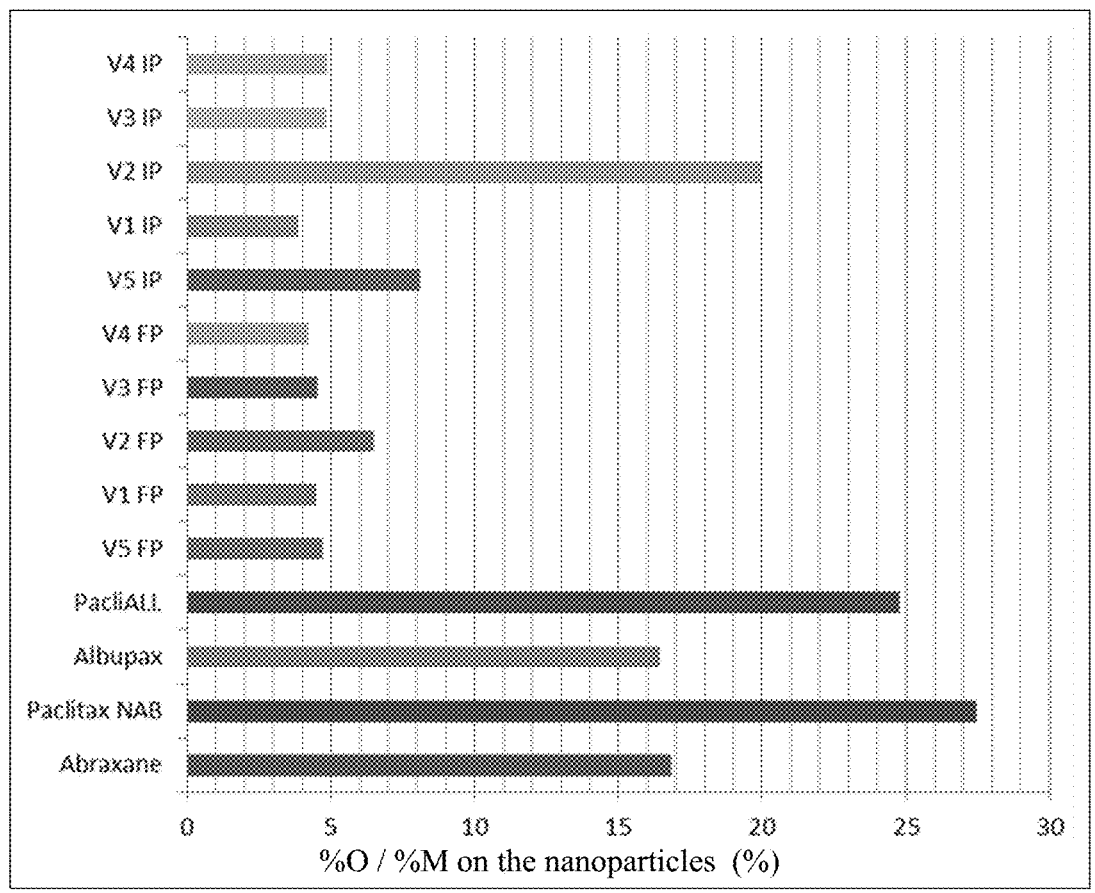
FIG. 22 shows a bar graph of the ratio (reported as a percentage) of the percentage of albumin on the nanoparticles in the form of oligomers (O) divided by the percentage of albumin on the nanoparticles in the form of monomers (M).

A comparison of the ratio (as reported as a percentage) of the percentage of albumin on the nanoparticles in the form of oligomers (O) divided by the percentage of albumin on the nanoparticles in the form of monomers (M) (Table 25) is illustrated in the bar graph of FIG. 22. Amongst all the compositions, the nab-paclitaxel sold under the trademark ABRAXANE® and Paclitax NAB are most stable.

Figure 23:
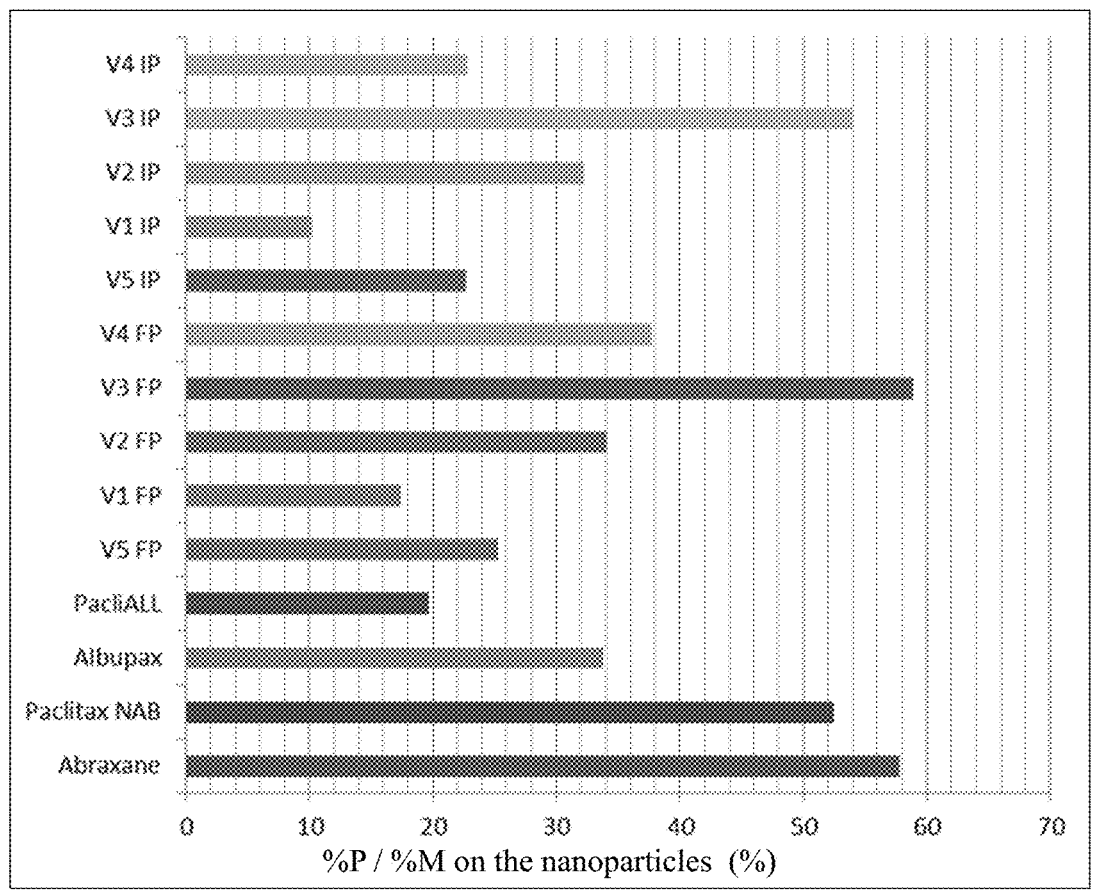
FIG. 23 shows a bar graph of the ratio (reported as a percentage) of the percentage of albumin on the nanoparticles in the form of polymers (P) divided by the percentage of albumin on the nanoparticles in the form of monomers (M).

A comparison of the ratio (as reported as a percentage) of the percentage of albumin on the nanoparticles in the form of polymers (P) divided by the percentage of albumin on the nanoparticles in the form of monomers (M) (Table 25) is illustrated in the bar graph of FIG. 23. Amongst all the compositions, the nab-paclitaxel sold under the trademark ABRAXANE® and Paclitax NAB are most stable.

Figure 24:
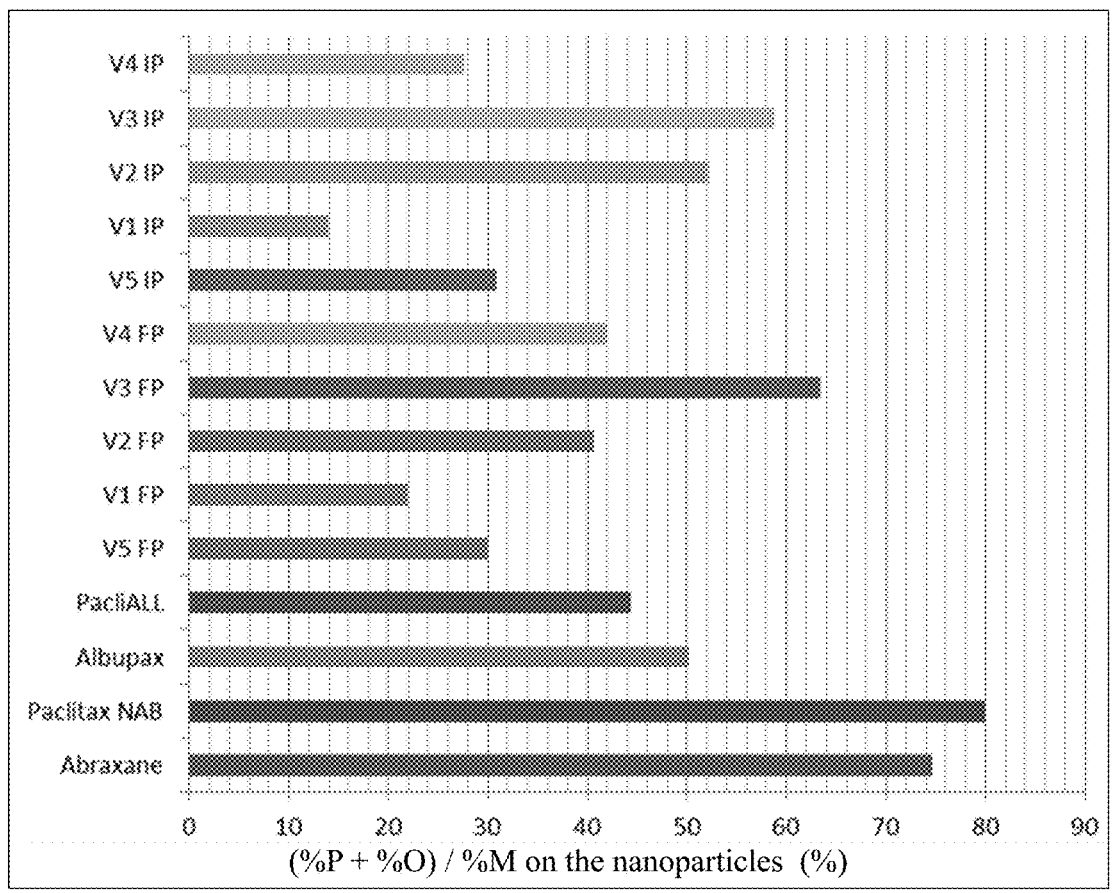
FIG. 24 shows a bar graph of the ratio (reported as a percentage) of the percentage of albumin on the nanoparticles in the form of polymers (P) and oligomers (O) divided by the percentage of albumin on the nanoparticles in the form of monomers (M).

A comparison of the ratio (as reported as a percentage) of the percentage of albumin on the nanoparticles in the form of polymers (P) and oligomers (O) divided by the percentage of albumin on the nanoparticles in the form of monomers (M) (Table 25) is illustrated in the bar graph of FIG. 24. Amongst all the compositions, the nab-paclitaxel sold under the trademark ABRAXANE® and Paclitax NAB are most stable.

Figure 25:
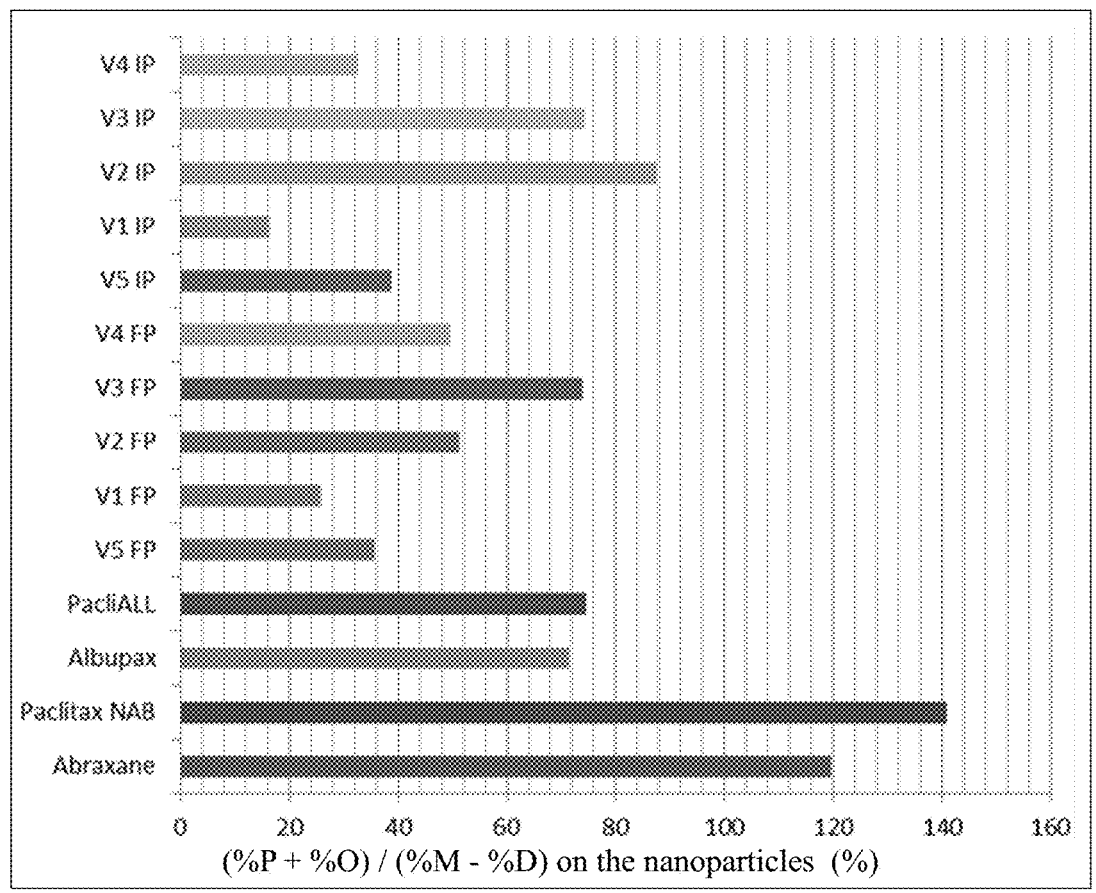
FIG. 25 shows a bar graph of the ratio (reported as a percentage) of the percentage of albumin on the nanoparticles in the form of polymers (P) and oligomers (O) divided by the percentage of albumin on the nanoparticles in the form of monomers (M) minus dimers (D).

A comparison of the ratio (as reported as a percentage) of the percentage of albumin on the nanoparticles in the form of polymers (P) and oligomers (O) divided by the percentage of albumin on the nanoparticles in the form of monomers (M) minus dimers (D) (Table 25) is illustrated in the bar graph of FIG. 25. Amongst all the compositions, the nab-paclitaxel sold under the trademark ABRAXANE® and Paclitax NAB are most stable.

TABLE 26

Solubility (µg/ml) and dissolution kinetics of the composition immediately after reconstitution.

| Sample Name | N (number) | Mean | Margin of error | Min | Max | Dissolution kinetics comment |
| --- | --- | --- | --- | --- | --- | --- |
| ABRAXANE ® | 11 | 66.1 | 5.3 | 53.5 | 82.2 | Normal |
| Paclitax NAB | 1 | 63.3 | — | 63.3 | 63.3 | Normal |
| Albupax | 1 | 40.0 | — | 40.0 | 40.0 | — |
| PacliALL | 3 | 85.0 | 21.2 | 76.0 | 93.0 | Normal |
| V5 FP | 3 | 80.0 | 39.8 | 62.3 | 93.5 | Normal |
| V1 FP | 3 | 66.2 | 22.4 | 58.0 | 75.9 | Normal |
| V2 FP | 2 | 70.9 | 183.0 | 56.5 | 85.3 | None |
| V3 FP | 3 | 74.8 | 13.6 | 68.8 | 79.5 | Normal |
| V4 FP | 3 | 69.1 | 22.1 | 59.8 | 77.5 | Slower than normal |

TABLE 27

Degree of sedimentation (stability) based on visual observation of the composition (1 indicates no sedimentation) immediately after reconstitution.

| Sample Name | N (number) | Mean | Margin of error | Min | Max |
| --- | --- | --- | --- | --- | --- |
| ABRAXANE ® | 17 | 1 | 0 | 1 | 1 |
| Paclitax NAB | 2 | 1 | 0 | 1 | 1 |
| Albupax | — | — | — | — | — |
| PacliALL | 3 | 1 | 0 | 1 | 1 |
| V5 FP | 3 | 1 | 0 | 1 | 1 |
| V1 FP | 3 | 1 | 0 | 1 | 1 |
| V2 FP | 3 | 1 | 0 | 1 | 1 |

TABLE 27-continued

Degree of sedimentation (stability) based on visual observation of the composition (1 indicates no sedimentation) immediately after reconstitution.

| Sample Name | N (number) | Mean | Margin of error | Min | Max |
|---|---|---|---|---|---|
| V3 FP | 3 | 1 | 0 | 1 | 1 |
| V4 FP | 3 | 1 | 0 | 1 | 1 |

*The degree of sedimentation recited as: 1 - No visible sedimentation (NVS); 2 - Streaming with NVS; 3 - Very slight sedimentation; 4 - Slight sedimentation; 5 - Sedimentation; 6 - Phase separation.

TABLE 28

Percentage of paclitaxel recovered after filtration through a 0.2-μm syringe filter immediately after reconstitution.

| Sample Name | N (number) | Mean | Margin of error | Min | Max |
|---|---|---|---|---|---|
| ABRAXANE ® | 21 | 98.2 | 1.4 | 93.3 | 106.2 |
| Paclitax NAB | 2 | 104.0 | 76.2 | 98 | 110 |
| Albupax | — | — | — | — | — |
| PacliALL | 5 | 43.0 | 24.1 | 27 | 72 |
| V5 FP | 3 | 95.7 | 8.7 | 92 | 99 |
| V1 FP | 3 | 92.3 | 18.0 | 84 | 97 |
| V2 FP | 2 | 92.0 | 63.5 | 87 | 97 |
| V3 FP | 3 | 97.0 | 7.5 | 94 | 100 |
| V4 FP | 3 | 99.0 | 13.1 | 95 | 105 |

Table 29

Solubility (μg/ml) and dissolution kinetics of the composition after storage of the reconstituted suspension for 24 hours at 40° C.

| Sample Name | N (number) | Mean | Margin of error | Min | Max | Solubility comment | Dissolution kinetics comment |
|---|---|---|---|---|---|---|---|
| ABRAXANE ® | 12 | 66.8 | 7.5 | 54.0 | 96.8 | Regular | Normal |
| Paclitax NAB | 1 | 44.9 | — | 44.9 | 44.9 | Low solubility | Normal |
| Albupax | — | — | — | — | — | — | Normal |
| PacliALL | 3 | 46.9 | 101.1 | 0.0 | 73.5 | Insoluble/Regular | — |
| V5 FP | 2 | 74.1 | 2.5 | 73.9 | 74.3 | ~Regular | Normal |
| V1 FP | 2 | 0.0 | 0.0 | 0.0 | 0.0 | Insoluble | None |
| V2 FP | 1 | 0.0 | — | 0.0 | 0.0 | Insoluble | None |
| V3 FP | 2 | 0.0 | 0.0 | 0.0 | 0.0 | Insoluble | None |
| V4 FP | 2 | 0.0 | 0.0 | 0.0 | 0.0 | Insoluble | None |

TABLE 30

Degree of sedimentation (stability) based on visual observation (1 indicates no sedimentation) and crystallinity (1 indicates presence of crystalline paclitaxel) of the composition after storage of the reconstituted suspension for 24 hours at 40° C.

| Sample Name | N (number) | Mean* | Margin of error | Min | Max | Crystallinity | Crystallinity value |
|---|---|---|---|---|---|---|---|
| ABRAXANE ® | 17 | 1 | 0 | 1 | 1 | No Birefringence | 0 |
| Paclitax NAB | 2 | 1 | 0 | 1 | 1 | No Birefringence | 0 |
| Albupax | 1 | 5 | — | 5 | 5 | Birefringence | 1 |
| PacliALL | 5 | 5 | 0 | 5 | 5 | Birefringence | 1 |
| V5 FP | 2 | 5 | 0 | 5 | 5 | Birefringence | 1 |
| V1 FP | 2 | 5.5 | 6.4 | 5 | 6 | Birefringence | 1 |
| V2 FP | 1 | 6 | 0 | 6 | 6 | Birefringence | 1 |
| V3 FP | 2 | 6 | 0 | 6 | 6 | Birefringence | 1 |
| V4 FP | 2 | 6 | 0 | 6 | 6 | Birefringence | 1 |

*The degree of sedimentation recited as: 1 - No visible sedimentation (NVS); 2 - Streaming with NVS; 3 - Very slight sedimentation; 4 - Slight sedimentation; 5 - Sedimentation; 6 - Phase separation.

TABLE 31

Degree of sedimentation (stability) based on visual observation (1 indicates no sedimentation) and crystallinity (1 indicates presence of crystalline paclitaxel) of the composition after storage of the reconstituted suspension at 40° C. for 16 hours.

| Sample Name | Mean | Crystallinity value |
|---|---|---|
| V5 FP | 2.7 | 0 |
| V1 FP | 5 | 1 |
| V2 FP | 5.5 | 1 |
| V3 FP | 5.3 | 0.66 |
| V4 FP | 5 | 0.66 |

TABLE 32

Percentage of paclitaxel recovered after filtration through a 0.2-μm syringe filter afterstorage of the reconstituted suspension at 40° C. for 16 hours.

| Sample Name | Mean |
|---|---|
| V5 FP | 96.5 |
| V1 FP | 59.2 |
| V2 FP | 22.6 |
| V3 FP | 50.1 |
| V4 FP | 36.2 |

TABLE 33

Degree of sedimentation (stability) based on visual observation (1 indicates no sedimentation) and crystallinity (1 indicates presence of crystalline paclitaxel) of the composition after storage of the reconstituted suspension at 5° C. for 8 hours followed by storage at 25° C. for 8 hours.

| Sample Name | Mean | Crystallinity value |
|---|---|---|
| V5 FP | 1 | 0.333 |
| V1 FP | 1.33 | 1 |
| V2 FP | 1.5 | 0 |
| V3 FP | 1.33 | 0 |
| V4 FP | 1 | 0 |

TABLE 34

Percentage of paclitaxel recovered after filtration through a 0.2-μm syringe filter after storage of the reconstituted suspension at 5° C. for 8 hours followed by storage at 25° C. for 8 hours.

| Sample Name | Mean |
|---|---|
| V5 FP | 98.7 |
| V1 FP | 72.7 |
| V2 FP | 64.0 |
| V3 FP | 91.0 |
| V4 FP | 92.0 |

TABLE 35

Percentage of paclitaxel recovered after filtration through a 0.2-μm syringe filter after storage of the reconstituted suspension for 24 hours at 40° C.

| Sample Name | N (number) | Mean | Margin of error | Min | Max |
|---|---|---|---|---|---|
| ABRAXANE ® | 18 | 96.4 | 1.7 | 92.2 | 106.7 |
| Paclitax NAB | — | — | — | — | — |
| Albupax | 1 | 61 | — | 61 | 61 |
| PacliALL | 1 | 69 | — | 69 | 69 |
| V5 FP | 2 | 86.3 | 36.8 | 83.4 | 89.2 |
| V1 FP | 2 | 13.5 | 170.9 | 0.0 | 26.9 |
| V2 FP | 1 | 0.0 | — | 0.0 | 0.0 |
| V3 FP | 2 | 9.7 | 91.5 | 2.5 | 16.9 |
| V4 FP | 2 | 0.0 | 0.0 | 0.0 | 0.0 |

TABLE 36

$D_{v4,3}$ (nm) measured after storage of the reconstituted suspension for 24 hours at 40° C.

| Sample Name | N (number) | Mean | Margin of error | Min | Max |
|---|---|---|---|---|---|
| ABRAXANE ® | 20 | 155.8 | 3.6 | 143.5 | 169.1 |
| Paclitax NAB | 2 | 118.4 | 48.9 | 114.5 | 122.2 |
| Albupax | 1 | 150.9 | — | 150.9 | 150.9 |
| PacliALL | 5 | 1052.5 | 3531.3 | 231.5 | 2694 |
| V5 FP | 2 | 172.9 | 90.8 | 165.7 | 180 |
| V1 FP | 2 | 2556.5 | 7096.4 | 1998 | 3115 |
| V2 FP | 1 | 2475.0 | — | 2475 | 2475 |
| V3 FP | 2 | 2408.0 | 5539.9 | 1972 | 2844 |
| V4 FP | 2 | 2431.0 | 7814.3 | 1816 | 3046 |

TABLE 37

Z average (nm) measured after storage of the reconstituted suspension for 24 hours at 40° C.

| Sample Name | N (number) | Mean | Margin of error | Min | Max |
|---|---|---|---|---|---|
| ABRAXANE ® | 20 | 147.7 | 2.2 | 139.5 | 155.8 |
| Paclitax NAB | 2 | 121.7 | 37.4 | 118.8 | 124.7 |
| Albupax | 1 | 157.7 | — | 157.7 | 157.7 |
| PacliALL | 5 | 1411.3 | 2634.2 | 183.4 | 5098 |
| V5 FP | 2 | 156.9 | 60.3 | 152.2 | 161.7 |
| V1 FP | 2 | 2361.8 | 25414.2 | 361.7 | 4362 |
| V2 FP | 1 | 3435.0 | — | 3435 | 3435 |
| V3 FP | 2 | 692.0 | 4459.2 | 341.1 | 1043 |
| V4 FP | 2 | 5338.5 | 946.6 | 5264 | 5413 |

TABLE 38

Polydispersity index (PDI) measured after storage of the reconstituted suspension for 24 hours at 40° C.

| Sample Name | N (number) | Mean | Margin of error | Min | Max |
|---|---|---|---|---|---|
| ABRAXANE ® | 20 | 0.11555 | 0.007141 | 0.092 | 0.156 |
| Paclitax NAB | 2 | 0.1015 | 0.069884 | 0.096 | 0.107 |
| Albupax | 1 | 0.214 | — | 0.214 | 0.214 |
| PacliALL | 5 | 0.3806 | 0.353505 | 0.178 | 0.862 |
| V5 FP | 2 | 0.141 | 0.1270619 | 0.131 | 0.151 |
| V1 FP | 2 | 0.6135 | 2.12829 | 0.446 | 0.781 |
| V2 FP | 1 | 0.315 | — | 0.315 | 0.315 |
| V3 FP | 2 | 0.8545 | 0.603542 | 0.807 | 0.902 |
| V4 FP | 2 | 0.368 | 1.4358 | 0.255 | 0.481 |

TABLE 39

DV5 (nm) measured after storage of the
reconstituted suspension for 24 hours at 40° C.

| Sample Name | N (number) | Mean | Margin of error | Min | Max |
|---|---|---|---|---|---|
| ABRAXANE ® | 20 | 76.2 | 2.4 | 65.2 | 84.7 |
| Paclitax NAB | 2 | 63.2 | 6.3 | 62.7 | 63.7 |
| Albupax | 1 | 86.3 | — | 86.3 | 86.3 |
| PacliALL | 5 | 611.2 | 944.5 | 73.8 | 1760 |
| V5 FP | 2 | 73.8 | 94.0 | 66.4 | 81.2 |
| V1 FP | 2 | 834 | 8716.4 | 148 | 1520 |
| V2 FP | 1 | 1500.0 | — | 1500 | 1500 |
| V3 FP | 2 | 172.5 | 209.6 | 156 | 189 |
| V4 FP | 2 | 1715.0 | 4637.7 | 1350 | 2080 |

TABLE 40

DV50 (nm) measured after storage
of the reconstituted suspension for 24 hours at 40° C.

| Sample Name | N (number) | Mean | Margin of error | Min | Max |
|---|---|---|---|---|---|
| ABRAXANE ® | 20 | 140.2 | 4.138 | 124 | 154 |
| Paclitax NAB | 2 | 107 | 38.11875 | 104 | 110 |
| Albupax | 1 | 142 | — | 142 | 142 |
| PacliALL | 5 | 1075.2 | 1466.9505 | 200 | 2500 |
| V5 FP | 2 | 151 | 139.768 | 140 | 162 |
| V1 FP | 2 | 2795 | 10355.52 | 1980 | 3610 |
| V2 FP | 1 | 2337 | — | 2337 | 2337 |
| V3 FP | 2 | 2445 | 6035.44 | 1970 | 2920 |
| V4 FP | 2 | 2390 | 7369.59 | 1810 | 2970 |

TABLE 41

DV95 (nm) measured after storage of the reconstituted
suspension for 24 hours at 40° C.

| Sample Name | N (number) | Mean | Margin of error | Min | Max |
|---|---|---|---|---|---|
| ABRAXANE ® | 20 | 290.9 | 7.695 | 267 | 336 |
| Paclitax NAB | 2 | 214.5 | 133.41495 | 204 | 225 |
| Albupax | 1 | 249 | — | 249 | 249 |
| PacliALL | 5 | 3062.4 | 2951.1995 | 496 | 5450 |
| V5 FP | 2 | 346 | 63.531 | 341 | 351 |
| V1 FP | 2 | 4305 | 21664 | 2600 | 6010 |
| V2 FP | 1 | 3917 | — | 3917 | 3917 |
| V3 FP | 2 | 4265 | 15565.1 | 3040 | 5490 |
| V4 FP | 2 | 3345 | 13023.82 | 2320 | 4370 |

TABLE 42

(DV90-DV10)/DV50 measured after storage of the
reconstituted suspension for 24 hour at 40° C.

| Sample Name | N (number) | Mean | Margin of error | Min | Max |
|---|---|---|---|---|---|
| ABRAXANE ® | 20 | 1.20616 | 0.055545 | 1.03684 | 1.46048 |
| Paclitax NAB | 2 | 1.08277 | 0.611737 | 1.03462 | 1.13091 |
| Albupax | 1 | 0.88803 | — | 0.88803 | 0.88803 |
| PacliALL | 5 | 3.76422 | 6.98718 | 0.736 | 13.8008 |
| V5 FP | 2 | 1.43079 | 2.077525 | 1.26728 | 1.59429 |
| V1 FP | 2 | 0.955875 | 6.498385 | 0.44444 | 1.46731 |
| V2 FP | 1 | 0.82713 | — | 0.82713 | 0.82713 |
| V3 FP | 2 | 1.17052 | 6.101 | 0.69036 | 1.65068 |
| V4 FP | 2 | 0.517895 | 1.0347265 | 0.43646 | 0.59933 |

What is claimed is:

1. A method of validating a commercial batch of a pharmaceutical composition for medical use in a human individual, wherein the pharmaceutical composition comprises (a) nanoparticles comprising paclitaxel coated with a coating comprising albumin and (b) a non-nanoparticle portion comprising albumin and paclitaxel, the method comprising:

(1) obtaining a sample from the commercial batch; and (2) assessing suitability of the pharmaceutical composition for medical use in a human individual, comprising:
separating the nanoparticles from the non-nanoparticle portion,
measuring a weight percentage of albumin in the form of albumin polymers in the coating of the separated nanoparticles among the total albumin in the coating of the separated nanoparticles, and
assessing the suitability of the pharmaceutical composition for medical use in a human individual, wherein the weight percentage of albumin in the form of albumin polymers in the coating of the separated nanoparticles among the total albumin in the coating of the separated nanoparticles being from about 15% to about 40% is indicative of suitability of the pharmaceutical composition for medical use; and (3) validating the commercial batch if the pharmaceutical composition is suitable for medical use.

2. The method of claim 1, wherein the method further comprises measuring a weight percentage of albumin in the form of albumin monomers in the coating of the separated nanoparticles among the total albumin in the coating of the separated nanoparticles, wherein the weight percentage of albumin in the form of albumin monomers in the coating of the separated nanoparticles among the total albumin in the coating of the separated nanoparticles being from about 40% to about 60% is indicative of suitability of the pharmaceutical composition for medical use.

3. The method of claim 1, wherein the method further comprises measuring a weight percentage of the albumin in the coating of the separated nanoparticles compared to the total weight of the separated nanoparticles, wherein the weight percentage of the albumin in the coating of the separated nanoparticles compared to the total weight of the separated nanoparticles being from about 15% to about 30% is indicative of suitability of the pharmaceutical composition for medical use.

4. The method of claim 1, further comprising determining a weight ratio of albumin in the coating of the separated nanoparticles to paclitaxel in the nanoparticles, wherein the weight ratio of albumin in the coating of the separated nanoparticles to paclitaxel in the nanoparticles being from about 1:2 to about 1:6 in the nanoparticles is indicative of suitability of the pharmaceutical composition for medical use.

5. The method of claim 1, further comprising determining a thickness of the coating of the nanoparticles by cryogenic transmission electron microscopy, wherein the thickness being about 5-7 nm as determined by cryogenic transmission electron microscopy is indicative of suitability of the pharmaceutical composition for medical use.

6. The method of claim 1, further comprising determining a solubility of the nanoparticles in a 5% albumin solution by dynamic light scattering, wherein the solubility of the nanoparticles being from about 50 µg/ml to about 100 µg/ml in the 5% human albumin solution is indicative of suitability of the pharmaceutical composition for medical use.

7. The method of claim 1, further comprising determining a paclitaxel crystallinity of the paclitaxel in the nanoparticles of the pharmaceutical composition by X-ray diffraction or polarized light microscopy, wherein a non-crystalline state of the paclitaxel is indicative of suitability of the pharmaceutical composition for medical use.

8. The method of claim 1, further comprising determining a paclitaxel recovery following a 0.2 micron filtration of the pharmaceutical composition, wherein the paclitaxel recovery being at least 80% is indicative of suitability of the pharmaceutical composition for medical use.

9. The method of claim 6, wherein the determination of solubility is carried out after storage.

10. The method of claim 1, further comprising measuring a weight percentage of albumin in the form of albumin dimers in the coating of the separated nanoparticles among the total albumin in the coating of the separated nanoparticles, wherein the weight percentage of albumin in the form of albumin dimers in the coating of the separated nanoparticles among the total albumin in the coating of the separated nanoparticles being from about 15% to about 30% is indicative of suitability of the pharmaceutical composition for medical use.

11. The method of claim 1, further comprising measuring a weight percentage of albumin in the form of albumin oligomers in the coating of the separated nanoparticles among the total albumin in the coating of the separated nanoparticles, wherein the weight percentage of albumin in the form of albumin oligomers in the coating of the separated nanoparticles among the total albumin in the coating of the separated nanoparticles being from about 7% to about 15% is indicative of suitability of the pharmaceutical composition for medical use.

12. The method of claim 1, further comprising determining a particle size of the nanoparticles using dynamic light scattering, wherein the particle size of the nanoparticles being less than 200 nm is indicative of suitability of the pharmaceutical composition for medical use.

13. The method of claim 1, further comprising determining a polydispersity index of the nanoparticles in the pharmaceutical composition using dynamic light scattering, wherein the polydispersity index of the nanoparticles being less than 0.3 is indicative of suitability of the pharmaceutical composition for medical use.

14. The method of claim 1, further comprising determining a span of size distribution of the nanoparticles in the pharmaceutical composition as $(D_{v90}-D_{v10})/D_{v50}$ using dynamic light scattering, wherein $D_{v90}$ is the particle diameter where 90% of the volume of all nanoparticles is contained in nanoparticles with smaller diameters; $D_{v10}$ is the particle diameter where 10% of the volume of all nanoparticles is contained in nanoparticles with smaller diameters; and $D_{v50}$ is the volume-weighted median particle diameter; and wherein the span of size distribution being from about 0.8 to about 1.5 is indicative of suitability of the pharmaceutical composition for medical use.

15. The method of claim 1, further comprising determining a surface potential of the nanoparticles using microelectrophoresis, electrophoretic light scattering, dynamic electrophoretic mobility, or tunable resistive pulse sensing, wherein the surface potential of the nanoparticles being from about −20 mV to about −35 mV is indicative of suitability of the nanoparticles for medical use.

16. The method of claim 1, further comprising measuring a weight percentage of the paclitaxel in the separated nanoparticles among the total paclitaxel in the pharmaceutical composition using reversed-phase high performance liquid chromatography, wherein the weight percentage of the paclitaxel in the separated nanoparticles among the total paclitaxel in the pharmaceutical composition being at least 95% is indicative of suitability of the pharmaceutical composition for medical use.

17. The method of claim 1, further comprising measuring a weight percentage of the albumin that is in the non-nanoparticle portion among the total albumin in the pharmaceutical composition using size-exclusion chromatography, wherein the weight percentage of the albumin that is in the non-nanoparticle portion among the total albumin in the pharmaceutical composition being at least 95% is indicative of suitability of the pharmaceutical composition for medical use.

18. The method of claim 1, wherein the pharmaceutical composition has a weight ratio of total albumin to total paclitaxel in the range from about 3:1 to about 7.9:1 or from about 10:1 to about 17:1.

19. The method of claim 1, wherein the albumin is human albumin.

20. The method of claim 1, wherein the average diameter of the nanoparticles in the pharmaceutical composition is less than about 200 nm as determined by dynamic light scattering.

21. A commercial batch of a pharmaceutical composition for medical use in a human individual, wherein the pharmaceutical composition comprises (a) nanoparticles comprising paclitaxel coated with a coating comprising albumin and (b) a non-nanoparticle portion comprising albumin and paclitaxel, and wherein the commercial batch is validated by method of claim 1.

22. The method of claim 1, further comprising measuring a weight percentage of albumin in the form of albumin monomers in the coating of the separated nanoparticles among the total albumin in the coating of the separated nanoparticles, wherein the weight percentage of albumin in the form of albumin monomers in the coating of the separated nanoparticles among the total albumin in the coating of the separated nanoparticles being less than about 51% is indicative of the pharmaceutical composition for medical use.

23. The method of claim 1, further comprising measuring a weight percentage of albumin in the form of albumin monomers, albumin oligomers, and albumin polymers in the coating of the separated nanoparticles among the total albumin in the coating of the separated nanoparticles, wherein a ratio of the sum of the weight percentage of albumin in the form of albumin polymers in the coating of the separated nanoparticles and the weight percentage of the albumin in the form of albumin oligomers in the coating of the separated nanoparticles compared to the weight percentage of albumin in the form of albumin monomers in the coating of the separated nanoparticles being more than about 65% is indicative of the pharmaceutical composition for medical use.

24. A method of releasing a commercial batch of a pharmaceutical composition comprising (a) nanoparticles comprising paclitaxel coated with a coating comprising albumin and (b) a non-nanoparticle portion comprising albumin and paclitaxel, the method comprising:
  (1) assessing suitability of the pharmaceutical composition for medical use in a human individual, comprising:
    separating the nanoparticles from the non-nanoparticle portion,
    measuring a weight percentage of albumin in the form of albumin polymers in the coating of the separated nanoparticles among the total albumin in the coating of the separated nanoparticles, and assessing the suitability of the pharmaceutical composition for medical use in a human individual, wherein the weight percentage of albumin in the form of albumin polymers in the coating of the separated nanoparticles among the total albumin in the coating of the separated nanoparticles being from about 15% to about 40% is indicative of suitability of the pharmaceutical composition for medical use; and (2) releasing the commercial batch if the pharmaceutical composition is suitable for medical use.

25. A method of processing a sample of a pharmaceutical composition to assess suitability of the pharmaceutical composition for medical use in a human individual, the pharmaceutical composition comprising (a) nanoparticles comprising paclitaxel coated with a coating comprising albumin and (b) a non-nanoparticle portion comprising albumin and paclitaxel, the method comprising:

(1) obtaining the sample from a commercial batch; and
(2) processing the sample to assess suitability of the pharmaceutical composition for medical use in a human individual, comprising:
separating the nanoparticles from the non-nanoparticle portion,
measuring a weight percentage of albumin in the form of albumin polymers in the coating of the separated nanoparticles among the total albumin in the coating of the separated nanoparticles, and
assessing the suitability of the pharmaceutical composition for medical use in a human individual, wherein the weight percentage of albumin in the form of albumin polymers in the coating of the separated nanoparticles among the total albumin in the coating of the separated nanoparticles being from about 15% to about 40% is indicative of suitability of the pharmaceutical composition for medical use.

* * * * *

UNITED STATES PATENT AND TRADEMARK OFFICE
CERTIFICATE OF CORRECTION

PATENT NO. : 10,900,951 B1
APPLICATION NO. : 16/517967
DATED : January 26, 2021
INVENTOR(S) : Viktor Peykov et al.

It is certified that error appears in the above-identified patent and that said Letters Patent is hereby corrected as shown below:

On the Title Page

On page 3, Column 2, item (56) under OTHER PUBLICATIONS, Line 23, please replace "Celegene" with -- Celgene --;
On page 3, Column 2, item (56) under OTHER PUBLICATIONS, Line 58, please replace "Parentheral" with -- Parenteral --;
On page 3, Column 2, item (56) under OTHER PUBLICATIONS, Line 68, please replace "Reseach." with -- Research. --;
On page 4, Column 1, item (56) under OTHER PUBLICATIONS, Line 21, please replace ""Anaphylactiod" with -- "Anaphylactoid --;
On page 4, Column 1, item (56) under OTHER PUBLICATIONS, Line 22, please replace "Infusin" with -- Infusion --;
On page 4, Column 1, item (56) under OTHER PUBLICATIONS, Line 57, please replace "Cremophore" with -- Cremophor --;
On page 4, Column 2, item (56) under OTHER PUBLICATIONS, Line 65, please replace "Supensions" with -- Suspensions --;
On page 5, Column 1, item (56) under OTHER PUBLICATIONS, Line 5, please replace "in Endotherlial" with -- in Endothelial --;
On page 5, Column 1, item (56) under OTHER PUBLICATIONS, Line 5, please replace "Endotherlial" with -- Endothelial --;
On page 5, Column 1, item (56) under OTHER PUBLICATIONS, Line 28, please replace ""Anaphylactiod" with -- "Anaphylactoid --;
On page 5, Column 1, item (56) under OTHER PUBLICATIONS, Line 41, please replace "Interactiono f" with -- Interaction of --;
On page 5, Column 2, item (56) under OTHER PUBLICATIONS, Line 2, please replace "Maligiancies,"" with -- Malignancies," --;

In the Specification

On Column 230, Line 43, please replace "50 μM or" with -- 50 μM, or --;

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,900,951 B1

On Column 236, Line 55, please replace "-diamindino-" with -- -diamidino- --;
On Column 245, Line 27, please replace "litocholic" with -- lithocholic --;
On Column 245, Lines 36-37, please replace "di stearoylphosphatidylcholine" with -- distearoylphosphatidylcholine --;
On Column 245, Lines 50-51, please replace "(vinylpyrolidone);" with -- (vinylpyrrolidone); --;
On Column 271, Line 9, please replace "Nude-Foxnlnu" with -- Nude-Foxn1nu --;
On Column 271, Line 51, please replace "-diamindino-" with -- -diamidino- --;
On Column 292, TABLE 27, Line 60, please replace "Mean" with -- Mean* --;
On Column 293, TABLE 27-continued, Line 9, please replace "Mean" with -- Mean* --;
On Column 295, TABLE 32, Line 27, please replace "afterstorage" with -- after storage --;
On Column 297, TABLE 42, Line 51, please replace "hour" with -- hours --;

In the Claims

On Column 299, Line 45, please replace "$D_{v90}$" with -- $Dv_{90}$ --;
On Column 299, Line 45, please replace "$D_{v10}$" with -- $Dv_{10}$ --;
On Column 299, Line 45, please replace "$D_{v50}$" with -- $Dv_{50}$ --;
On Column 299, Line 46, please replace "$D_{v90}$" with -- $Dv_{90}$ --;
On Column 299, Line 48, please replace "$D_{v10}$" with -- $Dv_{10}$ --; and
On Column 299, Line 51, please replace "$D_{v50}$" with -- $Dv_{50}$ --.